US008372852B2

(12) United States Patent
Shaginian et al.

(10) Patent No.: US 8,372,852 B2
(45) Date of Patent: Feb. 12, 2013

(54) PURINES AS REVERSE TRANSCRIPTASE INHIBITORS

(75) Inventors: Alex Shaginian, San Diego, CA (US); Samedy Ouk, San Diego, CA (US); Jean-Michel Vernier, San Diego, CA (US); Anthony B. Pinkerton, San Diego, CA (US)

(73) Assignee: Ardea Biosciences, Inc., San Diego, CA (US)

( * ) Notice: Subject to any disclaimer, the term of this patent is extended or adjusted under 35 U.S.C. 154(b) by 0 days.

(21) Appl. No.: 13/470,122

(22) Filed: May 11, 2012

(65) Prior Publication Data

US 2012/0277206 A1 Nov. 1, 2012

Related U.S. Application Data

(62) Division of application No. 12/334,371, filed on Dec. 12, 2008, now Pat. No. 8,207,178.

(60) Provisional application No. 61/013,983, filed on Dec. 14, 2007.

(51) Int. Cl.

| | |
|---|---|
| ***C07D 473/28*** | (2006.01) |
| ***C07D 473/34*** | (2006.01) |
| ***A61K 31/52*** | (2006.01) |
| ***A61P 31/18*** | (2006.01) |
| *C07D 487/04* | (2006.01) |
| *A61K 31/519* | (2006.01) |

(52) U.S. Cl. ........... 514/263.2; 514/263.22; 514/263.37; 514/265.1; 514/280; 514/262.1; 514/263.3; 544/265; 544/276; 544/254; 544/280; 544/262

(58) Field of Classification Search .................. 544/265, 544/276; 514/263.22, 263.2, 263.37
See application file for complete search history.

(56) References Cited

U.S. PATENT DOCUMENTS 6,271,370 B1 8/2001 Scott
6,414,147 B1 7/2002 Currie et al.

FOREIGN PATENT DOCUMENTS

| | | | |
|---|---|---|---|
| WO | WO 00-27850 A2 | 5/2000 | |
| WO | WO-00-43394 A1 | 7/2000 | |
| WO | WO-03-016306 A1 | 2/2003 | |
| WO | WO-2004-069812 A1 | 8/2004 | |
| WO | WO-2005-028479 A2 | 3/2005 | |
| WO | WO-2006-045828 A1 | 5/2006 | |
| WO | WO-2006-122003 A2 | 11/2006 | |

OTHER PUBLICATIONS

Badger et al., "Azaindoles," Aust. J. Chem. 18:1267-1271 (1965).
Balzarm, J., "Current Status of the Non-nucleoside Reverse Transcriptase Inhibitors of Human Immunodeficiency Virus Type 1," Cur. Top. Med. Chem. 4:921-944 (2004).
Banker et al., "Modern Pharmaceutics, 3ed., " Marcel Dekker, New York, 1996, p. 596.
Berge et al., "Pharmaceutical Salts," J. Pharm. Sci. 66:1-19 (1977).
Bitterli, "Uber einíge Derivate des Triazolo-pyrimidins," Helvetica Chimica Acta 34:835-840 (1951).
Bontems et al., "Guanosine Analogues. Synthesis of Nucleosides of Certain 3-Substituted 6-Aminopyrazolo[3,4-d]pyrmidin-4(5H)-ones as Potential Immunotherapeutic Agents," J. Med. Chem. 33:2 174-2178 (1990).
Buckheit, "Non-nucleoside reverse transcriptase inhibitors: perspectives onnovel therapeutic compounds and strategies for the treatment of HIV infection," Exp. Op. Investig. Drugs 10(8):1423-1442 (2001).
Bundgaard, "Design and Application of Prodrugs," in Textbook of Drug Design and Development, Krosgaard-Larsen and Bundgaard, ed. 1991, Chapter 5, pp. 113-191 (1991).
Bundgaard, H., "Means to Enhance Penetration: (1) Prodrugs as a means to improve the delivery of peptide drugs," Advanced Drug Delivery Reviews 8:1-38 (1992).
CDC website, <http://wonder.cdc.gov/wonder/prevguid/p0000072.asp >downloaded Mar. 29, 2012.
Combellas et al., "Synthesis of 4-(3,5-dialkyl-4-hydroxyphenyl)pyridines," Tetrahedron Letters 33:4923-4926 (1992).
Connor et at, "Characterization of the Functional Properties of *env* Genes from Long-Term Survivors of Human Immunodeficiency Virus Type 1 Infection," J. Virol. 70:5306-5311 (1996).
De Clercq et al., "Antiviral drug discovery and development: Where chemistry meets with biomedieinal," Antiviral Res. 67(2):56-75 (2005).
Fleisher et al., "Improved oral drug delivery: solubility limitations overcome byt he use of prodrugs," Advanced Drug Delivery Reviews 19:115-130 (1996).
Furniss et al., eds., Vogel's Encyclopedia of Practical Organic Chemistry, $5^{th}$ Supp., Longman Scientific and Technical Ltd., Essex, 1991, pp. 809-816.

(Continued)

*Primary Examiner* — Susanna Moore
(74) *Attorney, Agent, or Firm* — Wilson, Sonsini, Goodrich & Rosati

(57) ABSTRACT

Described herein are novel enzyme inhibitors. In some embodiments, the enzyme inhibitors are reverse transcriptase inhibitors, particularly HIV reverse transcriptase inhibitors. Also described herein are compositions containing them and methods of using them. Thus, the compounds and compositions described herein are useful for the in vitro and in vivo inhibition of HIV reverse transcriptase as a method of treating or preventing HIV, AIDS or related disorders. In some embodiments, the enzyme inhibitors are compounds of formula (I) or a pharmaceutically acceptable salt or tautomer thereof:

(I)

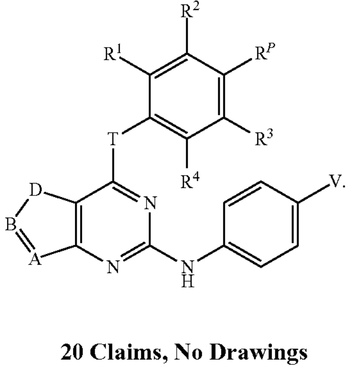

20 Claims, No Drawings

OTHER PUBLICATIONS

Harrington, R. et al., "Direct detection of infectious HIV-1 in blood using a certrifugation-indicator cell assay." J. Virol. Methods 88:111-115 (2000).
Lewis et al., "Pyrazolopyrimidine Nucleosides. 13. Synthesis of the Novel C-Nucleoside 5-Amino-3-(β-D-ribofuranosyl)pyrazolo[4,3-d]pyrimidin-7-one, a Guanosine Analogue Related to the Nucleoside Antibiotic Formyein B,". Chem. Soc. 104:1073-1078 (1982).
Liu, M, et al., "An Improved Synthesis of 9-Deazaguanine," Synthetic Comrimnicationsvol. 32(24):3797-3802 (2002).
Ludovici, D.W. et al., "Evolution of Anti-HIV Drug Candidates. Part 3. Diarylpyrimidine (DAPY) Analogues,"Bioorg. Med. Chem. Lett, 11:2235-2239 (2002).
Miles, K. "The growing HIV pandemic," Community Pract., Aug. 2005;78(8) abstract only.
Popik et al., "Human Immunodeficiency Virus Type 1 Uses Lipid Raft-Colocalized CD4 and Chemokine Receptors for Productive Entry into CD4+ T Cells," J. Virol. 76:4706-4722 (2002).
Roos, J. W. et al., "LuSIV Cells: A Receptor Cell Line for the Detection and Quantitation of a Single Cycle of HIV and SIV Replication," Virology 273:307-315 (2000).
Saulnier et al., "An Efficient Method for the Synthesis of Guandino Prodrugs," Med. Chem. Ltrs. 4(16):1985-1990 (1994).
Schang, "Cyclin-dependent kinases as cellular targets for antiviral drugs," J. Antimicrobial Chemotherapy 50(6):779-792 (2002).
Schow et al., "Synthesis and activity of 2,6,9-trisubstituted purines," Bioorg. Med. Chem. Ltrs. 7(21):2697-2702 (1997).
Seela, F. et al., "The High-Anti Conformation of 7-Halogenated 8-Axa-7-deaza-2'-deoxyguanosines. A Study of the Influence of Modified Bases on the Sugar Structure of Nucleosides," Helv. Chim. Act. 82:105-124 (1999).
Seela, F., "Synthesis of 2'-Deoxyribofuranosides of 8-Aza-7-deazaguanine and Related Pyrazolo[3,4-d]pyrimidines," Helv. Chim. Act. 69:1602-1613 (1986).
Taylor, E.C., "Synthesis of Pyralzolo[3,4-d]pyrimidine Analogues of the Potent Antitumor Agent N-{4[2-(2-Amino-4(3H)-oxo-7H-pyrrolo[2,3-d]pyrimidin-5-yl)ethyl]benzoyl}-L-glutamic Acid (LY231514)," Tetrahedron 48:8089-8100 (1992).
Van Heeswijk et al., "Combination of Protease Inhibitors for the Treatment of HIV-1-infected patients: a review of pharmacokinetics and clinical experience," Antivir Ther Dec. 2001 6(4), abstract only.
Vittori et al., "Sixth International Conference on Antiviral Research; Venice, Italy, Apr. 25-30, 1993; 1-Deazapurine derivatives: A new class of antiviral compounds," Antiviral Res. 20(Supp 1) (1993).
Vogel, Textbook of Practical Organic Chemistry 5th ed., 1989: Ch. 5.19 Resolution of Racemates, pp. 809-823.
Wolff, Manfred E., "Burger's Medicinal Chemistry, 5ed, Part 1," John Wiley & Sons, 1995, pp. 975-977.
Youssif et al., "A Facile One-pot Synthesis of Fused 2-Thiouracils: Dipyrimidinopyridine, Pyrazolopyrimidine and Pyridazinopyrimidines," Bull. Kor. Chem. Soc. 24:1429-1432 (2003).
PCT/EP03/50659 application filed Sep. 13, 2005.
PCT/US06/17677 Search Report dated Nov. 3, 2006.
PCT/US08/86703 Search Report dated Jun. 23, 2009.
EP06759292.3 Search Report dated Sep. 11, 2008.

PURINES AS REVERSE TRANSCRIPTASE INHIBITORS

This application is a divisional patent application of co-vending U.S. application Ser. No. 12/334,371, filed Dec. 12, 2008, now U.S. Pat. No. 8,207,178 entitled "Fused Pyrimidines as Reverse Transcriptase Inhibitors," which claims the benefit of U.S. Provisional Application No. 61/013,983, filed Dec. 14, 2007, all of which applications are incorporated herein by reference.

BACKGROUND OF THE INVENTION

In certain instances, human immunodeficiency virus (HIV), particularly the HIV type-1 (HIV-1) and type-2 (HIV-2) strains of the virus, is the causative agent of acquired immunodeficiency syndrome (AIDS). In certain instances, HIV infected individuals are initially asymptomatic but then develop AIDS related complex (ARC, characterized by symptoms such as persistent generalized lymphadenopathy, fever and weight loss) and eventually progress to AIDS.

In certain instances, replication of HIV by a host cell requires integration of the viral genome into the host cell's DNA. In certain instances, transcription of the viral RNA genome into the host cell DNA requires the reverse transcriptase (RT) enzyme.

SUMMARY OF THE INVENTION

Disclosed herein, in certain embodiments, are novel compounds and their metabolites, pharmaceutically acceptable salts, prodrugs, solvates, polymorphs, tautomers and isomers. In some embodiments, the compounds described herein are used to inhibit reverse transcriptases. In some embodiments, the compounds described herein are used to inhibit HIV reverse transcriptases. Further disclosed herein, in certain embodiments, are compositions comprising the novel compounds and their pharmaceutically acceptable salts, prodrugs, solvates, polymorphs, tautomers and isomers. Additionally disclosed herein, in certain embodiments, are methods for inhibiting reverse transcriptases. In some embodiments, the methods described herein are used for inhibiting HIV reverse transcriptases. Further disclosed herein, in certain embodiments, are methods useful in the treatment of diseases. In some embodiments, the compounds described herein are useful in the treatment of diseases such as viral infection, particularly infection with HIV.

In some embodiments, a compound disclosed herein, and the metabolites, pharmaceutically acceptable salts, pharmaceutically active metabolites, pharmaceutically acceptable prodrugs, and pharmaceutically acceptable solvates thereof, modulate the activity of reverse transcriptase enzymes; and, as such, are useful for treating diseases or conditions in which infection with a virus comprising a reverse transcriptase enzyme contributes to the pathology and/or symptoms of a disease or condition.

Described herein are compounds of Formula I and their metabolites, pharmaceutically acceptable salts, solvates, polymorphs, esters, tautomers or prodrugs:

(I)

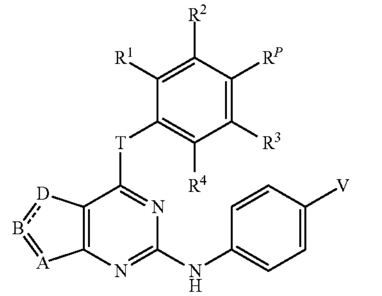

wherein

---- represents a double bond between either A and B or B and D;

A is —N=, —NZ— or —CZ=;

B is —CY= or —N=;

D is —N=, —NW— or —CW=;

provided that at least one of A and D is —N= or NZ or NR;

W, Y and Z are each independently selected from H, F, Cl, Br, $C_1$-$C_6$ alkyl, $C_2$-$C_6$ alkenyl, $OC_1$-$C_6$ alkyl, $C_3$-$C_6$ cycloalkyl, $OC_3$-$C_6$ cycloalkyl, phenyl or benzyl, wherein the alkyl, alkenyl, cycloalkyl, phenyl and the phenyl moiety of the benzyl group are optionally substituted with 1-3 substituents selected from F, Cl, Br, I, OH, $CF_3$, $C_1$-$C_3$ alkyl and $OC_1$-$C_3$ alkyl;

V is H, F, Cl, CN, $CF_3$, $SO_2CH_3$, $SO_2NH_2$, $SO_2NHCH_3$, $NH_2$, NH($C_1$-$C_6$ alkyl) or N($C_1$-$C_6$ alkyl)$_2$;

T is NH, O or S;

$R^P$ is aryl, substituted aryl, heterocyclyl, substituted heterocyclyl, heteroaryl or substituted heteroaryl; and $R^1$, $R^2$, $R^3$ and $R^4$ are independently selected from H, F, Cl, Br, I, $CFH_2$, $CF_2H$, $CF_3$, CN, CH=CHCN, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R'', OH, OR', SH, SR', C(O)R', $CO_2H$, COOR', $CONH_2$, CONHR', CONR'R'', $SO_3H$, $S(O)_2R'$, $S(O)_2NH_2$, $S(O)_2NHR'$, $S(O)_2NR'R''$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R'' is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R'' together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$, and $OC_1$-$C_3$ alkyl.

In further or additional embodiments, a compound disclosed herein is provided as a pharmaceutically acceptable salt. In further or additional embodiments, a compound disclosed herein is provided as a metabolite. In further or additional embodiments, a compound disclosed herein is provided as a solvate. In further or additional embodiments, a compound disclosed herein is provided as a pharmaceutically acceptable polymorph. In further or additional embodiments, a compound disclosed herein is provided as a pharmaceutically acceptable ester. In further or additional embodiments, a compound disclosed herein is provided as a pharmaceutically acceptable tautomer. In further or additional embodiments, a compound disclosed herein is provided as a pharmaceutically acceptable prodrug.

In some embodiments, A is —N═. In other embodiments A is —NZ—. In yet other embodiments A is —CZ═. In some embodiments, D is —N═. In other embodiments D is —NR. In yet other embodiments D is —CW—. In some embodiments, B is —CY═. In other embodiments B is —N═. In further or additional embodiments, A is —CZ═; B is —CY═; and D is —NW—. In some embodiments, Z is H, F, Cl or methyl. In some embodiments, Y is H. In some embodiments, W is $C_1$-$C_6$ alkyl or $C_1$-$C_6$ alkyl substituted with 1-3 substituents selected from F, Cl, Br, I, OH, $CF_3$. In further or additional embodiments, W is methyl, ethyl, $CH_2CF_3$ or $CH_2CH_2OH$. In some embodiments, Z is H, F, Cl or methyl; Y is H; and W is methyl, ethyl, $CH_2CF_3$ or $CH_2CH_2OH$. In some embodiments, W, Y and Z are each independently selected from H, F, Cl, Br, $C_1$-$C_6$ alkyl or $C_1$-$C_6$ alkyl substituted with 1-3 substituents selected from F, Cl, Br, I, OH, $CF_3$. In some embodiments, Y is H. In some embodiments, V is CN. In some embodiments, T is O. In further or additional embodiments, T is S. In further or additional embodiments, T is NH. In some embodiments, V is CN and T is O or S. In further or additional embodiments, A is —CZ═; B is —CH═; D is —NW—; Z is H, F, Cl or methyl; W is methyl, ethyl, $CH_2CF_3$ or $CH_2CH_2OH$; V is CN; and T is O or S. In some embodiments, $R^1$, $R^2$, $R^3$ and $R^4$ are independently selected from H, F, Cl, Br, I, $CFH_2$, $CF_2H$, $CF_3$, CN, CH═CHCN, methyl, ethyl, n-propyl, propyl, n-butyl, i-butyl, s-butyl, t-butyl, cyclopropyl, cyclobutyl, cyclopentyl, cyclohexyl and cyclopropylmethyl. In further or additional embodiments, $R^1$, $R^2$, $R^3$ and $R^4$ are independently selected from H, methyl, ethyl, n-propyl and i-propyl. In further or additional embodiments, $R^1$ and $R^4$ are independently selected from methyl, ethyl, n-propyl and i-propyl; and $R^2$ and $R^3$ are H. In some embodiments, $R^P$ is aryl or substituted aryl. In further or additional embodiments, $R^P$ is unsubstituted phenyl. In further or additional embodiments, $R^P$ is substituted phenyl. In some embodiments, $R^P$ is heterocyclyl, substituted heterocyclyl, heteroaryl or substituted heteroaryl. In further or additional embodiments, $R^P$ is unsubstituted heteroaryl. In further or additional embodiments, $R^P$ is substituted heteroaryl. In some embodiments, $R^P$ is a substituted or unsubstituted 5- or 6-membered heterocycle comprising 1, 2 or 3 heteroatoms independently selected from O, N or S. In further or additional embodiments, $R^P$ is a substituted or unsubstituted 5- or 6-membered heterocycle comprising 1, 2 or 3 N atoms. In further or additional embodiments, $R^P$ is a substituted or unsubstituted 5- or 6-membered heterocycle comprising 1 N atom. In further or additional embodiments, $R^P$ is a substituted or unsubstituted 5- or 6-membered heterocycle comprising 2 N atoms. In further or additional embodiments, $R^P$ is a substituted or unsubstituted 5- or 6-membered heterocycle comprising 3 N atoms. In further or additional embodiments, $R^P$ is a substituted or unsubstituted 5- or 6-membered heterocycle comprising 1 O atom. In further or additional embodiments, $R^P$ is a substituted or unsubstituted 5- or 6-membered heterocycle comprising 1 S atom. In further or additional embodiments, $R^P$ is a substituted or unsubstituted 5- or 6-membered heterocycle comprising 1 N atom and 1 O or S atom. In further or additional embodiments, $R^P$ is a substituted or unsubstituted heterocycle selected from furanyl, thiofuranyl, pyrrolyl, pyrrolinyl, pyrrolidinyl, oxazolyl, thiazolyl, imidazolyl, imidazolinyl, pyrazolyl, pyrazolinyl, pyrazolidinyl, isoxazolyl, isothiazolyl, oxadizolyl, thiazolyl, thiadiazolyl, triazolyl, pyranyl, pyridyl, piperidinyl, morpholinyl, pyridazyl, pyrimidyl, pyrazinyl, piperazinyl, triazinyl or tetrazolyl. In further or additional embodiments, $R^P$ is pyridyl, substituted pyridyl, furanyl, substituted furanyl, thiofuranyl, substituted thiofuranyl, pyrrolyl, substituted pyrrolyl, pyrazolyl, substituted pyrazolyl, pyrimidyl or substituted pyrimidyl. In some embodiments, $R^P$ is a 5-membered aryl, 5-membered substituted aryl, 5-membered heterocyclyl, 5-membered substituted heterocyclyl, 5-membered heteroaryl or 5-membered substituted heteroaryl. In other embodiments, $R^P$ is a 6-membered aryl, 6-membered substituted aryl, 6-membered heterocyclyl, 6-membered substituted heterocyclyl, 6-membered heteroaryl or 6-membered substituted heteroaryl. In yet other embodiments, $R^P$ is a 7-membered aryl, 7-membered substituted aryl, 7-membered heterocyclyl, 7-membered substituted heterocyclyl, 7-membered heteroaryl or 7-membered substituted heteroaryl.

Also described herein are compounds of Formula (IA), (1B), (IC-1), (IC-2), (ID), (ID-1), (ID-2), (ID-3), (ID-4), (IE), (IE-1), (IE-2), (IE-3) and (IE-4):

(IA)

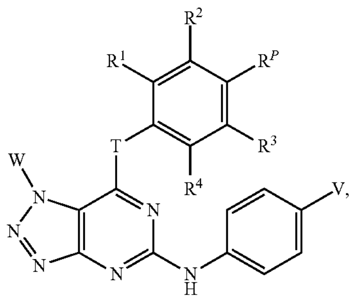

(IB)

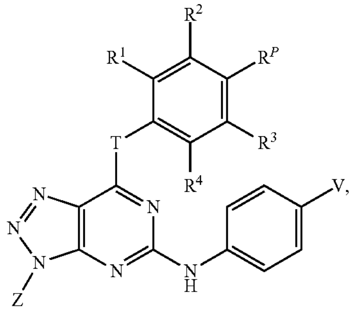

(IC-1)

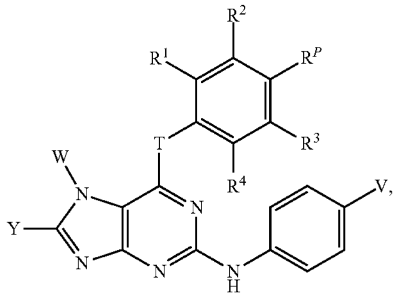

-continued
(IC-2)
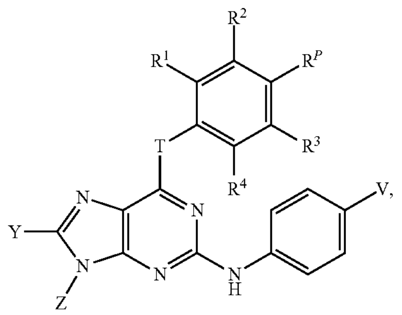
(ID)
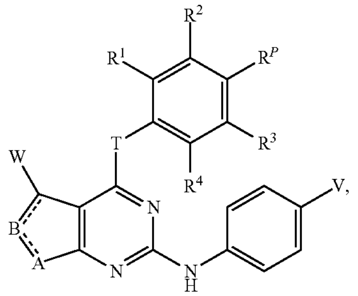
(IE)
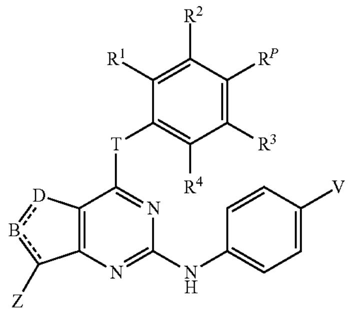
(ID-1)
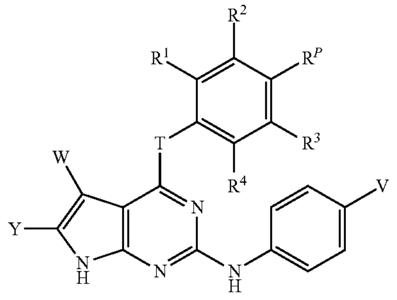
(ID-2)
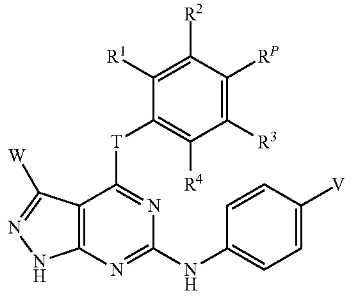
-continued
(ID-3)
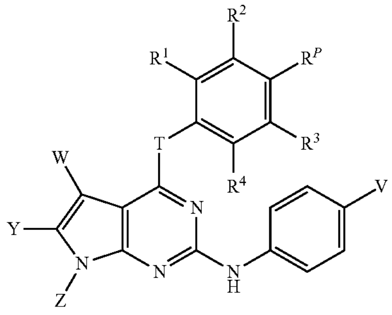
(ID-4)
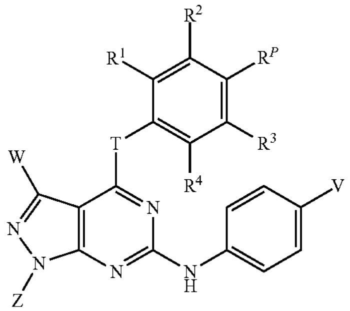
(IE-1)
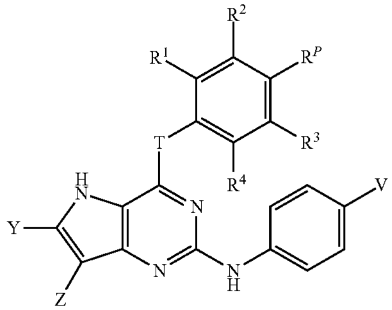
(IE-2)
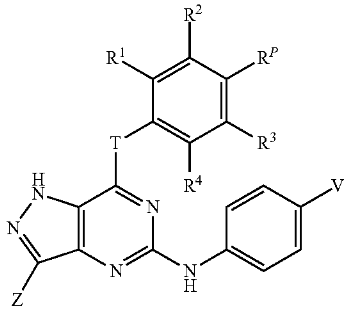
(IE-3)
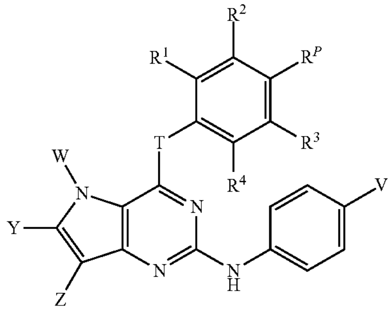

-continued (IE-4)

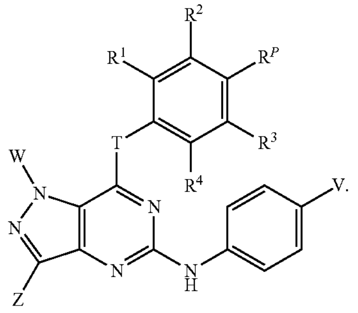

In some embodiments, of the compound of formula (IE), Y is H. In other embodiments, Z is H, F, Cl or methyl. In other embodiments, W is methyl, ethyl, $CH_2CF_3$ or $CH_2CH_2OH$. In further or additional embodiments, Z is H, F, Cl or methyl; Y is H; and W is methyl, ethyl, $CH_2CF_3$ or $CH_2CH_2OH$. In some embodiments, V is CN. In other embodiments, T is O. In other embodiments, T is S. In other embodiments, T is NH. In further or additional embodiments, Z is H, F, Cl or methyl; Y is H; W is methyl, ethyl, $CH_2CF_3$ or $CH_2CH_2OH$; V is CN; and T is O or S.

In some embodiments, of the compound of formula (IE-3), Y is H. In other embodiments, Z is H, F, Cl or methyl. In other embodiments, W is methyl, ethyl, $CH_2CF_3$ or $CH_2CH_2OH$. In further or additional embodiments, Z is H, F, Cl or methyl; Y is H; and W is methyl, ethyl, $CH_2CF_3$ or $CH_2CH_2OH$. In some embodiments, V is CN. In other embodiments, T is O. In other embodiments, T is S. In other embodiments, T is NH. In further or additional embodiments, Z is H, F, Cl or methyl; Y is H; W is methyl, ethyl, $CH_2CF_3$ or $CH_2CH_2OH$; V is CN; and T is O or S.

Also described herein are compounds of Formula (IC-3a):

(IE-3a)

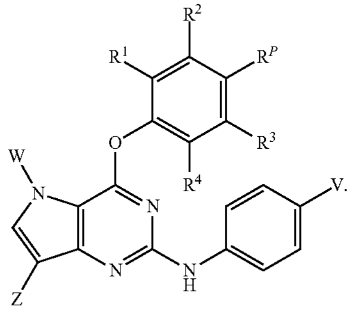

In some embodiments, of the compound of formula (IE-3a), Z is H, F, Cl or methyl. In other embodiments, W is methyl, ethyl, $CH_2CF_3$ or $CH_2CH_2OH$. In further or additional embodiments, Z is H, F, Cl or methyl; and W is methyl, ethyl, $CH_2CF_3$ or $CH_2CH_2OH$. In some embodiments, V is CN. In further or additional embodiments, Z is H, F, Cl or methyl; and W is methyl, ethyl, $CH_2CF_3$ or $CH_2CH_2OH$, and V is CN. In some embodiments, of the compound of formula (IE-3a), $R^1$, $R^2$, $R^3$ and $R^4$ are independently selected from H, methyl, ethyl, n-propyl and i-propyl. In further or additional embodiments, $R^1$ and $R^4$ are independently selected from methyl, ethyl, n-propyl and i-propyl; and $R^2$ and $R^3$ are H. In further or additional embodiments, $R^P$ is aryl or substituted aryl. In further or additional embodiments, $R^P$ is phenyl or substituted phenyl. In further or additional embodiments, $R^P$ is a substituted or unsubstituted 5- or 6-membered heterocycle comprising 1, 2 or 3 heteroatoms independently selected from O, N or S. In further or additional embodiments, $R^P$ is heterocyclyl or substituted heterocyclyl. In further or additional embodiments, $R^P$ is heteroaryl or substituted heteroaryl. In further or additional embodiments, $R^P$ is pyridyl, substituted pyridyl, furanyl, substituted furanyl, thiofuranyl, substituted thiofuranyl, pyrimidyl or substituted pyrimidyl.

Also described herein are compounds of Formula (IF):

(IF)

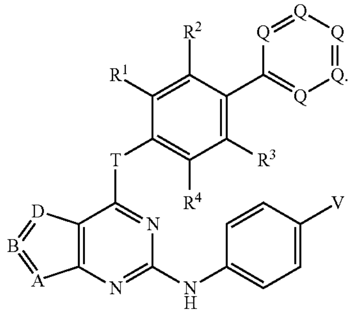

where each Q is independently $CR^a$ or N, provided that at least one Q is $CR^a$; and each $R^a$ is independently selected from H, F, Cl, Br, I, $CFH_2$, $CF_2H$, $CF_3$, CN, CH=CHCN, $CH_2CF_3$, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R'', OH, OR', SH, SR', C(O)R', $CO_2H$, COOR', $CONH_2$, CONHR', CONR'R'', $SO_3H$, $S(O)_2R'$, $S(O)_2NH_2$, $S(O)_2NHR'$, $S(O)_2NR'R''$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R'' is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R'' together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$, and $OC_1$-$C_3$ alkyl.

In some embodiments, one Q is N and the rest are $CR^a$. In further or additional embodiments, two Qs are N and the rest are $CR^a$. In further or additional embodiments, three Qs are N and the rest are $CR^a$. In further or additional embodiments, four Qs are N and the rest are $CR^a$.

Also described herein are compounds of Formula (IG-1) and (IG-2):

(IG-1)

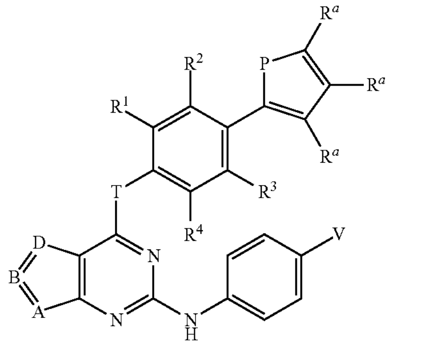

(IG-2)

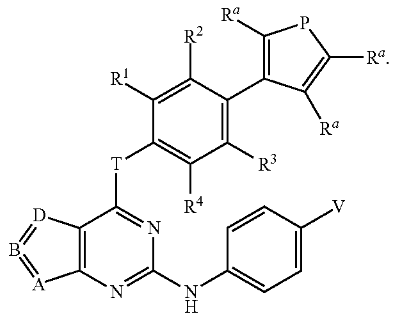

where

P is independently NH, O or S; and each $R^a$ is independently selected from H, F, Cl, Br, I, $CFH_2$, $CF_2H$, $CF_3$, CN, CH═CHCN, $CH_2CF_3$, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$, and $OC_1$-$C_3$ alkyl.

Also described herein are compounds of Formula (IH-1) and (1H-2):

(IH-1)

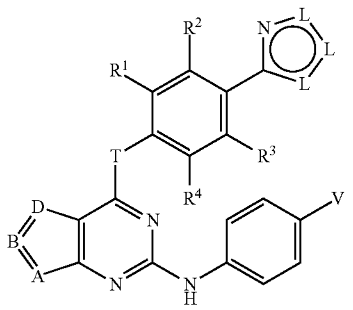

(IH-2)

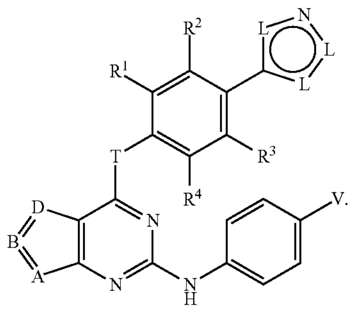

where one L is NH, O or S and the other two are $CR^a$; and each $R^a$ is independently selected from H, F, Cl, Br, I, $CFH_2$, $CF_2H$, $CF_3$, CN, CH═CHCN, $CH_2CF_3$, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$, and $OC_1$-$C_3$ alkyl.

In some embodiments, a compound disclosed herein or a metabolite, pharmaceutically acceptable salt, solvate, polymorph, ester, tautomer or prodrug thereof is selected from:

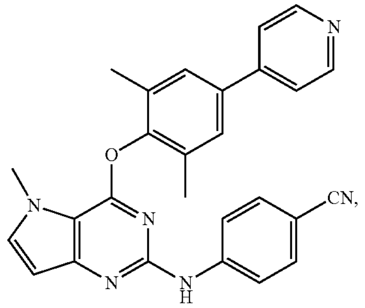
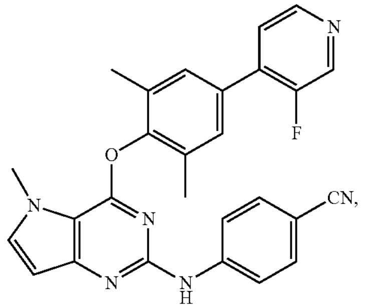
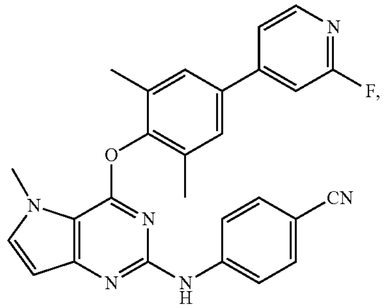
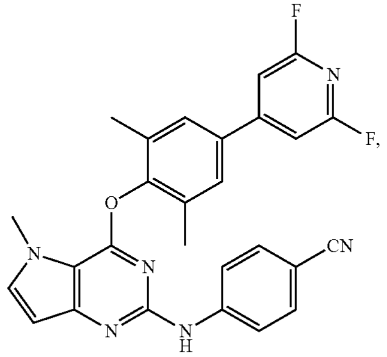
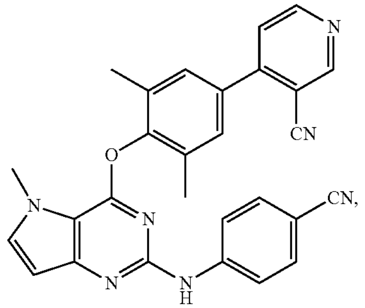
-continued
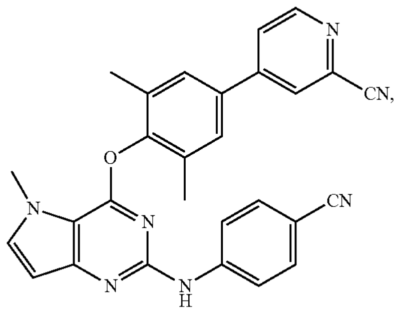
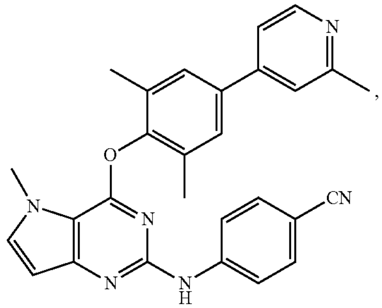
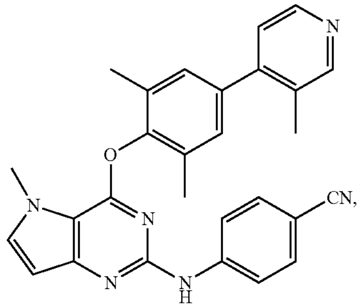
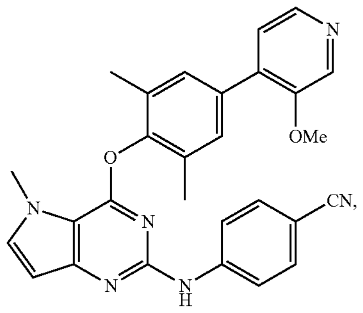
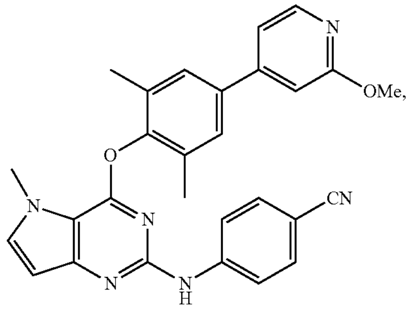

-continued
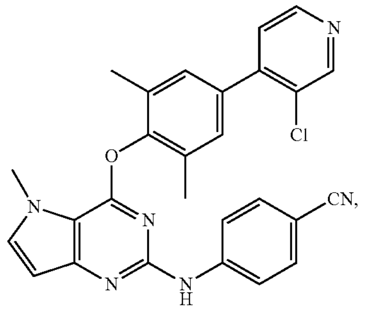
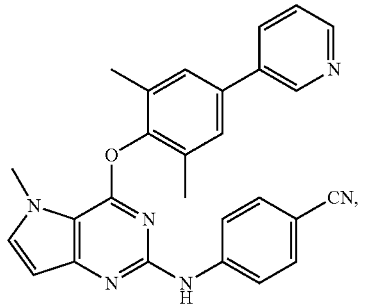
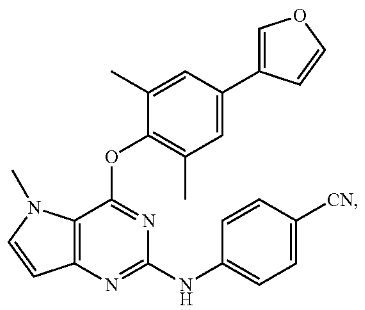
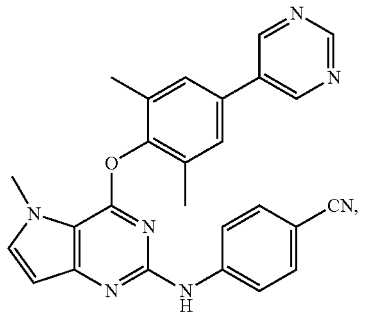
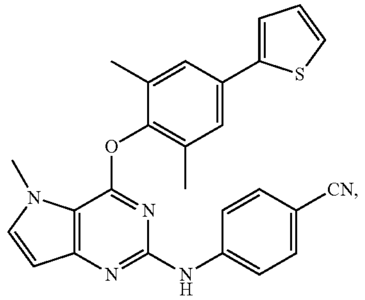
-continued
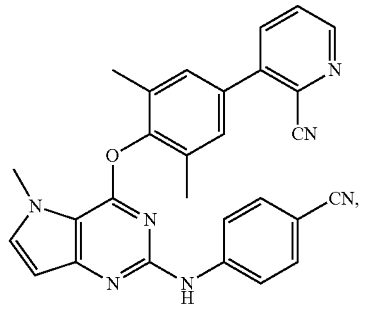
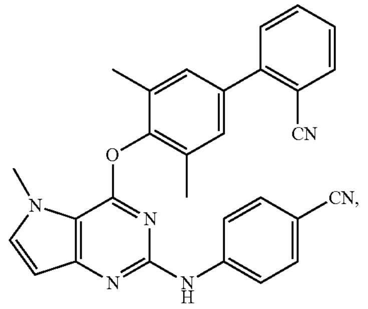
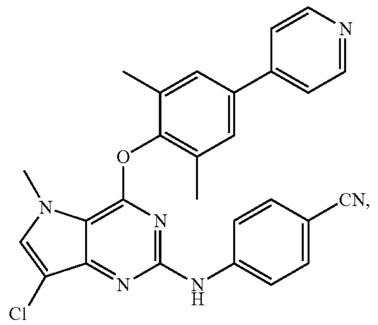
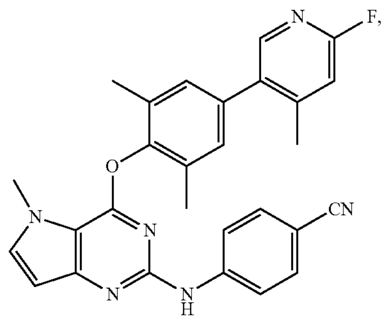
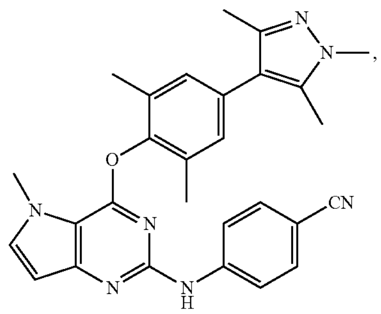

-continued
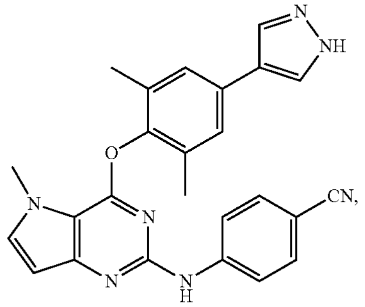
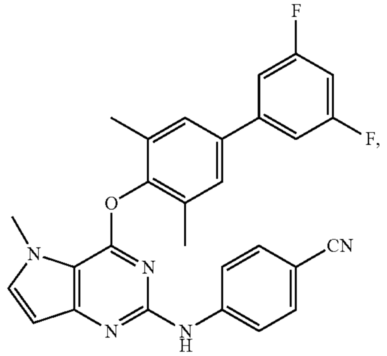
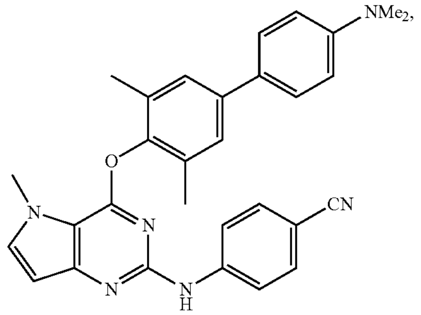
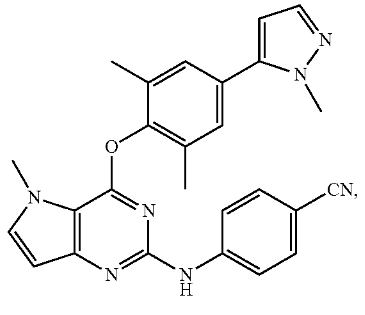
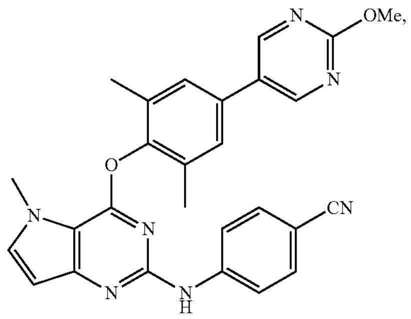
-continued
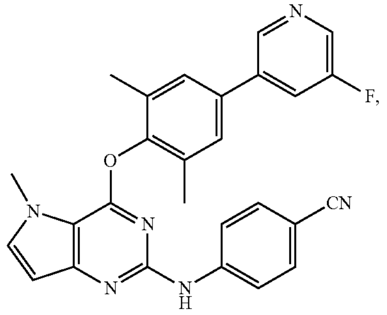
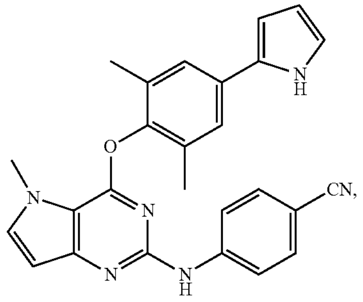
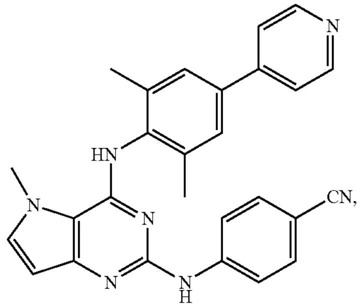
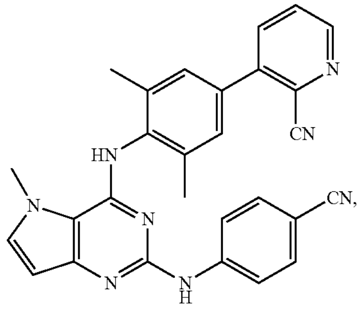
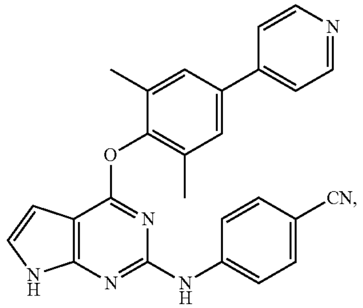

-continued
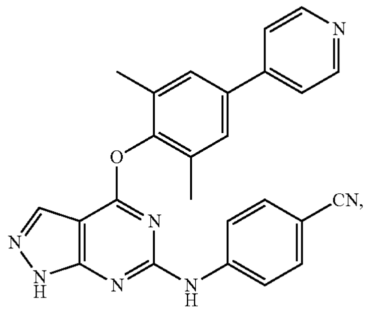
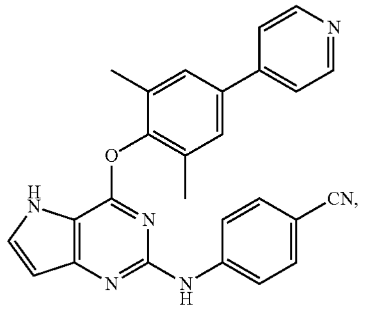
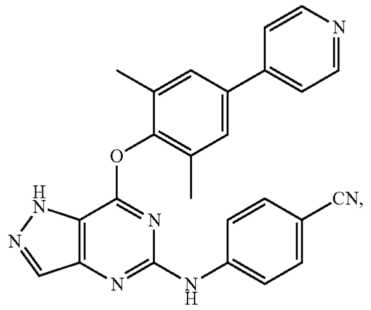
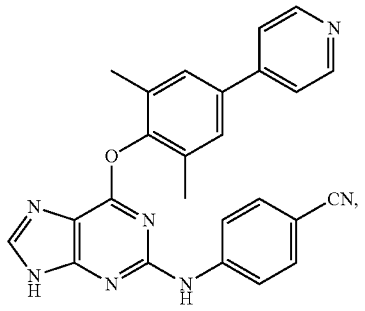
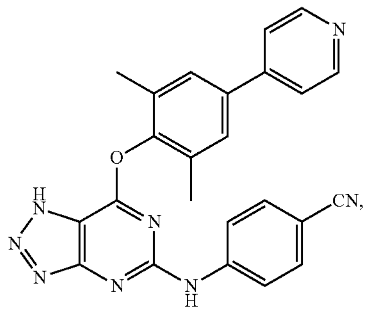
-continued
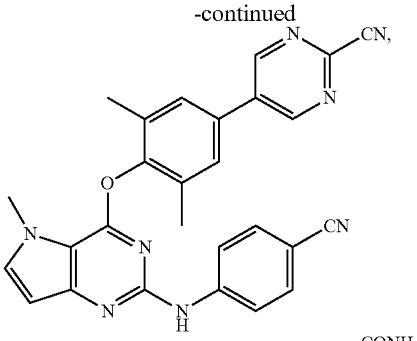
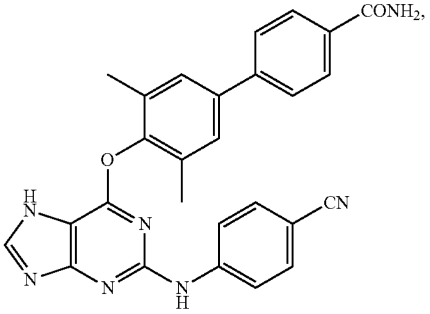
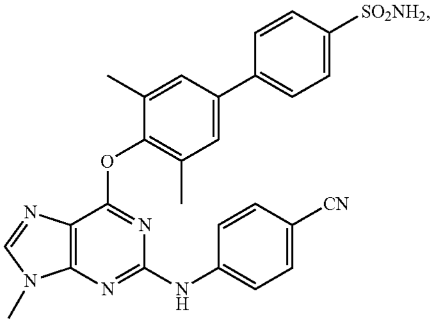
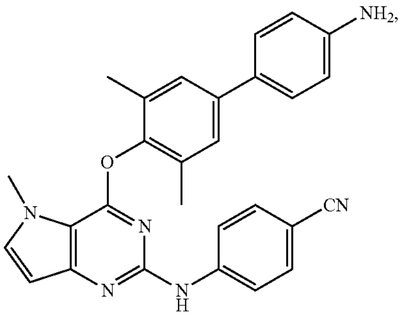
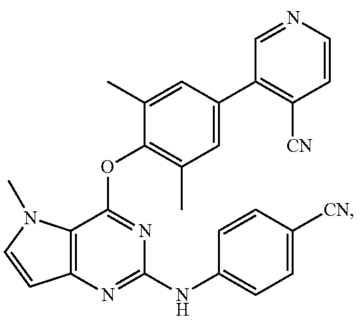

-continued
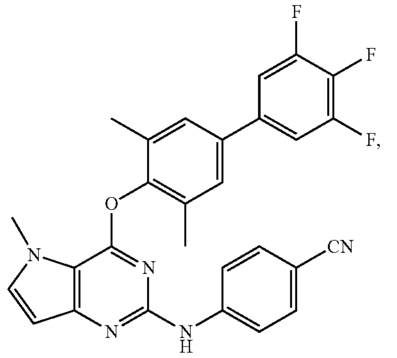
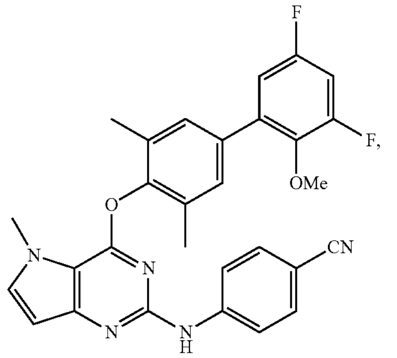
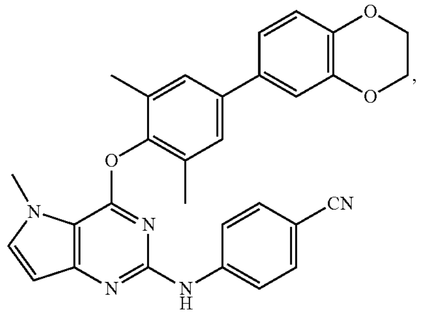
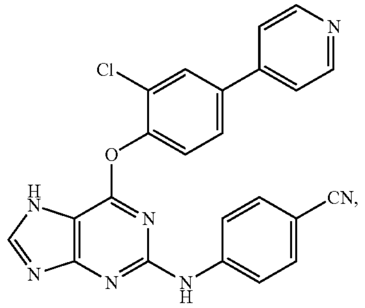
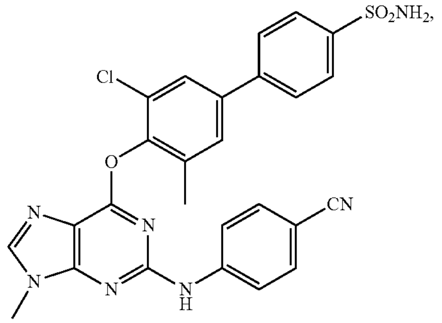
-continued
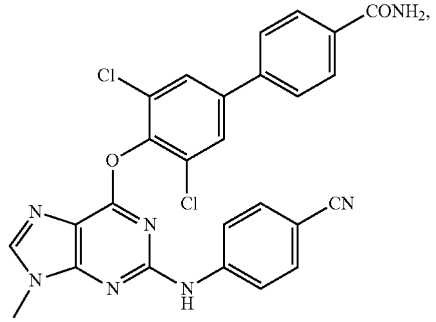
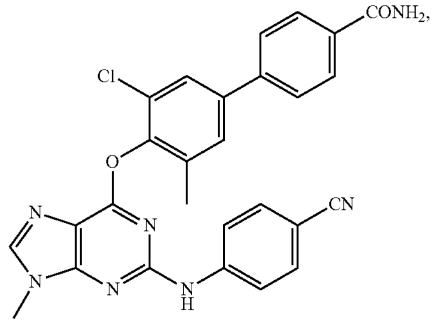
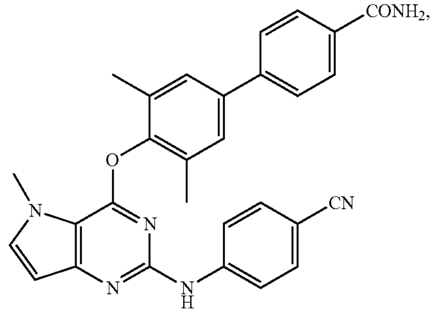
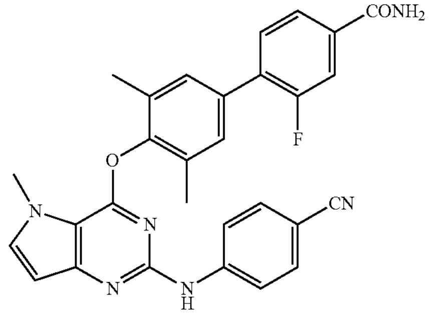
and
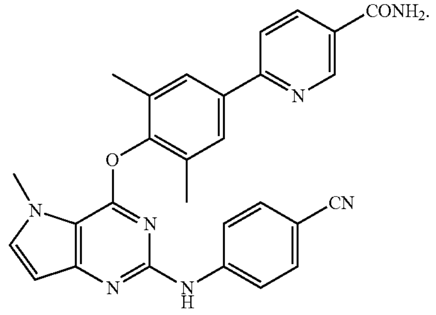
In some embodiments, a compound disclosed herein or a metabolite, pharmaceutically acceptable salt, solvate, polymorph, ester, tautomer or prodrug thereof is selected from:

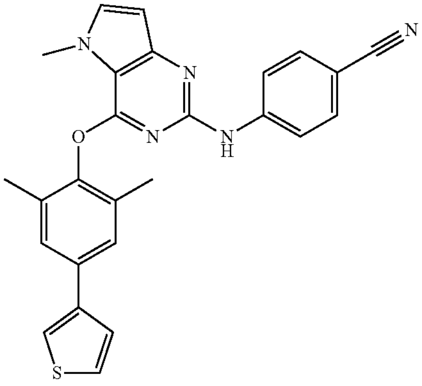
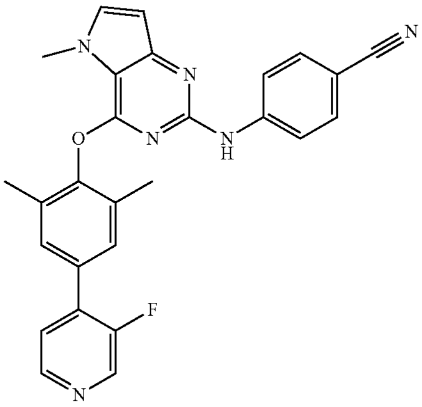
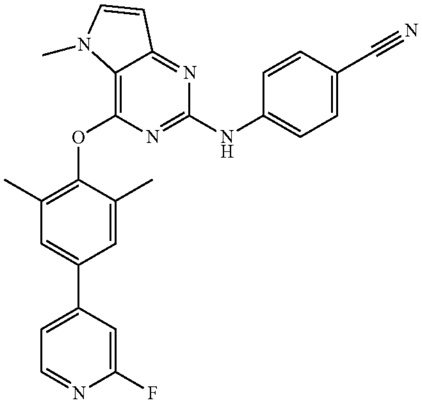
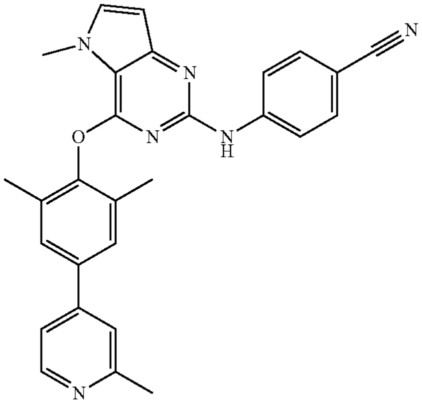
-continued
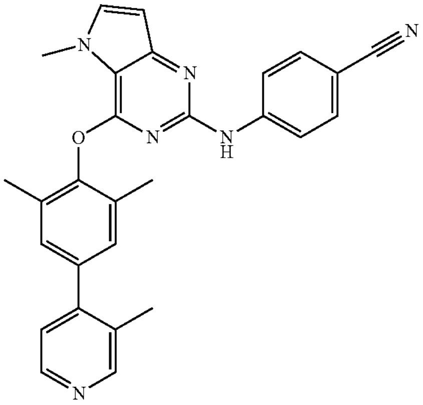
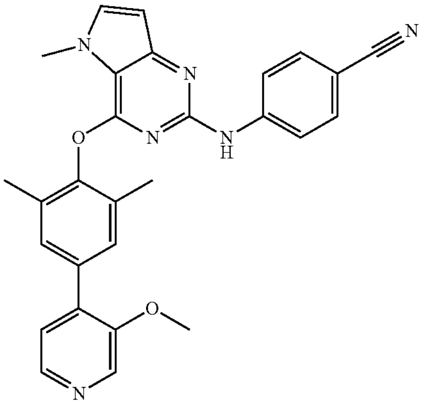
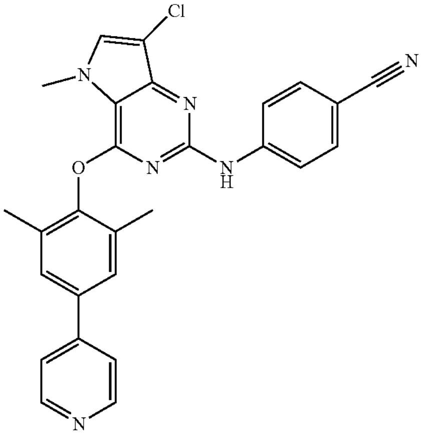
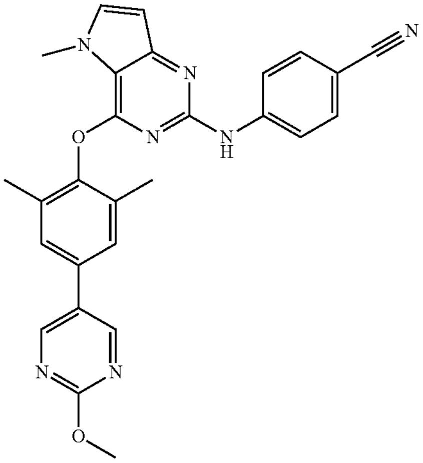

-continued
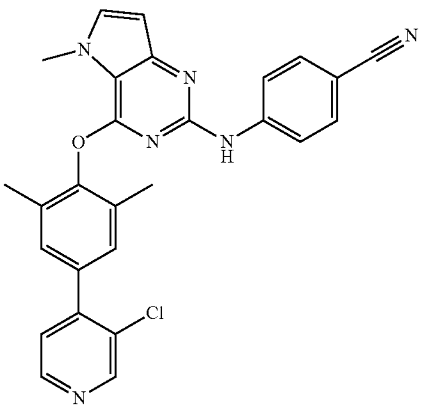
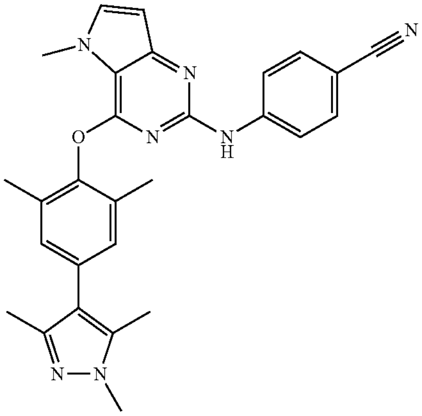
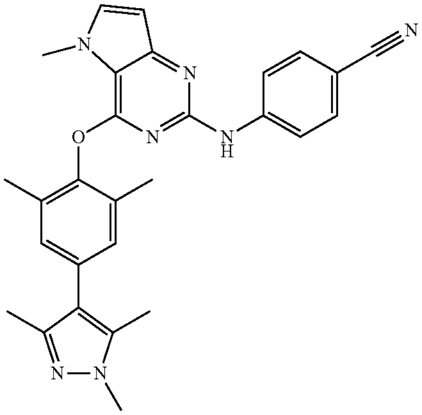
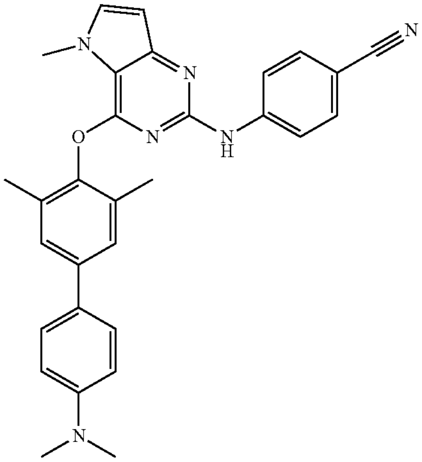
-continued
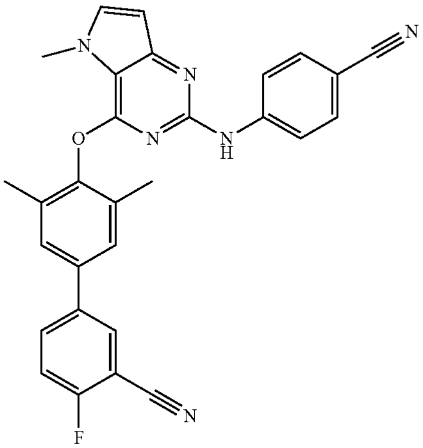
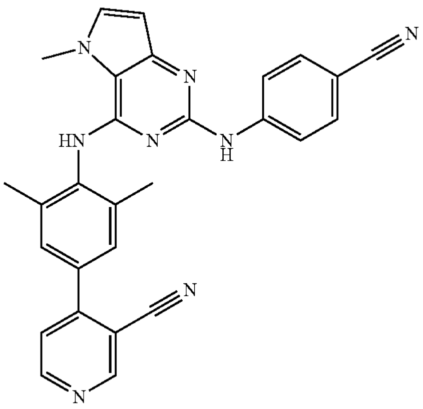
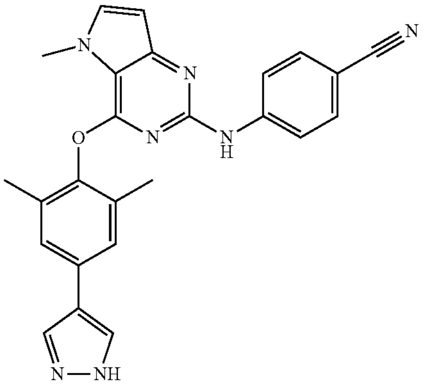
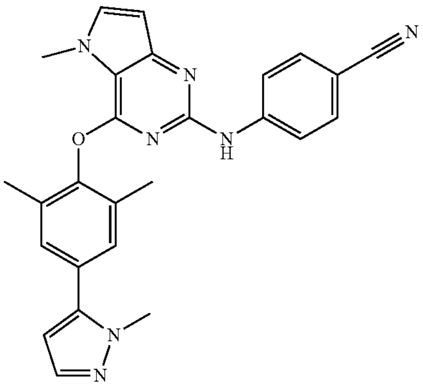

-continued
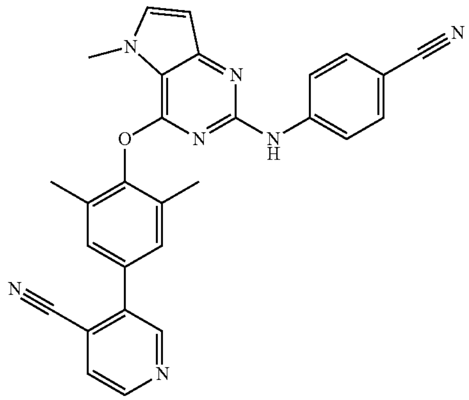
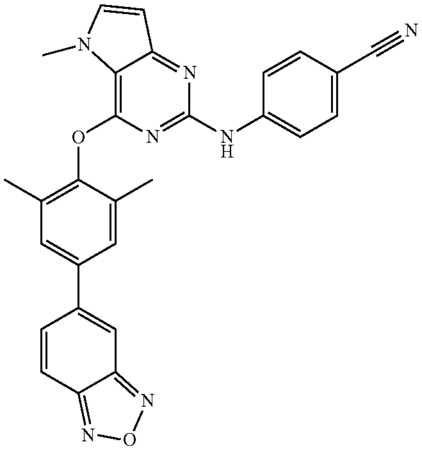
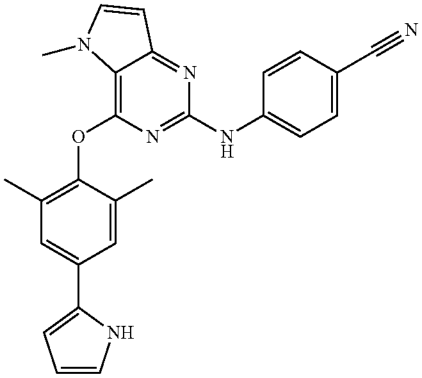
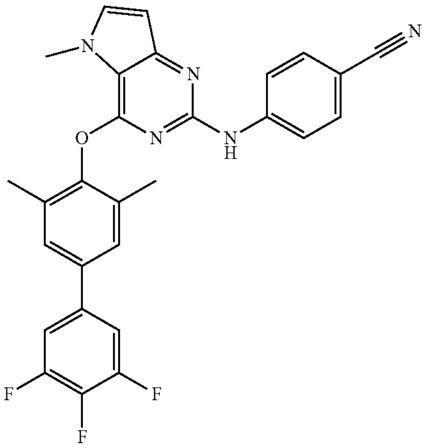
-continued
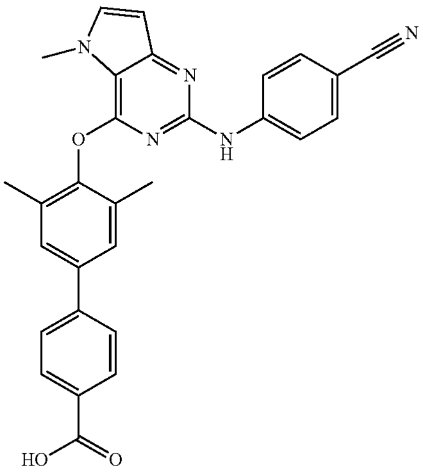
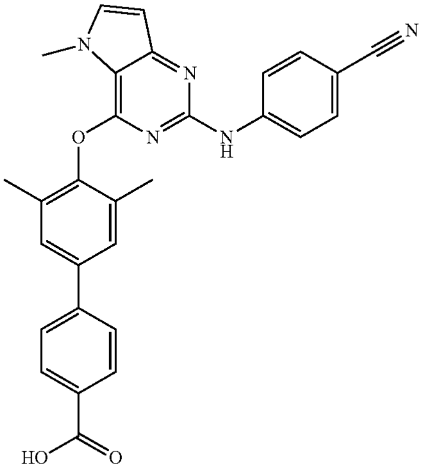
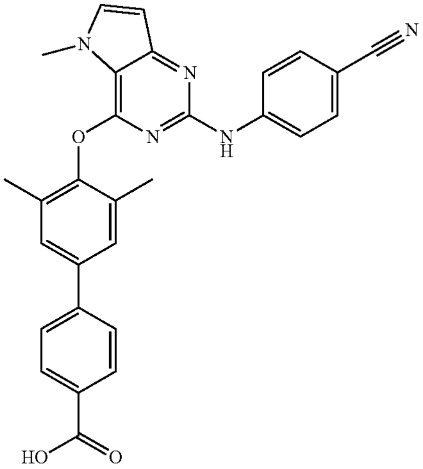

-continued
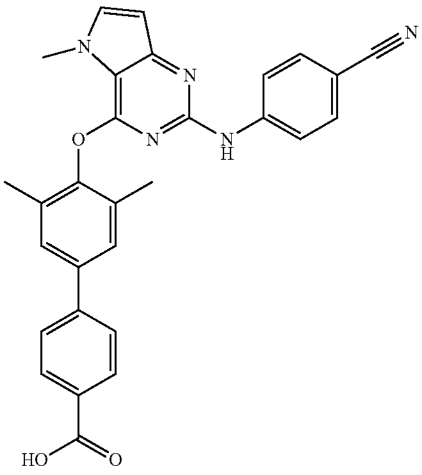
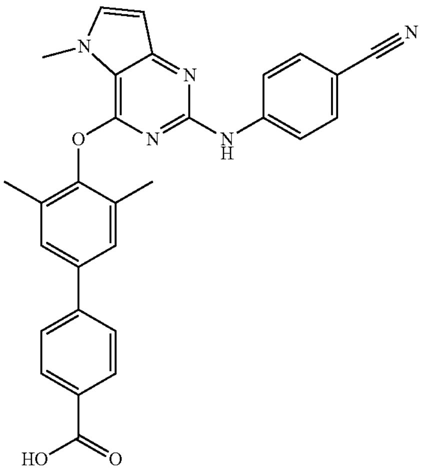
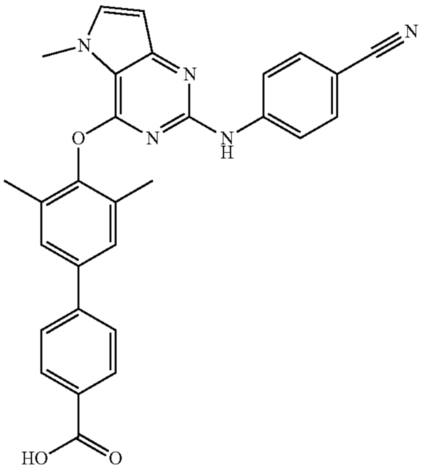
-continued
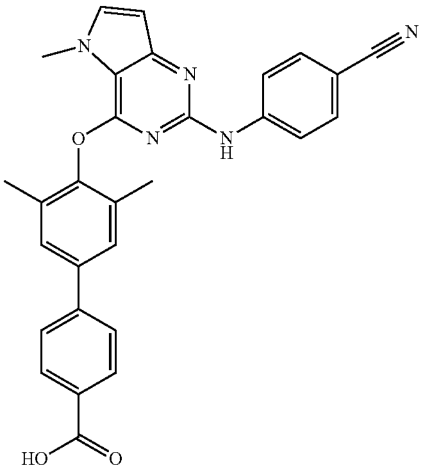
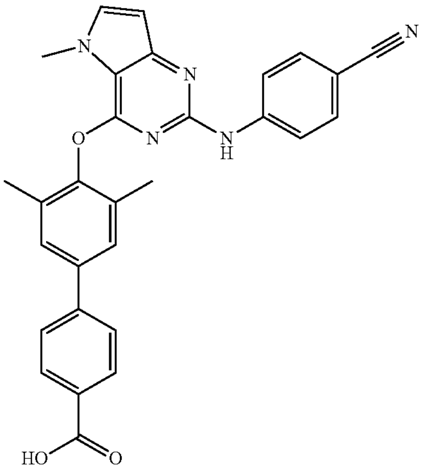
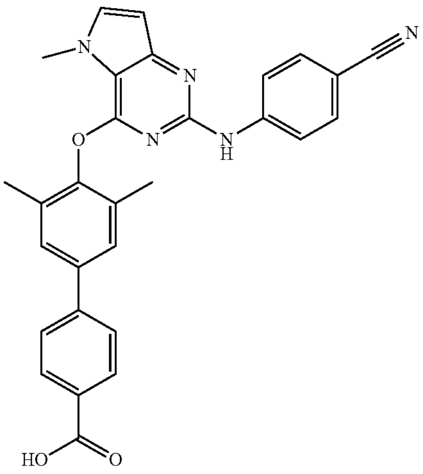

-continued
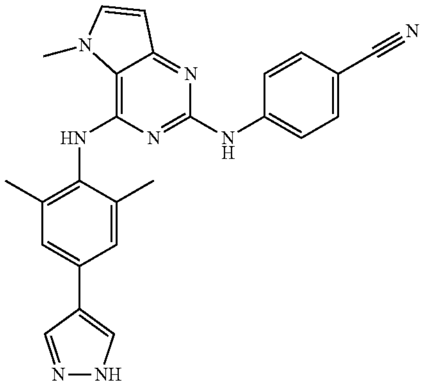
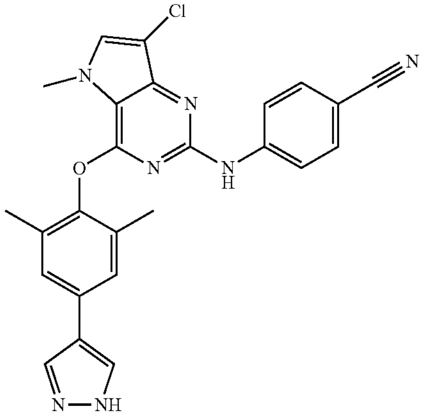
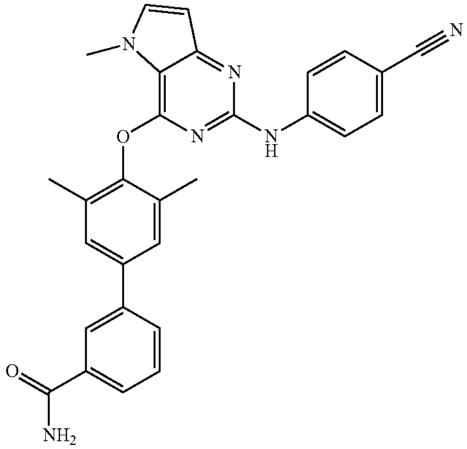
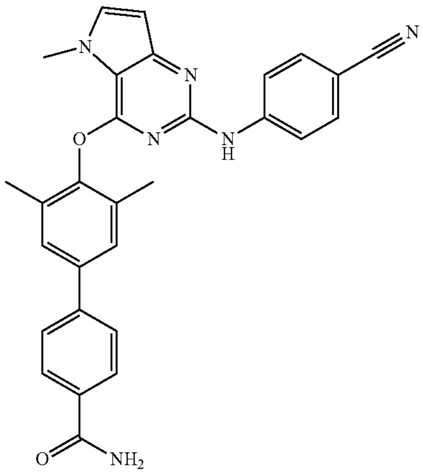
-continued
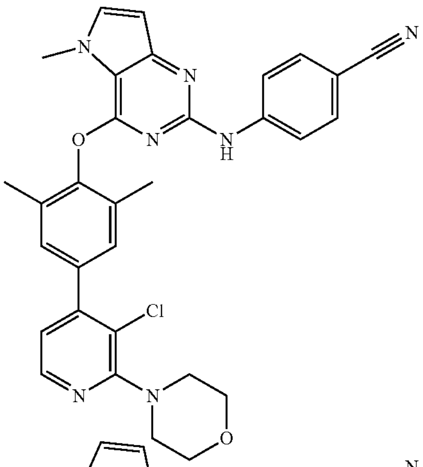
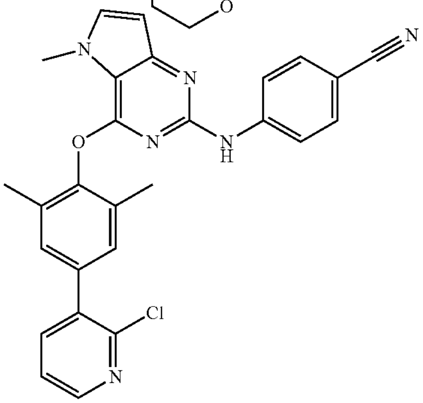
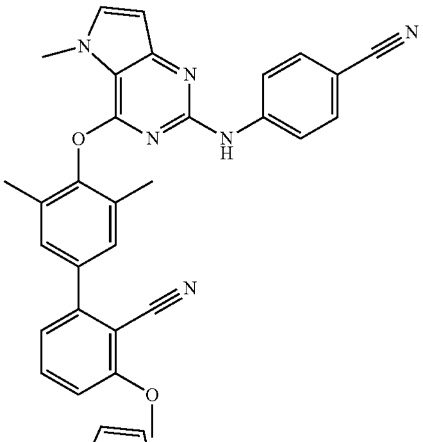
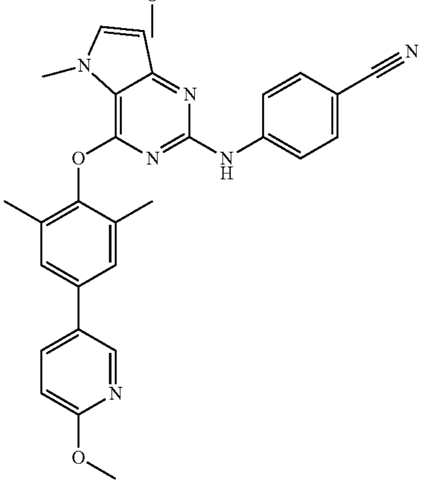

-continued
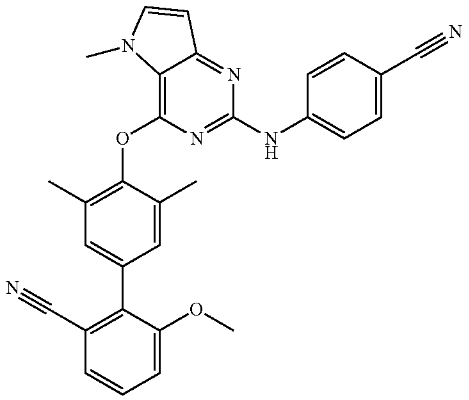
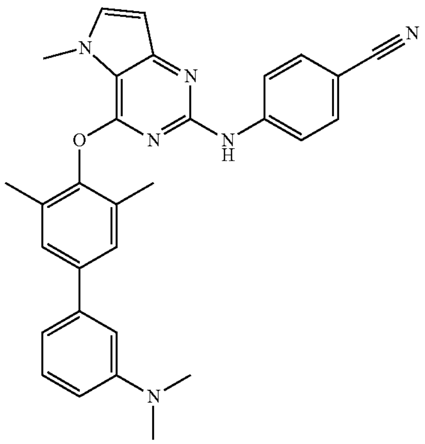
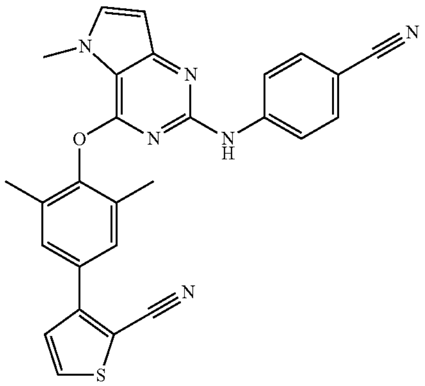
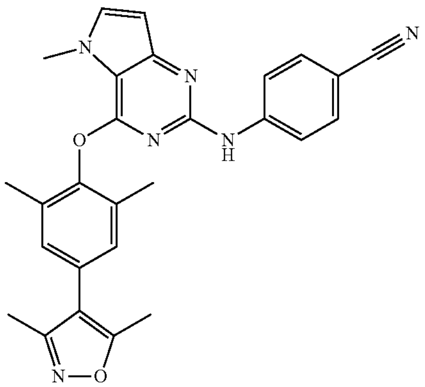
-continued
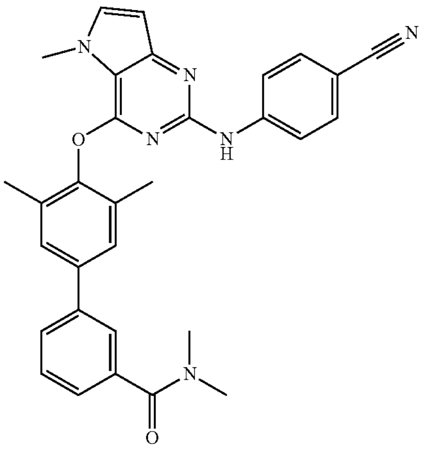
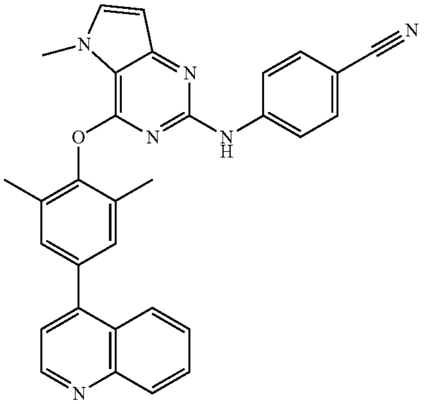
(?) indicates text missing or illegible when filed
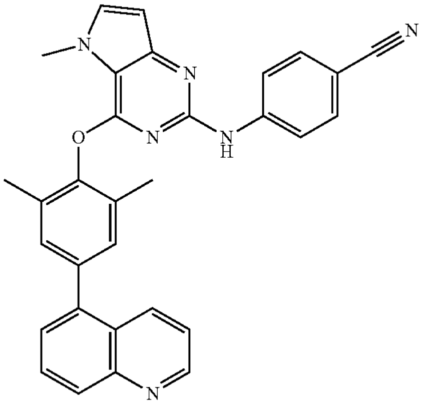
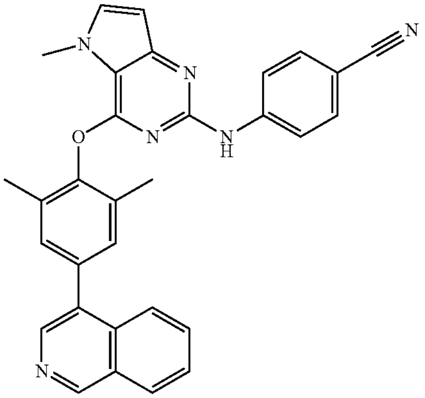

-continued
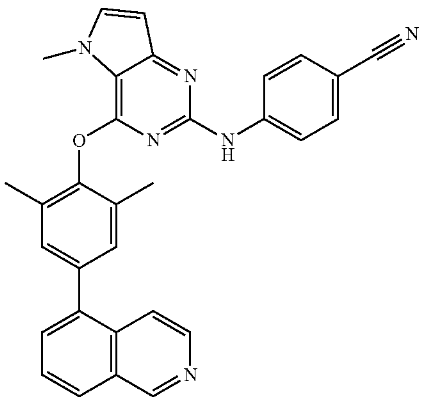
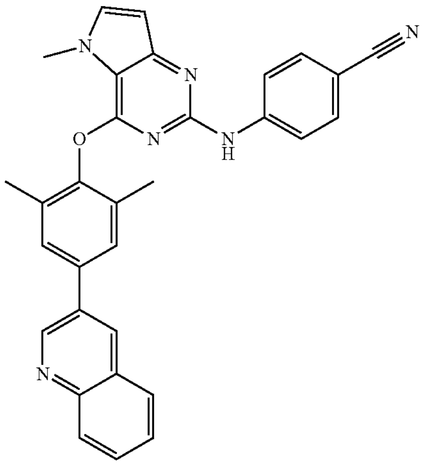
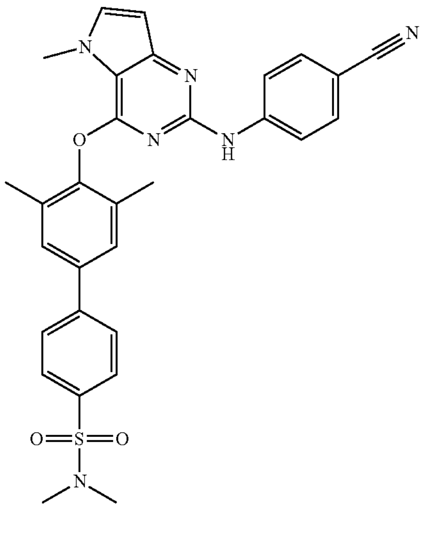
-continued
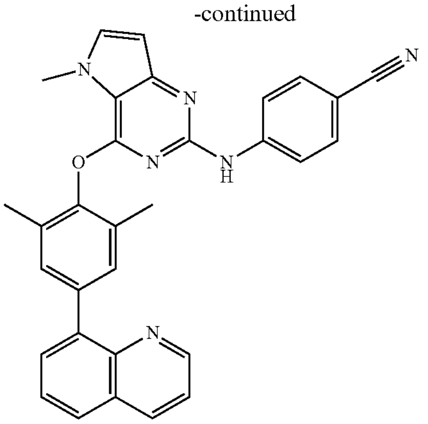
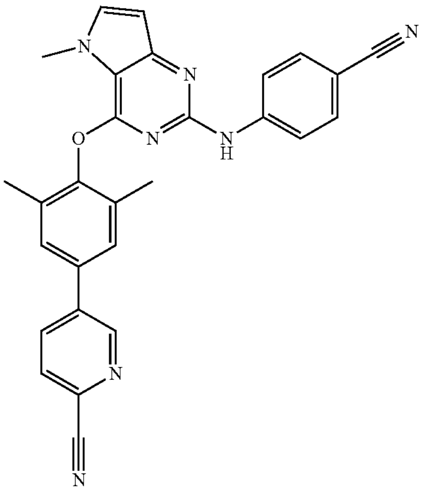
? indicates text missing or illegible when filed
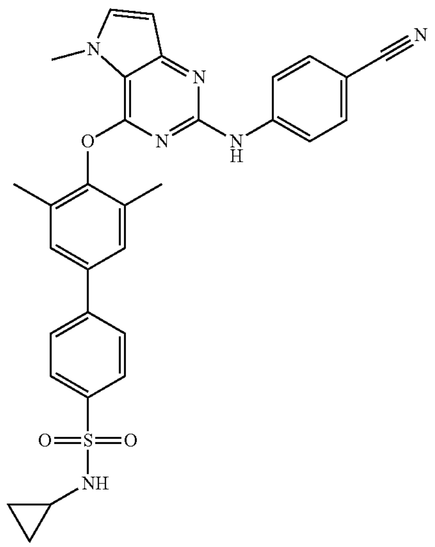

-continued
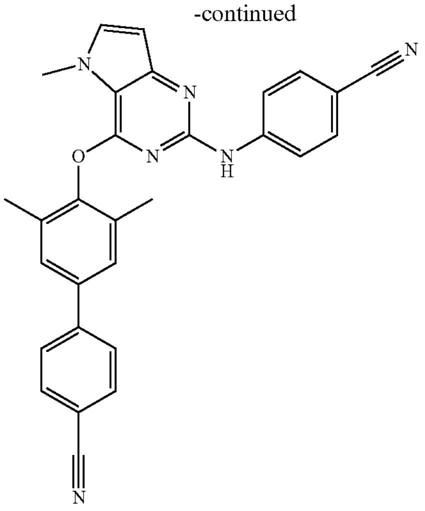
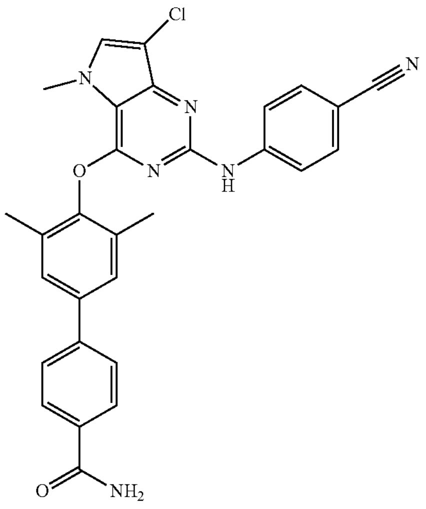
ⓘ indicates text missing or illegible when filed
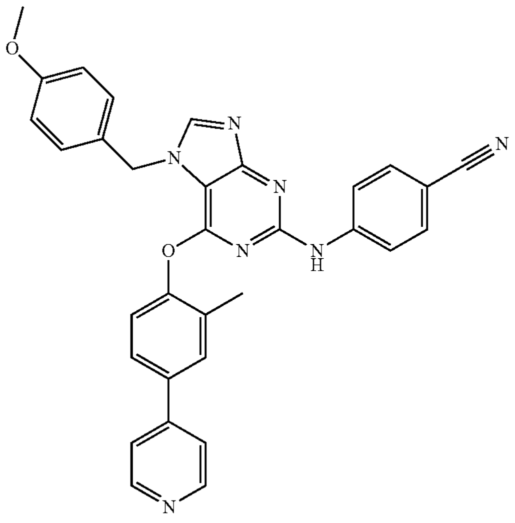
-continued
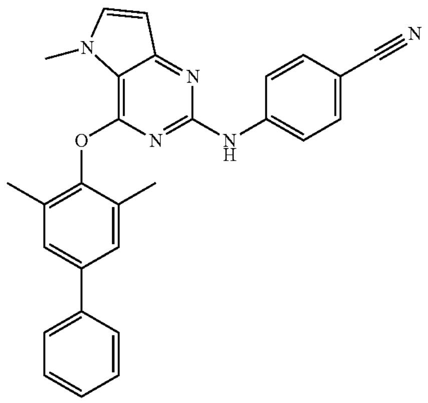
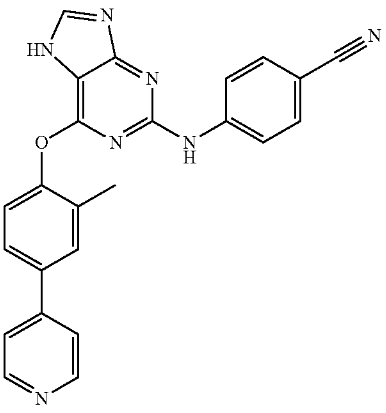
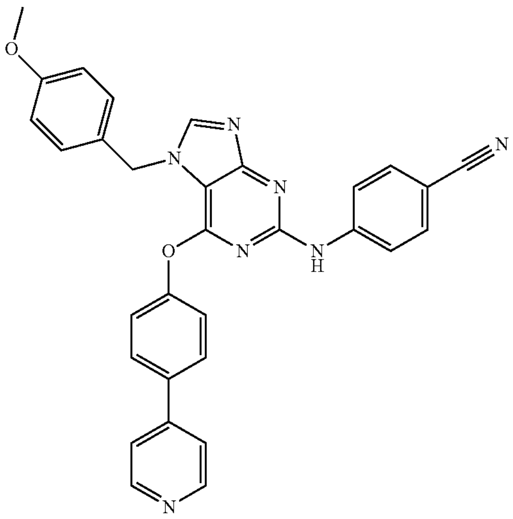
ⓘ indicates text missing or illegible when filed -continued
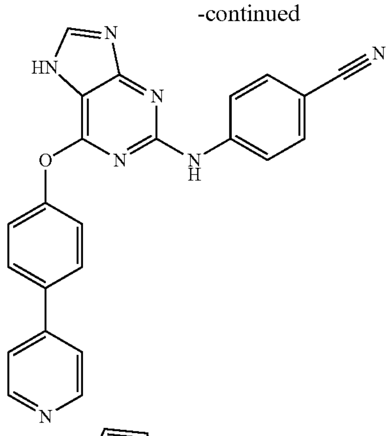
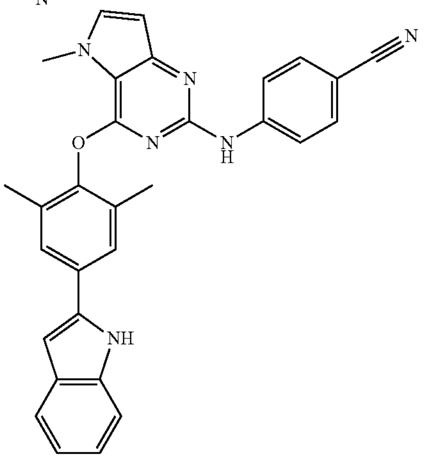
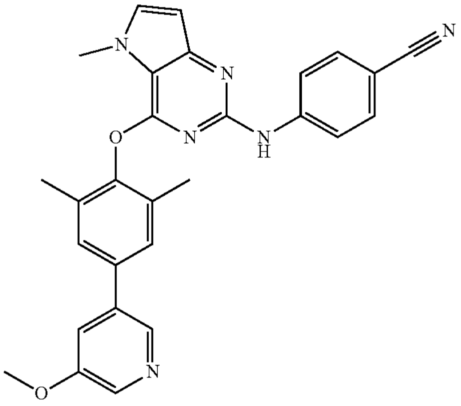
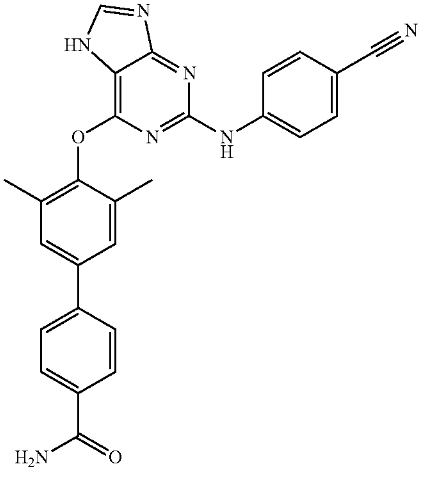
-continued
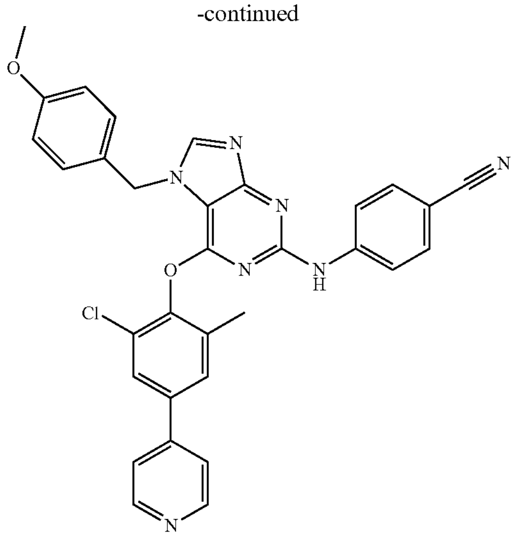
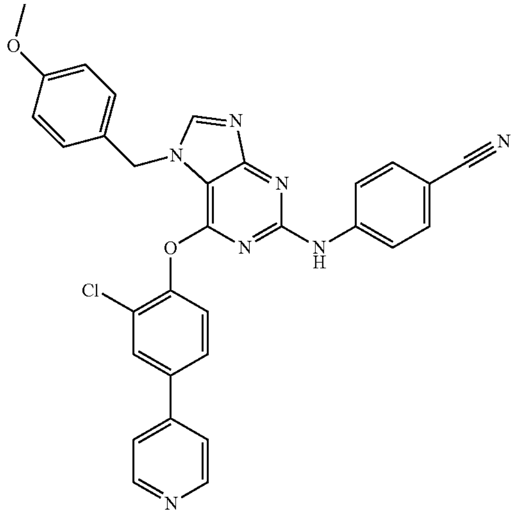
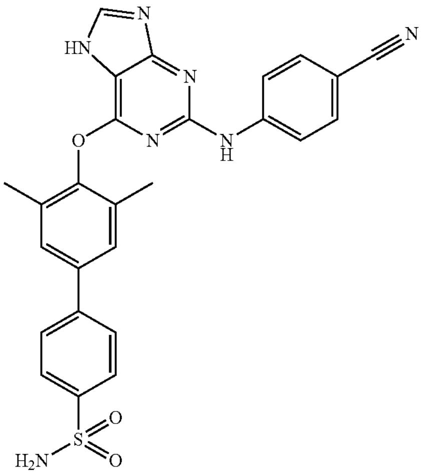
? indicates text missing or illegible when filed -continued
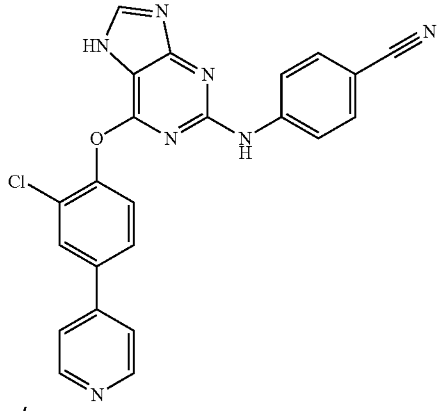
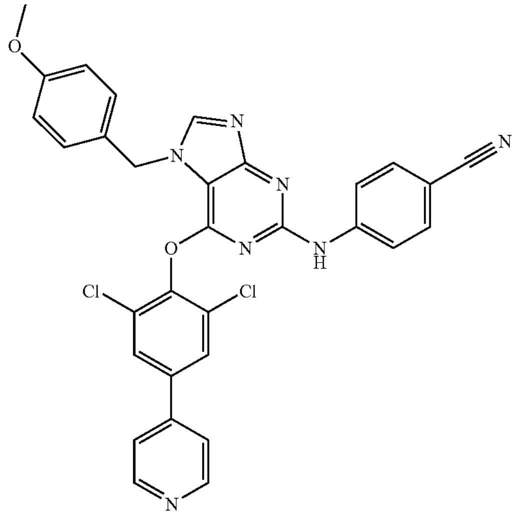
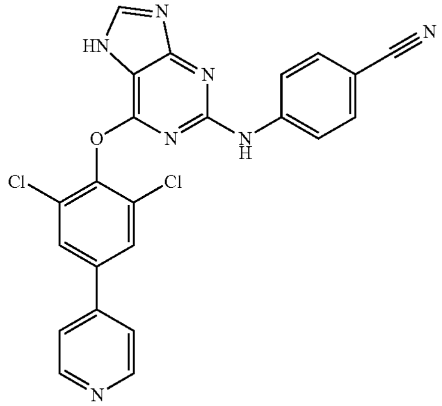
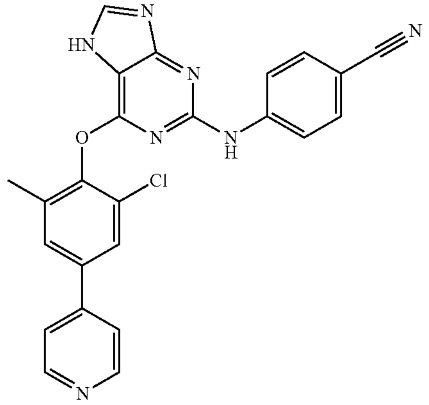
-continued
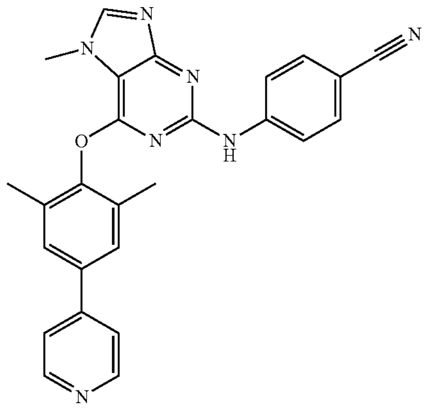
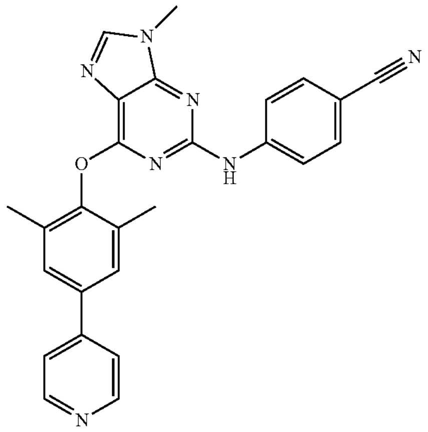
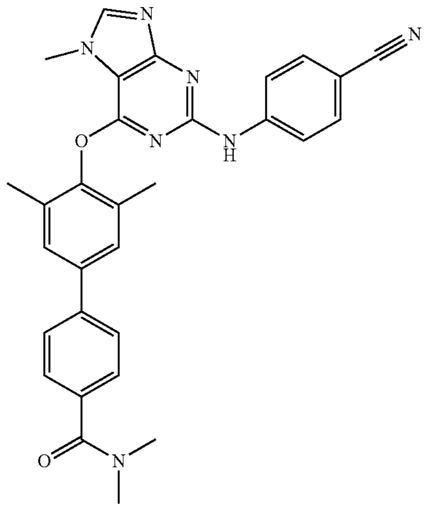

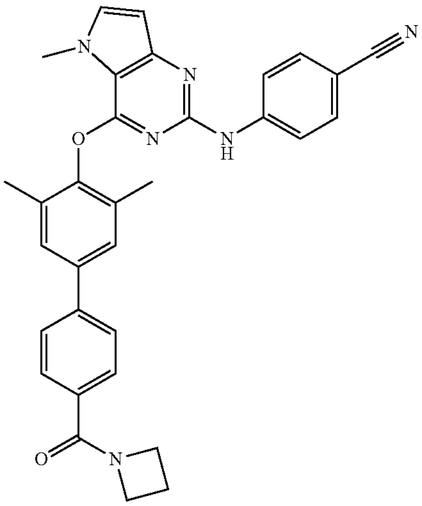
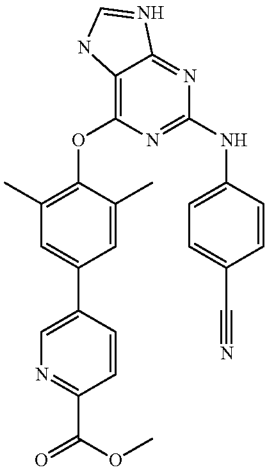
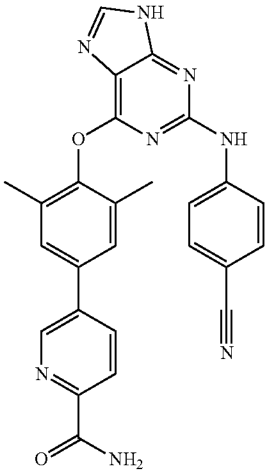
ⓘ indicates text missing or illegible when filed
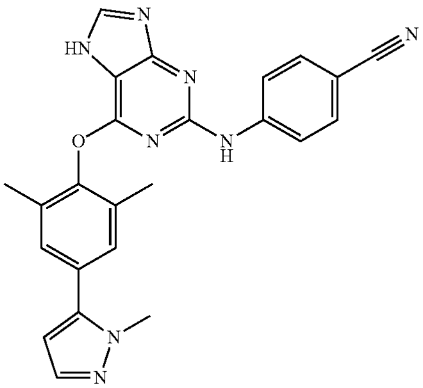
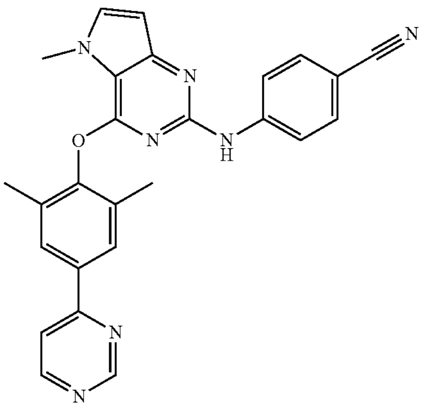
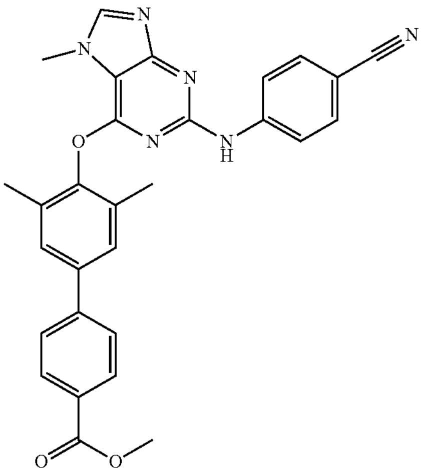

-continued
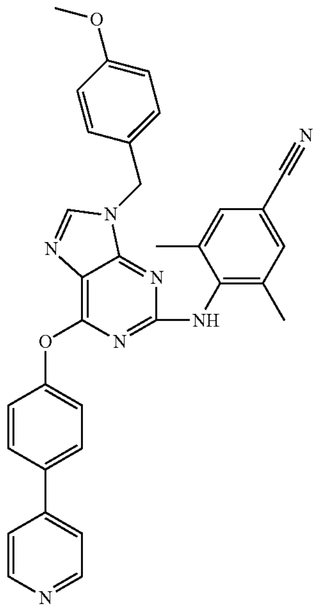
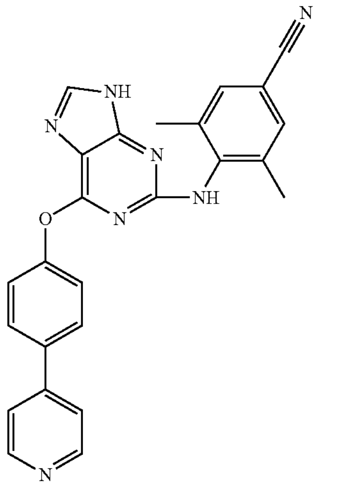
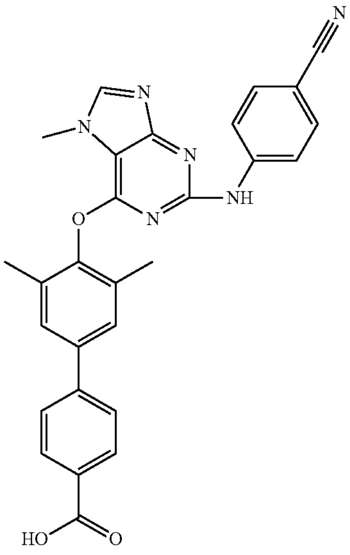
(?) indicates text missing or illegible when filed
-continued
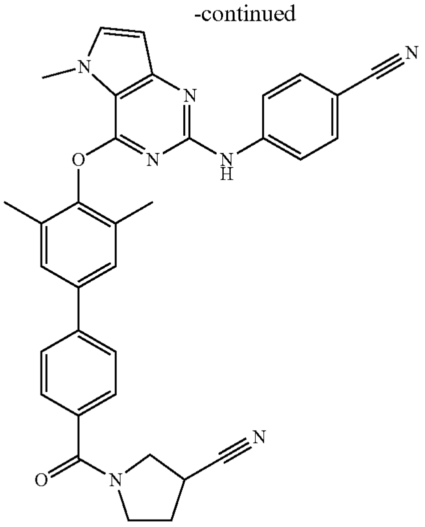
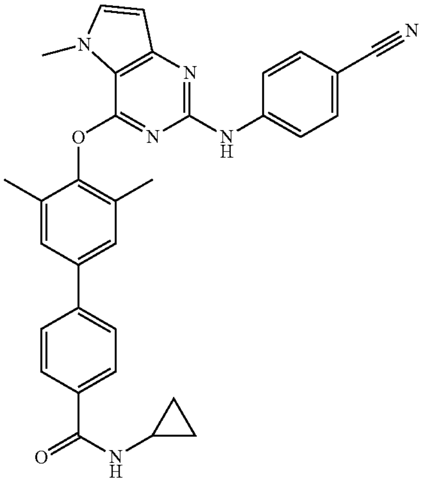
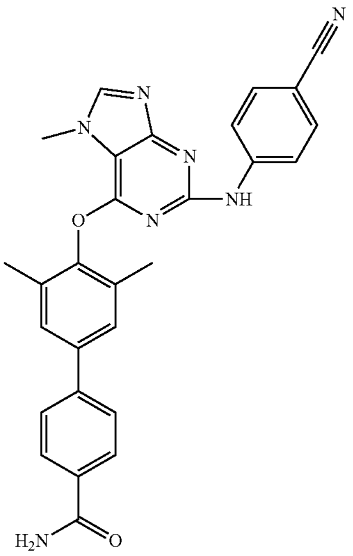
(?) indicates text missing or illegible when filed -continued
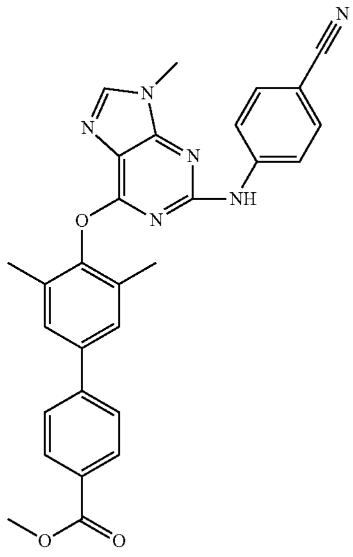
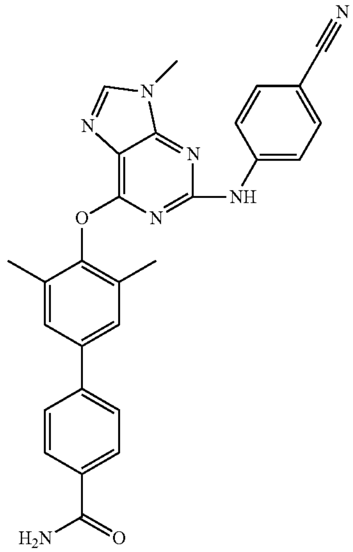
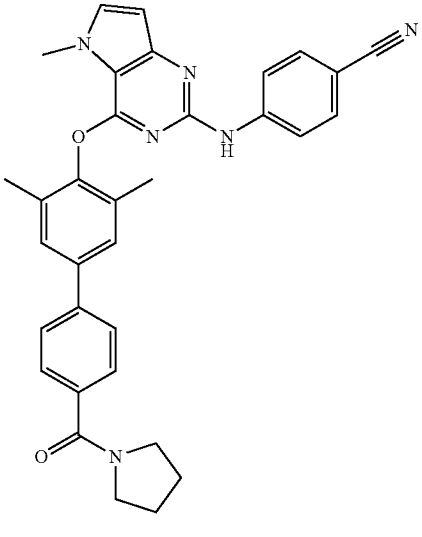
? indicates text missing or illegible when filed
-continued
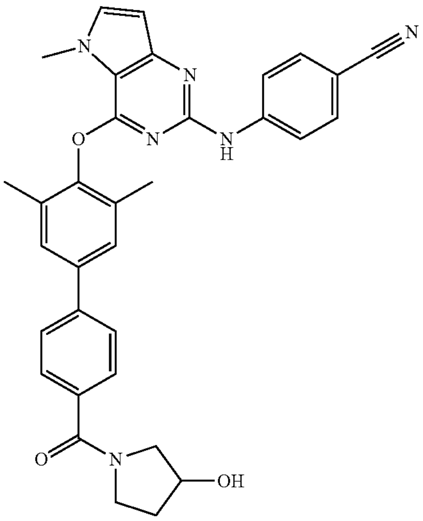
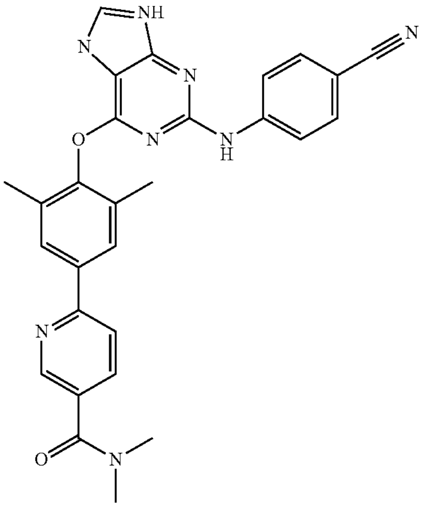
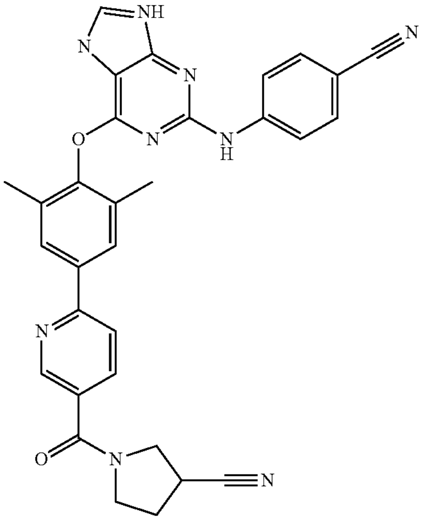
? indicates text missing or illegible when filed -continued
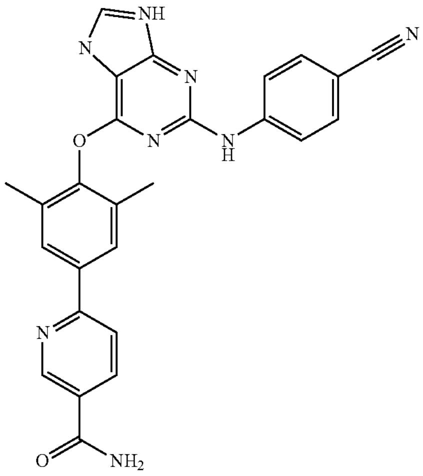
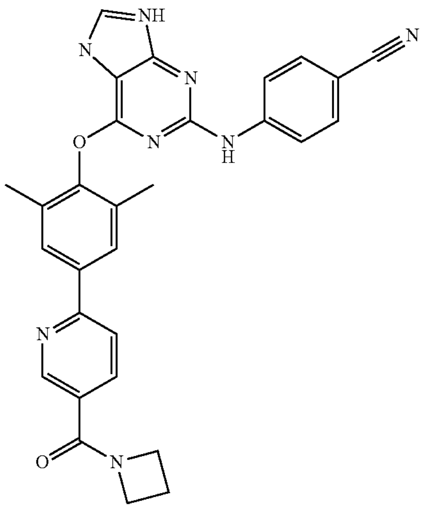
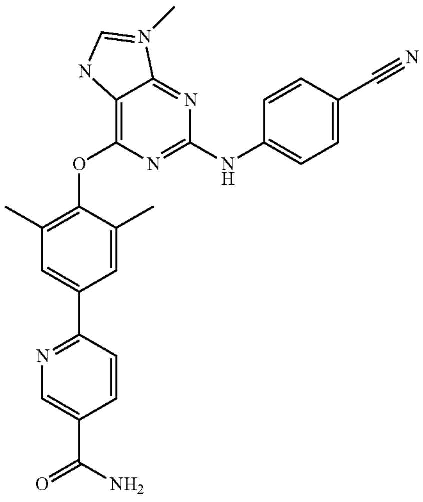
-continued
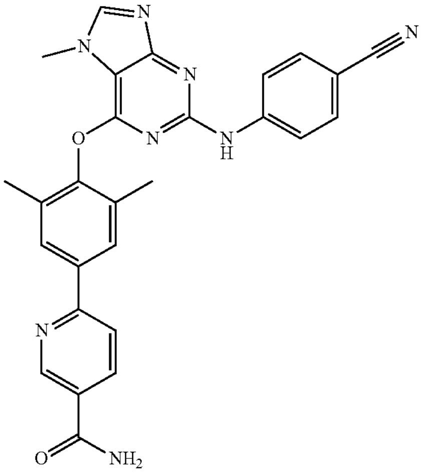
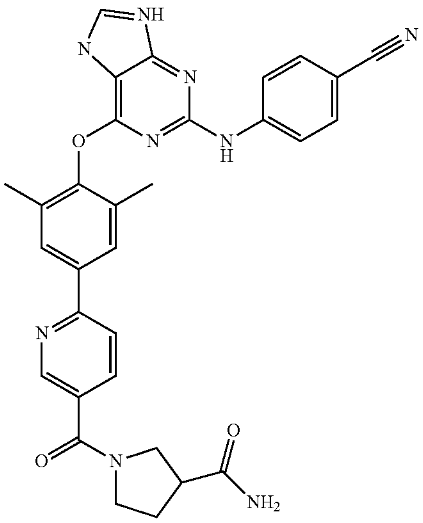
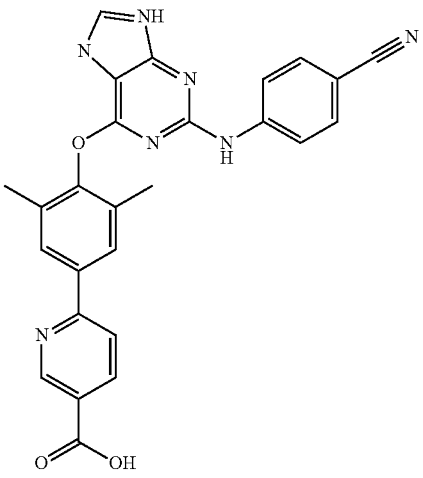

-continued
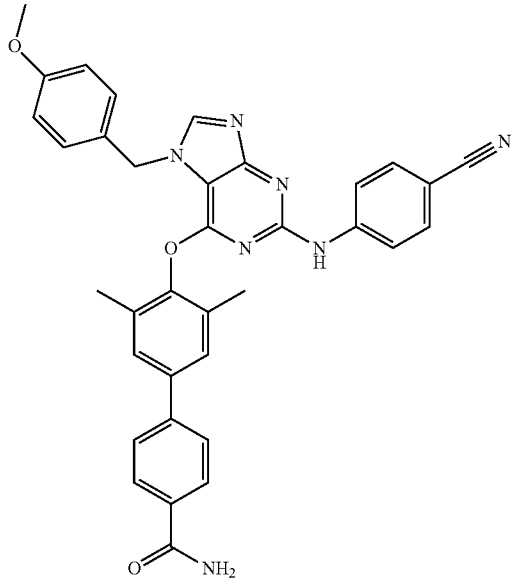
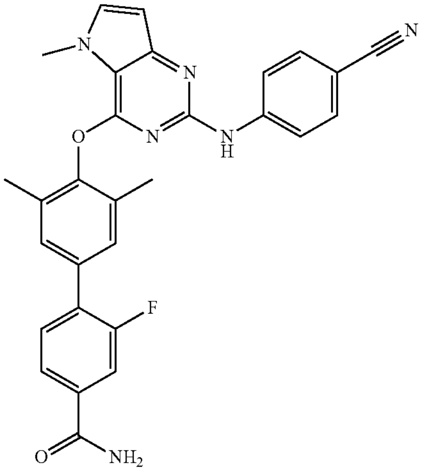
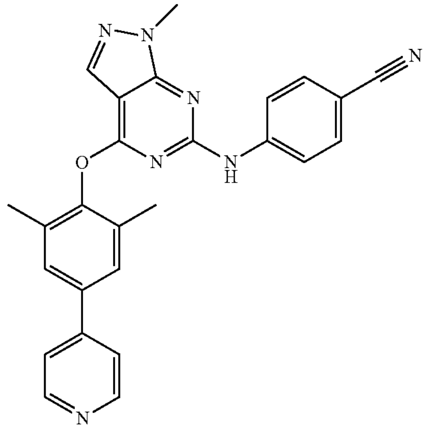
-continued
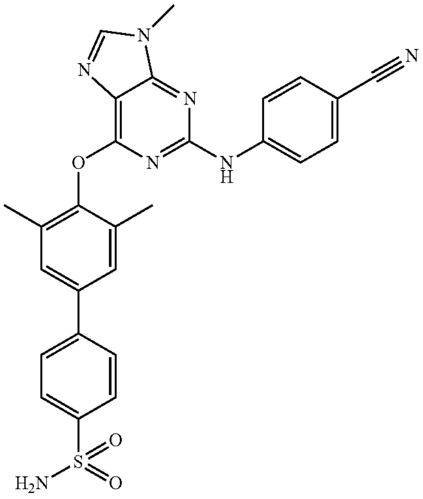
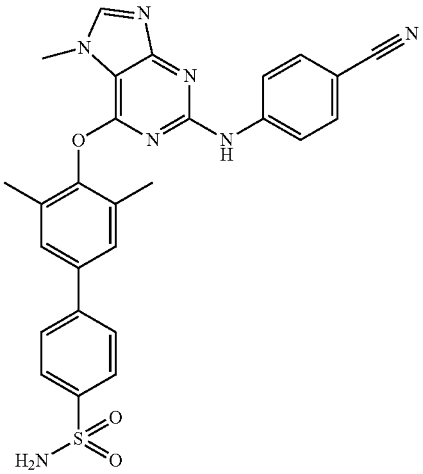
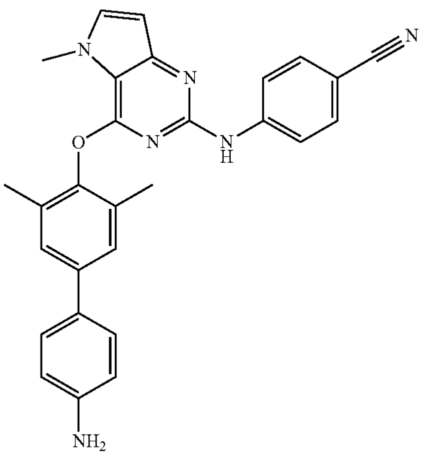
(?) indicates text missing or illegible when filed -continued
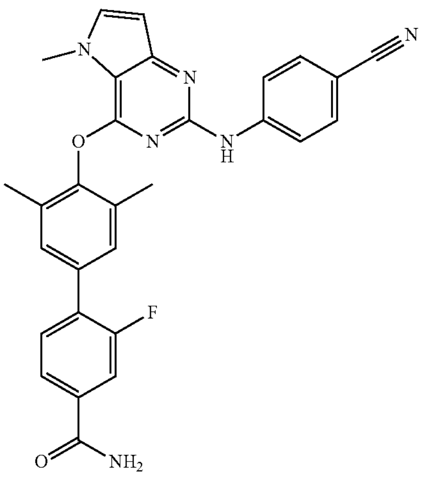
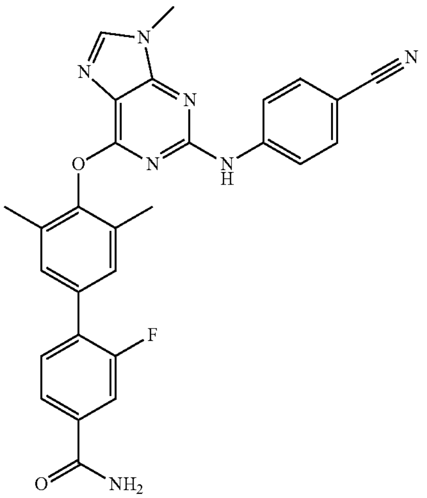
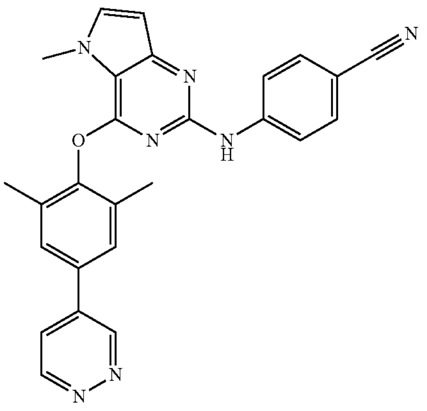
ⓘ indicates text missing or illegible when filed
-continued
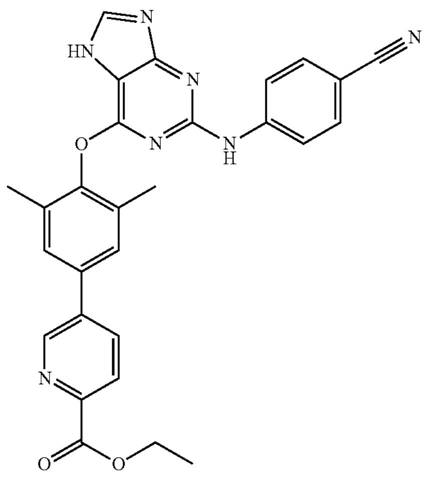
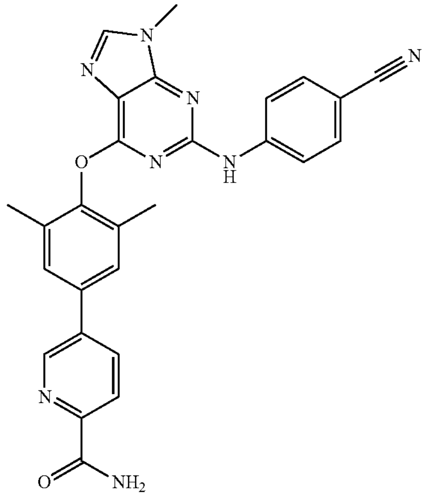
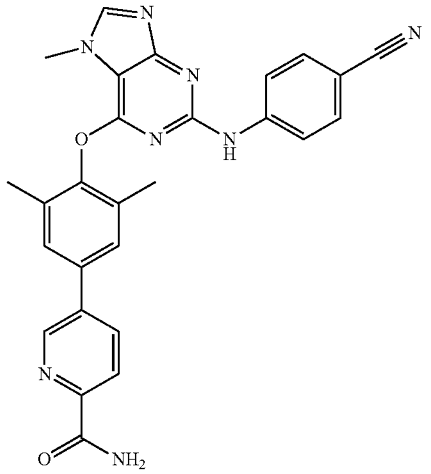
ⓘ indicates text missing or illegible when filed -continued
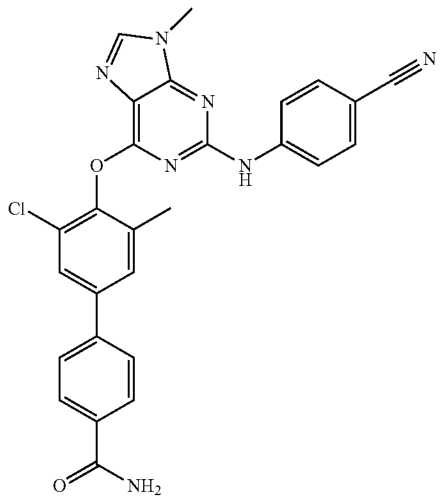
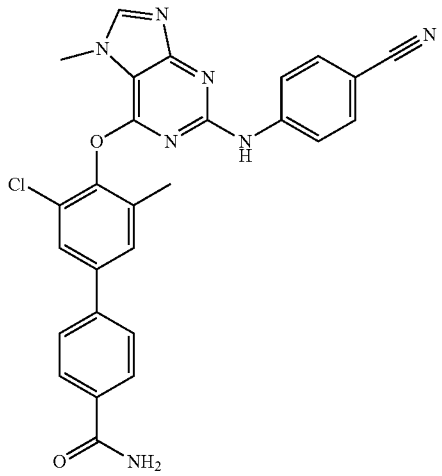
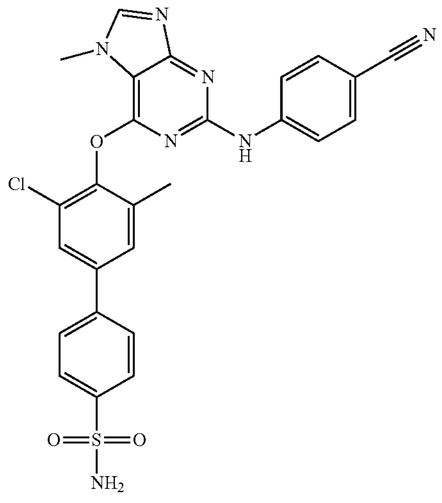
-continued
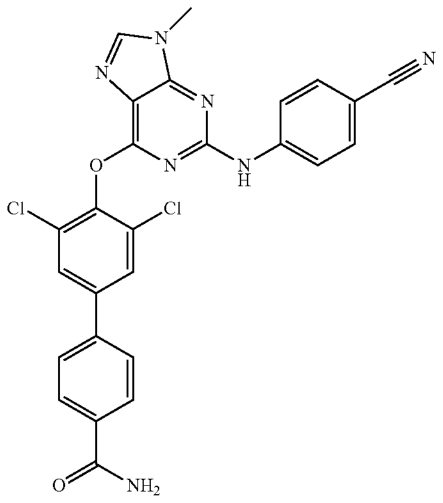
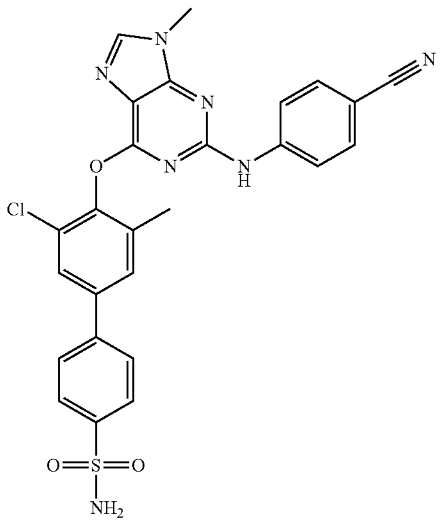
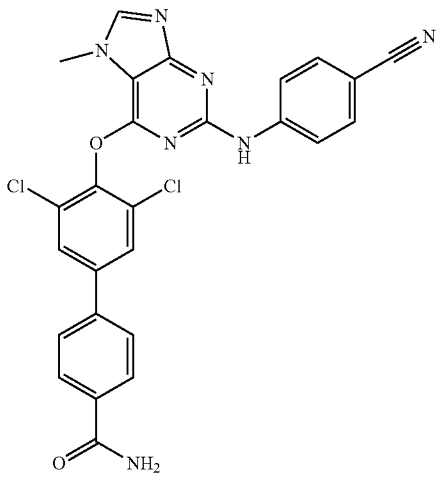
(?) indicates text missing or illegible when filed -continued

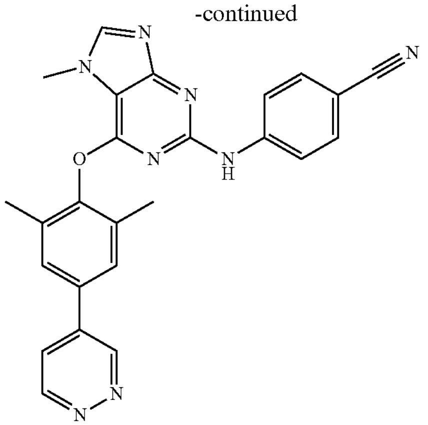

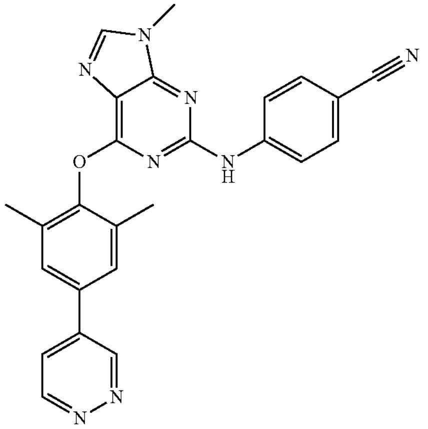

In some embodiments, $R^P$ is aryl or substituted aryl.

In further or additional embodiments, $R^P$ is heterocyclyl, substituted heterocyclyl, heteroaryl or substituted heteroaryl. In further or additional embodiments, $R^P$ is a substituted or unsubstituted heterocycle selected from furanyl, thiofuranyl, pyrrolyl, pyrrolinyl, pyrrolidinyl, oxazolyl, thiazolyl, imidazolyl, imidazolinyl, pyrazolyl, pyrazolinyl, pyrazolidinyl, isoxazolyl, isothiazolyl, oxadizolyl, thiazolyl, thiadiazolyl, triazolyl, pyranyl, pyridyl, piperidinyl, morpholinyl, pyridazyl, pyrimidyl, pyrazinyl, piperazinyl, triazinyl, tetrazolyl, quinolinyl, isoquinolinyl or indolyl. In further or additional embodiments, $R^P$ is pyridyl, substituted pyridyl, furanyl, substituted furanyl, thiofuranyl, substituted thiofuranyl, pyrrolyl, substituted pyrrolyl, pyrazolyl, substituted pyrazolyl, pyrimidyl, substituted pyrimidyl, isoxazolyl, substituted isoxazolyl, quinolinyl, substituted quinolinyl, isoquinolinyl, substituted isoquinolinyl, indolyl, or substituted indolyl. In further or additional embodiments, $R^P$ is phenyl, substituted phenyl, heteroaryl or substituted heteroaryl. In further or additional embodiments, $R^P$ is heteroaryl. In further or additional embodiments, $R^P$ is substituted heteroaryl. In further or additional embodiments, $R^P$ is pyridyl. In further or additional embodiments, $R^P$ is 2-pyridyl. In further or additional embodiments, $R^P$ is 3-pyridyl. In further or additional embodiments, $R^P$ is 4-pyridyl. In further or additional embodiments, $R^P$ is substituted pyridyl. In further or additional embodiments, $R^P$ is substituted 2-pyridyl. In further or additional embodiments, $R^P$ is substituted 3-pyridyl. In further or additional embodiments, $R^P$ is substituted 4-pyridyl. In further or additional embodiments, $R^P$ is phenyl. In further or additional embodiments, $R^P$ is substituted phenyl. In further or additional embodiments, $R^P$ is 2-substituted phenyl. In further or additional embodiments, $R^P$ is 3-substituted phenyl. In further or additional embodiments, $R^P$ is 4-substituted phenyl. In further or additional embodiments, $R^P$ is substituted pyridyl or substituted phenyl. In further or additional embodiments, $R^P$ is substituted pyridyl or substituted phenyl, substituted in the 2-position. In further or additional embodiments, $R^P$ is substituted pyridyl or substituted phenyl, substituted in the 3-position. In further or additional embodiments, $R^P$ is substituted pyridyl or substituted phenyl, substituted in the 4-position. In further or additional embodiments, $R^P$ is monosubstituted pyridyl or monosubstituted phenyl. In further or additional embodiments, $R^P$ is disubstituted pyridyl or disubstituted phenyl.

In further or additional embodiments, $R^P$ is substituted aryl, substituted heterocyclyl or substituted heteroaryl, wherein the substituents are independently selected from:

F, Cl, Br, I, $CFH_2$, $CF_2H$, $CF_3$, CN, CH═CHCN, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, benzyl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$, and $OC_1$-$C_3$ alkyl.

In further or additional embodiments, $R^P$ is substituted aryl, substituted heterocyclyl or substituted heteroaryl, wherein the substituents are independently selected from F, Cl, Br, I, methyl, ethyl, n-propyl, i-propyl, n-butyl, i-butyl, s-butyl, t-butyl, cyclopropyl, cyclobutyl, cyclopentyl, cyclohexyl, cyclopropylmethyl, C(O)R', $CO_2H$, COOR', $CONH_2$, CONHR', CONR'R", $SO_3H$, $S(O)_2R'$, $S(O)_2NH_2$, $S(O)_2NHR'$ and $S(O)_2NR'R"$.

In further or additional embodiments, $R^P$ is substituted phenyl or substituted pyridyl, wherein the substituents are independently selected from:

F, Cl, Br, I, $CFH_2$, $CF_2H$, $CF_3$, CN, CH═CHCN, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, benzyl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$, and $OC_1$-$C_3$ alkyl.

Also described herein are pharmaceutical compositions comprising an effective amount of a compound of formula (I), or a metabolite, pharmaceutically acceptable salt, solvate, polymorph, ester, tautomer or prodrug thereof. In some embodiments, the pharmaceutical compositions further comprise a pharmaceutically acceptable carrier, diluent or excipient. In further or additional embodiments, the pharmaceutical compositions further comprise a therapeutic agent. In further or additional embodiments, the therapeutic agent is an anti HIV or AIDS drug. In further or additional embodiments, the therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof.

Also described herein are pharmaceutical compositions for treating or preventing an immunodeficiency viral infection, comprising an effective amount of a compound of formula (I), or a metabolite, pharmaceutically acceptable salt, solvate, polymorph, ester, tautomer or prodrug thereof. In some embodiments, the pharmaceutical compositions further comprise a pharmaceutically acceptable carrier, diluent or excipient. In further or additional embodiments, the pharmaceutical compositions further comprise a therapeutic agent. In further or additional embodiments, the therapeutic agent is an anti HIV or AIDS drug. In further or additional embodiments, the therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof. In some embodiments, the infection occurs in a mammal and the pharmaceutical composition is intended for administration to the mammal. In some embodiments, the infection occurs in a human and the pharmaceutical composition is intended for administration to humans.

Also described herein are pharmaceutical compositions for treating or preventing a human immunodeficiency virus (HIV) infection, or treating AIDS or ARC comprising an effective amount of a compound of formula (I), or a metabolite, pharmaceutically acceptable salt, solvate, polymorph, ester, tautomer or prodrug thereof. In some embodiments, the pharmaceutical compositions further comprise a pharmaceutically acceptable carrier, diluent or excipient. In further or additional embodiments, the pharmaceutical compositions further comprise a therapeutic agent. In further or additional embodiments, the therapeutic agent is an anti HIV or AIDS drug. In further or additional embodiments, the pharmaceutical compositions comprising an effective amount of a compound of formula (I), or a metabolite, pharmaceutically acceptable salt, solvate, polymorph, ester, tautomer or prodrug thereof, are administered to an individual who has be prescribed an anti HIV or AIDS drug. In further or additional embodiments, the therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof.

Also described herein are methods for inhibiting a reverse transcriptase, comprising contacting the reverse transcriptase with a compound of formula (I), or a metabolite, pharmaceutically acceptable salt, solvate, polymorph, ester, tautomer or prodrug thereof. In some embodiments, the reverse transcriptase is a retroviral reverse transcriptase. In further or additional embodiments, the retroviral reverse transcriptase is an HIV reverse transcriptase. In further or additional embodiments, the HIV reverse transcriptase is HIV-1 or HIV-2 reverse transcriptase. In further or additional embodiments, the HIV reverse transcriptase is wild type reverse transcriptase. In further or additional embodiments, the retroviral reverse transcriptase exhibits a mutation compared to wild type virus. In further or additional embodiments, the mutation imparts drug resistance to the mutant virus as compared to the wild type virus. In further or additional embodiments, the mutation imparts multi-drug resistance to the mutant virus as compared to the wild type virus. In further or additional embodiments, the mutation imparts resistance to nucleoside reverse transcriptase inhibitors. In further or additional embodiments, the mutation imparts resistance to non-nucleoside reverse transcriptase inhibitors. In further or additional embodiments, the mutation imparts resistance to protease inhibitors. In further or additional embodiments, the contacting occurs in vitro. In further or additional embodiments, the contacting occurs in vivo. In further or additional embodiments, the contacting occurs in a cell. In further or additional embodiments, the cell is a mammalian cell. In further or additional embodiments, the cell is a human cell. In further or additional embodiments, the reverse transcriptase is inhibited at least about 10%. In further or additional embodiments, the reverse transcriptase is inhibited at least about 20%. In further or additional embodiments, the reverse transcriptase is inhibited at least about 50%.

Also described herein are methods for inhibiting HIV replication comprising contacting the HIV with a compound of formula (I), or a metabolite, pharmaceutically acceptable salt, solvate, polymorph, ester, tautomer or prodrug thereof. In some embodiments, the HIV is HIV-1 or HIV-2. In further or additional embodiments, the HIV is wild type HIV. In further or additional embodiments, the HIV exhibits a mutation compared to wild type HIV. In further or additional embodiments, the mutation imparts drug resistance to the mutant virus as compared to the wild type virus. In further or additional embodiments, the mutation imparts multi-drug resistance to the mutant virus as compared to the wild type virus. In further or additional embodiments, the mutation imparts resistance to nucleoside reverse transcriptase inhibitors. In further or additional embodiments, the mutation imparts resistance to non-nucleoside reverse transcriptase inhibitors. In further or additional embodiments, the mutation imparts resistance to protease inhibitors. In further or additional embodiments, the contacting occurs in vitro. In further or additional embodiments, the contacting occurs in vivo. In further or additional embodiments, the contacting occurs in a cell. In further or additional embodiments, the contacting occurs in a mammalian cell. In further or additional embodiments, the contacting occurs in a human cell. In further or additional embodiments, the HIV replication is inhibited at least about 10%. In further or additional embodiments, the HIV replication is inhibited at least about 20%. In further or additional embodiments, the HIV replication is inhibited at least about 30%.

Also described herein are methods for treating a viral infection in an individual in need thereof comprising administering to said individual an effective amount of a compound of formula (I), or a metabolite, pharmaceutically acceptable salt, solvate, polymorph, ester, tautomer or prodrug thereof. In some embodiments, the viral infection is caused by a virus selected from the group consisting of human immunodeficiency viruses 1 (HIV-1), human immunodeficiency viruses 2 (HIV-2), human T-cell leukemia viruses 1 (HTLV-1), human T-cell leukemia viruses 2 (HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 (HSV-1), herpes simplex viruses 2 (HSV-2), human herpes virus 8 (HHV-8) Yellow Fever virus, Dengue virus, Japanese Encephalitis and West Nile virus.

Also described herein are methods for preventing immunodeficiency virus (HIV) infection in an individual in need thereof, comprising administering to the individual a therapeutically effective amount of a compound of formula (I), or a metabolite, pharmaceutically acceptable salt, solvate, polymorph, ester, tautomer or prodrug thereof. In some embodiments, the method further comprises administering an effective amount of a second therapeutic agent. In further or additional embodiments, the second therapeutic agent is an anti HIV or AIDS drug. In further or additional embodiments, the second therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the second therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof. In some embodiments, the compound of formula (I) and the second therapeutic agent are administered sequentially. In further or additional embodiments, the sequential administration is a cycling therapy. In further or additional embodiments, the compound of formula (I) is administered before the second therapeutic agent. In further or additional embodiments, the compound of formula (I) is administered after the second therapeutic agent. In further or additional embodiments, the administration is simultaneous.

Also described herein are methods for treating immunodeficiency virus (HIV) infection in an individual in need thereof, comprising administering to the individual a therapeutically effective amount of a compound of formula (I), or a metabolite, pharmaceutically acceptable salt, solvate, polymorph, ester, tautomer or prodrug thereof. In some embodiments, the HIV is HIV-1 or HIV-2. In further or additional embodiments, the HIV is a strain that exhibits a mutation compared to wild type HIV. In further or additional embodiments, the HIV is a drug resistant strain of HIV. In further or additional embodiments, the HIV is a multidrug resistant strain of HIV. In further or additional embodiments, the HIV is a strain that exhibits reduced susceptibility to reverse transcriptase inhibitors. In further or additional embodiments, the mutation conveys resistance to an AIDS or HIV therapeutic. In some embodiments, the method further comprises administering an effective amount of a second therapeutic agent. In further or additional embodiments, the therapeutic agent is an anti HIV or AIDS drug. In further or additional embodiments, the therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof. In some embodiments, the compound of formula (I) and the other therapeutic agent are administered sequentially. In further or additional embodiments, the sequential administration is a cycling therapy. In further or additional embodiments, the compound of formula (I) is administered before the other therapeutic agent. In further or additional embodiments, the compound of formula (I) is administered after the therapeutic agent. In further or additional embodiments, the administration is simultaneous.

Also described herein are methods for treating AIDS-related complex (ARC) in an individual in need thereof, comprising administering to the individual a therapeutically effective amount of a compound of formula (I), or a metabolite, pharmaceutically acceptable salt, solvate, polymorph, ester, tautomer or prodrug thereof. In some embodiments, the HIV is HIV-1 or HIV-2. In further or additional embodiments, the HIV is a strain that exhibits a mutation compared to wild type HIV. In further or additional embodiments, the HIV is a drug resistant strain of HIV. In further or additional embodiments, the HIV is a multidrug resistant strain of HIV. In further or additional embodiments, the HIV is a strain that exhibits reduced susceptibility to reverse transcriptase inhibitors. In further or additional embodiments, the mutation conveys resistance to an AIDS or HIV therapeutic. In some embodiments, the method further comprises administering an effective amount of a second therapeutic agent. In further or additional embodiments, the therapeutic agent is an anti HIV or AIDS drug. In further or additional embodiments, the therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof. In some embodiments, the compound of formula (I) and the other therapeutic agent are administered sequentially. In further or additional embodiments, the sequential administration is a cycling therapy. In further or additional embodiments, the compound of formula (I) is administered before the other therapeutic agent. In further or additional embodiments, the compound of formula (I) is administered after the therapeutic agent. In further or additional embodiments, the administration is simultaneous.

Also described herein are methods for prophylaxis of ARC in an individual in need thereof, comprising administering to the individual a therapeutically effective amount of a compound of formula (I), or a metabolite, pharmaceutically acceptable salt, solvate, polymorph, ester, tautomer or prodrug thereof. In some embodiments, the HIV is HIV-1 or HIV-2. In further or additional embodiments, the HIV is a strain that exhibits a mutation compared to wild type HIV. In further or additional embodiments, the HIV is a drug resistant strain of HIV. In further or additional embodiments, the HIV is a multidrug resistant strain of HIV. In further or additional embodiments, the HIV is a strain that exhibits reduced susceptibility to reverse transcriptase inhibitors. In further or additional embodiments, the mutation conveys resistance to an AIDS or HIV therapeutic. In some embodiments, the method further comprises administering an effective amount of a second therapeutic agent. In further or additional embodiments, the therapeutic agent is an anti HIV or AIDS drug. In further or additional embodiments, the therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof. In some embodiments, the compound of formula (I) and the other therapeutic agent are administered sequentially. In further or additional embodiments, the sequential administration is a cycling therapy. In further or additional embodiments, the compound of formula (I) is administered before the other therapeutic agent. In further or additional embodiments, the compound of formula (I) is administered after the therapeutic agent. In further or additional embodiments, the administration is simultaneous.

Also described herein are methods for delaying the onset of ARC in an individual in need thereof, comprising administering to the individual a therapeutically effective amount of a compound of formula (I), or a metabolite, pharmaceutically acceptable salt, solvate, polymorph, ester, tautomer or prodrug thereof. In some embodiments, the HIV is HIV-1 or HIV-2. In further or additional embodiments, the HIV is a strain that exhibits a mutation compared to wild type HIV. In further or additional embodiments, the HIV is a drug resistant strain of HIV. In further or additional embodiments, the HIV is a multidrug resistant strain of HIV. In further or additional embodiments, the HIV is a strain that exhibits reduced susceptibility to reverse transcriptase inhibitors. In further or additional embodiments, the mutation conveys resistance to an AIDS or HIV therapeutic. In some embodiments, the method further comprises administering an effective amount of a second therapeutic agent. In further or additional embodiments, the therapeutic agent is an anti HIV or AIDS drug. In further or additional embodiments, the therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof. In some embodiments, the compound of formula (I) and the other therapeutic agent are administered sequentially. In further or additional embodiments, the sequential administration is a cycling therapy. In further or additional embodiments, the compound of formula (I) is administered before the other therapeutic agent. In further or additional embodiments, the compound of formula (I) is administered after the therapeutic agent. In further or additional embodiments, the administration is simultaneous.

Also described herein are methods for treating AIDS in an individual in need thereof, comprising administering to the individual a therapeutically effective amount of a compound of formula (I), or a metabolite, pharmaceutically acceptable salt, solvate, polymorph, ester, tautomer or prodrug thereof. In some embodiments, the HIV is HIV-1 or HIV-2. In further or additional embodiments, the HIV is a strain that exhibits a mutation compared to wild type HIV. In further or additional embodiments, the HIV is a drug resistant strain of HIV. In further or additional embodiments, the HIV is a multidrug resistant strain of HIV. In further or additional embodiments, the HIV is a strain that exhibits reduced susceptibility to reverse transcriptase inhibitors. In further or additional embodiments, the mutation conveys resistance to an AIDS or HIV therapeutic. In some embodiments, the method further comprises administering an effective amount of a second therapeutic agent. In further or additional embodiments, the therapeutic agent is an anti HIV or AIDS drug. In further or additional embodiments, the therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof. In some embodiments, the compound of formula (I) and the other therapeutic agent are administered sequentially. In further or additional embodiments, the sequential administration is a cycling therapy. In further or additional embodiments, the compound of formula (I) is administered before the other therapeutic agent. In further or additional embodiments, the compound of formula (I) is administered after the therapeutic agent. In further or additional embodiments, the administration is simultaneous.

Also described herein are methods for the prophylaxis of AIDS in an individual in need thereof, comprising administering to the individual a therapeutically effective amount of a compound of formula (I), or a metabolite, pharmaceutically acceptable salt, solvate, polymorph, ester, tautomer or prodrug thereof. In some embodiments, the HIV is HIV-1 or HIV-2. In further or additional embodiments, the HIV is a strain that exhibits a mutation compared to wild type HIV. In further or additional embodiments, the HIV is a drug resistant strain of HIV. In further or additional embodiments, the HIV is a multidrug resistant strain of HIV. In further or additional embodiments, the HIV is a strain that exhibits reduced susceptibility to reverse transcriptase inhibitors. In further or additional embodiments, the mutation conveys resistance to an AIDS or HIV therapeutic. In some embodiments, the method further comprises administering an effective amount of a second therapeutic agent. In further or additional embodiments, the therapeutic agent is an anti HIV or AIDS drug. In further or additional embodiments, the therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof. In some embodiments, the compound of formula (I) and the other therapeutic agent are administered sequentially. In further or additional embodiments, the sequential administration is a cycling therapy. In further or additional embodiments, the compound of formula (I) is administered before the other therapeutic agent. In further or additional embodiments, the compound of formula (I) is administered after the therapeutic agent. In further or additional embodiments, the administration is simultaneous.

Also described herein are methods for delaying the onset of AIDS in an individual in need thereof, comprising administering to the individual a therapeutically effective amount of a compound of formula (I), or a metabolite, pharmaceutically acceptable salt, solvate, polymorph, ester, tautomer or prodrug thereof. In some embodiments, the HIV is HIV-1 or HIV-2. In further or additional embodiments, the HIV is a strain that exhibits a mutation compared to wild type HIV. In further or additional embodiments, the HIV is a drug resistant strain of HIV. In further or additional embodiments, the HIV is a multidrug resistant strain of HIV. In further or additional embodiments, the HIV is a strain that exhibits reduced susceptibility to reverse transcriptase inhibitors. In further or additional embodiments, the mutation conveys resistance to an AIDS or HIV therapeutic. In some embodiments, the method further comprises administering an effective amount of a second therapeutic agent. In further or additional embodiments, the therapeutic agent is an anti HIV or AIDS drug. In further or additional embodiments, the therapeutic agent is a reverse transcriptase inhibitor, a viral protease inhibitor, a fusion inhibitor, a cytokine, a cytokine inhibitor, a glycosylation inhibitor, a viral mRNA processing inhibitor, an entry inhibitor, an integrase inhibitor or a maturation inhibitor. In further or additional embodiments, the therapeutic agent is adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof. In some embodiments, the compound of formula (I) and the other therapeutic agent are administered sequentially. In further or additional embodiments, the sequential administration is a cycling therapy. In further or additional embodiments, the compound of formula (I) is administered before the other therapeutic agent. In further or additional embodiments, the compound of formula (I) is administered after the therapeutic agent. In further or additional embodiments, the administration is simultaneous.

Also described herein are methods for treating HIV infection in an individual in need thereof with combination therapy, comprising administering to said individual an effective amount of a combination of a compound of formula (I) with a second compound selected from the group consisting of reverse transcriptase inhibitors, viral protease inhibitors, cytokines, cytokine inhibitors, glycosylation inhibitors, viral mRNA processing inhibitors, entry inhibitors, integrase inhibitors or maturation inhibitors.

Also described herein are methods for treating HIV infection in an individual in need thereof with combination therapy, comprising administering to said individual an effective amount of a combination of a compound of formula (I) with a second compound selected from the group consisting of adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof.

Also described herein are kits, comprising a compound of formula (I), or a metabolite, pharmaceutically acceptable salt, solvate, polymorph, ester, tautomer or prodrug thereof. In some embodiments, the kit further comprises instructions for administration of the compound to a mammal to treat HIV infection, ARC or AIDS.

Further disclosed herein is a method of treating a disorder or condition resulting form infection with a virus in a mammal, including a human, comprising administering to said mammal an effective amount of a compound disclosed herein, or a pharmaceutically acceptable salt, ester, prodrug, solvate, hydrate or derivative thereof, effective to modulate said cascade. The appropriate dosage for a particular individual is determined by any suitable method.

Further disclosed herein, in certain embodiments, is a pharmaceutical composition comprising a compound disclosed herein or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the amount of a compound disclosed herein is in the range of about 0.001 to about 1000 mg/kg body weight/day. In further or additional embodiments, the amount of a compound disclosed herein is in the range of about 0.5 to about 50 mg/kg/day. In further or additional embodiments, the amount of a compound disclosed herein is about 0.001 to about 7 g/day. In further or additional embodiments, the amount of a compound disclosed herein is about 0.002 to about 6 g/day. In further or additional embodiments, the amount of a compound disclosed herein is about 0.005 to about 5 g/day. In further or additional embodiments, the amount of a compound disclosed herein is about 0.01 to about 5 g/day. In further or additional embodiments, the amount of a compound disclosed herein is about 0.02 to about 5 g/day. In further or additional embodiments, the amount of a compound disclosed herein is about 0.05 to about 2.5 g/day. In further or additional embodiments, the amount of a compound disclosed herein is about 0.1 to about 1 g/day. In further or additional embodiments, dosage levels below the lower limit of the aforesaid ranges are adequate. In further or additional embodiments, dosage levels above the upper limit of the aforesaid ranges are required. In further or additional embodiments, a compound disclosed herein is administered in a single dose, once daily. In further or additional embodiments, a compound disclosed herein is administered in multiple doses, more than once per day. In further or additional embodiments, a compound disclosed herein is administered twice daily. In further or additional embodiments, a compound disclosed herein is administered three times per day. In further or additional embodiments, a compound disclosed herein is administered four times per day. In further or additional embodiments, a compound disclosed herein is administered more than four times per day. In some embodiments, the pharmaceutical composition is for administration to a mammal. In further or additional embodiments, the mammal is human. In further or additional embodiments, the pharmaceutical composition further comprises a pharmaceutical carrier, excipient and/or adjuvant. In further or additional embodiments, the pharmaceutical composition comprises a pharmaceutically acceptable salt of a compound disclosed herein.

Disclosed herein, in certain embodiments, is a method for inhibiting a reverse transcriptase enzyme. In some embodiments, the method comprises contacting said reverse transcriptase enzyme with an amount of a composition comprising a compound disclosed herein or a pharmaceutically acceptable salt, solvate, polymorph, ester, tautomer or prodrug thereof, sufficient to inhibit said enzyme, wherein said enzyme is inhibited. In further or additional embodiments, the enzyme is at least about 1% inhibited. In further or additional embodiments, the enzyme is at least about 2% inhibited. In further or additional embodiments, the enzyme is at least about 3% inhibited. In further or additional embodiments, the enzyme is at least about 4% inhibited. In further or additional embodiments, the enzyme is at least about 5% inhibited. In further or additional embodiments, the enzyme is at least about 10% inhibited. In further or additional embodiments, the enzyme is at least about 20% inhibited. In further or additional embodiments, the enzyme is at least about 25% inhibited. In further or additional embodiments, the enzyme is at least about 30% inhibited. In further or additional embodiments, the enzyme is at least about 40% inhibited. In further or additional embodiments, the enzyme is at least about 50% inhibited. In further or additional embodiments, the enzyme is at least about 60% inhibited. In further or additional embodiments, the enzyme is at least about 70% inhibited. In further or additional embodiments, the enzyme is at least about 75% inhibited. In further or additional embodiments, the enzyme is at least about 80% inhibited. In further or additional embodiments, the enzyme is at least about 90% inhibited. In further or additional embodiments, the enzyme is essentially completely inhibited . . . . In further or additional embodiments, the contacting occurs within a cell. In further or additional embodiments, the cell is a mammalian cell. In further or additional embodiments, the mammalian cell is a human cell. In further or additional embodiments, the reverse transcriptase enzyme is inhibited with a composition comprising a pharmaceutically acceptable salt of a compound disclosed herein.

Disclosed herein, in certain embodiments, is a method of treating a disease in an individual suffering from said disease comprising administering to said individual an effective amount of a composition comprising a compound disclosed herein or a pharmaceutically acceptable salt, solvate, polymorph, ester, tautomer or prodrug thereof.

Disclosed herein, in certain embodiments, is a method of treatment of immunodeficiency viral infection in an individual infected with an immunodeficiency virus, comprising administering to said individual an effective amount of a composition comprising a compound disclosed herein or a pharmaceutically acceptable salt, solvate, polymorph, ester, tautomer or prodrug thereof. In some embodiments, the composition comprising a compound disclosed herein is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release formulations, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant.

In further or additional embodiments, the amount of a compound disclosed herein is in the range of about 0.001 to about 1000 mg/kg body weight/day. In further or additional embodiments, the amount of a compound disclosed herein is in the range of about 0.5 to about 50 mg/kg/day. In further or additional embodiments, the amount of a compound disclosed herein is about 0.001 to about 7 g/day. In further or additional embodiments, the amount of a compound disclosed herein is about 0.01 to about 7 g/day. In further or additional embodiments, the amount of a compound disclosed herein is about 0.02 to about 5 g/day. In further or additional embodiments, the amount of a compound disclosed herein is about 0.05 to about 2.5 g/day. In further or additional embodiments, the amount of a compound disclosed herein is about 0.1 to about 1 g/day. In further or additional embodiments, dosage levels below the lower limit of the aforesaid range are adequate. In further or additional embodiments, dosage levels above the upper limit of the aforesaid range are required. In further or additional embodiments, a compound disclosed herein is administered in a single dose, once daily. In further or additional embodiments, a compound disclosed herein is administered in multiple doses, more than once per day. In further or additional embodiments, a compound disclosed herein is administered twice daily. In further or additional embodiments, a compound disclosed herein is administered three times per day. In further or additional embodiments, a compound disclosed herein is administered four times per day. In further or additional embodiments, a compound disclosed herein is administered more than four times per day. In some embodiments, the individual infected with HIV is a mammal. In further or additional embodiments, the individual is a human. In some embodiments, the composition comprising a compound disclosed herein is administered in combination with an additional therapy.

Disclosed herein, in certain embodiments, is a method for degrading, inhibiting the growth of or killing a cell infected with an immunodeficiency virus comprising contacting said cell with an amount of a composition effective to degrade, inhibit the growth of or to kill said cell, the composition comprising a compound disclosed herein or a pharmaceutically acceptable salt, solvate, polymorph, ester, tautomer or prodrug thereof. In some embodiments, the cells are killed. In further or additional embodiments, 1% of the cells are killed. In further or additional embodiments, 2% of the cells are killed. In further or additional embodiments, 3% of the cells are killed. In further or additional embodiments, 4% of the cells are killed. In further or additional embodiments, 5% of the cells are killed. In further or additional embodiments, 10% of the cells are killed. In further or additional embodiments, 20% of the cells are killed. In further or additional embodiments, 25% of the cancer cells are killed. In further or additional embodiments, 30% of the cells are killed. In further or additional embodiments, 40% of the cells are killed. In further or additional embodiments, 50% of the cells are killed. In further or additional embodiments, 60% of the cells are killed. In further or additional embodiments, 70% of the cells are killed. In further or additional embodiments, 75% of the cells are killed. In further or additional embodiments, 80% of the cells are killed. In further or additional embodiments, 90% of the cells are killed. In further or additional embodiments, 100% of the cells are killed. In further or additional embodiments, essentially all of the cells are killed. In further or additional embodiments, the growth of the cells is inhibited. In further or additional embodiments, the growth of the cells is about 1% inhibited. In further or additional embodiments, the growth of the cells is about 2% inhibited. In further or additional embodiments, the growth of the cells is about 3% inhibited. In further or additional embodiments, the growth of the cells is about 4% inhibited. In further or additional embodiments, the growth of the cells is about 5% inhibited. In further or additional embodiments, the growth of the cells is about 10% inhibited. In further or additional embodiments, the growth of the cells is about 20% inhibited. In further or additional embodiments, the growth of the cells is about 25% inhibited. In further or additional embodiments, the growth of the cells is about 30% inhibited. In further or additional embodiments, the growth of the cells is about 40% inhibited. In further or additional embodiments, the growth of the cells is about 50% inhibited. In further or additional embodiments, the growth of the cells is about 60% inhibited. In further or additional embodiments, the growth of the cells is about 70% inhibited. In further or additional embodiments, the growth of the cells is about 75% inhibited. In further or additional embodiments, the growth of the cells is about 80% inhibited. In further or additional embodiments, the growth of the cells is about 90% inhibited. In further or additional embodiments, the growth of the cells is about 100% inhibited. In further or additional embodiments, a composition comprising a pharmaceutically acceptable salt of a compound disclosed herein is used.

DETAILED DESCRIPTION

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference for the disclosures they are cited as illustrating. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definitions of standard chemistry terms are found in reference works, such as Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Any suitable technique is used for chemical syntheses, chemical analyses, pharmaceutical preparation, formulation, and delivery, and treatment of individuals. In some embodiments, reactions and purification techniques are performed e.g., using kits of manufacturer's specifications or as commonly accomplished in the art or as described herein. The foregoing techniques and procedures are performed by any suitable method. Throughout the specification, groups and substituents thereof are chosen to provide stable moieties and compounds.

Where substituent groups are specified by their conventional chemical formulas, written from left to right, they equally encompass the chemically identical substituents that would result from writing the structure from right to left. As a non-limiting example, $—CH_2O—$ is equivalent to $—OCH_2—$.

Unless otherwise noted, the use of general chemical terms, such as though not limited to "alkyl," "amine," "aryl," are equivalent to their optionally substituted forms. For example, "alkyl," as used herein, includes optionally substituted alkyl.

In some embodiments, the compounds presented herein possess one or more stereocenters and each center exists in the R or S configuration, or combinations thereof. Likewise, in some embodiments, the compounds presented herein possess one or more double bonds and each exists in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. For techniques of inverting or leaving unchanged a particular stereocenter, and/or resolving mixtures of stereoisomers see, for example, Furniss et al. (eds.), VOGEL'S TEXTBOOK OF PRACTICAL ORGANIC CHEMISTRY $5^{th}$ Edition, Longman Scientific and Technical Ltd., Essex, UK, 1991, 809-816 which is herein incorporated by reference for such disclosures.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "catalytic group" refers to a chemical functional group that assists catalysis by acting to lower the activation barrier to reaction.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, in some embodiments, an optionally substituted group is unsubstituted (e.g., $—CH_2CH_3$), fully substituted (e.g., $—CF_2CF_3$), mono-substituted (e.g., $—CH_2CH_2F$) or substituted at a level anywhere in-between fully substituted and mono-substituted (e.g., $—CH_2CHF_2$, $—CH_2CF_3$, $—CF_2CH_3$, $—CFHCHF_2$, etc). Such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-$C_X$ includes $C_1$-$C_2$, $C_1$-$C_3$ . . . $C_1$-$C_X$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that, in some embodiments, the group has 1 carbon atom; in some embodiments, 2 carbon atoms; in some embodiments, 3 carbon atoms; in some embodiments, 4 carbon atoms; in some embodiments, 5 carbon atoms; in some embodiments, 6 carbon atoms; in some embodiments, 7 carbon atoms; in some embodiments, 8 carbon atoms; in some embodiments, 9 carbon atoms; or, in some embodiments, 10 carbon atoms.

The term "hydrocarbon" as used herein, alone or in combination, refers to a compound or chemical group containing only carbon and hydrogen atoms.

The terms "heteroatom" or "hetero" as used herein, alone or in combination, refer to an atom other than carbon or hydrogen. Heteroatoms are independently selected from among oxygen, nitrogen, sulfur, phosphorous, silicon, selenium and tin but are not limited to these atoms. In some embodiments, in which two or more heteroatoms are present, the two or more heteroatoms are the same as each another, or some or all of the two or more heteroatoms each different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that in some embodiments, the alkyl group consists of 1 carbon atom; in some embodiments, 2 carbon atoms; in some embodiments, 3 carbon atoms; in some embodiments, 4 carbon atoms; in some embodiments, 5 carbon atoms; or, in some embodiments, 6 carbon atoms, although the present definition also covers the occurrence of the term "alkyl" where no numerical range is designated.

The term "alkylene" as used herein, alone or in combination, refers to a diradical derived from the above-defined monoradical, alkyl. Examples include, but are not limited to methylene ($—CH_2—$), ethylene ($—CH_2CH_2—$), propylene ($—CH_2CH_2CH_2—$), isopropylene ($—CH(CH_3)CH_2—$) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. In some embodiments, the group is in the cis conformation about the double bond(s). In some embodiments, the group is in the trans conformation about the double bond(s). As used herein, the term should be understood to include both isomers. Examples include, but are not limited to ethenyl ($—CH{=}CH_2$), 1-propenyl ($—CH_2CH{=}CH_2$), isopropenyl [$C(CH_3){=}CH_2$], butenyl, 1,3-butadienyl and the like. Whenever it appears herein, a numerical range such as "$C_2$-$C_6$ alkenyl" or "$C_{2-6}$ alkenyl", means that, in some embodiments, the alkenyl group consists of 2 carbon atoms; in some embodiments, 3 carbon atoms; in some embodiments, 4 carbon atoms; in some embodiments, 5 carbon atoms; or, in some embodiments, 6 carbon atoms, although the present definition also covers the occurrence of the term "alkenyl" where no numerical range is designated.

The term "alkenylene" as used herein, alone or in combination, refers to a diradical derived from the above-defined monoradical alkenyl. Examples include, but are not limited to ethenylene ($—CH{=}CH—$), the propenylene isomers (e.g., $—CH_2CH{=}CH—$ and $—C(CH_3){=}CH—$) and the like.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that, in some embodiments, the alkynyl group consists of 2 carbon atoms; in some embodiments, 3 carbon atoms; in some embodiments, 4 carbon atoms; in some embodiments, 5 carbon atoms; or, in some embodiments, 6 carbon atoms, although the present definition also covers the occurrence of the term "alkynyl" where no numerical range is designated.

The term "alkynylene" as used herein, alone or in combination, refers to a diradical derived from the above-defined monoradical, alkynyl. Examples include, but are not limited to ethynylene propargylene ($—CH_2—C{\equiv}C—$) and the like.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, =N—N=, —N=N—, —N=N—NH—, $—P(O)_2—$, $—O—P(O)_2—$, $—P(O)_2—O—$, —S(O)—, $—S(O)_2—$, $—SnH_2—$ and the like.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments, two or more hydrogen atoms are replaced with halogen atoms that are the same as each another (e.g. difluoromethyl); in other embodiments two or more hydrogen atoms are replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The term "perhalo" as used herein, alone or in combination, refers to groups in which all of the hydrogen atoms are replaced by fluorines, chlorines, bromines, iodines, or combinations thereof. Thus, as a non-limiting example, the term "perhaloalkyl" refers to an alkyl group, as defined herein, in which all of the H atoms have been replaced by fluorines, chlorines, bromines or iodines, or combinations thereof. A non-limiting example of a perhaloalkyl group is bromo, chloro, fluoromethyl. A non-limiting example of a perhaloalkenyl group is trichloroethenyl. A non-limiting example of a perhaloalkynyl group is tribromopropynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. In some embodiments, rings are optionally substituted. In some embodiments, rings form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though, in some embodiments, includes additional, non-ring carbon atoms as substituents (e.g. methylcyclopropyl). Whenever it appears herein, a numerical range such as "$C_3$-$C_6$ cycloalkyl" or "$C_{3-6}$ cycloalkyl", means that, in some embodiments, the cycloalkyl group consists of 3 carbon atoms; in some embodiments, 4 carbon atoms; in some embodiments, 5 carbon atoms; or, in some embodiments, 6 carbon atoms, i.e., is cyclopropyl, cyclobutyl, cyclopentyl or cyclohepty, although the present definition also covers the occurrence of the term "cycloalkyl" where no numerical range is designated. The term includes fused, non-fused, bridged and spiro radicals. In some embodiments, a fused cycloalkyl contains from two to four fused rings where the ring of attachment is a cycloalkyl ring. In some embodiments, the other individual rings are alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

, , , 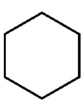, 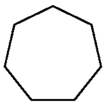,

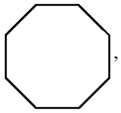, 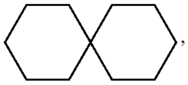, 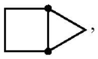,

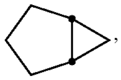, 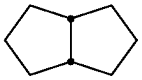, 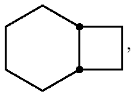,

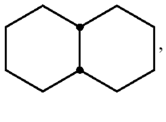, 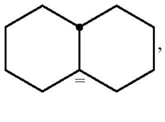, 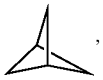,

-continued

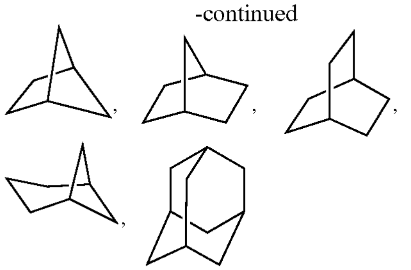

and the like.

The term "cycloalkenyl" as used herein, alone or in combination, refers to an optionally substituted hydrocarbon non-aromatic, monoradical ring, having one or more carbon-carbon double-bonds and from three to about twenty ring carbon atoms, three to about twelve ring carbon atoms, or from three to about ten ring carbon atoms. The term includes fused, non-fused, bridged and spiro radicals. In some embodiments, a fused cycloalkenyl contains from two to four fused rings where the ring of attachment is a cycloalkenyl ring. In some embodiments, the other individual rings are alicyclic, heterocyclic, aromatic, heteroaromatic or any combination thereof. In some embodiments, fused ring systems are fused across a bond that is a carbon-carbon single bond or a carbon-carbon double bond. Examples of cycloalkenyls include, but are not limited to cyclohexenyl, cyclopentadienyl and bicyclo[2.2.1]hept-2-ene ring systems. Illustrative examples include, but are not limited to the following moieties:

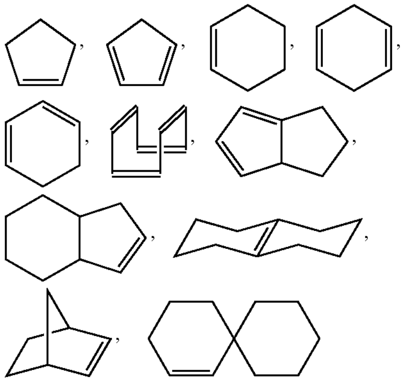

and the like.

The terms "alicyclyl" or "alicyclic" as used herein, alone or in combination, refer to an optionally substituted, saturated, partially unsaturated, or fully unsaturated nonaromatic hydrocarbon ring systems containing from three to about twenty ring carbon atoms, three to about twelve ring carbon atoms, or from three to about ten ring carbon atoms. Thus, the terms collectively include cycloalkyl and cycloalkenyl groups.

The terms "non-aromatic heterocyclyl" and "heteroalicyclyl" as used herein, alone or in combination, refer to optionally substituted, saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. In embodiments in which two or more heteroatoms are present in the ring, the two or more heteroatoms are the same as each another, or some or all of the two or more heteroatoms are each different from the others. The terms include fused, non-fused, bridged and spiro radicals. A fused non-aromatic heterocyclic radical contains from two to four fused rings where the attaching ring is a non-aromatic heterocycle; the other individual rings are alicyclic, heterocyclic, aromatic, heteroaromatic or any combination thereof. In some embodiments, fused ring systems are fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. In some embodiments, attachment of a non-aromatic heterocyclic subunit to its parent molecule is via a heteroatom or a carbon atom. Likewise, in some embodiments, additional substitution is via a heteroatom or a carbon atom. As a non-limiting example, an imidazolidine non-aromatic heterocycle is attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

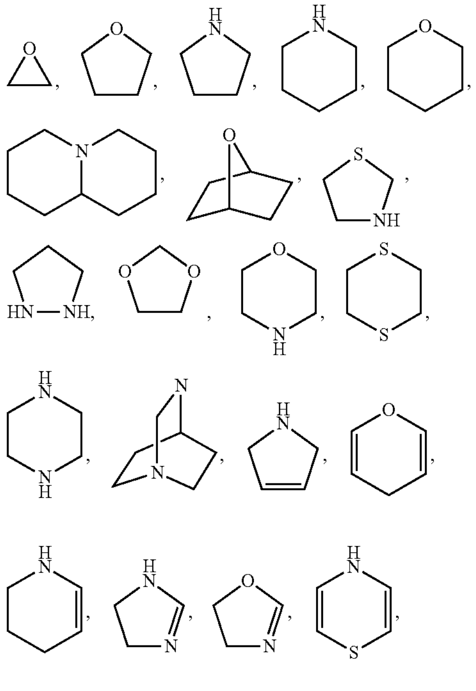

-continued

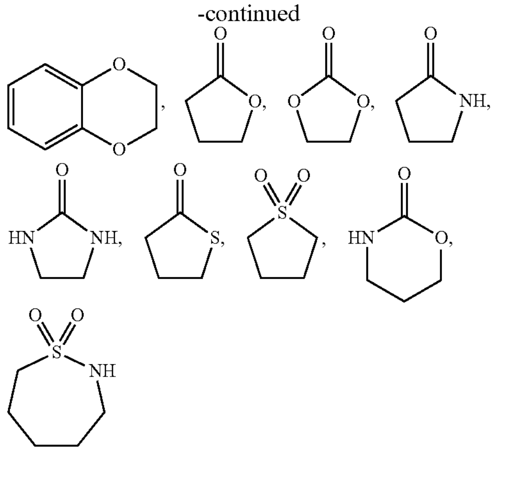

and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized π-electron system containing $4n+2\pi$ electrons, where n is an integer. In certain instances, aromatic rings are formed by five, six, seven, eight, nine, or more than nine atoms. In certain instances, aromatics are optionally substituted and are monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings are alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "arylene" as used herein, alone or in combination, refers to a diradical derived from the above-defined monoradical, aryl. Examples include, but are not limited to 1,2-phenylene, 1,3-phenylene, 1,4-phenylene, 1,2-naphthylene and the like.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms are the same as each another, or some or all of the two or more heteroatoms are different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. In certain instances, bonding to a heteroaryl group is via a carbon atom or a heteroatom. Thus, as a non-limiting example, an imidiazole group is attached to a parent molecule via any of its carbon atoms (imidazol-2-yl, imidazol-4-yl or imidazol-5-yl), or its nitrogen atoms (imidazol-1-yl or imidazol-3-yl). Likewise, in some embodiments, a heteroaryl group is further substituted via any or all of its carbon atoms, and/or any or all of its heteroatoms. A fused heteroaryl radical contains from two to four fused rings where the ring of attachment is a heteroaromatic ring and the other individual rings are alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

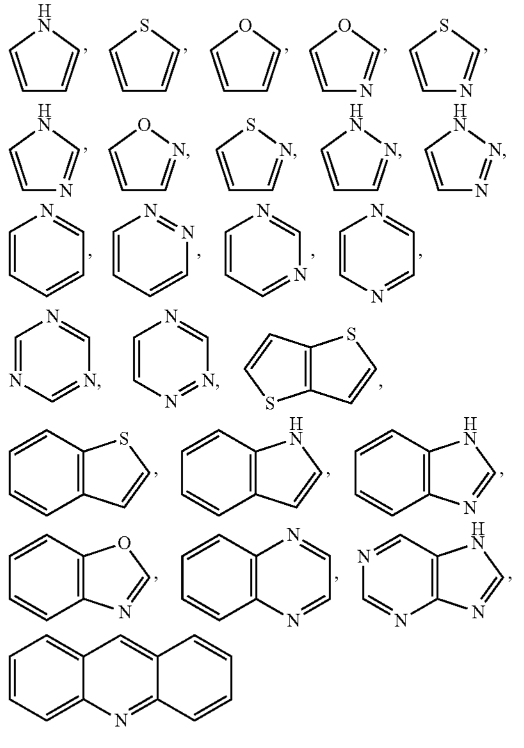

and the like.

The term "heteroarylene" as used herein, alone or in combination, refers to a diradical derived from the above-defined monoradical heteroaryl. Examples include, but are not limited to pyridinyl and pyrimidinyl.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms are the same or different from one another. In some embodiments, heterocycles are optionally substituted. Non-aromatic heterocyclic groups include groups having only three atoms in the ring, while aromatic heterocyclic groups must have at least five atoms in the ring. In certain instances, bonding (i.e. attachment to a parent molecule or further substitution) to a heterocycle is via a heteroatom or a carbon atom.

The term "carbocyclyl" as used herein, alone or in combination, refers collectively to alicyclyl and aryl groups; i.e. all carbon, covalently closed ring structures, which are saturated, partially unsaturated, fully unsaturated or aromatic. In certain instances, carbocyclic rings are formed by three, four, five, six, seven, eight, nine, or more than nine carbon atoms. In some embodiments, carbocycles are optionally substituted. The term distinguishes carbocyclic from heterocyclic rings in which the ring backbone contains at least one atom which is different from carbon.

The terms "halogen", "halo" or "halide" as used herein, alone or in combination refer to fluoro, chloro, bromo and iodo.

The term "hydroxy" as used herein, alone or in combination, refers to the monoradical —OH.

The term "cyano" as used herein, alone or in combination, refers to the monoradical —CN.

The term "cyanomethyl" as used herein, alone or in combination, refers to the monoradical —$CH_2CN$.

The term "nitro" as used herein, alone or in combination, refers to the monoradical —$NO_2$.

The term "oxy" as used herein, alone or in combination, refers to the diradical —O—.

The term "oxo" as used herein, alone or in combination, refers to the diradical =O.

The term "carbonyl" as used herein, alone or in combination, refers to the diradical —C(=O)—, which are also written as —C(O)—.

The terms "carboxy" or "carboxyl" as used herein, alone or in combination, refer to the moiety —C(O)OH, which are also written as —COOH.

The term "alkoxy" as used herein, alone or in combination, refers to an alkyl ether radical, —O-alkyl, including the groups —O-aliphatic and —O-carbocyclyl, wherein, in some embodiments, the alkyl, aliphatic and carbocyclyl groups are optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "sulfinyl" as used herein, alone or in combination, refers to the diradical —S(=O)—.

The term "sulfonyl" as used herein, alone or in combination, refers to the diradical —$S(=O)_2$—.

The terms "sulfonamide", "sulfonamido" and "sulfonamidyl" as used herein, alone or in combination, refer to the diradical groups —$S(=O)_2$—NH— and —NH—$S(=O)_2$—.

The terms "sulfamide", "sulfamido" and "sulfamidyl" as used herein, alone or in combination, refer to the diradical group —NH—$S(=O)_2$—NH—.

The term "reactant," as used herein, refers to a nucleophile or electrophile used to create covalent linkages.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Certain Pharmaceutical Terminology

The term "reverse transcriptase inhibitor" as used herein refers to a compound that exhibits an $IC_{50}$ with respect to reverse transcriptase activity, of no more than about 100 μM or not more than about 50 μM, as measured in the reverse transcriptase enzyme assay described generally herein. "$IC_{50}$" is that concentration of inhibitor which reduces the activity of an enzyme to half-maximal level. Compounds described herein exhibit inhibition against reverse transcriptase, preferably exhibiting an $IC_{50}$ with respect to reverse transcriptase of no more than about 10 μM, more preferably, no more than about 5 μM, even more preferably not more than about 1 μM, and most preferably, not more than about 200 nM, as measured in the reverse transcriptase assay described herein.

The term "subject", "patient" or "individual" as used herein in reference to individuals suffering from a disorder, and the like, encompasses mammals and non-mammals. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments, of the methods and compositions provided herein, the individual is a mammal. In preferred embodiments, the individual is a human. None of the terms are to be interpreted as requiring the supervision or care of a medical professional.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual continues to be afflicted with the underlying disorder. For prophylactic benefit, the compositions are administered to an individual at risk of developing a particular disease, or to an individual reporting one or more of the physiological symptoms of a disease, even though a diagnosis of the disease has not made.

The terms "administer," "administering", "administration," and the like, as used herein, refer to the methods that are used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. In preferred embodiments, the compounds and compositions described herein are administered orally.

The terms "effective amount", "therapeutically effective amount" or "pharmaceutically effective amount" as used herein, refer to a sufficient amount of an agent or compound being administered which will relieve to some extent one or more of the symptoms of the disease or condition being treated. In some embodiments, the result is reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. In some embodiments, an appropriate "effective" amount differs from one individual to another. An appropriate "effective" amount in any individual case is determined using techniques, such as a dose escalation study.

The term "acceptable" as used herein, with respect to a formulation, composition or ingredient, means having no persistent detrimental effect on the general health of the individual being treated.

The term "pharmaceutically acceptable" as used herein, refers to a material, such as a carrier or diluent, which does not abrogate the biological activity or properties of the compounds described herein, and is relatively nontoxic, i.e., the material is administered to an individual without causing undesirable biological effects or interacting in a deleterious manner with any of the components of the composition in which it is contained.

The term "prodrug" as used herein, refers to a drug precursor that, following administration to an individual and subsequent absorption, is converted to an active, or a more active species via some process, such as conversion by a metabolic pathway. Thus, the term encompasses any derivative of a compound, which, upon administration to a recipient, is capable of providing, either directly or indirectly, a compound disclosed herein or a pharmaceutically active metabolite or residue thereof. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. For example, in certain instances, a prodrug is for instance, bioavailable by oral administration whereas the parent is not. Particularly favored derivatives or prodrugs are those that increase the bioavailability of a compound disclosed herein when such compounds are administered to an individual (e.g. by allowing an orally administered compound to be more readily absorbed into the blood) or which enhance delivery of the parent compound to a biological compartment (e.g. the brain or lymphatic system).

The term "pharmaceutically acceptable salt" as used herein, refers to salts that retain the biological effectiveness of the free acids and bases of the specified compound and that are not biologically or otherwise undesirable. In some embodiments, compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of a compound disclosed herein, or by separately reacting a purified compound in its free base form with a suitable organic or inorganic acid, and isolating the salt thus formed.

The term "pharmaceutical composition," as used herein, refers to a biologically active compound, optionally mixed with a pharmaceutically acceptable chemical component, such as, though not limited to carriers, stabilizers, diluents, dispersing agents, suspending agents, thickening agents, excipients and the like.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "pharmaceutical combination," "administering an additional therapy," "administering an additional therapeutic agent" and the like, as used herein, refer to a pharmaceutical therapy resulting from the mixing or combining of more than one active ingredient and includes both fixed and non-fixed combinations of the active ingredients. The term "fixed combination" means that a compound described herein, and a co-agent, are both administered to an individual simultaneously in the form of a single entity or dosage. The term "non-fixed combination" means that a compound described herein, and a co-agent, are administered to an individual as separate entities either simultaneously, concurrently or sequentially with variable intervening time limits, wherein such administration provides effective levels of the two or more compounds in the body of the individual. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single individual, and are intended to include treatment regimens in which the agents are administered by the same or different route of administration or at the same or different times. In some embodiments, the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, a compound disclosed herein and the other agent(s) are administered in a single composition. In some embodiments, a compound disclosed herein and the other agent(s) are admixed in the composition.

The term “metabolite,” as used herein, refers to a derivative of a compound which is formed when the compound is metabolized.

The term “active metabolite,” as used herein, refers to a biologically active derivative of a compound that is formed when the compound is metabolized.

The term “metabolized,” as used herein, refers to the sum of the processes (including, but not limited to, hydrolysis reactions and reactions catalyzed by enzymes) by which a particular substance is changed by an organism. Thus, enzymes produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. For further information on metabolism see Brunton (editor-in-chief), *Goodman & Gilman’s The Pharmacological Basis of Therapeutics,* 11th Edition, New York, N.Y., McGraw-Hill, 2006.

Compounds

Described herein are compounds of formula I, pharmaceutically acceptable salts, solvates, polymorphs, esters, tautomers or prodrugs thereof, (I)

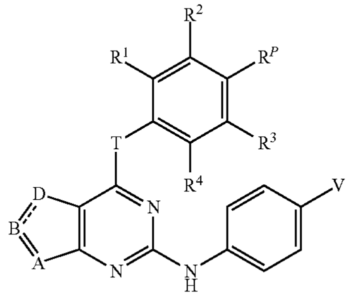

wherein

---- represents a double bond between either A and B or B and D;

A is —N═, —NZ— or —CZ═;

B is —CY═ or —N═;

D is —N═, —NW— or —CW═;

provided that at least one of A and D is —N═ or NZ or NR;

W, Y and Z are each independently selected from H, F, Cl, Br, $C_1$-$C_6$ alkyl, $C_2$-$C_6$ alkenyl, $OC_1$-$C_6$ alkyl, $C_3$-$C_6$ cycloalkyl, $OC_3$-$C_6$ cycloalkyl, phenyl or benzyl, wherein the alkyl, alkenyl, cycloalkyl, phenyl and the phenyl moiety of the benzyl group are optionally substituted with 1-3 substituents selected from F, Cl, Br, I, OH, $CF_3$, $C_1$-$C_3$ alkyl and $OC_1$-$C_3$ alkyl;

V is H, F, Cl, CN, $CF_3$, $SO_2CH_3$, $SO_2NH_2$, $SO_2NHCH_3$, $NH_2$, NH($C_1$-$C_6$ alkyl) or N($C_1$-$C_6$ alkyl)$_2$;

T is NH, O or S;

$R^P$ is aryl, substituted aryl, heterocyclyl, substituted heterocyclyl, heteroaryl or substituted heteroaryl; and $R^1$, $R^2$, $R^3$ and $R^4$ are independently selected from H, F, Cl, Br, I, $CFH_2$, $CF_2H$, $CF_3$, CN, CH═CHCN, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$, and $OC_1$-$C_3$ alkyl.

In further or additional embodiments, a compound disclosed herein is provided as a pharmaceutically acceptable salt. In further or additional embodiments, a compound disclosed herein is provided as a metabolite. In further or additional embodiments, a compound disclosed herein is provided as a solvate. In further or additional embodiments, a compound disclosed herein is provided as a pharmaceutically acceptable polymorph. In further or additional embodiments, a compound disclosed herein is provided as a pharmaceutically acceptable ester. In further or additional embodiments, a compound disclosed herein is provided as a pharmaceutically acceptable tautomer. In further or additional embodiments, a compound disclosed herein is provided as a pharmaceutically acceptable prodrug.

In some embodiments, A is —N═. In other embodiments A is —NZ—. In yet other embodiments A is —CZ═. In some embodiments, D is —N═. In other embodiments D is —NR. In yet other embodiments D is —CW—. In some embodiments, B is —CY═. In other embodiments B is —N═. In further or additional embodiments, A is —CZ═; B is —CY═; and D is —NW—. In some embodiments, Z is H, F, Cl or methyl. In some embodiments, Y is H. In some embodiments, W is $C_1$-$C_6$ alkyl or $C_1$-$C_6$ alkyl substituted with 1-3 substituents selected from F, Cl, Br, I, OH, $CF_3$. In further or additional embodiments, W is methyl, ethyl, $CH_2CF_3$ or $CH_2CH_2OH$. In some embodiments, Z is H, F, Cl or methyl; Y is H; and W is methyl, ethyl, $CH_2CF_3$ or $CH_2CH_2OH$. In some embodiments, W, Y and Z are each independently selected from H, F, Cl, Br, $C_1$-$C_6$ alkyl or $C_1$-$C_6$ alkyl substituted with 1-3 substituents selected from F, Cl, Br, I, OH, $CF_3$. In some embodiments, Y is H. In some embodiments, V is CN. In some embodiments, T is O. In further or additional embodiments, T is S. In further or additional embodiments, T is NH. In some embodiments, V is CN and T is O or S. In further or additional embodiments, A is —CZ═; B is —CH═; D is —NW—; Z is H, F, Cl or methyl; W is methyl, ethyl, $CH_2CF_3$ or $CH_2CH_2OH$; V is CN; and T is O or S. In some embodiments, $R^1$, $R^2$, $R^3$ and $R^4$ are independently selected from H, F, Cl, Br, I, $CFH_2$, $CF_2H$, $CF_3$, CN, CH═CHCN, methyl, ethyl, n-propyl, propyl, n-butyl, i-butyl, s-butyl, t-butyl, cyclopropyl, cyclobutyl, cyclopentyl, cyclohexyl and cyclopropylmethyl. In further or additional embodiments, $R^1$, $R^2$, $R^3$ and $R^4$ are independently selected from H, methyl, ethyl, n-propyl and i-propyl. In further or additional embodiments, $R^1$ and $R^4$ are independently selected from methyl, ethyl, n-propyl and i-propyl; and $R^2$ and $R^3$ are H. In some embodiments, $R^P$ is aryl or substituted aryl. In further or additional embodiments, $R^P$ is unsubstituted phenyl. In further or additional embodiments, $R^P$ is substituted phenyl. In some embodiments, $R^P$ is heterocyclyl, substituted heterocyclyl, heteroaryl or substituted heteroaryl. In further or additional embodiments, $R^P$ is unsubstituted heteroaryl. In further or additional embodiments, $R^P$ is substituted heteroaryl. In some embodiments, $R^P$ is a substituted or unsubstituted 5- or 6-membered heterocycle comprising 1, 2 or 3 heteroatoms independently selected from O, N or S. In further or additional embodiments, $R^P$ is a substituted or unsubstituted 5- or 6-membered heterocycle comprising 1, 2 or 3 N atoms. In further or additional embodiments, $R^P$ is a substituted or unsubstituted 5- or 6-membered heterocycle comprising 1 N atom. In further or additional embodiments, $R^P$ is a substituted or unsubstituted 5- or 6-membered heterocycle comprising 2 N atoms. In further or additional embodiments, $R^P$ is a substituted or unsubstituted 5- or 6-membered heterocycle comprising 3 N atoms. In further or additional embodiments, $R^P$ is a substituted or unsubstituted 5- or 6-membered heterocycle comprising 1 O atom. In further or additional embodiments, $R^P$ is a substituted or unsubstituted 5- or 6-membered heterocycle comprising 1 S atom. In further or additional embodiments, $R^P$ is a substituted or unsubstituted 5- or 6-membered heterocycle comprising 1 N atom and 1 O or S atom. In further or additional embodiments, $R^P$ is a substituted or unsubstituted heterocycle selected from furanyl, thiofuranyl, pyrrolyl, pyrrolinyl, pyrrolidinyl, oxazolyl, thiazolyl, imidazolyl, imidazolinyl, pyrazolyl, pyrazolinyl, pyrazolidinyl, isoxazolyl, isothiazolyl, oxadizolyl, thiazolyl, thiadiazolyl, triazolyl, pyranyl, pyridyl, piperidinyl, morpholinyl, pyridazyl, pyrimidyl, pyrazinyl, piperazinyl, triazinyl or tetrazolyl. In further or additional embodiments, $R^P$ is pyridyl, substituted pyridyl, furanyl, substituted furanyl, thiofuranyl, substituted thiofuranyl, pyrrolyl, substituted pyrrolyl, pyrazolyl, substituted pyrazolyl, pyrimidyl or substituted pyrimidyl. In some embodiments, $R^P$ is a 5-membered aryl, 5-membered substituted aryl, 5-membered heterocyclyl, 5-membered substituted heterocyclyl, 5-membered heteroaryl or 5-membered substituted heteroaryl. In other embodiments, $R^P$ is a 6-membered aryl, 6-membered substituted aryl, 6-membered heterocyclyl, 6-membered substituted heterocyclyl, 6-membered heteroaryl or 6-membered substituted heteroaryl. In yet other embodiments, $R^P$ is a 7-membered aryl, 7-membered substituted aryl, 7-membered heterocyclyl, 7-membered substituted heterocyclyl, 7-membered heteroaryl or 7-membered substituted heteroaryl.

Also described herein are compounds of Formula (IA), (1B), (IC-1), (IC-2), (ID), (ID-1), (ID-2), (ID-3), (ID-4), (IE), (IE-1), (IE-2), (IE-3) and (IE-4):

(IA)

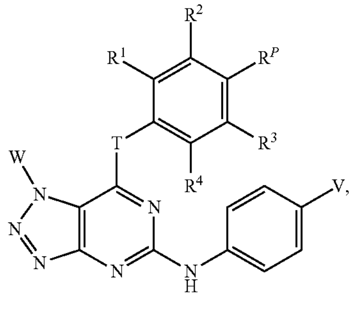

-continued (IB)

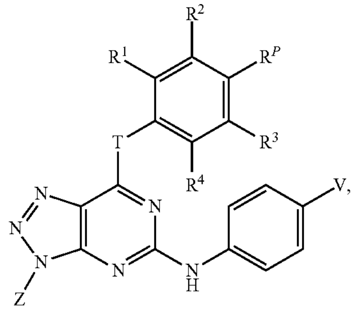

(IC-1)

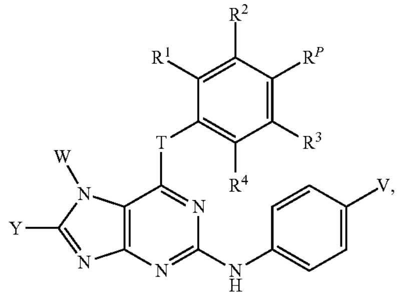

(IC-2)

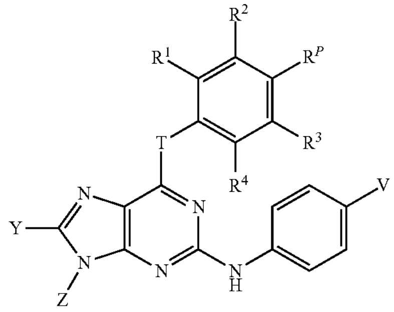

(ID)

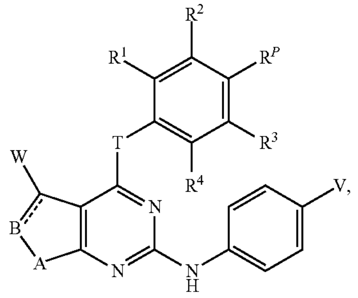

(IE)

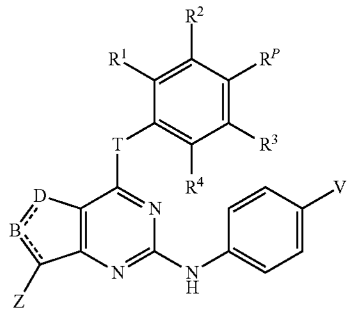

-continued (ID-1)

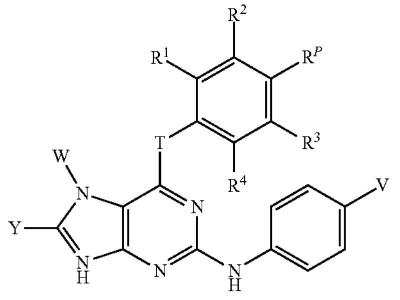

(ID-2)

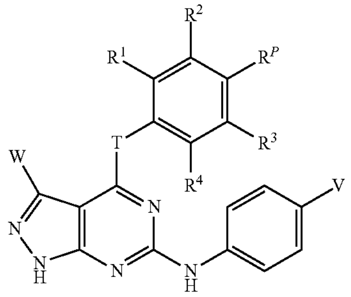

(ID-3)

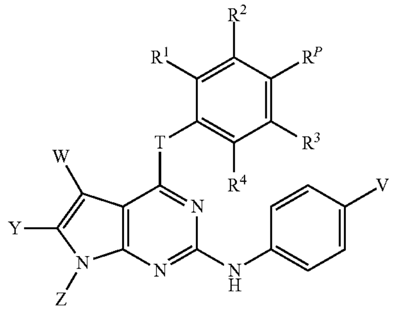

(ID-4)

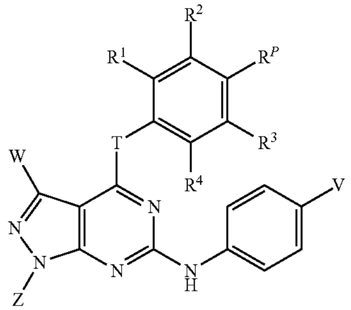

(IE-1)

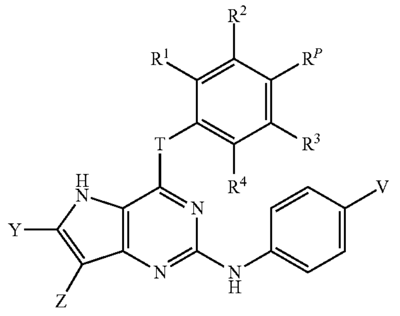

-continued (IE-2)

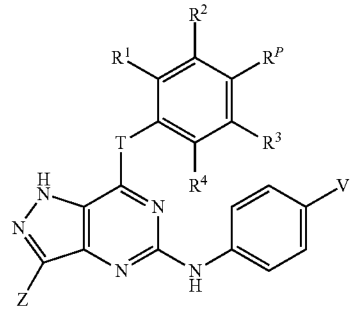

(IE-3)

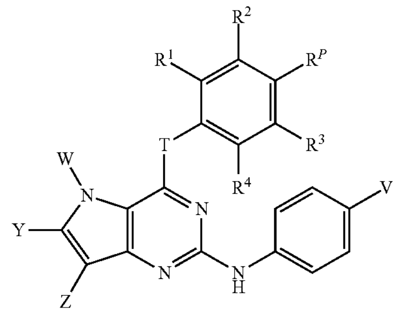

(IE-4)

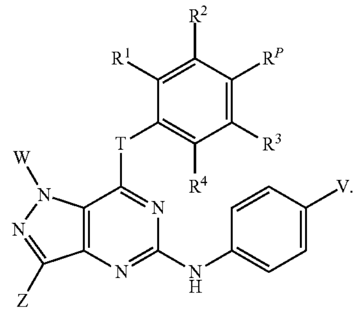

In some embodiments, of the compound of formula (IE), Y is H. In other embodiments, Z is H, F, Cl or methyl. In other embodiments, W is methyl, ethyl, $CH_2CF_3$ or $CH_2CH_2OH$. In further or additional embodiments, Z is H, F, Cl or methyl; Y is H; and W is methyl, ethyl, $CH_2CF_3$ or $CH_2CH_2OH$. In some embodiments, V is CN. In other embodiments, T is O. In other embodiments, T is S. In other embodiments, T is NH. In further or additional embodiments, Z is H, F, Cl or methyl; Y is H; W is methyl, ethyl, $CH_2CF_3$ or $CH_2CH_2OH$; V is CN; and T is O or S.

In some embodiments, of the compound of formula (IE-3), Y is H. In other embodiments, Z is H, F, Cl or methyl. In other embodiments, W is methyl, ethyl, $CH_2CF_3$ or $CH_2CH_2OH$. In further or additional embodiments, Z is H, F, Cl or methyl; Y is H; and W is methyl, ethyl, $CH_2CF_3$ or $CH_2CH_2OH$. In some embodiments, V is CN. In other embodiments, T is O. In other embodiments, T is S. In other embodiments, T is NH. In further or additional embodiments, Z is H, F, Cl or methyl; Y is H; W is methyl, ethyl, $CH_2CF_3$ or $CH_2CH_2OH$; V is CN; and T is O or S.

Also described herein are compounds of Formula (IC-3a):

(IE-3a)

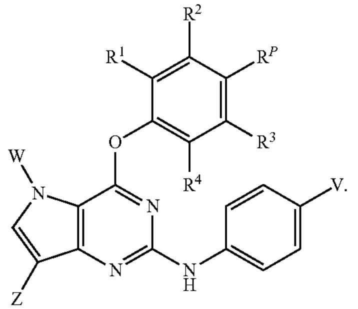

In some embodiments, of the compound of formula (IE-3a), Z is H, F, Cl or methyl. In other embodiments, W is methyl, ethyl, $CH_2CF_3$ or $CH_2CH_2OH$. In further or additional embodiments, Z is H, F, Cl or methyl; and W is methyl, ethyl, $CH_2CF_3$ or $CH_2CH_2OH$. In some embodiments, V is CN. In further or additional embodiments, Z is H, F, Cl or methyl; and W is methyl, ethyl, $CH_2CF_3$ or $CH_2CH_2OH$, and V is CN. In some embodiments, of the compound of formula (IE-3a), $R^1$, $R^2$, $R^3$ and $R^4$ are independently selected from H, methyl, ethyl, n-propyl and i-propyl. In further or additional embodiments, $R^1$ and $R^4$ are independently selected from methyl, ethyl, n-propyl and i-propyl; and $R^2$ and $R^3$ are H. In further or additional embodiments, $R^P$ is aryl or substituted aryl. In further or additional embodiments, $R^P$ is phenyl or substituted phenyl. In further or additional embodiments, $R^P$ is a substituted or unsubstituted 5- or 6-membered heterocycle comprising 1, 2 or 3 heteroatoms independently selected from O, N or S. In further or additional embodiments, $R^P$ is heterocyclyl or substituted heterocyclyl. In further or additional embodiments, $R^P$ is heteroaryl or substituted heteroaryl. In further or additional embodiments, $R^P$ is pyridyl, substituted pyridyl, furanyl, substituted furanyl, thiofuranyl, substituted thiofuranyl, pyrimidyl or substituted pyrimidyl.

Also described herein are compounds of Formula (IF):

(IF)

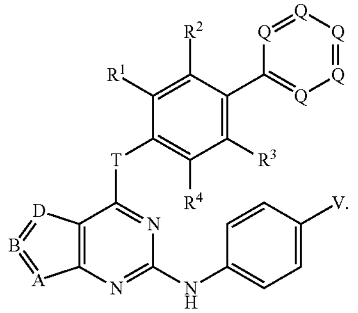

where each Q is independently $CR^a$ or N, provided that at least one Q is $CR^a$; and each $R^a$ is independently selected from H, F, Cl, Br, I, $CFH_2$, $CF_2H$, $CF_3$, CN, CH═CHCN, $CH_2CF_3$, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$, and $OC_1$-$C_3$ alkyl.

In some embodiments, one Q is N and the rest are $CR^a$. In further or additional embodiments, two Qs are N and the rest are $CR^a$. In further or additional embodiments, three Qs are N and the rest are $CR^a$. In further or additional embodiments, four Qs are N and the rest are $CR^a$.

Also described herein are compounds of Formula (IG-1) and (IG-2):

(IG-1)

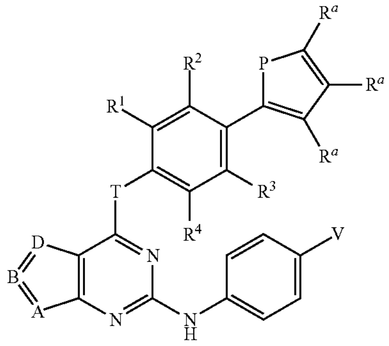

(IG-2)

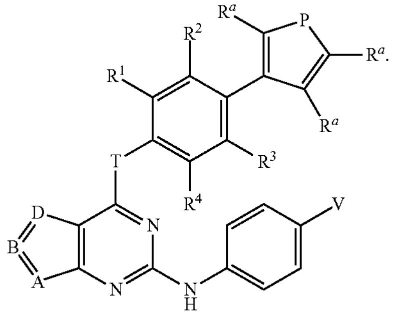

where

P is independently NH, O or S; and each $R^a$ is independently selected from H, F, Cl, Br, I, $CFH_2$, $CF_2H$, $CF_3$, CN, CH═CHCN, $CH_2CF_3$, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$, and $OC_1$-$C_3$ alkyl.

Also described herein are compounds of Formula (IH-1) and (1H-2):

(IH-1)

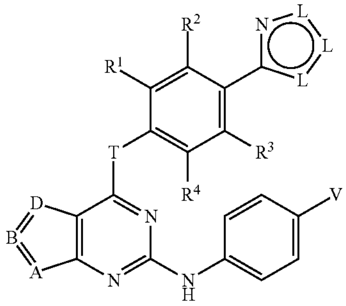

(IH-2)

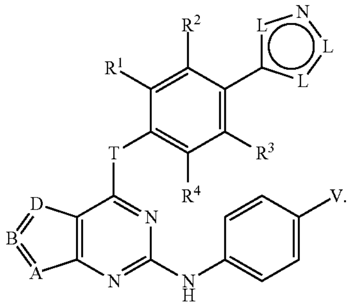

where one L is NH, O or S and the other two are $CR^a$; and each $R^a$ is independently selected from H, F, Cl, Br, I, $CFH_2$, $CF_2H$, $CF_3$, CN, CH═CHCN, $CH_2CF_3$, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$, and $OC_1$-$C_3$ alkyl.

In some embodiments, a compound disclosed herein or a metabolite, pharmaceutically acceptable salt, solvate, polymorph, ester, tautomer or prodrug thereof is selected from:

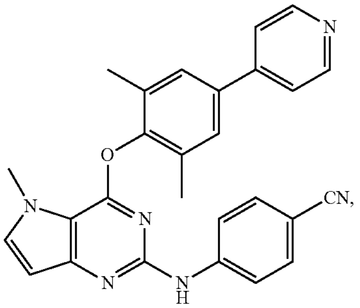

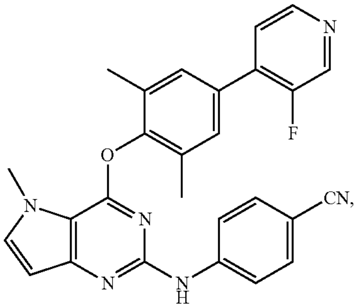

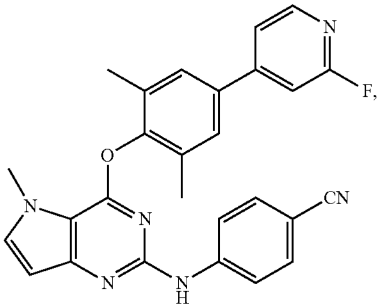

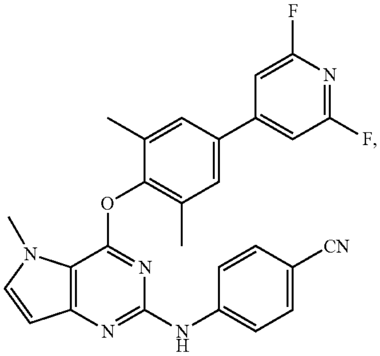

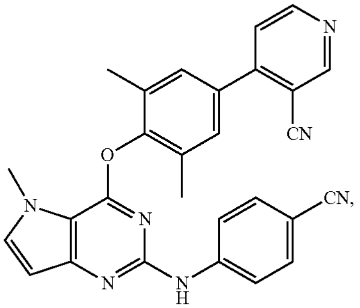

-continued
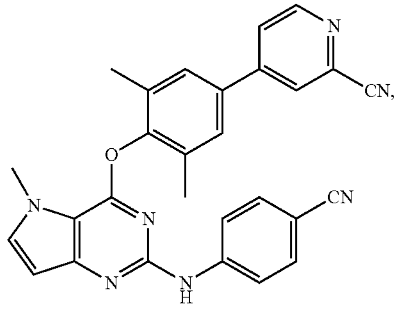
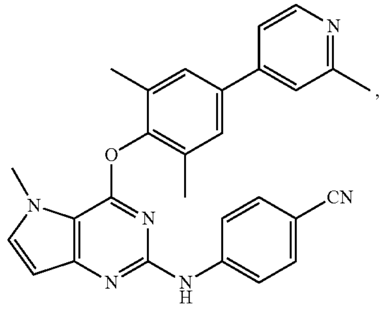
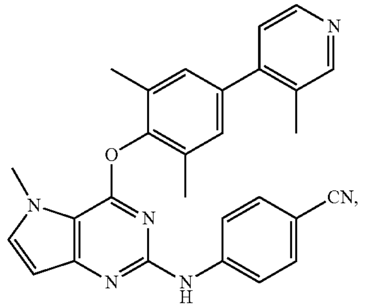
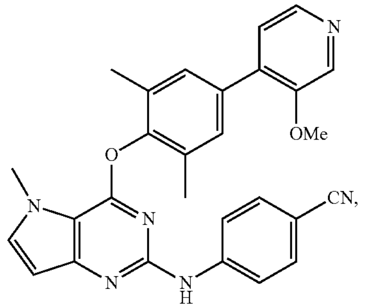
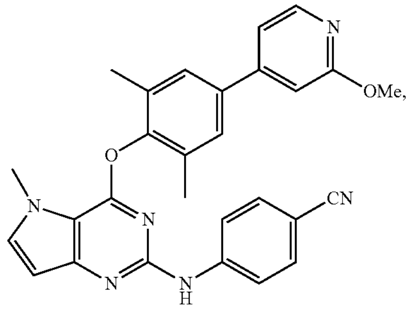
-continued
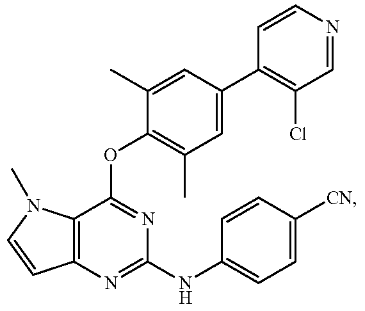
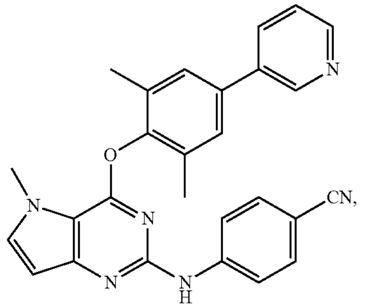
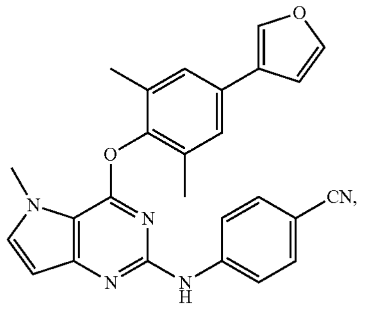
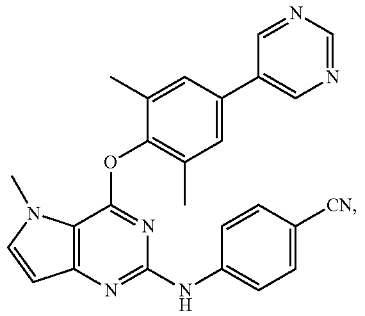
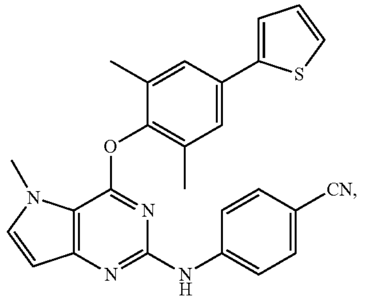

-continued
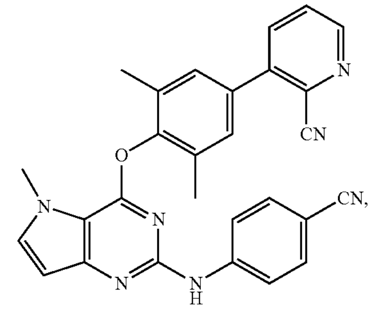
,
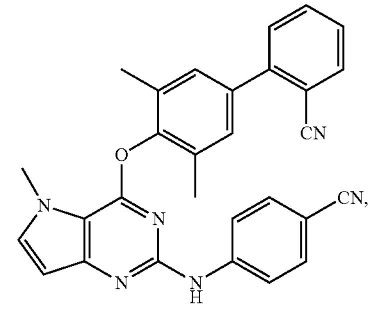
,
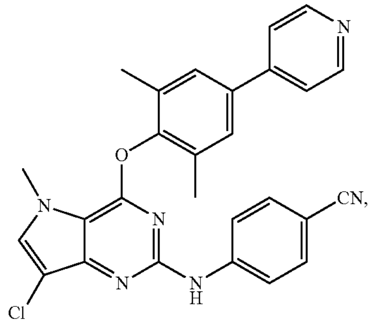
,
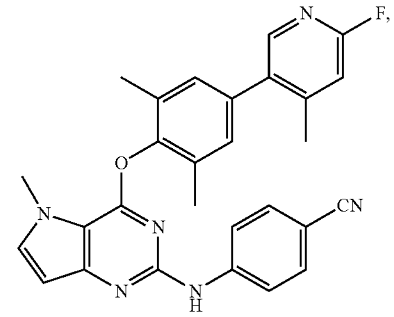
,
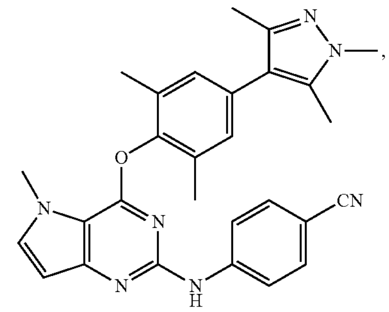
,
-continued
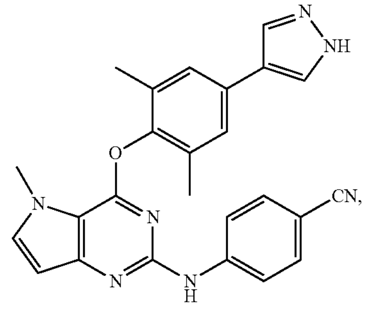
,
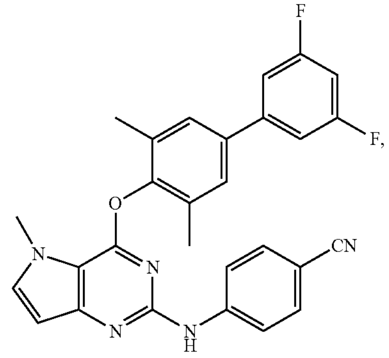
,
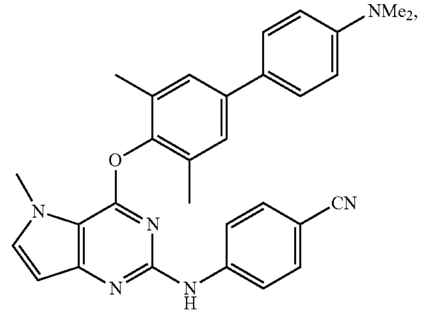
,
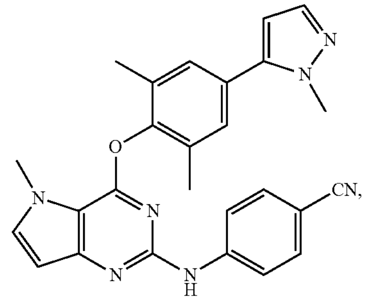
,
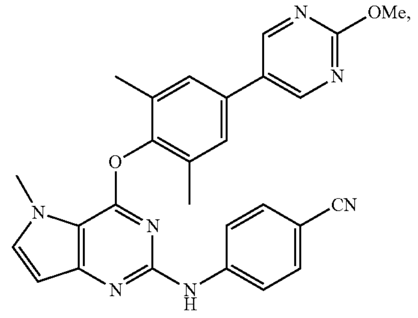
, -continued
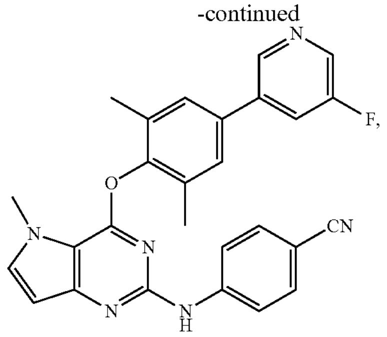
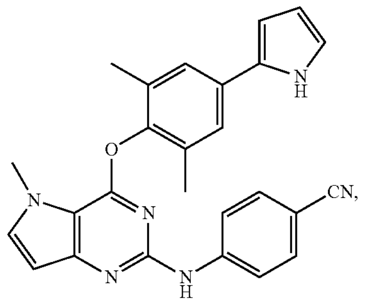
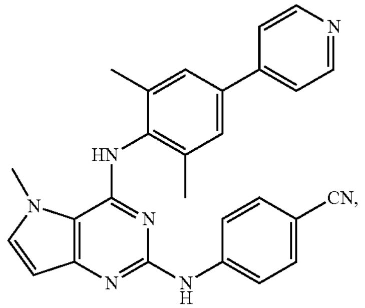
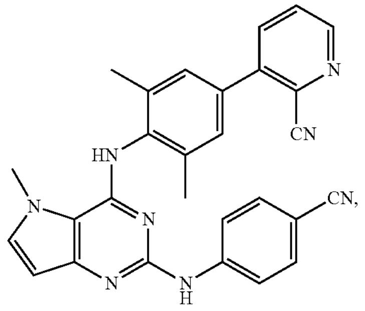
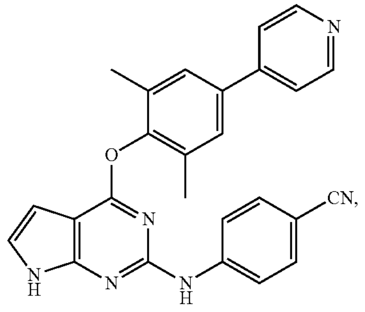
-continued
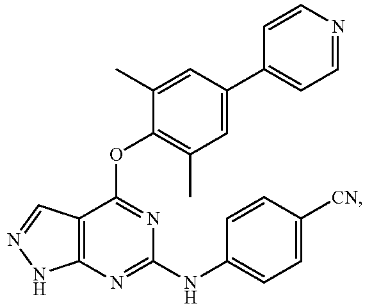
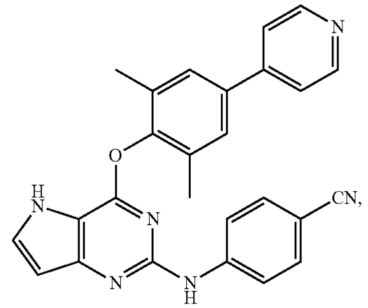
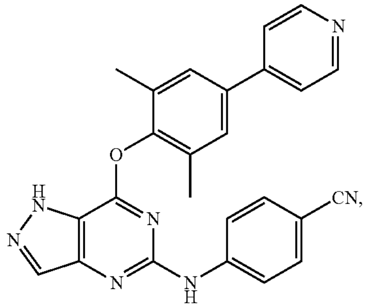
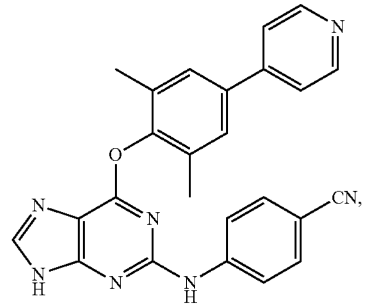
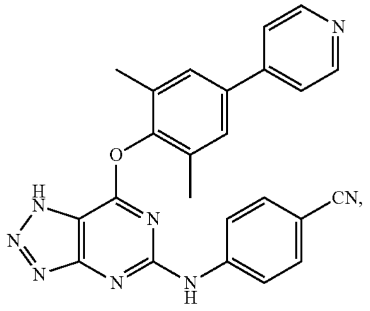

-continued
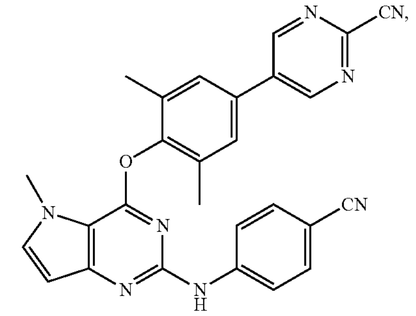
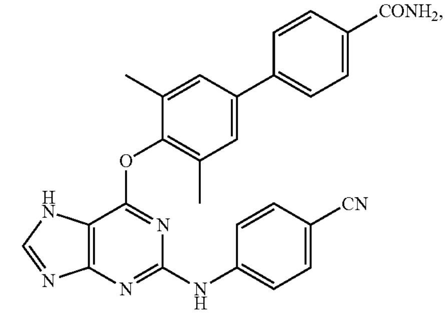
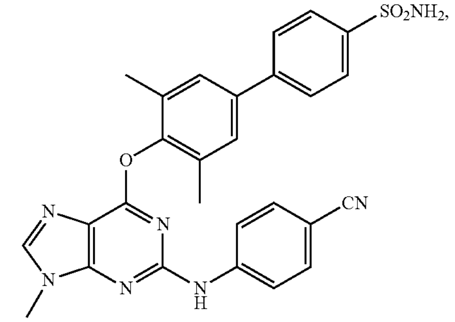
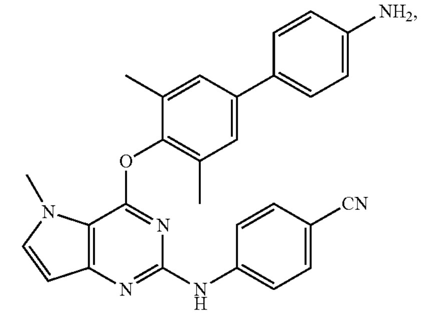
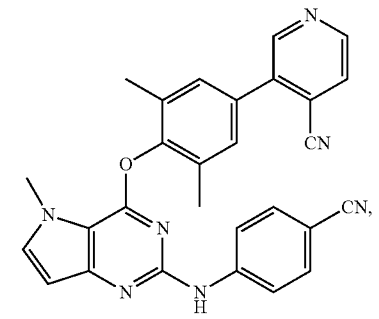
-continued
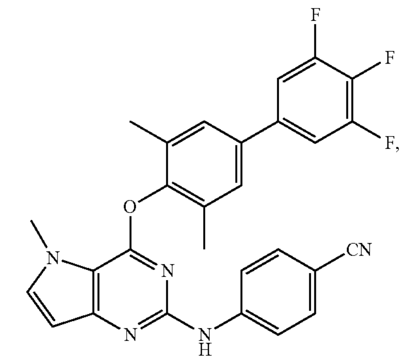
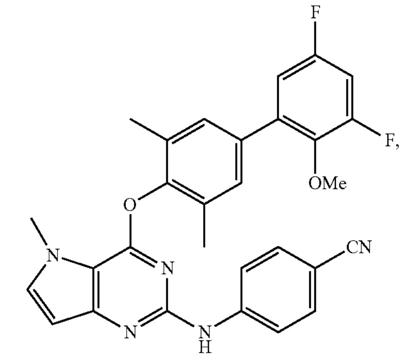
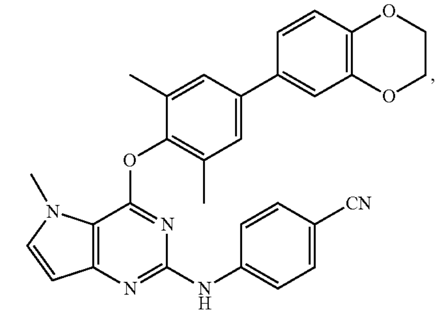
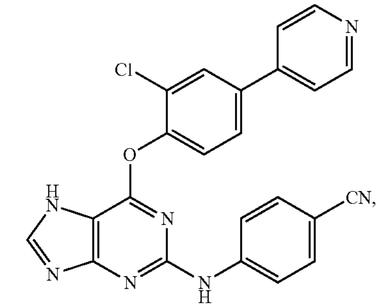
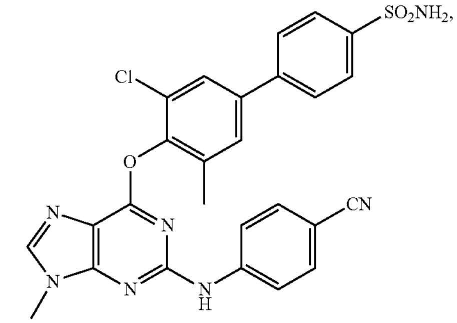

-continued
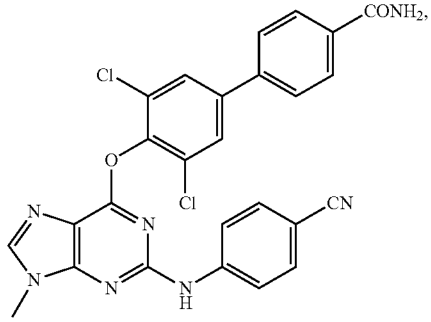
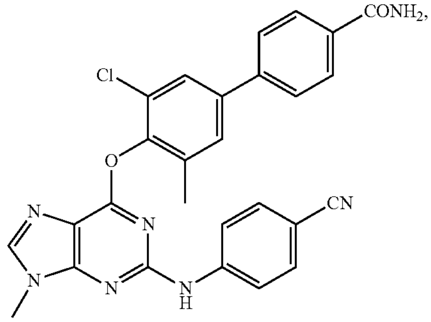
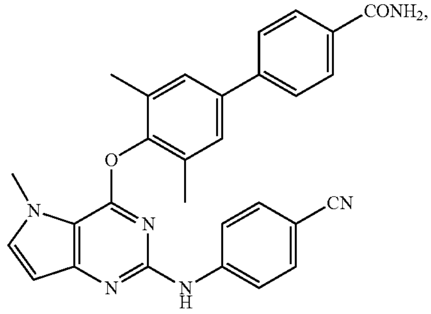
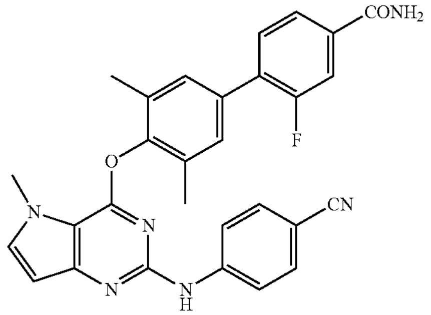
and
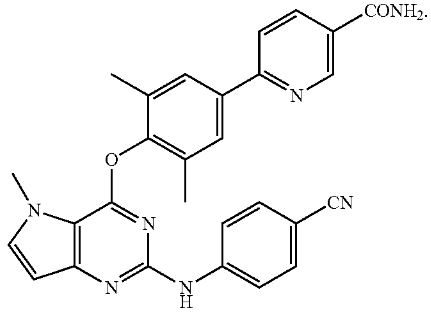
In some embodiments, a compound disclosed herein or a metabolite, pharmaceutically acceptable salt, solvate, polymorph, ester, tautomer or prodrug thereof is selected from:
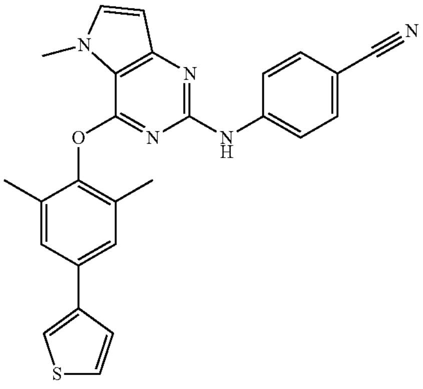
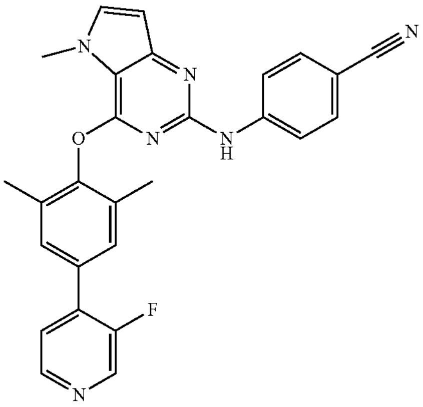
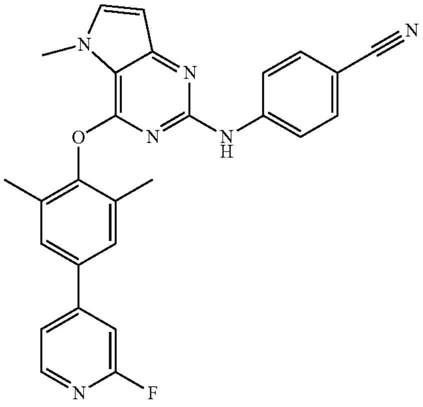
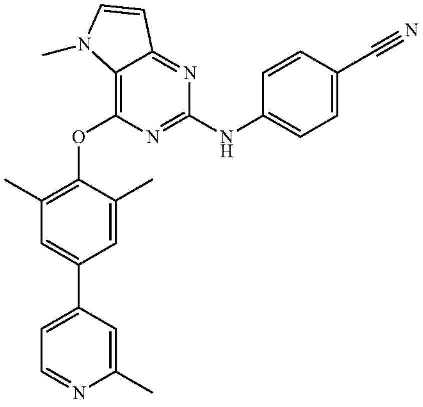

-continued
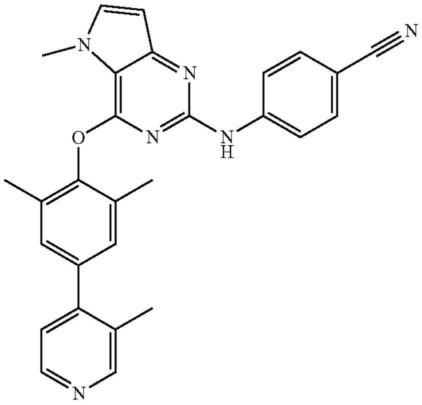
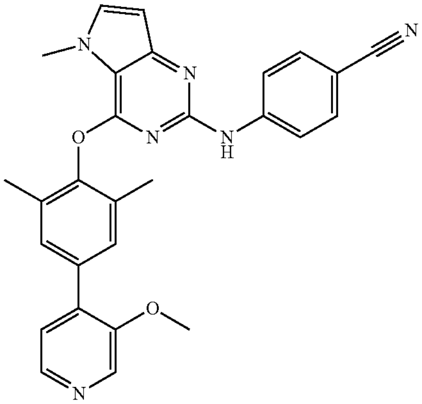
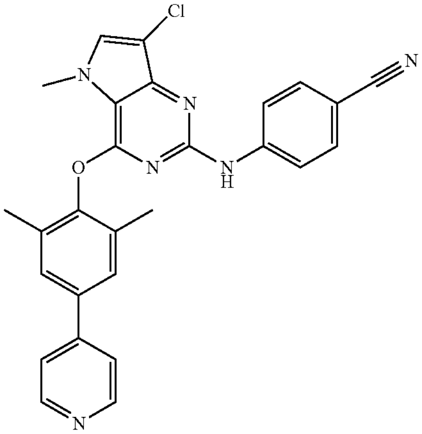
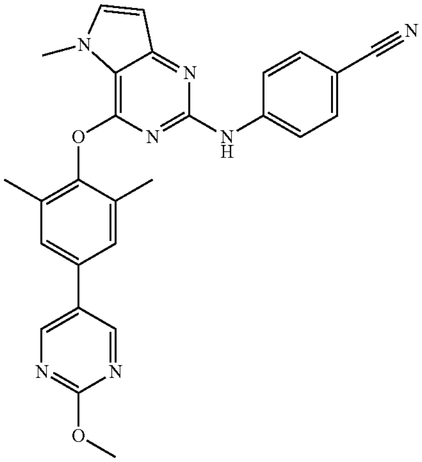
-continued
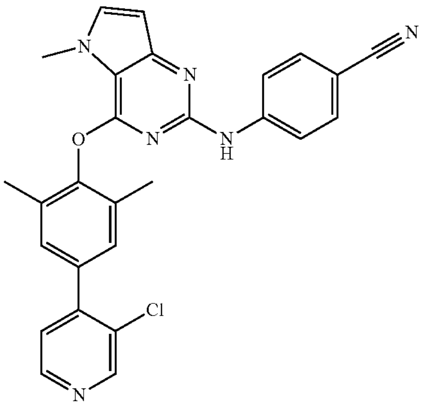
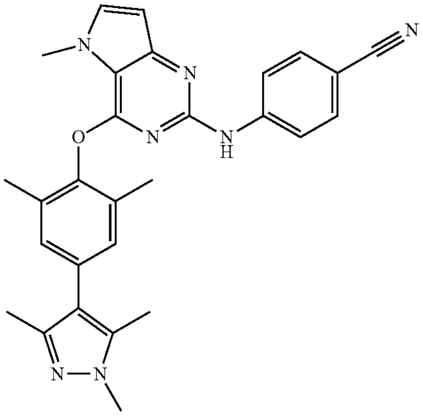
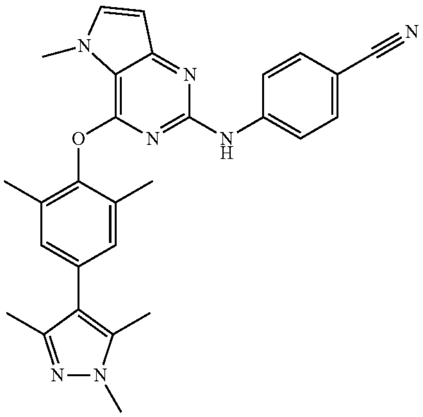
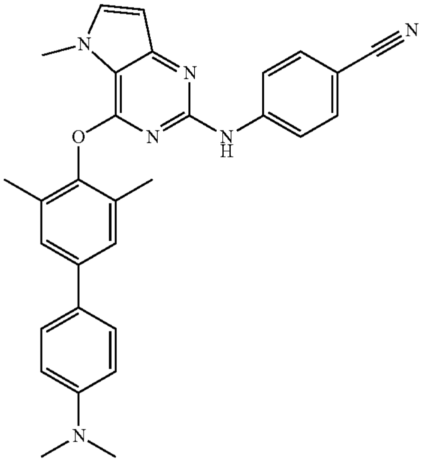

-continued
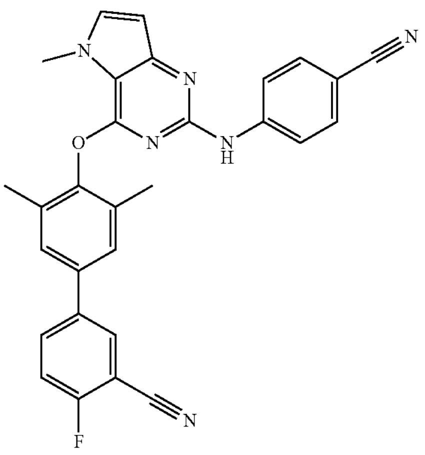
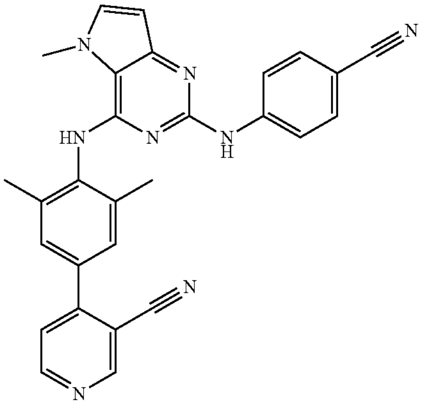
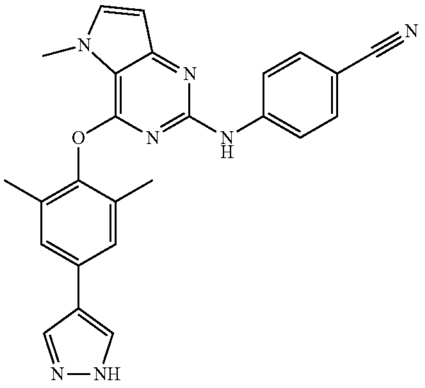
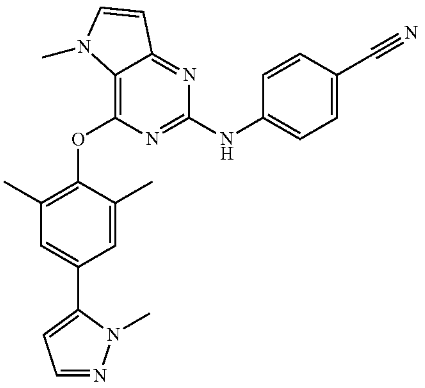
-continued
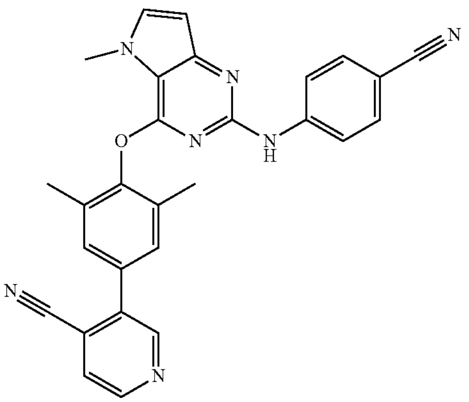
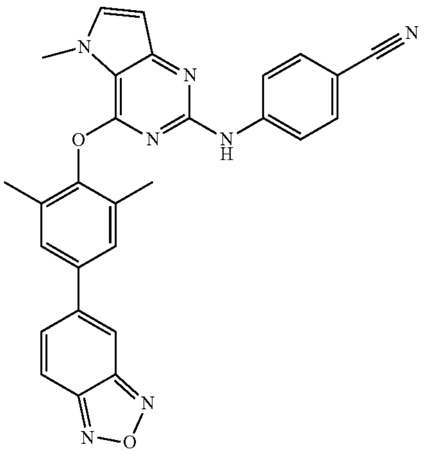
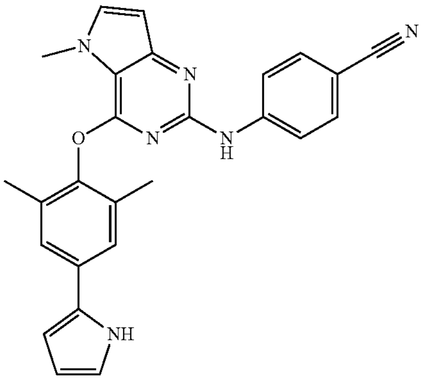
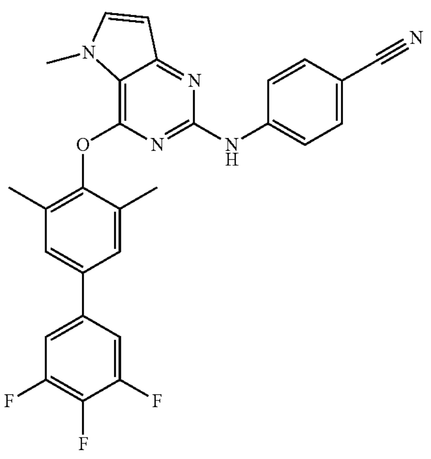

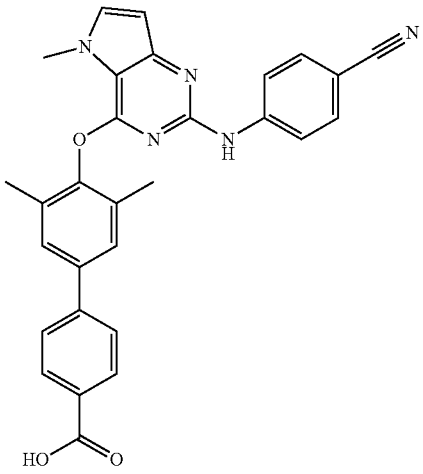
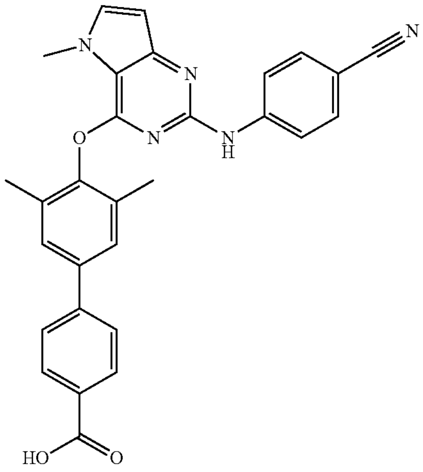
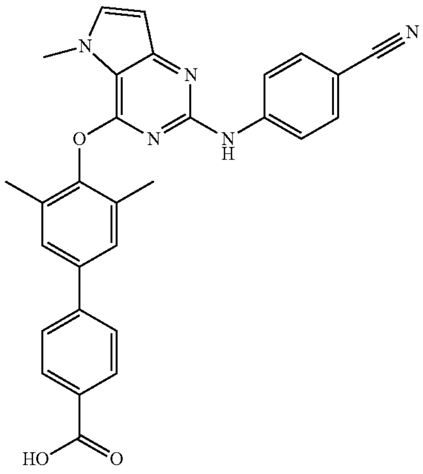
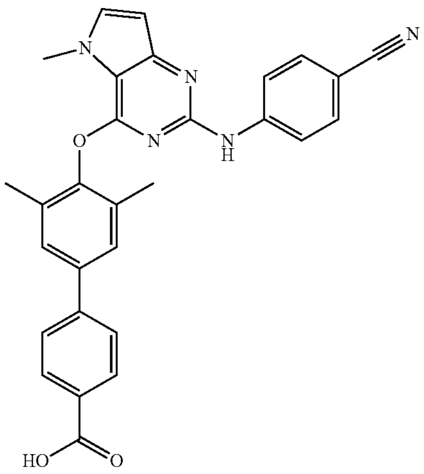
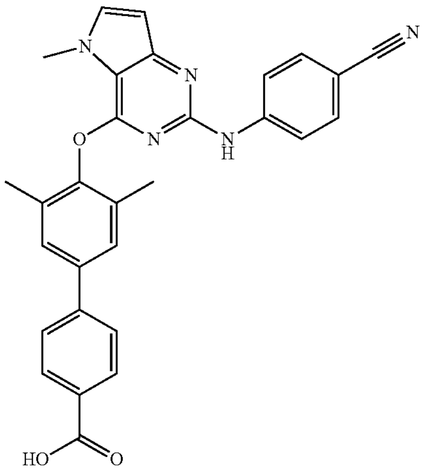
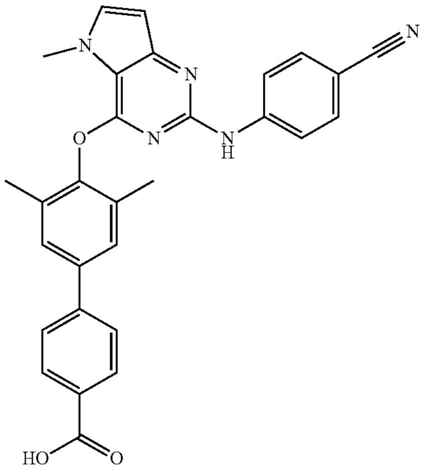

-continued
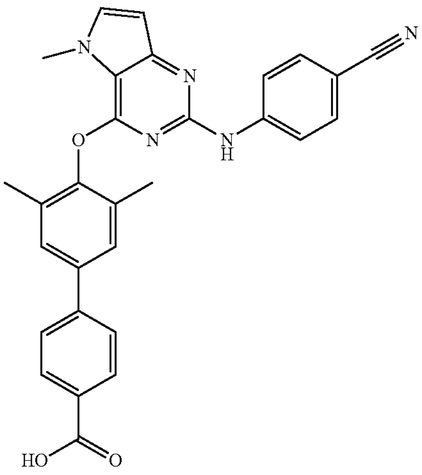
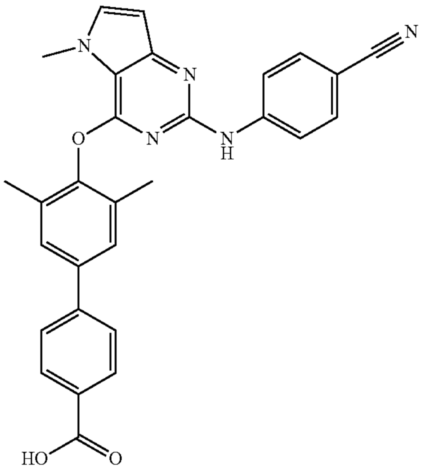
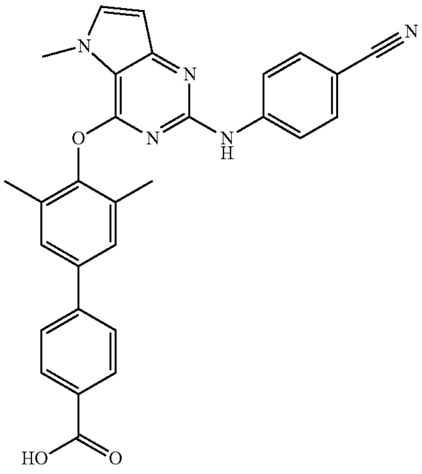
-continued
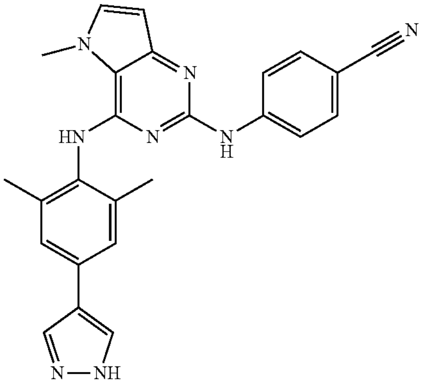
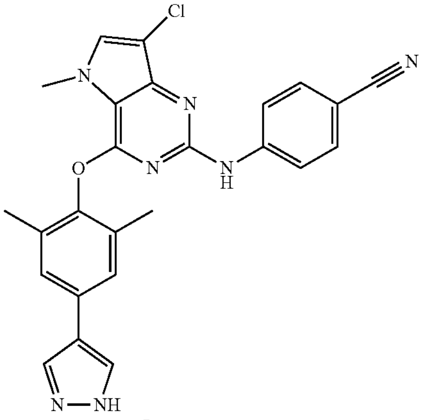
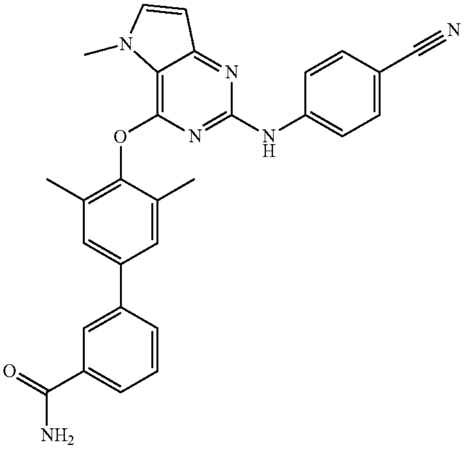
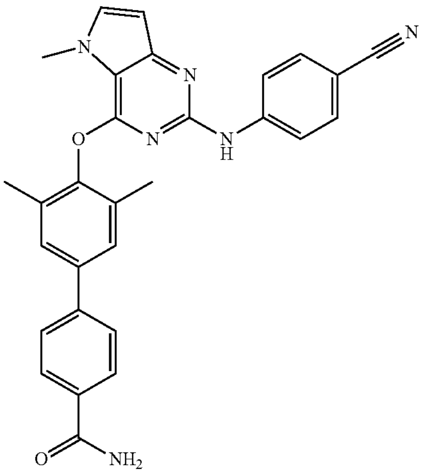

-continued
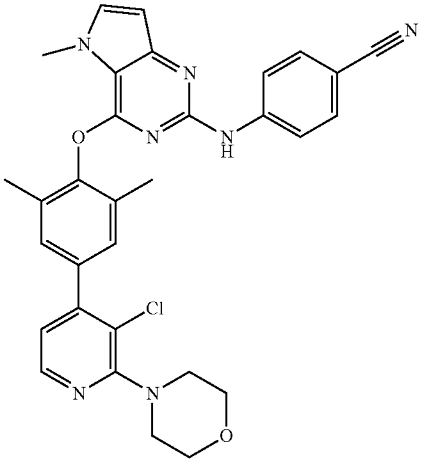
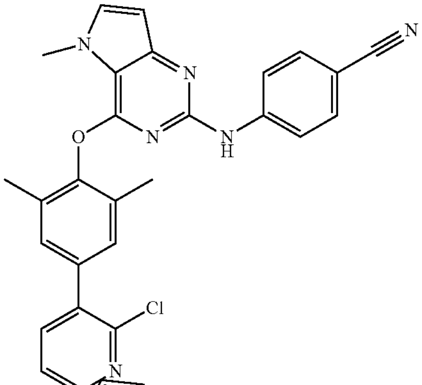
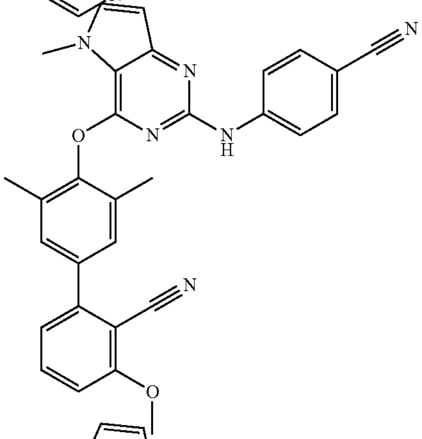
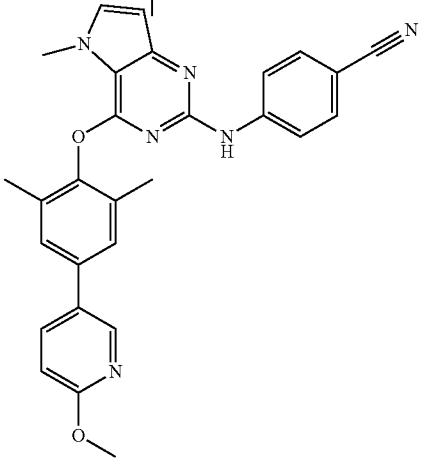
-continued
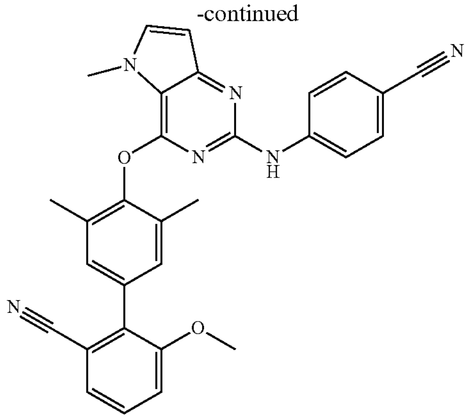
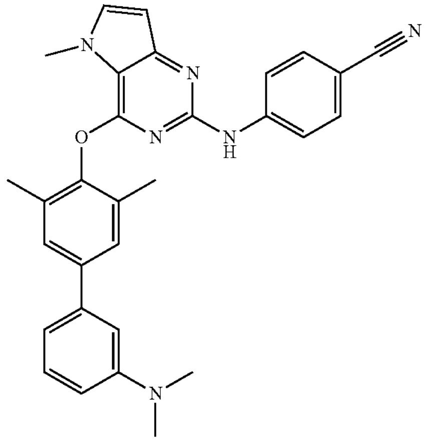
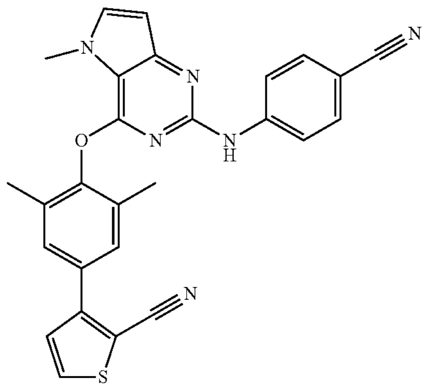
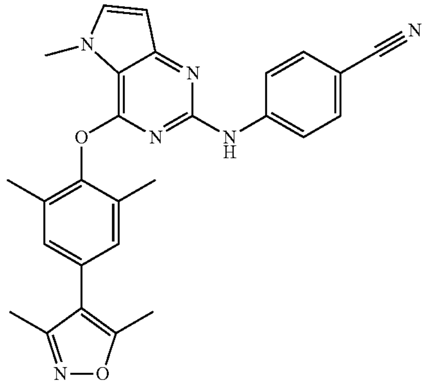

-continued
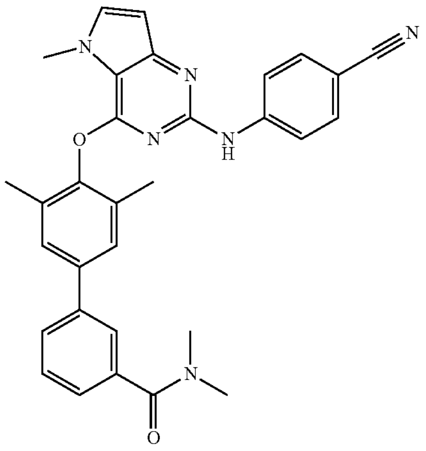
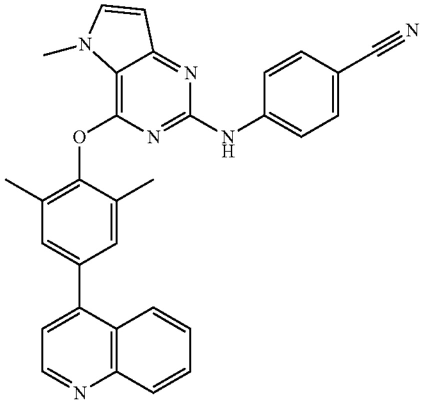
(?) indicates text missing or illegible when filed
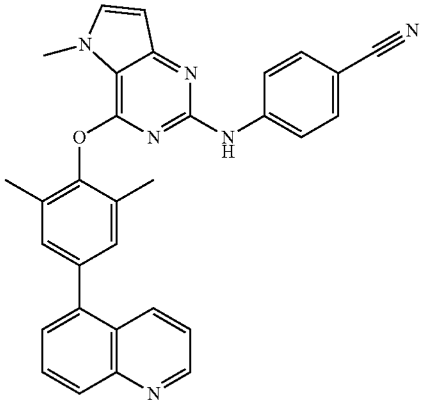
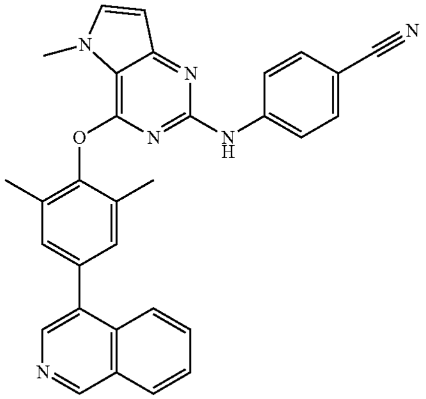
-continued
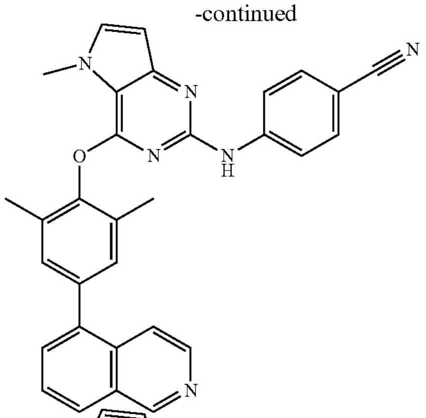
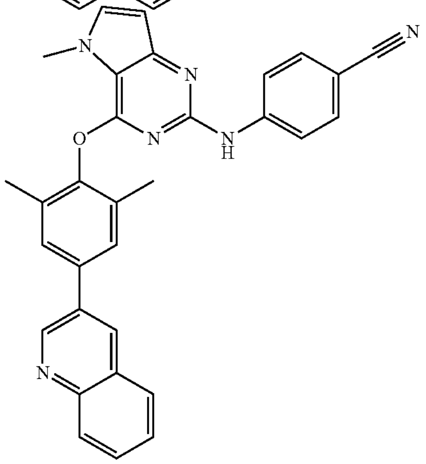
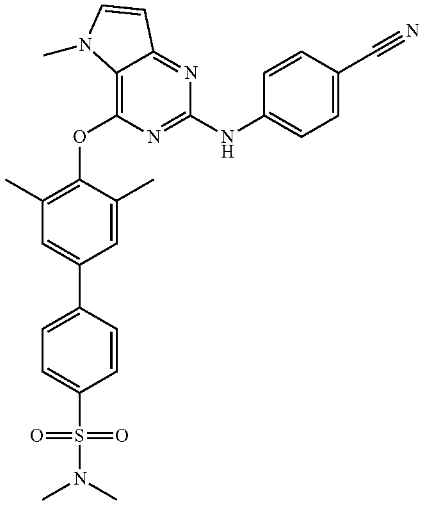
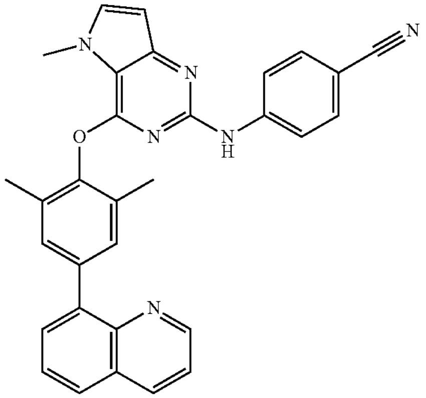

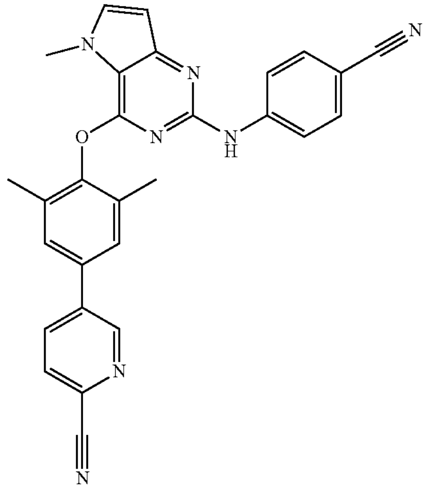
(?) indicates text missing or illegible when filed
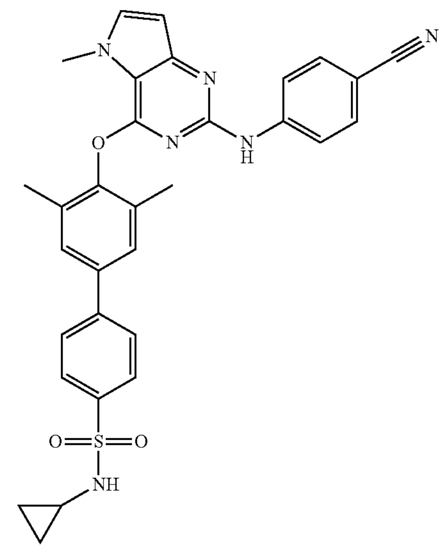
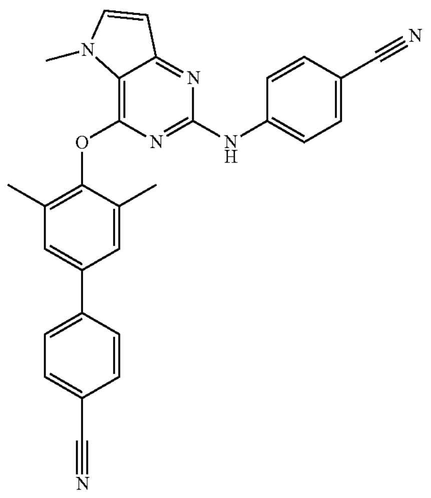
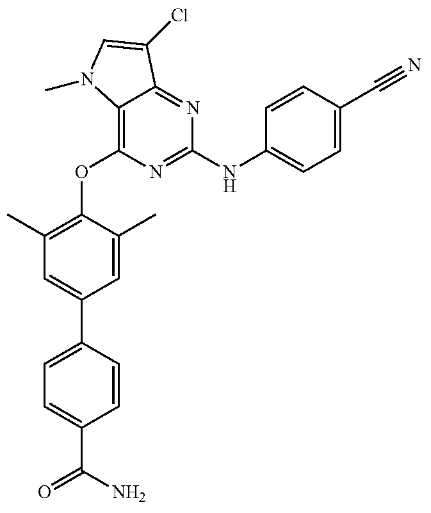
(?) indicates text missing or illegible when filed
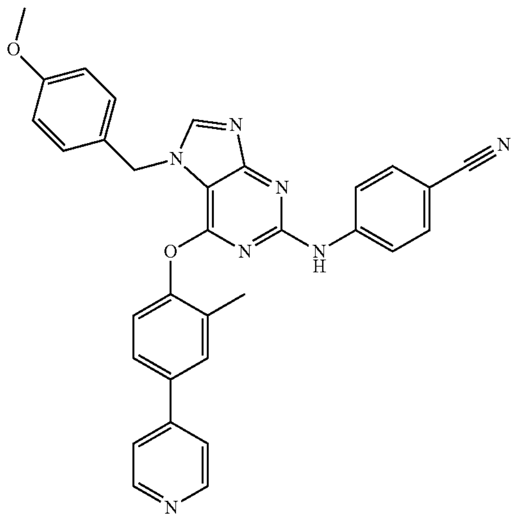
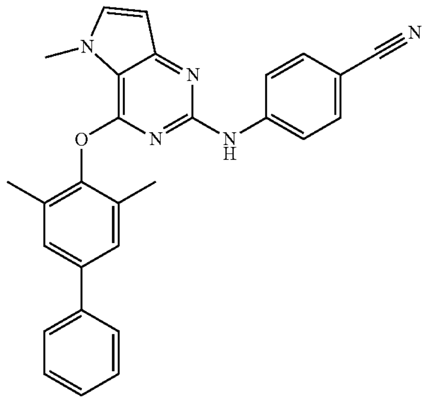

-continued
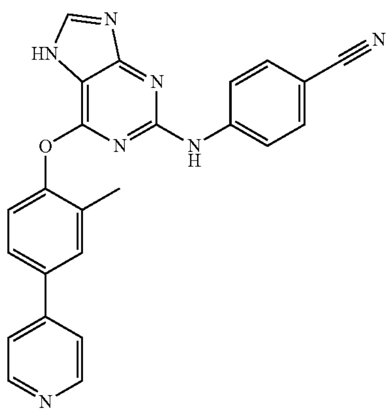
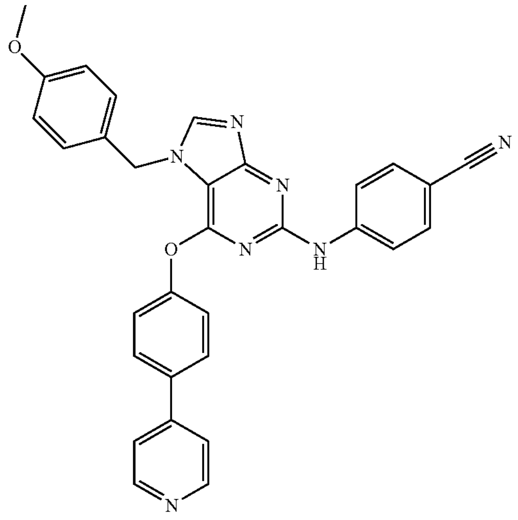
(?) indicates text missing or illegible when filed
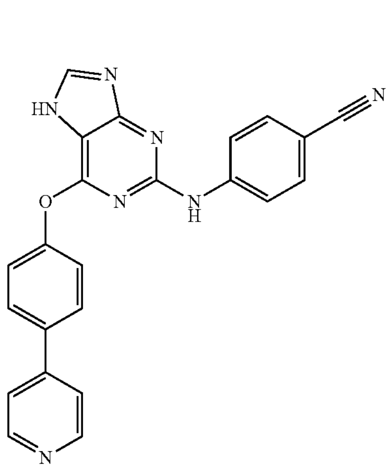
-continued
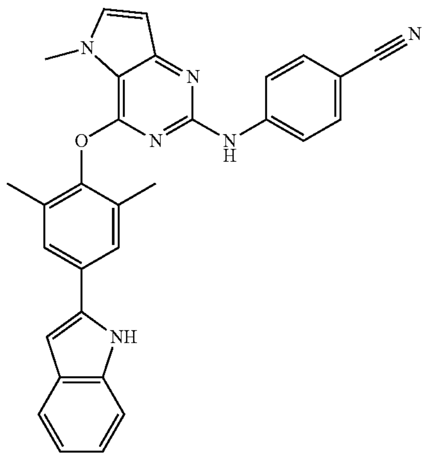
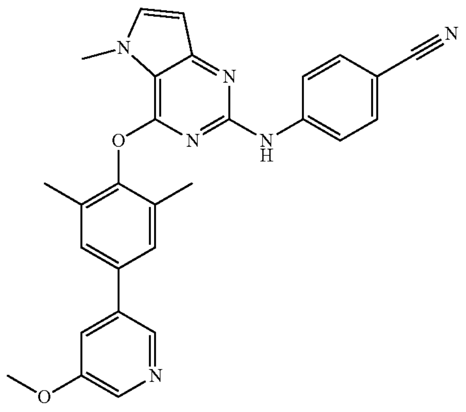
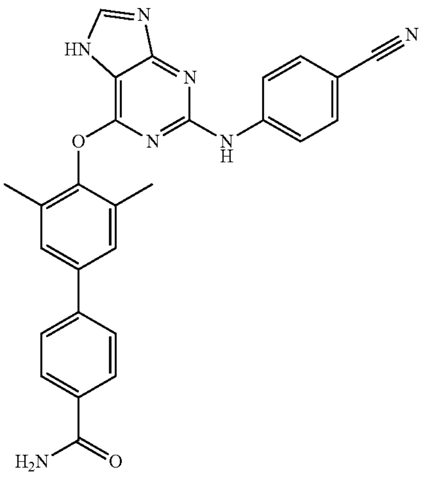

-continued
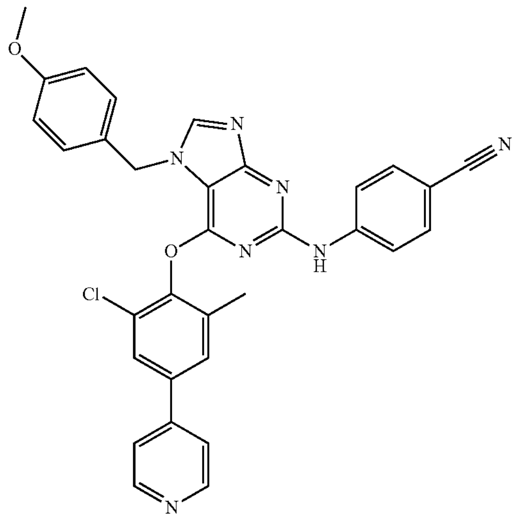
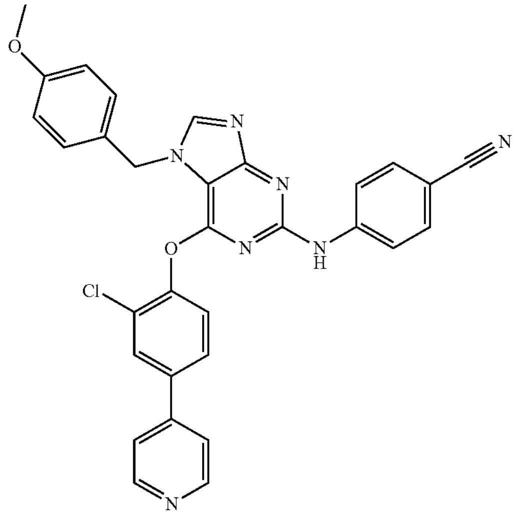
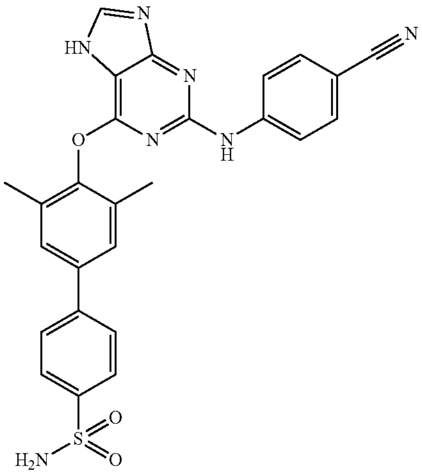
-continued
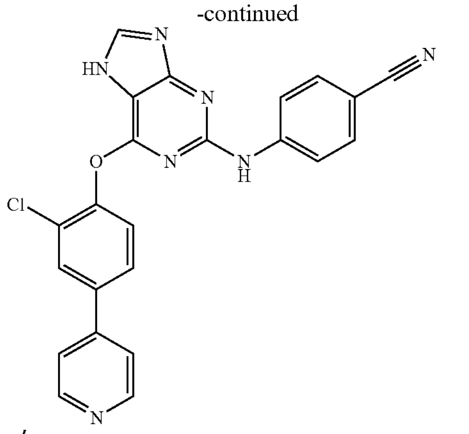
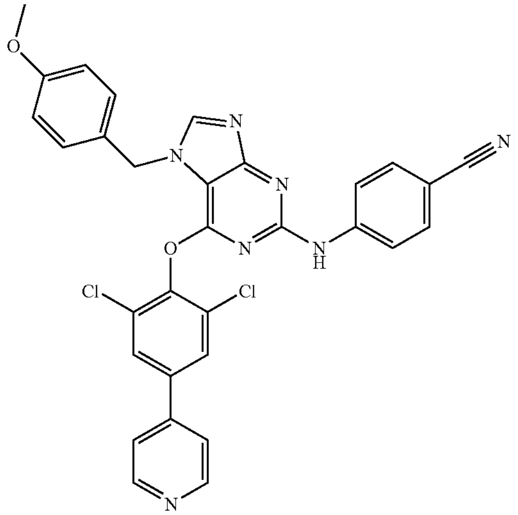
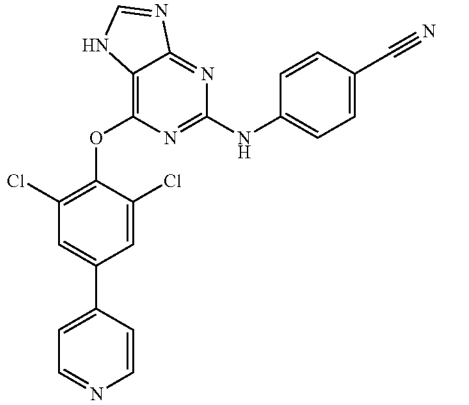
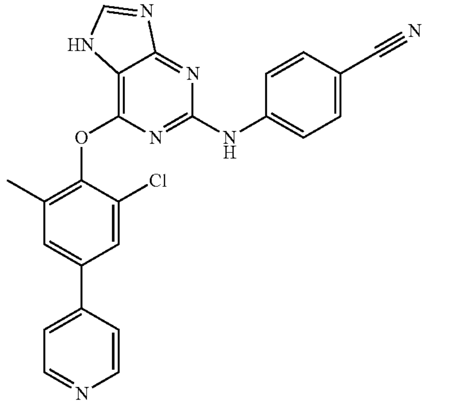
? indicates text missing or illegible when filed -continued
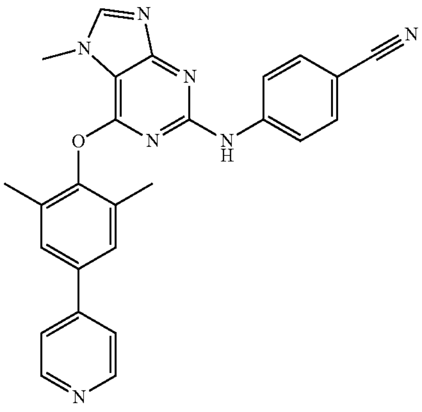
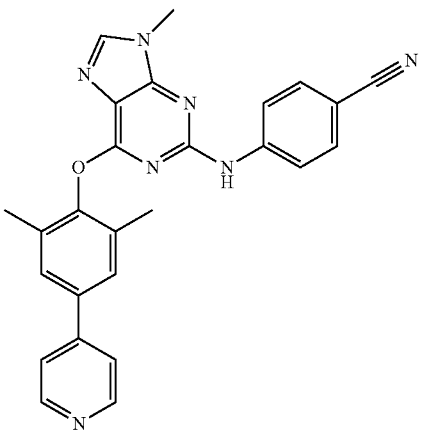
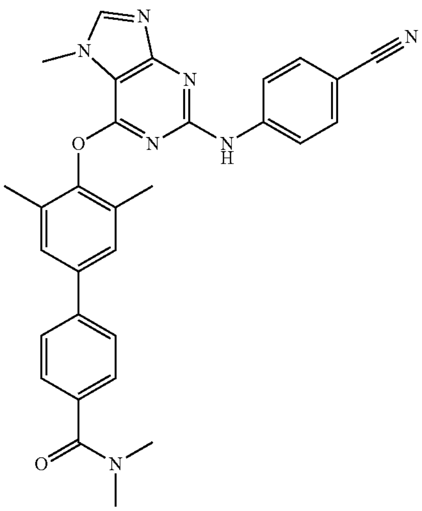
-continued
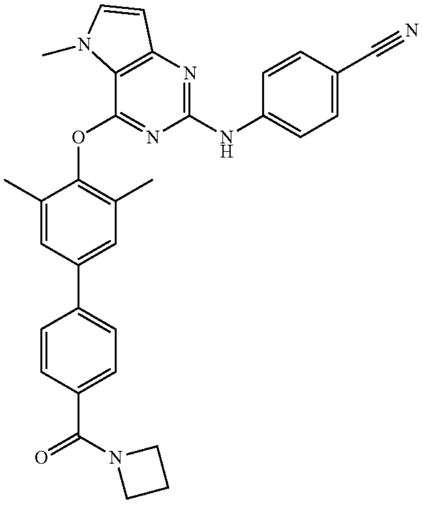
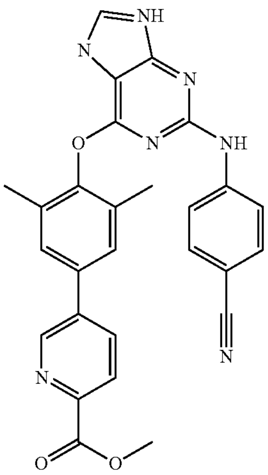
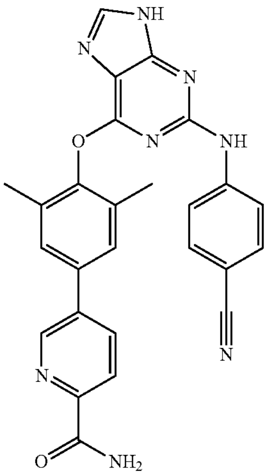
ⓘ indicates text missing or illegible when filed -continued
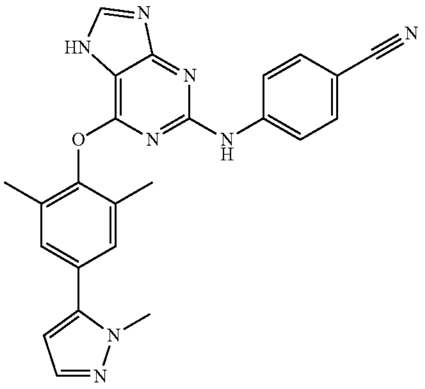
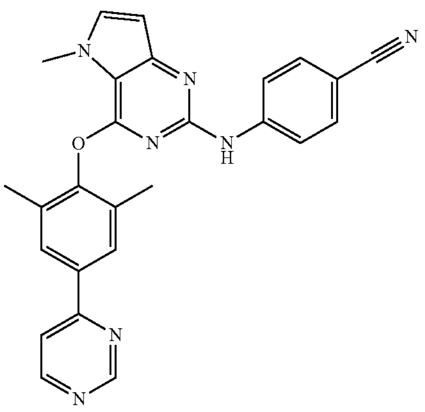
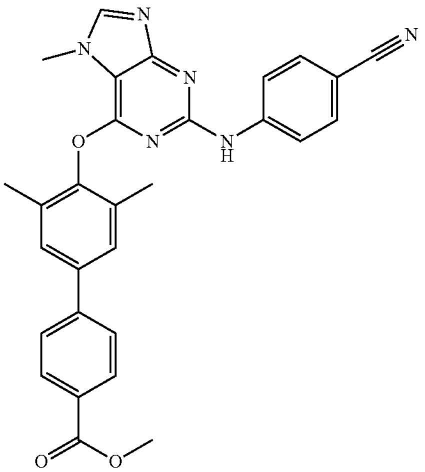
-continued
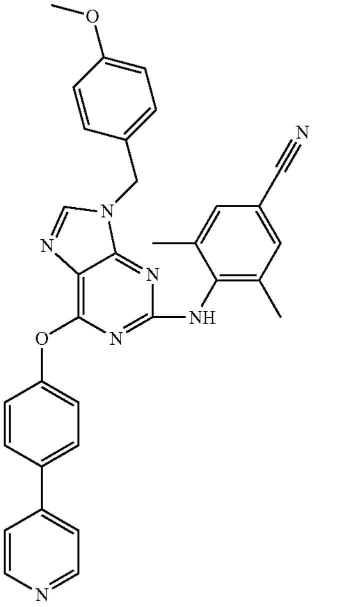
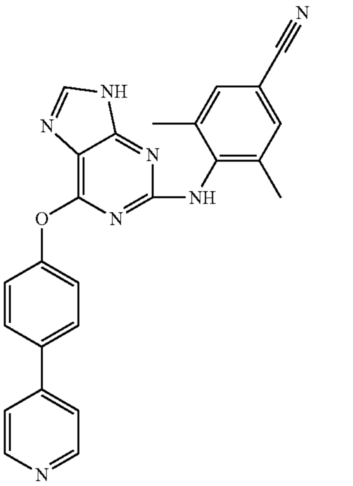
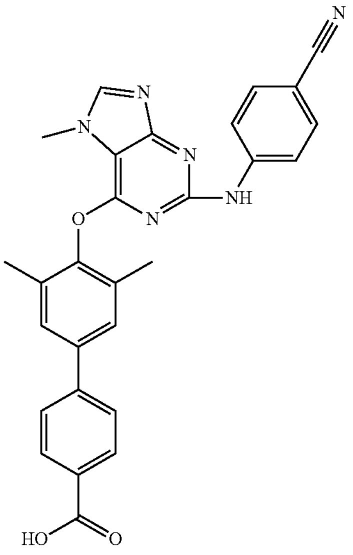
ⓘ indicates text missing or illegible when filed -continued
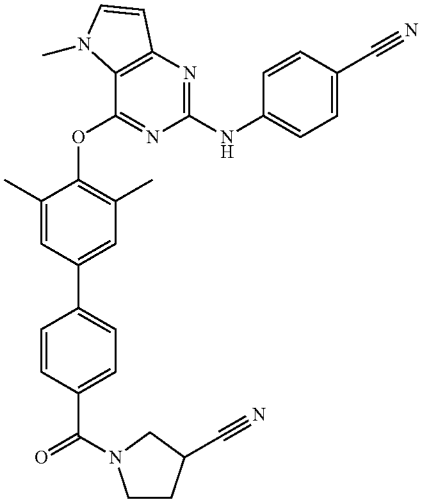
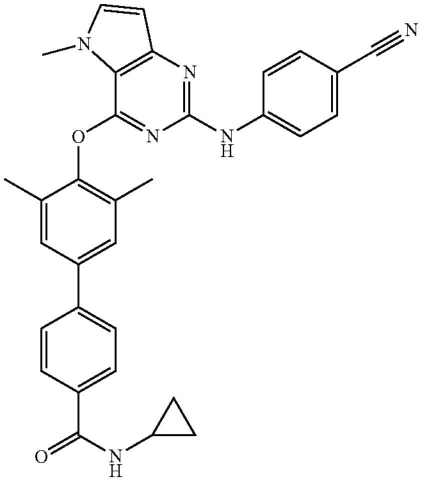
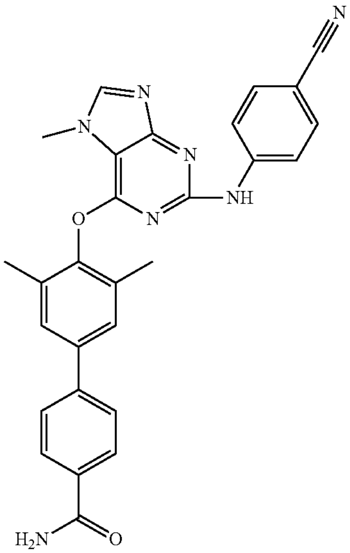
ⓘ indicates text missing or illegible when filed
-continued
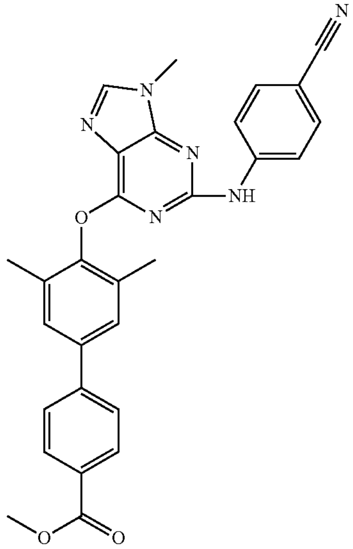
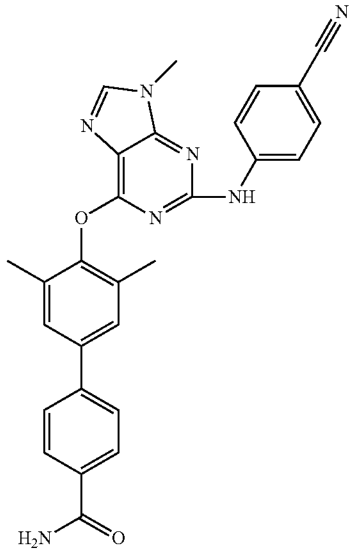
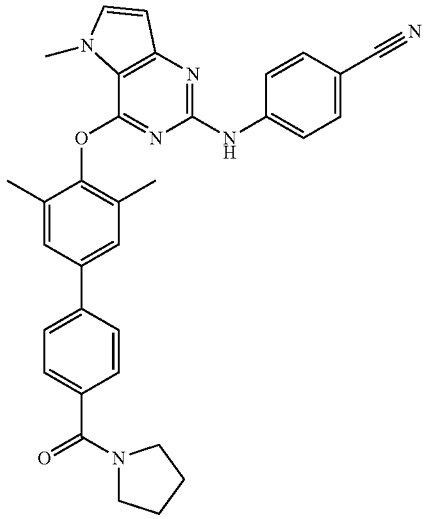
ⓘ indicates text missing or illegible when filed -continued
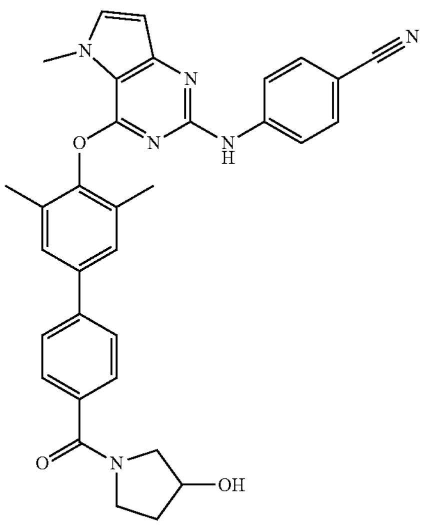
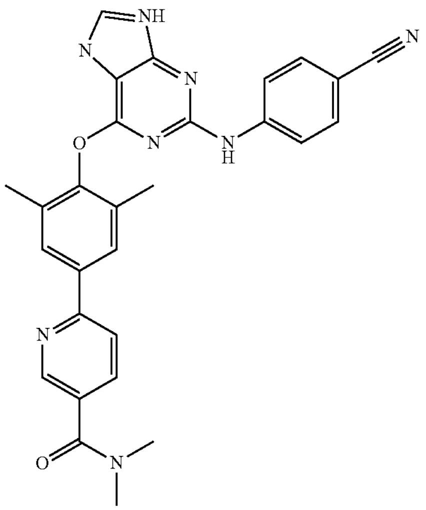
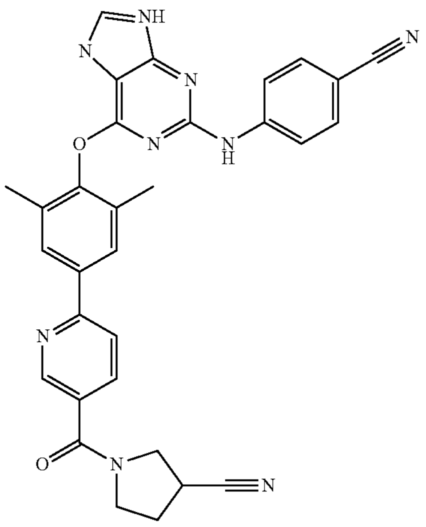
ⓘ indicates text missing or illegible when filed
-continued
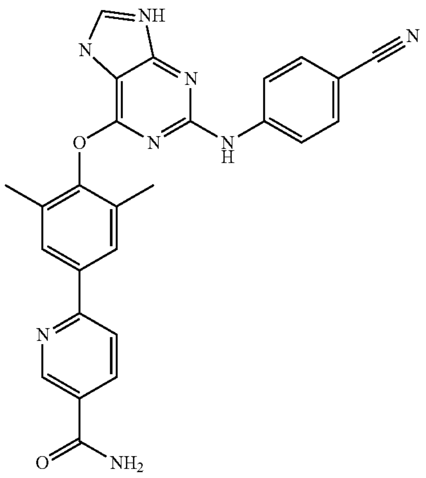
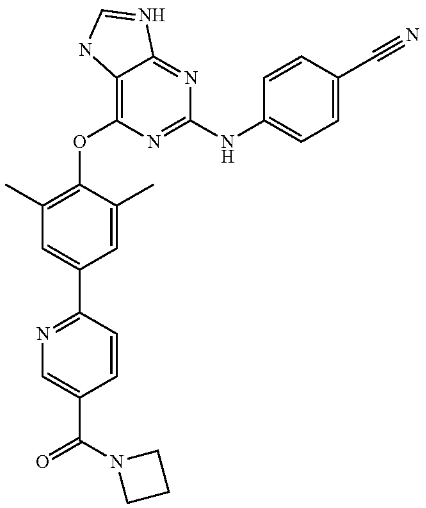
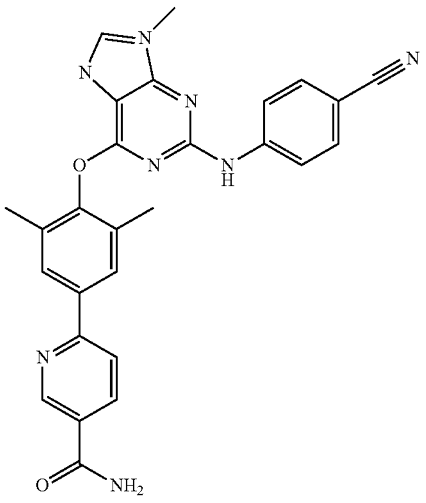

-continued
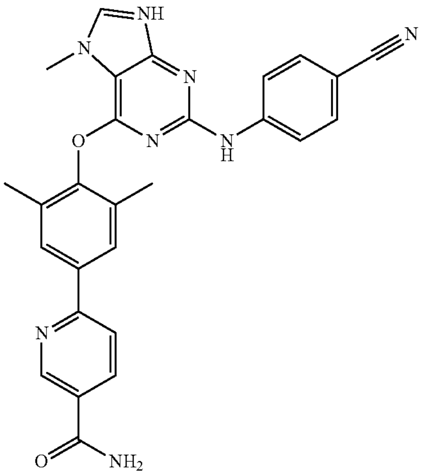
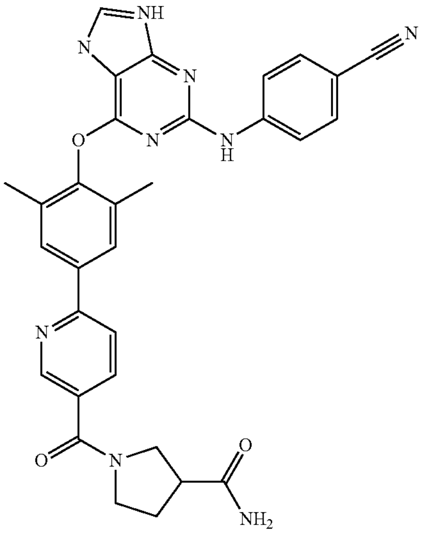
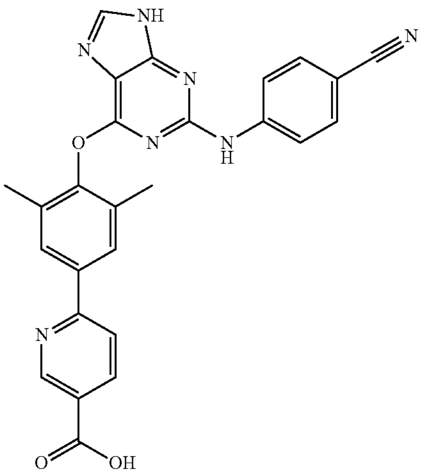
-continued
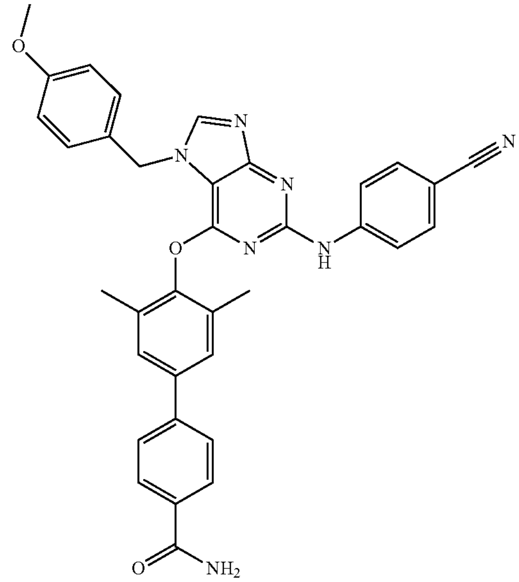
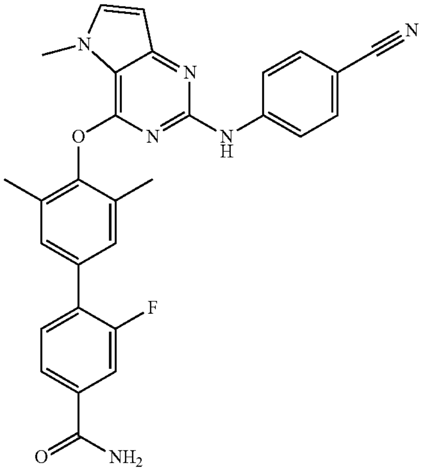
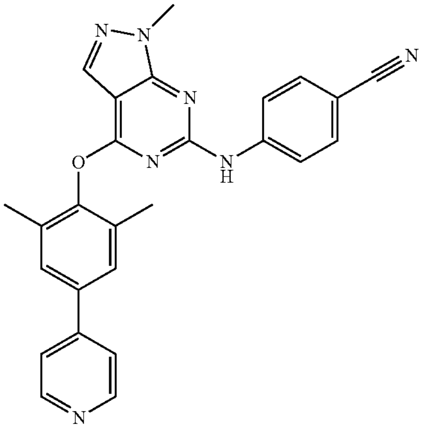

-continued
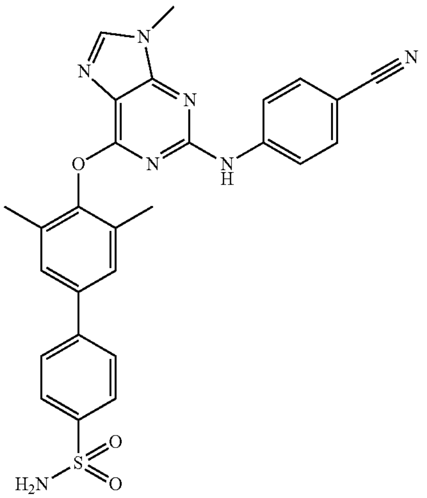
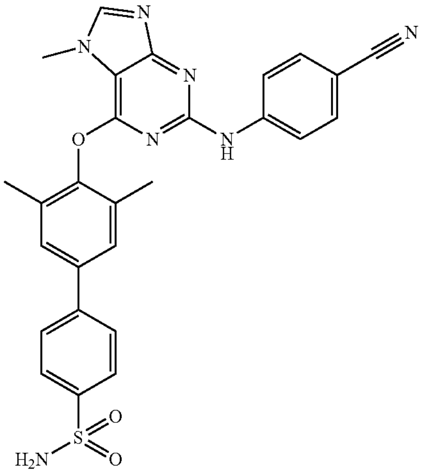
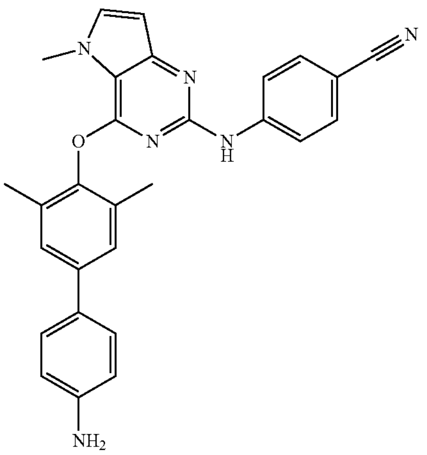
ⓘ indicates text missing or illegible when filed
-continued
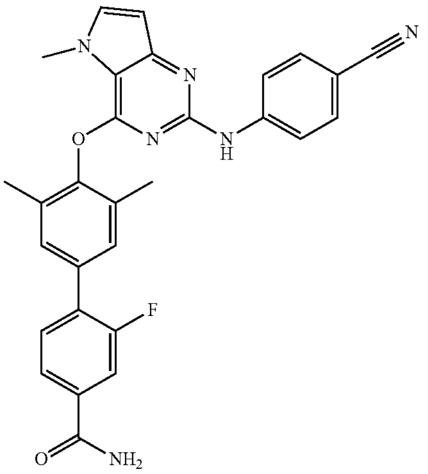
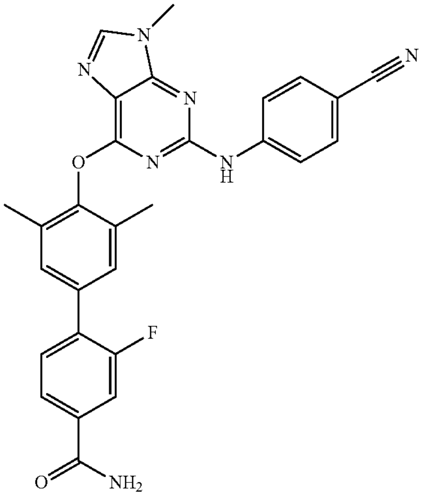
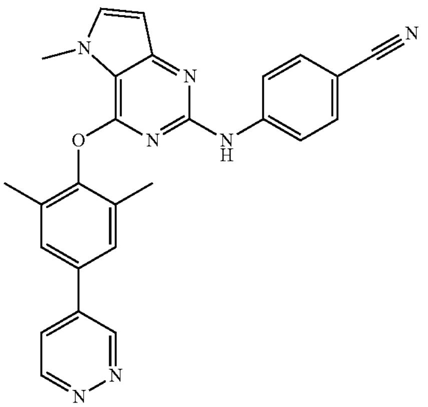
ⓘ indicates text missing or illegible when filed -continued
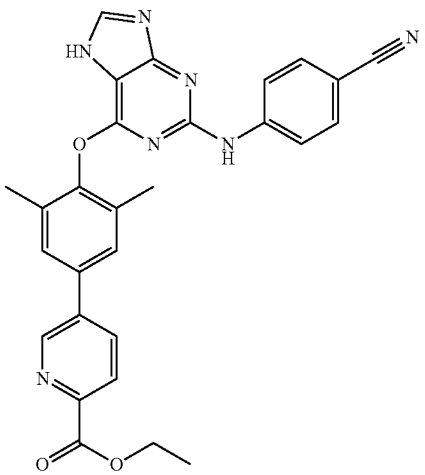
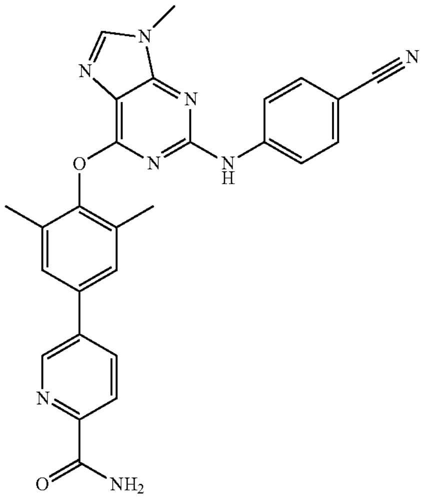
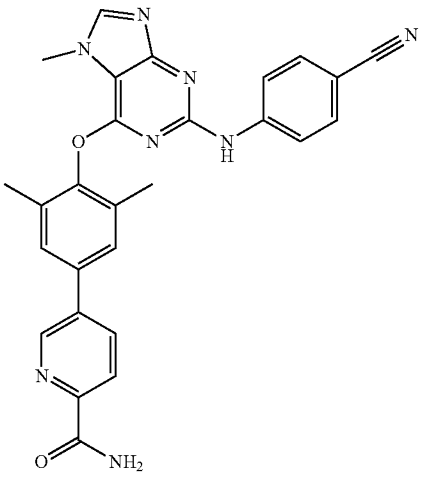
? indicates text missing or illegible when filed
-continued
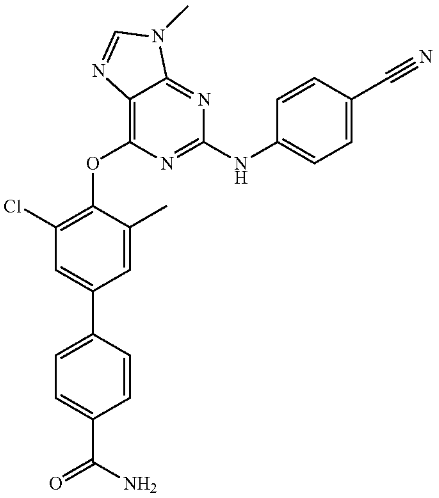
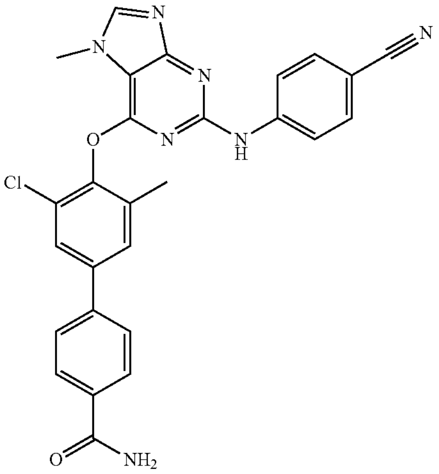
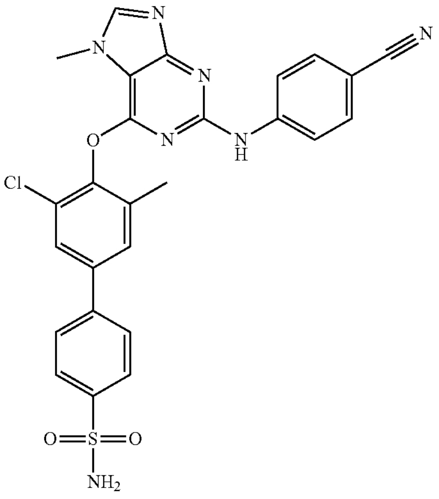

-continued

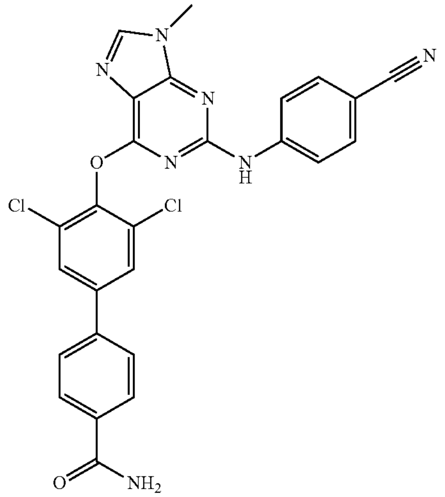

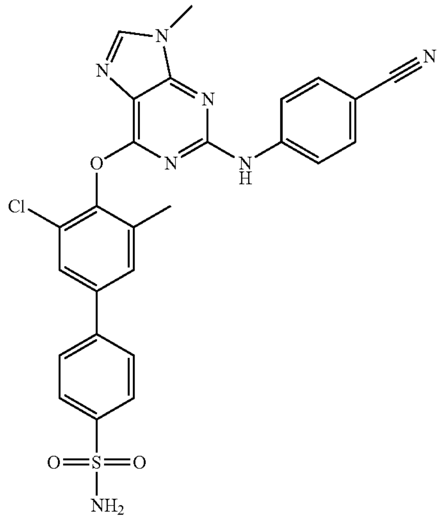

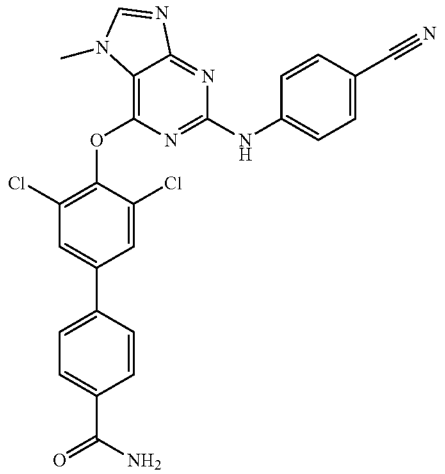

ⓘ indicates text missing or illegible when filed

-continued

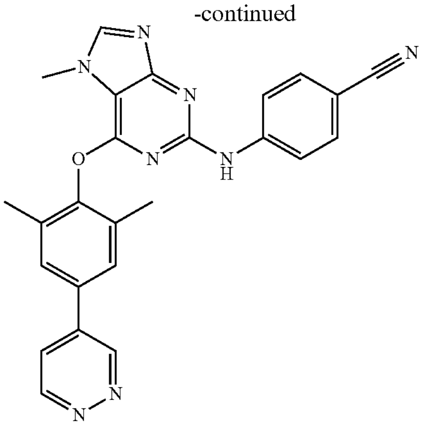

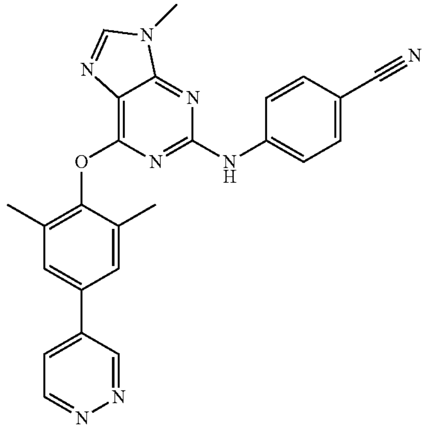

Synthetic Procedures

In another aspect, methods for synthesizing the compounds described herein are provided. In some embodiments, the compounds described herein are prepared by the methods described below. The procedures and examples below are intended to illustrate those methods. Neither the procedures nor the examples should be construed as limiting in any way. Compounds described herein are synthesized using any suitable method.

In some embodiments, the starting materials used for the synthesis of the compounds as described herein are obtained from commercial sources, such as Aldrich Chemical Co. (Milwaukee, Wis.), Sigma Chemical Co. (St. Louis, Mo.). In some embodiments, the starting materials are synthesized. The compounds described herein, and other related compounds having different substituents are synthesized using any suitable technique, such as described, for example, in March, ADVANCED ORGANIC CHEMISTRY 4th Edition (John Wiley and Sons, 1992) and Carey and Sundberg, ADVANCED ORGANIC CHEMISTRY 4th Edition, Vols. A and B (Plenum, 2000, 2001), (each of which are incorporated by reference for such disclosures). In some embodiments, general methods for the preparation of compounds as disclosed herein are derived from any suitable method, and the reactions are modified by the use of appropriate reagents and conditions for the introduction of the various moieties found in the formulae as provided herein. Suitable synthetic methods include, but are not limited to:

Formation of Covalent Linkages by Reaction of an Electrophile with a Nucleophile In some embodiments, the compounds described herein are modified using various electrophiles or nucleophiles to form new functional groups or substituents. The table below entitled "Examples of Covalent Linkages and Precursors Thereof" lists selected examples of covalent linkages and precursor functional groups which yield and are used as guidance toward the variety of electrophiles and nucleophiles combinations available. Precursor functional groups are shown as electrophilic groups and nucleophilic groups.

| Covalent Linkage Product | Electrophile | Nucleophile |
|---|---|---|
| Carboxamides | Activated esters | Amines/anilines |
| Carboxamides | Acyl azides | Amines/anilines |
| Carboxamides | Acyl halides | Amines/anilines |
| Esters | Acyl halides | Alcohols/phenols |
| Esters | Acyl nitriles | Alcohols/phenols |
| Carboxamides | Acyl nitriles | Amines/anilines |
| Imines | Aldehydes | Amines/anilines |
| Hydrazones | Aldehydes or ketones | Hydrazines |
| Oximes | Aldehydes or ketones | Hydroxylamines |
| Alkyl amines | Alkyl halides | Amines/anilines |
| Esters | Alkyl halides | Carboxylic acids |
| Thioethers | Alkyl halides | Thiols |
| Ethers | Alkyl halides | Alcohols/phenols |
| Thioethers | Alkyl sulfonates | Thiols |
| Esters | Alkyl sulfonates | Carboxylic acids |
| Ethers | Alkyl sulfonates | Alcohols/phenols |
| Esters | Anhydrides | Alcohols/phenols |
| Carboxamides | Anhydrides | Amines/anilines |
| Thiophenols | Aryl halides | Thiols |
| Aryl amines | Aryl halides | Amines |
| Thioethers | Azindines | Thiols |
| Boronate esters | Boronates | Glycols |
| Carboxamides | Carboxylic acids | Amines/anilines |
| Esters | Carboxylic acids | Alcohols |
| Hydrazines | Hydrazides | Carboxylic acids |
| N-acylureas or Anhydrides | Carbodiimides | Carboxylic acids |
| Esters | Diazoalkanes | Carboxylic acids |
| Thioethers | Epoxides | Thiols |
| Thioethers | Haloacetamides | Thiols |
| Ammotriazines | Halotriazines | Amines/anilines |
| Triazinyl ethers | Halotriazines | Alcohols/phenols |
| Amidines | Imido esters | Amines/anilines |
| Ureas | Isocyanates | Amines/anilines |
| Urethanes | Isocyanates | Alcohols/phenols |
| Thioureas | Isothiocyanates | Amines/anilines |
| Thioethers | Maleimides | Thiols |
| Phosphite esters | Phosphoramidites | Alcohols |
| Silyl ethers | Silyl halides | Alcohols |
| Alkyl amines | Sulfonate esters | Amines/anilines |
| Thioethers | Sulfonate esters | Thiols |
| Esters | Sulfonate esters | Carboxylic acids |
| Ethers | Sulfonate esters | Alcohols |
| Sulfonamides | Sulfonyl halides | Amines/anilines |
| Sulfonate esters | Sulfonyl halides | Phenols/alcohols |

Examples of Covalent Linkages and Precursors Thereof

Use of Protecting Groups

In some embodiments, of the reactions described, it will be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. In some embodiments, protective groups are removed by acid, base, and hydrogenolysis. In some embodiments, groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. In some embodiments, carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In some embodiments, arboxylic acid and hydroxy reactive moieties are also blocked with hydrolytically removable protective groups such as the benzyl group. In some embodiments, amine groups capable of hydrogen bonding with acids are blocked with base labile groups such as Fmoc. In some embodiments, carboxylic acid reactive moieties are protected by conversion to simple ester compounds as exemplified herein, or they are blocked with oxidatively-removable protective groups such as 2,4-dimethoxybenzyl, while co-existing amino groups are blocked with fluoride labile silyl carbamates.

Allyl blocking groups are useful in then presence of acid- and base-protecting groups since the former are stable and, in certain instances, are subsequently removed by metal or pi-acid catalysts. For example, an allyl-blocked carboxylic acid is deprotected with a Pd-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and cannot react. Once released from the resin, the functional group is available to react.

In some embodiments, protecting or blocking groups are selected from:

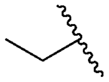
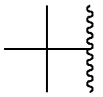

Methyl (Me) Ethyl (Et) t-Butyl (t-Bu)

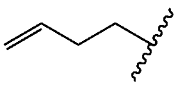
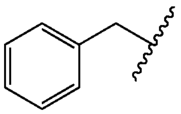
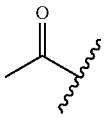

Allyl Benzyl (Bn) Acetyl

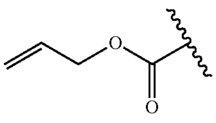
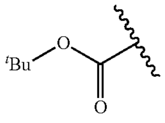

Alloc Boc

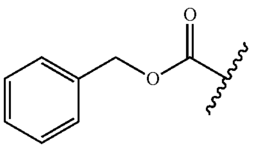
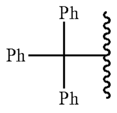

Cbx Trityl

-continued

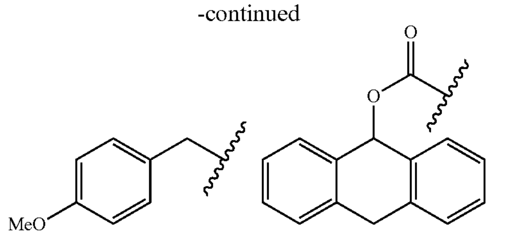

pMBn Fmoc

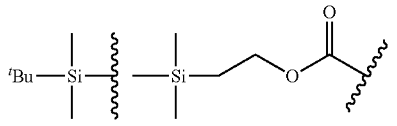

TBDMS Teoc

Other protecting groups, plus a detailed description of techniques applicable to the creation of protecting groups and their removal are described in Greene and Wuts, PROTECTIVE GROUPS IN ORGANIC SYNTHESIS, 3rd Edition (John Wiley and Sons, 1999), and Kocienski, PROTECTIVE GROUPS (Thieme Verlag, 1994), which are incorporated herein by reference for such disclosures.

Preparing a Compound Disclosed Herein

Described herein are processes for the preparation of a compound disclosed herein, which are synthesized according to the reaction schemes below.

I. Preparation of a compound disclosed herein wherein A is —CH═; B is —CH═; D is —NW— and T' is O or NH as follows:

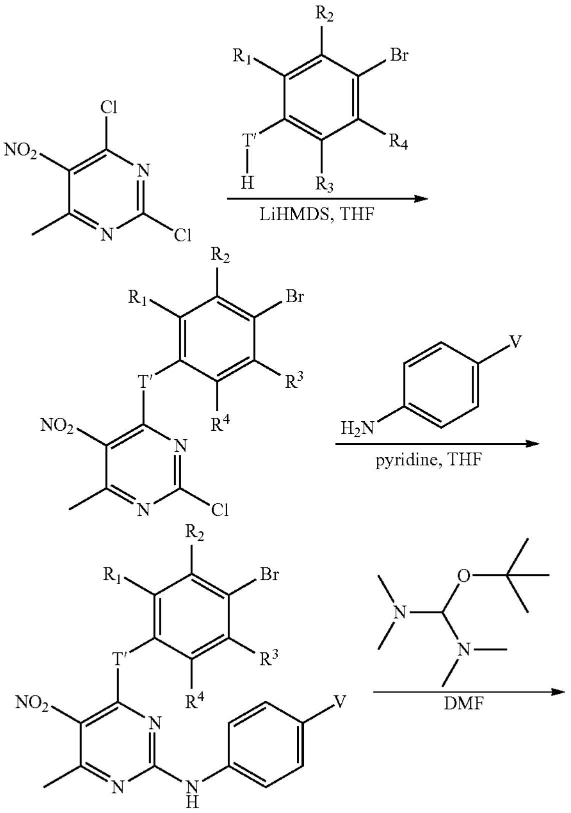

-continued

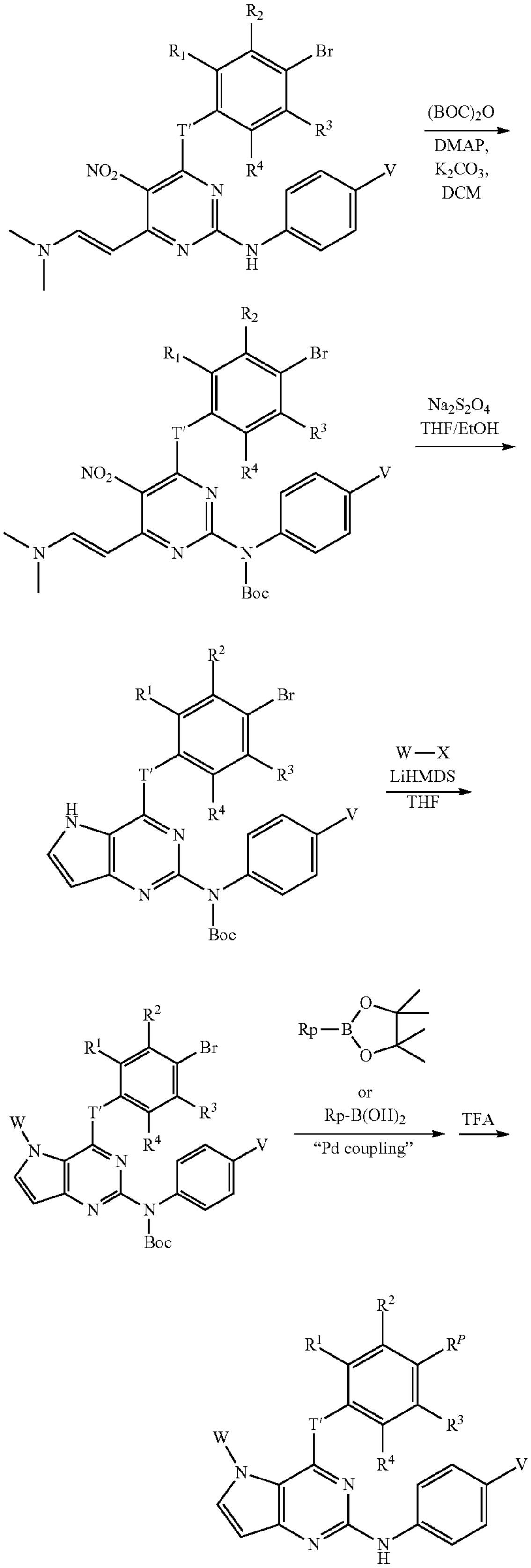

In some embodiments, 2,4-Dichloro-6-methyl-5-nitropyrimidine is coupled with an optionally substituted ($R^1$, $R^2$, $R^3$, $R^4$) para-bromophenol or para-bromoaniline. In some embodiments, formation of the diaryl amine is achieved via reaction with para-V-aniline. Reaction with tert-butoxy-N,N,N',N'-tetramethylmethanediamine forms the dimethylethenamine, which after Boc protection of the aryl amine(s) is cyclized to form the 2,4-disubstituted 5H-pyrrolo[3,2-d]pyrimidine. In some embodiments, deprotonation of the pyrrolo nitrogen using a strong base such as lithium hexamethyldisilazide (LiHMDS), followed by treatment with W—X (where X is a suitable leaving group) allows introduction of substituent W, if desired. In some embodiments, the aryl, substituted aryl, heteroaryl or substituted heteroaryl, $R^P$, group is introduced by palladium coupling and lastly the Boc protecting group is removed by treatment with TFA.

II. Preparation of a compound disclosed herein wherein A is —CH═; B is —CH═; D is —NH.

Preparation of starting material, 5-benzyl-4-chloro-5H-pyrrolo[3,2-d]pyrimidin-2-amine is performed as follows:

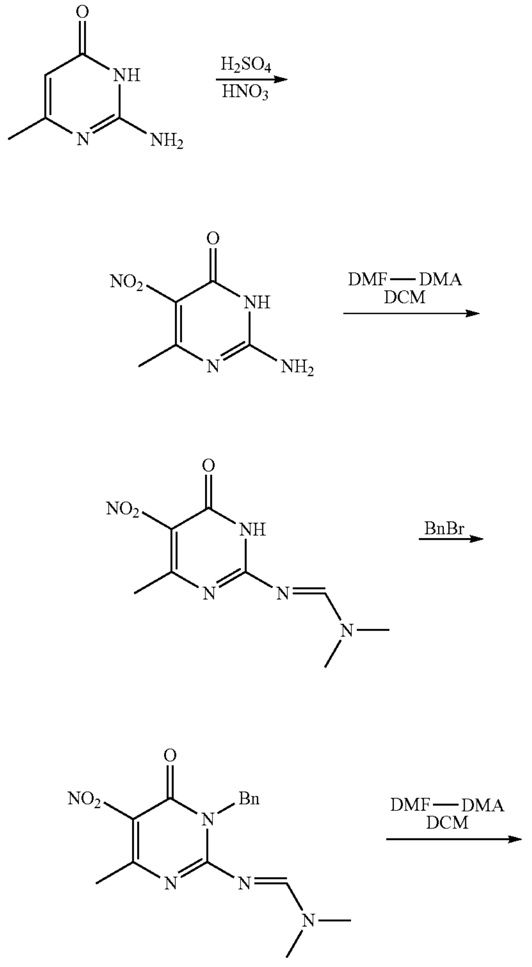

-continued

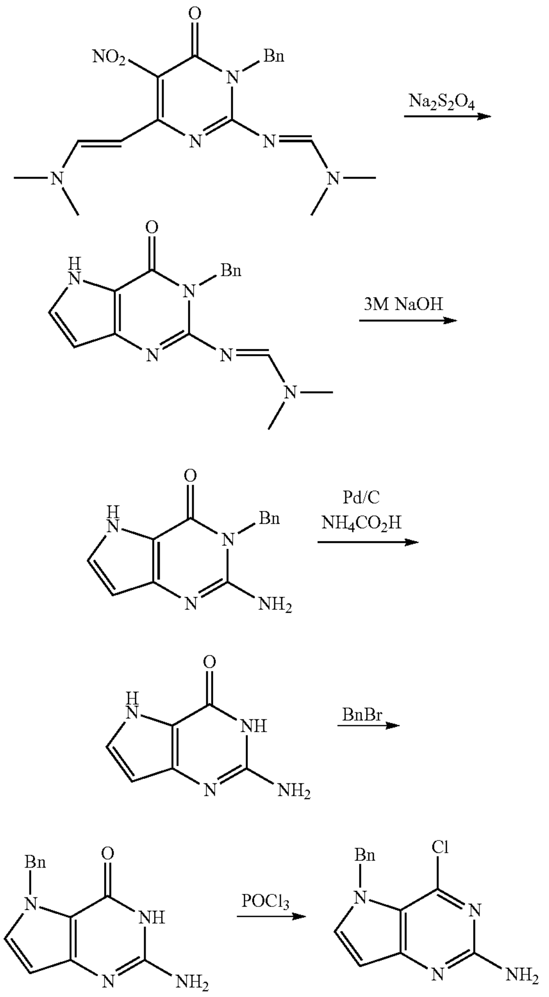

In some embodiments, 2-Amino-6-methylpyrimidin-4(3H)-one is nitrated with nitric acid followed by treatment of the nitrated product with N,N-dimethylformamide dimethyl acetal (DMF-DMA) to afford the corresponding 2-(dimethylamino)methyleneimino derivative. In some embodiments, benzylation gives 3-benzyl-2-[(dimethylamino)methyleneimino]-5-nitro-6-methylpyrimidin-4-one by treating with benzyl bromide which is then converted to the benzylated-2,6-bis-dimethylaminomethylene derivative with DMF-DMA. In some embodiments, reductive cyclization with sodium hydrosulfite followed by deprotection with sodium hydroxide and debenzylation with Pd/C and $NH_4CO_2H$ affords 9-deazaguanine. In some embodiments, benzylation of 9-deazaguanine followed by chlorination with $POCl_3$ gives the chlorinated 9-deazapurine product.

In some embodiments, conversion of 5-benzyl-4-chloro-5H-pyrrolo[3,2-d]pyrimidin-2-amine to the desired product is achieved by a variety of routes, some of which are exemplified below. The most suitable of these routes depends on various factors, such as desired substituents, availability of starting materials and reactants, etc.

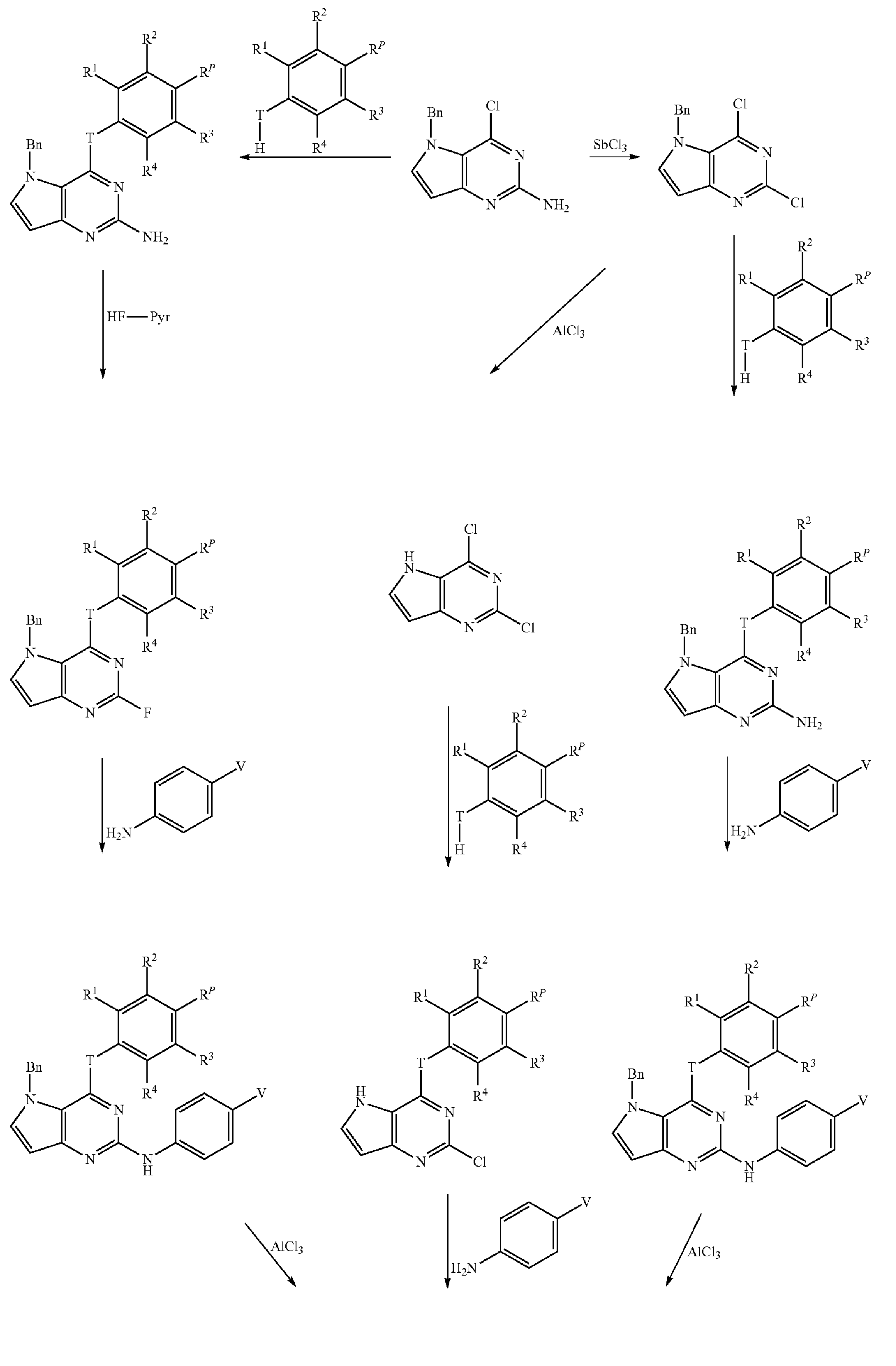
SbCl3
HF—Pyr
AlCl3
AlCl3
AlCl3

-continued

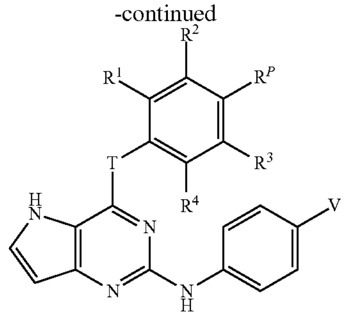

In some embodiments, 5-Benzyl-4-chloro-5H-pyrrolo[3,2-d]pyrimidin-2-amine is coupled with an aniline, phenol or thiophenol, followed by fluorination by treatment with HF-pyridine and t-butyl nitrite, coupling with para-V-aniline and finally benzyl deprotection with $AlCl_3$. Alternatively, in some embodiments, 5-benzyl-4-chloro-5H-pyrrolo[3,2-d]pyrimidin-2-amine is first converted to 5-benzyl-2,4-dichloro-5H-pyrrolo[3,2-d]pyrimidine, by treatment with $SbCl_3$ and t-butyl nitrite, followed by coupling with an aniline, phenol or thiophenol, coupling with para-V-aniline and finally benzyl deprotection with $AlCl_3$. Also, in some embodiments, 5-benzyl-2,4-dichloro-5H-pyrrolo[3,2-d]pyrimidine is first benzyl deprotected with $AlCl_3$ followed by coupling with an aniline, phenol or thiophenol, and finally coupling with para-V-aniline.

III. Preparation of a compound disclosed herein wherein A is —CH═; B is —CH═; D is —NW— and T is O as follows:

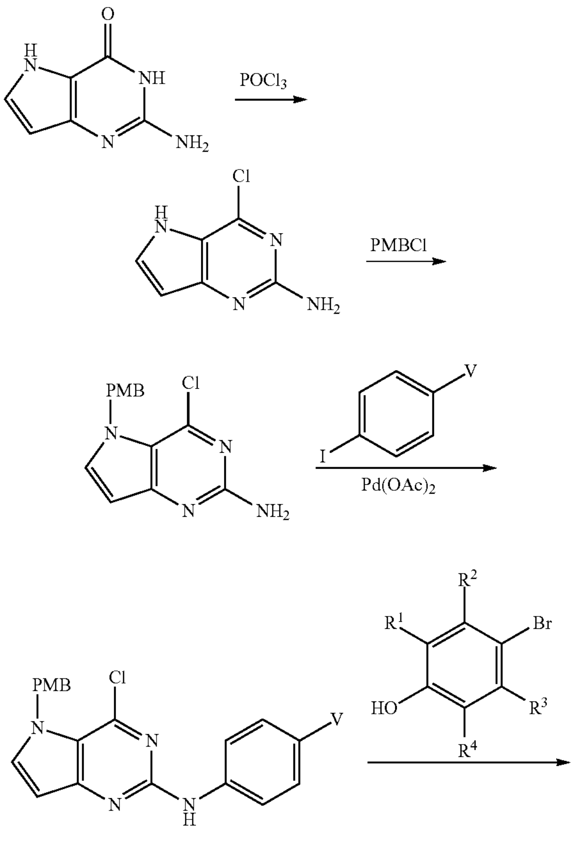

-continued

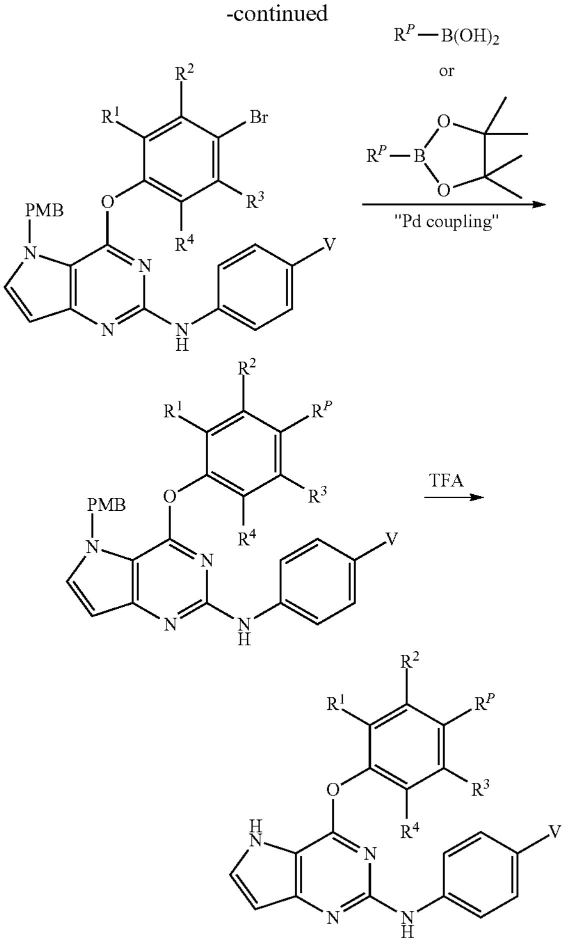

In some embodiments, 2-Amino-3H-pyrrolo[3,2-d]pyrimidin-4(5H)-one is converted to 4-chloro-5H-pyrrolo[3,2-d]pyrimidin-2-amine by treatment with $POCl_3$, and then amine protected by reaction with para-methoxy benzyl chloride (PMB-Cl). In some embodiments, formation of the diaryl amine is achieved via reaction with para-V-iodobenzene, which is then coupled with optionally substituted ($R^1$, $R^2$, $R^3$, $R^4$) para-bromophenol. In some embodiments, the aryl, substituted aryl, heteroaryl or substituted heteroaryl, $R^P$, group is then introduced by palladium coupling and the PMB protecting group removed with TFA. In some embodiments, 2-Amino-3H-pyrrolo[3,2-d]pyrimidin-4(5H)-one is prepared as described by Kielich, ed., *Synthetic Communications,* 2002, 32, 3797-3802, which is herein incorporated by reference for such disclosure.

IV. Preparation of a compound disclosed herein wherein A is —CCl═; B is —CH═; D is —NW— and T' is O or NH as follows:

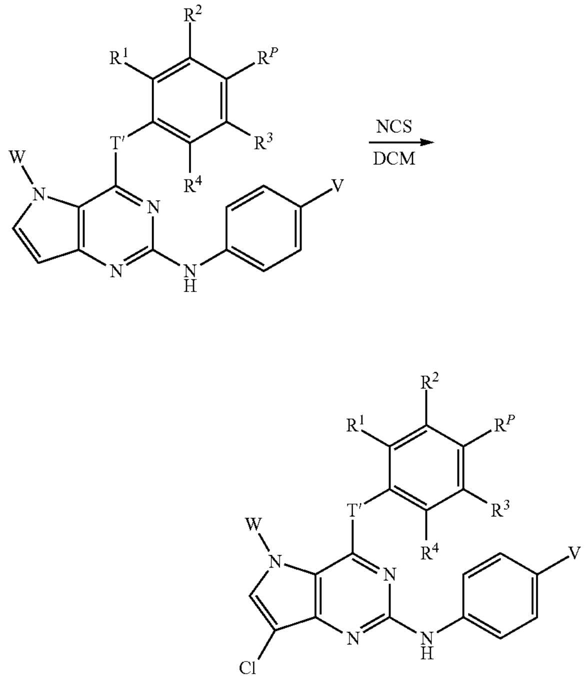

In some embodiments, the pyrrolo ring of the 2,4-disubstituted 5H-pyrrolo[3,2-d]pyrimidine, prepared as described above, is chlorinated in the 7-position by treatment with N-chlorosuccinimide.

V. Preparation of a compound disclosed herein wherein A is —NH—; B is —CH═; D is —CH═ and T is O, S or NH as follows:

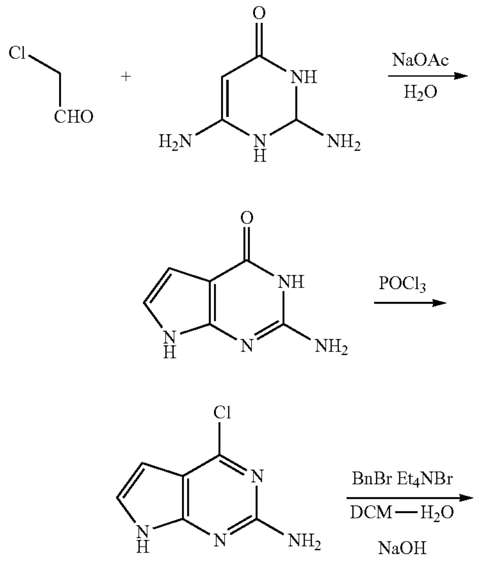

-continued

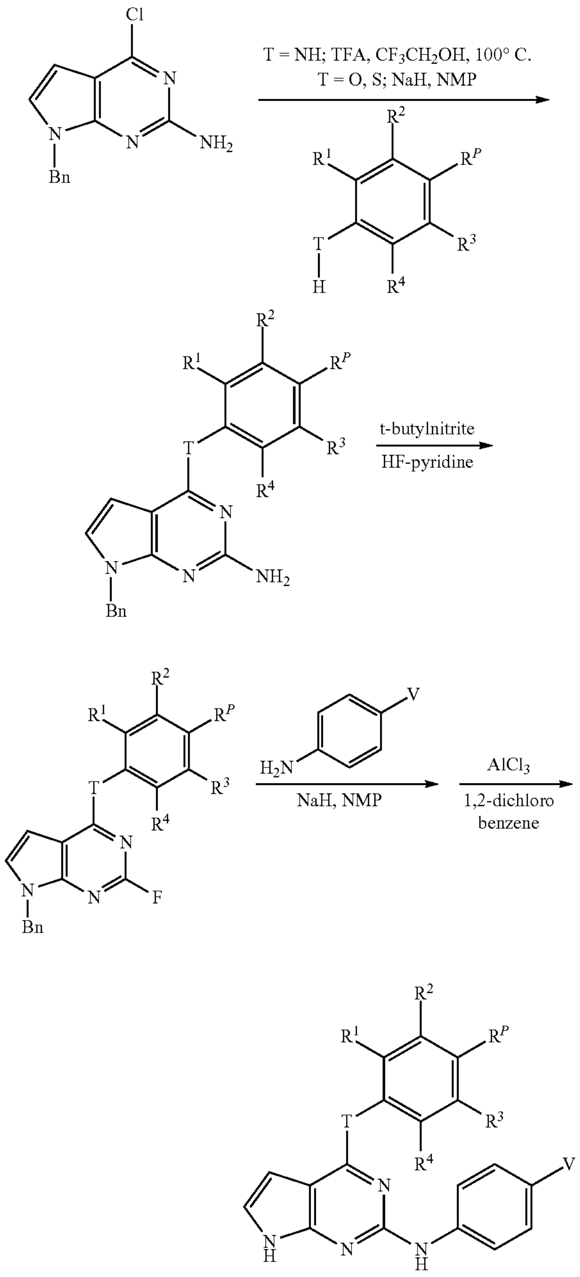

In some embodiments, condensation of 2,6-diamino-1,2-dihydro[3H]pyrimidin-4-one with chloroacetaldehyde, followed by treatment with phosphorus oxychloride and anime protection with benzyl bromide provides 7-benzyl-4-chloro-7H-pyrrolo[2,3-d]pyrimidin-2-amine. In some embodiments, this is coupled with optionally substituted ($R^1$, $R^2$, $R^3$, $R^4$) para-bromo phenol or thiol (T=O, S) or para-bromoaniline (T=NH). In some embodiments, conversion of amine to fluoro is achieved by treatment with HF-pyridine, and then coupled with para-V-aniline. In some embodiments, benzyl deprotection is achieved by treatment with aluminum chloride to give the desired compound.

VI. Preparation of a compound disclosed herein wherein A is —N═; B is —CH═; D is —NH— and T' is O or NH as follows:

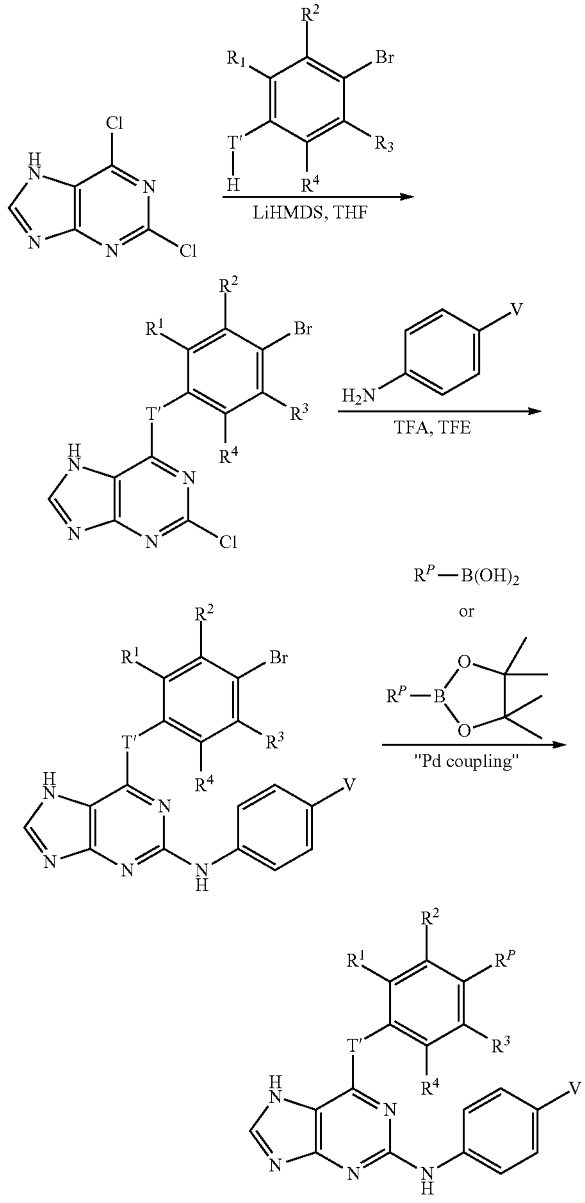

In some embodiments, 2,6-Dichloro-7H-purine is coupled with optionally substituted ($R^1$, $R^2$, $R^3$, $R^4$) para-bromophenol or para-bromoaniline. In some embodiments, formation of the diaryl amine is achieved via reaction with para-V-aniline. In some embodiments, the aryl, substituted aryl, hetero aryl or substituted heteroaryl, $R^P$, group is then introduced by palladium coupling with the 2-chloro purine.

VIIa. Preparation of a compound disclosed herein wherein A is —NH—; B is —N═; D is —CH═ and T is O as follows:

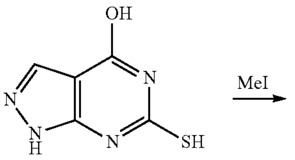

-continued

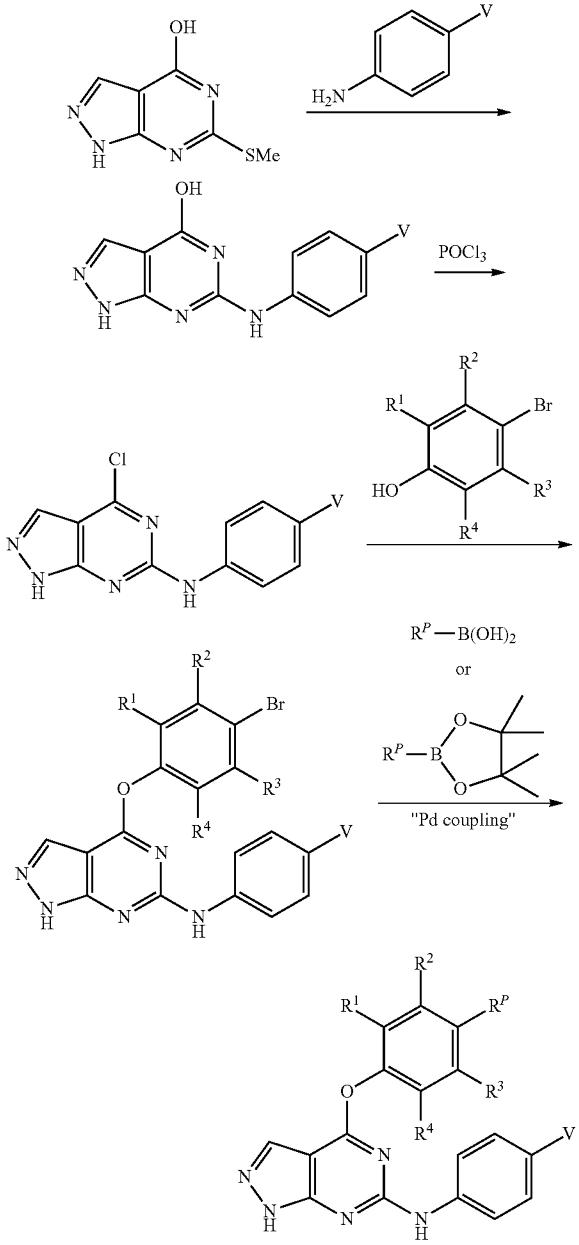

In some embodiments, 6-Mercapto-1H-pyrazolo[3,4-d]pyrimidin-4-ol (prepared according to published procedures, see Youssif, et al., *Bull. Kor. Chem. Soc.,* 2003, 24, 1429-32; Bontems, et al., *J. Med. Chem.* 1990, 33, 2174-8; Badger, et al., *Aust. J. Chem.* 1965, 18, 1267-71, all of which are herein incorporated by reference for such disclosures) is S-methylated with methyl iodide. In some embodiments, formation of the diaryl amine is achieved via reaction with para-V-aniline. In some embodiments, conversion of the hydroxy to the chloro is achieved by treatment with $POCl_3$, followed by coupling with optionally substituted ($R^1$, $R^2$, $R^3$, $R^4$) para-bromophenol. In some embodiments, the aryl, substituted aryl, heteroaryl or substituted heteroaryl, $R^P$, group is then introduced by palladium coupling.

VIIb. An alternate synthesis of the above compounds is as follows:

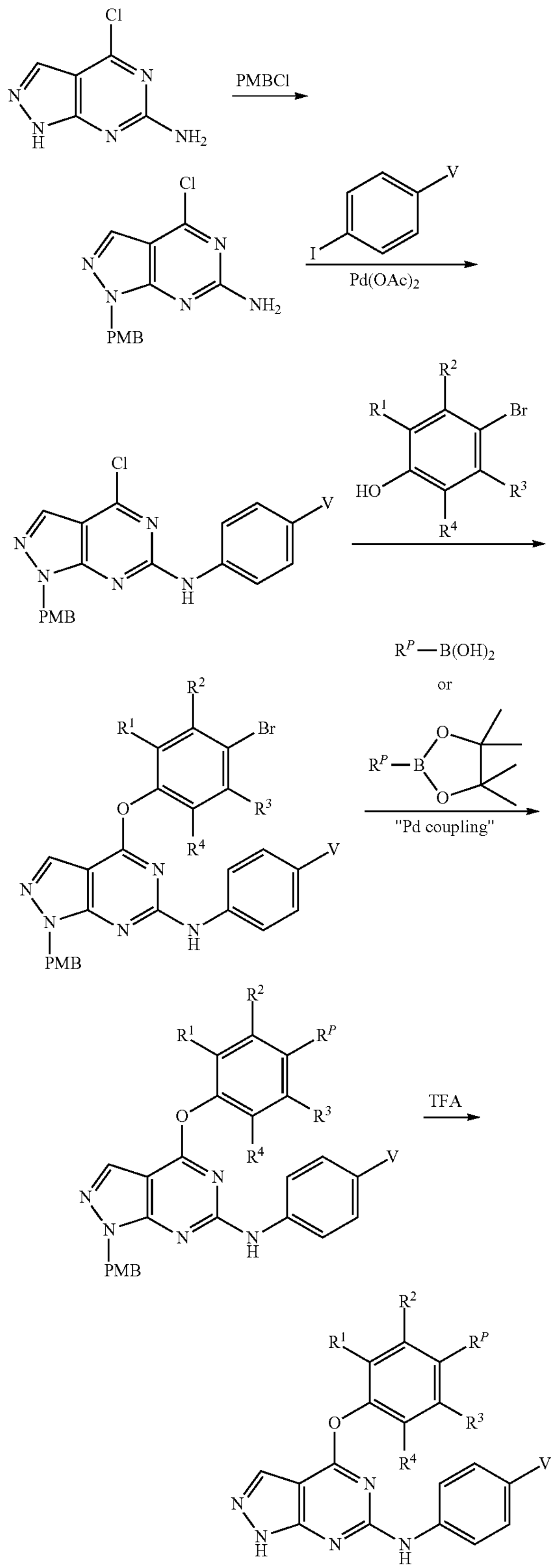

In some embodiments, the 1-amine of 4-Chloro-1H-pyrazolo[3,4-d]pyrimidin-6-amine (prepared according to published procedures, see Seela, *Helv. Chim. Act.* 1999, 82, 105-124; Taylor, *Tetrahedron* 1992, 48, 8089-100; Seela, *Helv. Chim. Act.* 1986, 69, 1602-1613, all of which are herein incorporated by reference for such disclosures) is protected by treatment with para-methoxy benzyl chloride (PMB-Cl). In some embodiments, formation of the diarly amine is achieved via Pd coupling with para-V-iodobenzene. In some embodiments, the aryl ether i prepared by coupling with optionally substituted ($R^1$, $R^2$, $R^3$, $R^4$) para-bromophenol. In some embodiments, the aryl, substituted aryl, heteroaryl or substituted heteroaryl, $R^P$, group is then introduced by palladium coupling and the PMB protecting group removed with TFA.

VIII. Preparation of a compound disclosed herein wherein A is —CH═; B is —N═; D is —NH— and T is O as follows:

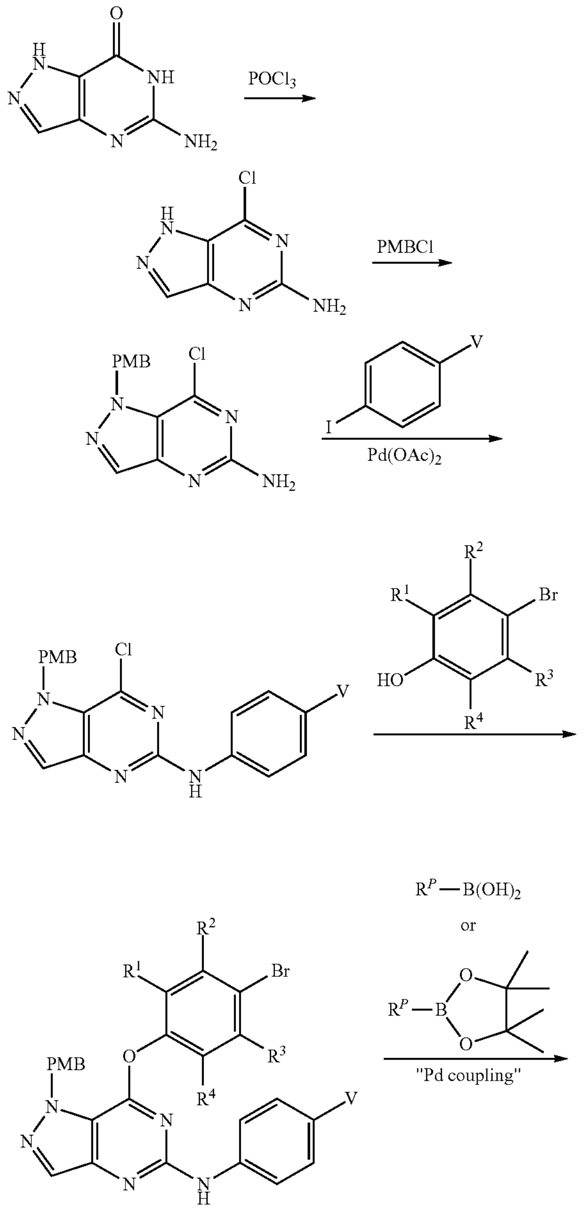

-continued

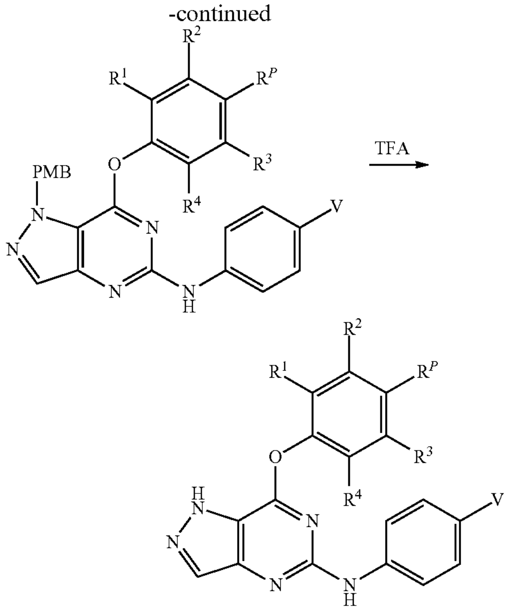

In some embodiments, 5-Amino-1H-pyrazolo[4,3-d]pyrimidin-7(6H)-one (prepared according to published procedures, see Lewis, et al., *J. Am. Chem. Soc.* 1982, 104, 1073-78, which is incorporated herein by reference for such disclosure) is treated with $POCl_3$ to form 7-chloro-1H-pyrazolo[4,3-d]pyrimidin-5-amine and the amine protected by reaction with para-methoxy benzyl chloride (PMB-Cl). In some embodiments, formation of the diaryl amine is achieved via reaction with para-V-iodobenzene, which is then coupled with optionally substituted ($R^1$, $R^2$, $R^3$, $R^4$) para-bromophenol. In some embodiments, the aryl, substituted aryl, heteroaryl or substituted heteroaryl, $R^P$, group is then introduced by palladium coupling and the PMB protecting group removed with TFA.

Further Forms of a Compound Disclosed Herein

Isomers of a Compound Disclosed Herein

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some embodiments, the compounds described herein possess one or more chiral centers and each center exists in the R or S configuration. The compounds described herein include all diastereomeric, enantiomeric, and epimeric forms as well as the corresponding mixtures thereof. In additional embodiments, of the compounds and methods provided herein, mixtures of enantiomers and/or diastereoisomers, resulting from a single preparative step, combination, or interconversion are also useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, resolution of enantiomers is carried out using covalent diastereomeric derivatives of the compounds described herein. In some embodiments, resolution of enantiomers is carried out using dissociable complexes (e.g., crystalline diastereomeric salts). In certain instances, diastereomers have distinct physical properties (e.g., melting points, boiling points, solubilities, reactivity, etc.) and are readily separated by taking advantage of these dissimilarities. In some embodiments, diastereomers are separated by chiral chromatography, or preferably, by separation/resolution techniques based upon differences in solubility. In certain instances, the optically pure enantiomer is then recovered, along with the resolving agent, by any practical means that would not result in racemization. A more detailed description of the techniques applicable to the resolution of stereoisomers of compounds from their racemic mixture is found in Jacques et al, "ENANTIOMERS, RACEMATES AND RESOLUTIONS" (John Wiley And Sons, New York, N.Y., 1981), herein is incorporated by reference for such disclosures.

Labeled a Compound Disclosed Herein

In some embodiments, the compounds described herein exist in their isotopically-labeled forms. Disclosed herein, in certain instances, are methods of treating diseases by administering such isotopically-labeled compounds. Disclosed herein, in certain instances, are methods of treating diseases by administering such isotopically-labeled compounds as pharmaceutical compositions. Thus, in some embodiments, a compound disclosed herein includes isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds disclosed herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}0$, $^{17}O$, $^{31}P$, $^{32}P$, $^{35}S$, $^{18}F$, and $^{36}Cl$, respectively. Compounds described herein, and the pharmaceutically acceptable salts, esters, prodrugs, solvate, hydrates or derivatives thereof which contain the aforementioned isotopes and/or other isotopes of other atoms are within the scope of this disclosure. In certain instances, certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, in some embodiments, substitution with heavy isotopes such as deuterium, i.e., $^{2}H$, can afford certain therapeutic advantages resulting from greater metabolic stability, for example increased in vivo half-life or reduced dosage requirements and, hence, are preferred in some circumstances. Isotopically labeled compounds, pharmaceutically acceptable salt, ester, prodrug, solvate, hydrate or derivative thereof can generally be prepared by carrying out procedures described herein, by substituting a readily available isotopically labeled reagent for a non-isotopically labeled reagent.

In some embodiments, the compounds described herein are labeled by other means, including, but not limited to, the use of chromophores or fluorescent moieties, bioluminescent labels, or chemiluminescent labels.

Pharmaceutically Acceptable Salts of a Compound Disclosed Herein

In some embodiments, the compounds described herein exist as their pharmaceutically acceptable salts. Disclosed herein, in certain instances, are methods of treating diseases by administering such pharmaceutically acceptable salts. Disclosed herein, in certain instances, are methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, in some embodiments, the compounds described herein are prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining a compound disclosed herein and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N^+(C_{1-4}$ alkyl)$_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In certain instances, water or oil-soluble or dispersible products are obtained by such quaternization. In some embodiments, the compounds described herein are prepared as pharmaceutically acceptable salts formed when an acidic proton present in the parent compound either is replaced by a metal ion, for example an alkali metal ion, an alkaline earth ion, or an aluminum ion; or coordinates with an organic base. In some embodiments, base addition salts are also prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, in some embodiments, the salt forms of the disclosed compounds are prepared using salts of the starting materials or intermediates. For additional information on pharmaceutical salts see for example Berge et al., *J. Pharm. Sci.* 1977, 66, 1-19, which is herein incorporated by reference for such disclosure.

Solvates of a Compound Disclosed Herein

In some embodiments, the compounds described herein exist as solvates. Disclosed herein, in certain instances, are methods of treating diseases by administering such solvates. Disclosed herein, in certain instances, are methods of treating diseases by administering such solvates as pharmaceutical compositions.

Solvates contain either stoichiometric or non-stoichiometric amounts of a solvent, and are formed during the process of crystallization with pharmaceutically acceptable solvents such as water, ethanol, and the like. In certain instances, hydrates are formed when the solvent is water, or alcoholates are formed when the solvent is alcohol. In some embodiments, solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, in some embodiments, the compounds provided herein exist in unsolvated as well as solvated forms. In general, the solvated forms are considered equivalent to the unsolvated forms for the purposes of the compounds and methods provided herein.

Polymorphs of a Compound Disclosed Herein

In some embodiments, the compounds described herein exist as polymorphs. Disclosed herein, in certain instances, are methods of treating diseases by administering such polymorphs Disclosed herein, in certain instances, are methods of treating diseases by administering such polymorphs as pharmaceutical compositions.

Thus, the compounds described herein include all their crystalline forms, known as polymorphs. In certain instances, polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

Prodrugs of a Compound Disclosed Herein

In some embodiments, the compounds described herein exist in prodrug form. Disclosed herein, in certain instances, are methods of treating diseases by administering such prodrugs. Disclosed herein, in certain instances, are methods of treating diseases by administering such prodrugs as pharmaceutical compositions.

In certain instances, prodrugs are drug precursors that, following administration to an individual and subsequent absorption, are converted to an active, or a more active species via some process, such as conversion by a metabolic pathway. In certain instances, prodrugs have a chemical group present on the prodrug that renders it less active and/or confers solubility or some other property to the drug. In certain instances, once the chemical group has been cleaved and/or modified from the prodrug the active drug is generated. In certain instances, prodrugs are useful because, in some situations, they are easier to administer than the parent drug. By way of non-limiting example, they are bioavailable by oral administration whereas the parent is not, or they have improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug is a short peptide (polyamino acid) bonded to an acid group where the peptide is metabolized to reveal the active moiety. For examples of prodrugs see Bundgaard, "Design and Application of Prodrugs" Chapter 5, 113-191 in *A Textbook of Drug Design and Development*, Krosgaard-Larsen et al., (Eds.), 1991; Bundgaard, A. (Ed.), *Design of Prodrugs*, Elsevier, 1985 and Bundgaard, H., *Advanced Drug Delivery Reviews,* 1992, 8, 1-38, each of which is incorporated herein by reference for such disclosure.)

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Prodrug derivatives of compounds described herein are prepared by any suitable method (for further details see Saulnier et al., *Bioorganic and Medicinal Chemistry Letters,* 1994, 4, 1985, which is herein incorporated by reference for such disclosure). By way of example only, in certain instances, appropriate prodrugs are prepared by reacting a non-derivatized compound with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for derivatives or active compounds.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of a compound disclosed herein. By way of non-limiting example, amino acid residues include the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound disclosed herein.

In some embodiments, pharmaceutically acceptable prodrugs of the compounds described herein are esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In certain instances, compounds having free amino, amido, hydroxy or carboxylic groups are converted into prodrugs. For instance, free carboxyl groups are derivatized as amides or alkyl esters. All of these prodrug moieties incorporate groups including but not limited to ether, amine and carboxylic acid functionalities.

Hydroxy prodrugs include esters, such as but not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, (see Fleisher, et al. *Advanced Drug Delivery Reviews* 1996, 19, 115).

Amine derived prodrugs include, but are not limited to the following groups and combinations of groups:

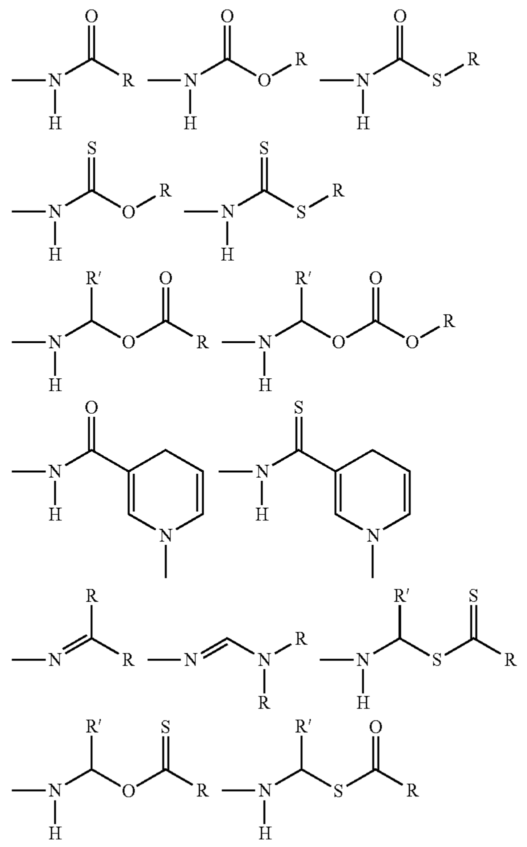

-continued

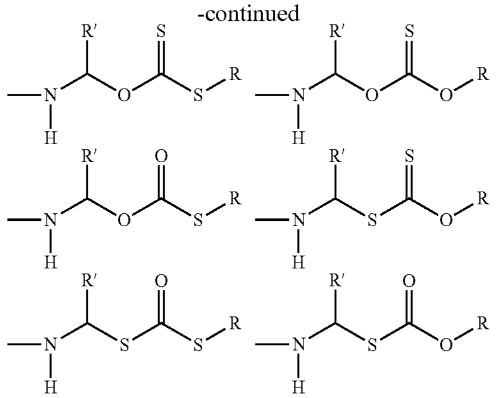

as well as sulfonamides and phosphonamides.

In certain instances, sites on any aromatic ring portions are susceptible to various metabolic reactions, therefore incorporation of appropriate substituents on the aromatic ring structures, can reduce, minimize or eliminate this metabolic pathway.

Pharmaceutical Compositions

Described herein are pharmaceutical compositions comprising a compound disclosed herein. In some embodiments, the pharmaceutical compositions comprise an effective amount of a compound disclosed herein, or a pharmaceutically acceptable salt, ester, prodrug, solvate, hydrate or derivative thereof. In some embodiments, the pharmaceutical compositions comprise an effective amount of a compound disclosed herein, or a pharmaceutically acceptable salt, ester, prodrug, solvate, hydrate or derivative thereof and a pharmaceutically acceptable carrier. In some embodiments, the pharmaceutical compositions are for the treatment of disorders (e.g. HIV infection). In some embodiments, the pharmaceutical compositions are for the treatment of disorders in a mammal. In some embodiments, the pharmaceutical compositions are for the treatment of disorders in a human.

Reverse Transcriptase Modulation

Also described herein are methods of modulating reverse transcriptase activity by contacting reverse transcriptase with an amount of a compound disclosed herein sufficient to modulate the activity of reverse transcriptase. As used herein, modulate means inhibiting or activating reverse transcriptase activity. Disclosed herein, in certain instances, are methods of inhibiting reverse transcriptase activity by contacting reverse transcriptase with an amount of a compound disclosed herein sufficient to inhibit the activity of reverse transcriptase. Disclosed herein, in certain instances, are methods of inhibiting reverse transcriptase activity in a solution by contacting said solution with an amount of a compound disclosed herein sufficient to inhibit the activity of reverse transcriptase in said solution. Disclosed herein, in certain instances, are methods of inhibiting reverse transcriptase activity in a cell by contacting the cell with an amount of a compound described herein sufficient to inhibit the activity of reverse transcriptase in said cell. Disclosed herein, in certain instances, are methods of inhibiting reverse transcriptase activity in a tissue by contacting said tissue with an amount of a compound described herein sufficient to inhibit the activity of reverse transcriptase in said tissue. Disclosed herein, in certain instances, are methods of inhibiting reverse transcriptase activity in an organism by contacting said organism with an amount of a compound described herein sufficient to inhibit the activity of reverse transcriptase in said organism. Disclosed herein, in certain instances, are methods of inhibiting reverse transcriptase activity in an animal by contacting said animal with an amount of a compound described herein sufficient to inhibit the activity of reverse transcriptase in said animal. Disclosed herein, in certain instances, are methods of inhibiting reverse transcriptase activity in a mammal by contacting said mammal with an amount of a compound described herein sufficient to inhibit the activity of reverse transcriptase in said mammal. Disclosed herein, in certain instances, are methods of inhibiting reverse transcriptase activity in a human by contacting said human with an amount of a compound described herein sufficient to inhibit the activity of reverse transcriptase in said human.

In some embodiments, the reverse transcriptase is an HIV reverse transcriptase. In some embodiments, the reverse transcriptase is an HIV-1 reverse transcriptase. In some embodiments, the reverse transcriptase is an HIV-2 reverse transcriptase. In some embodiments, the reverse transcriptase is a wild type reverse transcriptase. In some embodiments, the reverse transcriptase is a mutated reverse transcriptase.

Diseases

Described herein are methods of treating a disease in an individual suffering from said disease comprising administering to said individual an effective amount of a composition comprising a compound disclosed herein or a pharmaceutically acceptable salt, solvate, polymorph, ester, tautomer or prodrug thereof.

Also described herein are methods of preventing or delaying onset of a disease in an individual at risk for developing said disease comprising administering to said individual an effective amount to prevent or delay onset of said disease, of a composition comprising a compound disclosed herein or a pharmaceutically acceptable salt, solvate, polymorph, ester, tautomer or prodrug thereof.

The methods disclosed herein include the prophylaxis or treatment of any disease or disorder in which reverse transcriptase plays a role including, without limitation, reverse transcriptase in a human, or other mammal. The methods disclosed herein include the use of a compound disclosed herein for the manufacture of a medicament for treating such diseases or disorders. Further, the methods disclosed herein include the administration to a human of an effective amount of a compound disclosed herein for treating any such disease or disorder.

In some embodiments, individuals that are treated with the compounds described herein, or a pharmaceutically acceptable salt, ester, prodrug, solvate, hydrate or derivative of said compounds, have been diagnosed as having a viral infection.

Viral Infections

Disclosed herein are methods of treatment of viral infections, and/or preventing or delaying the onset of conditions related to viral. In some embodiments, a compound described herein is used to treat infections or conditions associated with viruses, including, but not limited to, human immunodeficiency viruses 1 and 2 (HIV-1 and HIV-2) including drug resistant strains, human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposis sarcoma-associated virus) and flaviviruses, including Yellow Fever virus, Dengue virus, Japanese Encephalitis and West Nile viruses. In some embodiments, a compound disclosed herein is used to treat HIV infections. In addition, in some embodiments, a compound disclosed herein is used to prevent and/or reduce the likelihood of a viral infection such as an HIV infection or a condition which occur secondary to a viral infection, such as AIDS, EBV-related lymphoma or HHV-8 associated cancer (sarcoma) will actually occur.

HIV and AIDS

In certain instances, the human immunodeficiency virus (HIV), particularly type-1 (HIV-1) and type-2 (HIV-2) strains, is the causative agent of acquired immunodeficiency syndrome (AIDS). In certain instances, individuals infected with HIV are initially asymptomatic but eventually undergo the gradual destruction of the immune system, (particularly $CD4^+$ T-cells), with a resultant debilitating and ultimately fatal susceptibility to opportunistic infections. In certain instances, prior to the onset of AIDS, infected individuals experience a precursor AIDS-related complex (ARC), a syndrome characterized by symptoms such as persistent generalized lymphadenopathy, fever and weight loss.

In certain instances, replication of HIV in a host cell requires integration of the HIV genome (which encodes protein precursors processed by the viral protease to produce the protease, reverse transcriptase, endonuclease/integrase and mature structural proteins of the virus core) into the host cell's DNA. In certain instances, HIV replication requires transcription of the viral RNA genome into DNA, via the reverse transcriptase (RT) enzyme.

In certain instances, reverse transcriptase has multiple enzymatic functions. In certain instances, the enzyme acts as an RNA-dependent DNA polymerase, as a ribonuclease, and/or as a DNA-dependent DNA polymerase. In its role as an RNA-dependent DNA polymerase, in certain instances, RT transcribes a single-stranded DNA copy of the viral RNA. As a ribonuclease, in certain instances, RT destroys the original viral RNA and frees the DNA just produced from the original RNA. As a DNA-dependent DNA polymerase, in certain instances, RT makes a second, complementary DNA strand using the first DNA strand as a template. In certain instances, the two strands form double-stranded DNA, which is integrated into the host cell's genome by the integrase enzyme.

Two general classes of reverse transcriptase inhibitors have been identified, namely the nucleoside reverse transcriptase inhibitors (NRTI) and the non-nucleoside reverse transcriptase inhibitors (NNRTI).

In certain instances, NNRTIs reversibly bind non-substrate binding sites on the HIV reverse transcriptase thereby altering the shape of the active site or blocking polymerase activity. (Buckheit, *Expert Opin. Investig. Drugs,* 2001, 10(8), 1423-1442). In certain instances, HIV has a relatively high mutation rate. In certain instances, strains of HIV have emerged with marked resistance reverse transcriptase inhibitors. In certain instances, resistance to RT inhibitors results from a mutation that occurs in the RT segment of the pol gene. Mutant strains of HIV include, but are not limited to, K103N (e.g., K103N-P225H, K103N-V108I, K103N-K101Q, K103N-L100I, K103N-F227L, K103N-Y188L and K103N-G190A), Y181C, K101E, G190S/A/E, Y188L/C, and V106I-Y188L.

Modes of Administration and Dosage Forms

In some embodiments, the compounds and compositions described herein are administered either alone or in combination with pharmaceutically acceptable carriers, excipients or diluents, in a pharmaceutical composition, according to standard pharmaceutical practice. In some embodiments, administration of the compounds and compositions described herein is effected by any method that enables delivery of the compounds to the site of action. These methods include, though are not limited to, delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration. In some embodiments, the most suitable route depends upon, for example, the condition and disorder of the recipient. In some embodiments, the compounds and compositions described herein are administered orally. For formulation and administration techniques see, for example, Goodman et al., in "Goodman and Gilman's: The Pharmacological Basis of Therapeutics", 9th edition, McGraw-Hill, New York, N.Y., 1996 and Gennaro, (Ed.), in "Remington's Pharmaceutical Sciences", 18th edition, Mack Publishing Co., Easton, Pa., 1990, all of which are herein incorporated by reference for such disclosure). In some embodiments, the pharmaceutical compounds and compositions described herein are in unit dosage forms suitable for single administration of precise dosages. In some embodiments, the pharmaceutical compounds and compositions are presented in multi-dose form in multi-dose containers with one or more added preservatives as required.

In some embodiments, the compounds described herein are administered locally to the area in need of treatment, by for example, local infusion during surgery, topical application such as creams or ointments, injection, catheter, or implant, said implant made for example, out of a porous, non-porous, or gelatinous material, including membranes, such as sialastic membranes, or fibers. In some embodiments, administration is also by direct injection at the site of a diseased tissue or organ.

In some embodiments, the compounds and pharmaceutical compositions described herein are in a form suitable for oral administration. By way of non-limiting example, oral preparations include tablets, troches, lozenges, pills, powders, granules, cachets, capsules including push-fit capsules made of gelatin, as well as soft, sealed capsules made of gelatin and a plasticizer, such as glycerol or sorbitol. Such forms are typically presented as discrete units containing a predetermined amount of the active ingredient. Other pharmaceutical preparations which are used orally include, but are not limited to, syrups, elixirs, solutions or suspensions in aqueous or non-aqueous liquids, oil-in-water liquid emulsions or water-in-oil liquid emulsions. In some embodiments, such preparations are presented in discrete, single-unit dosage forms suitable for single administration of precise dosages containing a predetermined amount of the active ingredient, or in multi-unit form in multi-dose containers with one or more added preservatives as required. In some embodiments, tablets are prepared by any suitable method (e.g., compression or molding, optionally with one or more accessory ingredients). In some embodiments, compressed tablets are prepared by compressing in a suitable machine the active ingredient in a free-flowing form such as a powder or granules, optionally mixed with binders, inert diluents, or lubricating, surface active or dispersing agents. In some embodiments, molded tablets are made by molding in a suitable machine a mixture of the powdered compound moistened with an inert liquid diluent. In some embodiments, the tablets are coated or scored. In some embodiments, tablets are formulated so as to provide immediate, controlled release (e.g., slow release, extended release, delayed release, continuous release, or timed release) of the active ingredient therein. In some embodiments, push-fit capsules contain the active ingredients in admixture with filler such as lactose, binders such as starches, and/or lubricants such as talc or magnesium stearate and, optionally, stabilizers. In some embodiments, a soft capsule is used, wherein the active compound is dissolved or suspended in suitable liquids, such as fatty oils, liquid paraffin, or liquid polyethylene glycols. In some embodiments, stabilizers are added. In some embodiments, dragee cores are provided with suitable coatings. In some embodiments, concentrated sugar solutions are used, which optionally contain gum arabic, talc, polyvinyl pyrrolidone, carbopol gel, polyethylene glycol, and/or titanium dioxide, lacquer solutions, and suitable organic solvents or solvent mixtures. In some embodiments, dyestuffs or pigments are added to the tablets or Dragee coatings for identification or to characterize different combinations of active compound doses. In some embodiments, pharmaceutical compositions intended for oral administration contain one or more sweetening, flavoring or coloring agents in order to provide palatable and elegant preparations.

In some embodiments, the compounds described herein are administered parenterally. In some embodiments, pharmaceutical formulations used for parenteral administration include aqueous and non-aqueous sterile solutions, suspensions or emulsions of one or more active compounds in sterile aqueous or oily vehicles, such as, though not limited to water, aqueous propylene glycol, dextrose solutions and the like. In some embodiments, such dosage forms are buffered. In some embodiments, the compositions contain formulatory agents such as though not limited to suspending, dispersing, thickening and stabilizing agents, antioxidants, buffers, bacteriostats and the like. In some embodiments, formulatory agents useful for rendering the formulation isotonic with the blood of the intended recipient are employed. Suitable lipophilic solvents or vehicles include fatty oils such as sesame oil, or synthetic fatty acid esters, such as ethyl oleate or triglycerides, or liposomes. In some embodiments, aqueous injection suspensions contain substances which increase the viscosity of the suspension, such as sodium carboxymethyl cellulose, sorbitol, or dextran. In some embodiments, the suspension contains suitable stabilizers or agents which increase the solubility of the compounds to allow for the preparation of highly concentrated solutions. In some embodiments, pharmaceutical preparations are formulated for parenteral administration by injection, for example by bolus injection or continuous infusion. In some embodiments, formulations for parenteral administration are presented in unit dosage form, suitable for single administration of precise dosages, for example in sealed containers, ampoules or vials. In some embodiments, the formulations for parenteral administration are presented in multi-dose form in multi-dose containers with one or more added preservatives as required. In some embodiments, the formulations for parenteral administration are stored in powder form or in a freeze-dried (lyophilized) condition requiring the addition of the sterile liquid carrier, for example, saline or sterile pyrogen-free water, immediately prior to use. In some embodiments, extemporaneous injection solutions and suspensions are prepared from sterile powders, granules and tablets of the kind previously described.

In some embodiments, pharmaceutical preparations are also formulated as a depot preparation. In some embodiments, the formulations are administered by implantation (for example subcutaneously or intramuscularly) or by intramuscular injection. Thus, for example, the compounds are formulated with suitable polymeric or hydrophobic materials (for example as an emulsion in an acceptable oil) or ion exchange resins, or as sparingly soluble derivatives, for example, as a sparingly soluble salt.

In some embodiments, the compositions are formulated for buccal or sublingual administration. In some embodiments, the compositions take the form of tablets, lozenges, pastilles, or gels. In some embodiments, the compositions comprise a flavoring agent (e.g., sucrose, acacia, or tragacanth).

In some embodiments, pharmaceutical preparations are also formulated in rectal compositions such as suppositories or retention enemas, e.g., containing conventional suppository bases such as cocoa butter, polyethylene glycol, or other glycerides.

In some embodiments, pharmaceutical preparations are administered topically, that is by non-systemic administration. In some embodiments, pharmaceutical preparations are administered externally to the epidermis or the buccal cavity. In some embodiments, pharmaceutical preparations are administered into the ear, eye and nose, such that the compound does not significantly enter the blood stream. In contrast, systemic administration refers to oral, intravenous, intraperitoneal and intramuscular administration.

Pharmaceutical preparations suitable for topical administration include, but are not limited to, liquid or semi-liquid preparations suitable for penetration through the skin to the site of inflammation such as gels, liniments, lotions, creams, ointments or pastes, and drops suitable for administration to the eye, ear or nose. In some embodiments, the active ingredient comprises, for topical administration, from 0.001% to 10% w/w, for instance from 1% to 2% by weight of the formulation. In some embodiments, the active ingredient comprises as much as 10% w/w but preferably will comprise less than 5% w/w, more preferably from 0.1% to 1% w/w of the formulation.

In some embodiments, pharmaceutical preparations are administered by inhalation. In some embodiments, the pharmaceutical preparations are delivered from an insufflator, nebulizer pressurized packs or other suitable means of delivering an aerosol spray. In certain instances, pressurized packs comprise a suitable propellant such as dichlorodifluoromethane, trichlorofluoromethane, dichlorotetrafluoroethane, carbon dioxide or other suitable gas. In certain instances, such as with a pressurized aerosol, the dosage unit is determined by providing a valve to deliver a metered amount.

In some embodiments, such as administration by inhalation or insufflation, the pharmaceutical preparations take the form of a dry powder composition. In some embodiments, the pharmaceutical preparation comprises a powder mix of the compound and a suitable powder base such as lactose or starch. In some embodiments, the powder composition is presented in unit dosage form, in for example, capsules, cartridges, gelatin or blister packs from which the powder is administered with the aid of an inhalator or insufflator.

Formulations

In some embodiments, the pharmaceutical compositions described herein contain a compound described herein in admixture with one or more non-toxic, pharmaceutically acceptable excipients (such as, though not limited to pharmaceutical carriers, excipients, adjuvants, and the like, as well as other medicinal or pharmaceutical agents) which are suitable for the manufacture and administration of the composition, formulated as appropriate for the desirable mode of administration. In some embodiments, the pharmaceutical compositions described herein contain the active ingredient in a form suitable for oral administration, for example, as tablets, troches, lozenges, aqueous or oily suspensions, dispersible powders or granules, emulsions, hard or soft capsules, or syrups or elixirs. In some embodiments, compositions intended for oral use are prepared according to any suitable method. In some embodiments, pharmaceutical compositions disclosed herein further comprise one or more agents selected from the group consisting of sweetening agents, flavoring agents, coloring agents and preserving agents in order to provide pharmaceutically elegant and palatable preparations.

In some embodiments, the pharmaceutical compositions described herein are administered as a tablet. In some embodiments, tablets contain the active ingredient in admixture with non-toxic pharmaceutically acceptable excipients, such as though not limited to inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. In some embodiments, the tablets are un-coated or coated to mask the taste of the drug or delay disintegration and absorption in the gastrointestinal tract and thereby provide a sustained action over a longer period. Examples of coating materials include, but are not limited to, a water soluble taste masking material such as hydroxypropylmethylcellulose or hydroxypropylcellulose, or a time delay material such as ethyl cellulose, or cellulose acetate butyrate.

In some embodiments, formulations for oral use are presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

In some embodiments, the compounds or compositions described herein are delivered in a vesicle, such as a liposome. In some embodiments, the compounds and pharmaceutical compositions described herein are delivered in a controlled release system, or a controlled release system is placed in proximity of the therapeutic target. In one embodiment, a pump is used.

In some embodiments, the pharmaceutical compositions described herein are administered as an aqueous suspension. In some embodiments, the aqueous suspension comprises the active material in admixture with excipients suitable for the manufacture of aqueous suspensions. Such excipients include, but are not limited to, suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents include, but are not limited to, a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. In some embodiments, the aqueous suspensions further comprises one or more preservatives, for example ethyl, or n-propyl p-hydroxybenzoate, one or more coloring agents, one or more flavoring agents, and one or more sweetening agents, such as sucrose, saccharin or aspartame.

In some embodiments, the compositions disclosed herein further comprise a pharmaceutical carrier (e.g., inert diluents or fillers, water and various organic solvents). In some embodiments, the pharmaceutical compositions further comprise additional ingredients such as flavorings, binders, excipients and the like. By way of non-limiting example, tablets containing various excipients, such as citric acid are employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. In some embodiments, solid compositions of a similar type are also employed in soft and hard filled gelatin capsules. Preferred materials, therefore, include lactose or milk sugar and high molecular weight polyethylene glycols. In some embodiments, the aqueous suspensions or elixirs comprise various sweetening or flavoring agents, coloring matters or dyes and, if desired, emulsifying agents or suspending agents, together with diluents such as water, ethanol, propylene glycol, glycerin, or combinations thereof.

In some embodiments, a pharmaceutical composition described herein is administered as an oily suspension. In some embodiments, oily suspensions are formulated by suspending the active ingredient in a vegetable oil, for example arachis oil, olive oil, sesame oil or coconut oil, or in mineral oil such as liquid paraffin. In some embodiments, an oily suspension further comprises a thickening agent, for example beeswax, hard paraffin or cetyl alcohol. In some embodiments, an oily suspension further comprises sweetening agents such as those set forth above, and flavoring agents. In some embodiments, an oily suspension further comprises an anti-oxidant such as butylated hydroxyanisol or alpha-tocopherol.

In some embodiments, a pharmaceutical composition described herein is administered as a dispersible powder and/or as dispersible granules. In some embodiments, a dispersible powder and/or dispersible granules a combined with water to yield an aqueous suspension. In some embodiments, the dispersible powder and/or dispersible granules further comprise a dispersing or wetting agent, suspending agent and one or more preservatives. Suitable dispersing or wetting agents and suspending agents are exemplified by those already mentioned above. In some embodiments, additional excipients, for example sweetening, flavoring and coloring agents, are also present. In some embodiments, these compositions are preserved by the addition of an anti-oxidant such as ascorbic acid.

In some embodiments, the pharmaceutical compositions are also in the form of oil-in-water emulsions. In some embodiments, the oily phase is a vegetable oil, for example olive oil or arachis oil, or a mineral oil, for example liquid paraffin or mixtures of these. Suitable emulsifying agents are naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. In some embodiments, the emulsions further comprise sweetening agents, flavoring agents, preservatives and antioxidants.

In some embodiments, the pharmaceutical compositions disclosed herein are formulated as syrups and/or elixirs. In some embodiments, the pharmaceutical compositions disclosed herein further comprise sweetening agents, for example glycerol, propylene glycol, sorbitol or sucrose. Such formulations also contain a demulcent, a preservative, flavoring and coloring agents and antioxidant.

In some embodiments, the pharmaceutical compositions disclosed herein are formulated as a sterile injectable aqueous solution. In some embodiments, vehicles and solvents that are employed for such solutions include, but are not limited to, water, Ringer's solution and isotonic sodium chloride solution.

In some embodiments, the sterile injectable preparation is a sterile injectable oil-in-water microemulsion. In some embodiments, the active ingredient is dissolved in the oily phase. In some embodiments, the active ingredient is first dissolved in a mixture of soybean oil and lecithin. In some embodiments, the oil solution then introduced into a water and glycerol mixture and processed to form a microemulsion.

In some embodiments, the injectable solutions or microemulsions are introduced into an individual's blood-stream by local bolus injection. In some embodiments, the injectable solutions or microemulsions are administered in such a way as to maintain a constant circulating concentration of the instant compound (e.g., by use of a continuous intravenous delivery device). Continuous intravenous delivery devices include, but are not limited to, the Deltec CADD-PLUS™ model 5400 intravenous pump.

In some embodiments, the pharmaceutical compositions are in the form of a sterile injectable aqueous or oleagenous suspension for intramuscular and subcutaneous administration. In some embodiments, the suspension comprises dispersing or wetting agents and suspending agents which have been mentioned above.

In some embodiments, the sterile injectable preparation is a sterile injectable solution or suspension in a non-toxic parenterally-acceptable diluent or solvent. In some embodiments, the diluent or solvent is 1,3-butane diol, synthetic mono- or diglycerides, fatty acids such as oleic acid, or combinations thereof.

In some embodiments, the pharmaceutical compositions disclosed herein are also administered in the form of suppositories for rectal administration of the drug. In some embodiments, the compositions are prepared by mixing the active ingredient with a suitable non-irritating excipient which is solid at ordinary temperatures but liquid at the rectal temperature and will therefore melt in the rectum to release the drug. Such materials include, but are not limited to, cocoa butter, glycerinated gelatin, hydrogenated vegetable oils, mixtures of polyethylene glycols of various molecular weights and fatty acid esters of polyethylene glycol.

In some embodiments, the pharmaceutical compositions disclosed herein are also administered topically. In some embodiments, the pharmaceutical compositions disclosed herein are formulated as creams, ointments, jellies, solutions or suspensions, etc. As used herein, topical application includes mouth washes and gargles.

In some embodiments, the pharmaceutical compositions disclosed herein are also administered in intranasal form via topical use of suitable intranasal vehicles and delivery devices, or via transdermal routes, using any suitable transdermal skin patch. In some embodiments, the dosage administration will be continuous rather than intermittent throughout the dosage regimen.

In some embodiments, the formulations disclosed herein are presented in unit dosage form and are prepared by any suitable method. In some embodiments, the methods include the step of bringing into association a compound disclosed herein or a pharmaceutically acceptable salt, ester, prodrug or solvate thereof ("active ingredient") with the carrier which constitutes one or more accessory ingredients. In some embodiments, the formulations are prepared by uniformly and intimately bringing into association the active ingredient with liquid carriers or finely divided solid carriers or both and then, if necessary, shaping the product into the desired formulation.

It should be understood that in addition to the ingredients particularly mentioned above, the compounds and compositions described herein include other agents conventional in the art having regard to the type of formulation in question.

Doses

The amount of pharmaceutical composition administered depends on a variety of factors. In some embodiments, the amount will firstly be dependent on the mammal being treated. In the instances where pharmaceutical compositions are administered to a human individual, the daily dosage will normally be determined by the prescribing physician with the dosage generally varying according to the age, sex, diet, weight, general health and response of the individual, the severity of the individual's symptoms, the precise indication or condition being treated, the severity of the indication or condition being treated, time of administration, route of administration, the disposition of the composition, rate of excretion, drug combination, and the discretion of the prescribing physician. In some embodiments, the route of administration varies depending on the condition and its severity. In some embodiments, the pharmaceutical composition is in unit dosage form. In some embodiments, the preparation is subdivided into unit doses containing appropriate quantities of the active component, e.g., an effective amount to achieve the desired purpose. In some embodiments, treatment is initiated with smaller dosages which are less than the optimum dose of the compound. In some embodiments, the dosage is increased by small amounts until the optimum effect under the circumstances is reached. In some embodiments, the total daily dosage is divided and administered in portions during the day. The amount and frequency of administration of the compounds described herein, and if applicable other therapeutic agents and/or therapies, will be regulated according to the judgment of the attending clinician (physician) considering such factors as described above.

In some embodiments, the dosage is between about 0.001 mg/kg of body weight to about 100 mg/kg of body weight per day (administered in single or divided doses), more preferably at least about 0.1 mg/kg of body weight per day. In some embodiments, the dosage is from about 0.01 mg to about 7000 mg of compound, and preferably includes, e.g., from about 0.05 mg to about 2500 mg. In some embodiments, the quantity of active compound in a unit dose of preparation is varied or adjusted from about 0.1 mg to 1000 mg, preferably from about 1 mg to 300 mg, more preferably 10 mg to 200 mg, according to the particular application. In some instances, dosage levels below the lower limit of the aforesaid range are more than adequate, while in other cases still larger doses are employed without causing any harmful side effect, e.g. by dividing such larger doses into several small doses for administration throughout the day. In some embodiments, the amount administered will vary depending on the particular $IC_{50}$ value of the compound used. In combinational applications in which the compound is not the sole therapy, it is possible to administer lesser amounts of compound and still have therapeutic or prophylactic effect.

Combination Therapies

In some embodiments, a compound described herein or a pharmaceutically acceptable salt, solvate, polymorph, ester, tautomer or prodrug thereof is administered as a sole therapy. In some embodiments, a compound described herein or a pharmaceutically acceptable salt, solvate, polymorph, ester, tautomer or prodrug thereof is administered in combination with another active agent.

In some embodiments, the therapeutic effectiveness of one of the compounds described herein is enhanced by administration of an adjuvant (i.e., by itself the adjuvant only have minimal therapeutic benefit, but in combination with another therapeutic agent, the overall therapeutic benefit to the individual is enhanced). Or, by way of example only, the benefit experienced by an individual is increased by administering one of the compounds described herein with another therapeutic agent (which also includes a therapeutic regimen) that also has therapeutic benefit. By way of example only, in a treatment for viral infection involving administration of one of the compounds described herein, increased therapeutic benefit result by also providing the individual with another therapeutic agent for viral infection. Or, by way of example only, if one of the side effects experienced by an individual upon receiving one of the compounds described herein is nausea, then it are appropriate to administer an anti-nausea agent in combination with the compound. Or, the additional therapy or therapies include, but are not limited to physiotherapy, psychotherapy, radiation therapy, application of compresses to a diseased area, rest, altered diet, and the like. In some embodiments, regardless of the disease, disorder or condition being treated, the overall benefit experienced by the individual is additive of the two therapies or therapeutic agents or the individual experience a synergistic benefit.

In the instances where the compounds described herein are administered with other active agents, the compounds described herein need not be administered in the same pharmaceutical composition as other therapeutic agents. In some embodiments, the compounds disclosed herein and an additional active agent are administered by a different route. For example, the compounds/compositions are administered orally to generate and maintain good blood levels thereof, while the other active agent is administered intravenously. In some embodiments, the compounds described herein and additional active agent are administered concurrently (e.g., simultaneously, essentially simultaneously or within the same treatment protocol), sequentially or dosed separately. In some embodiments, the dosage, modes of administration and times of administration are modified by the skilled clinician. The particular choice of compound and other therapeutic agent will depend upon the diagnosis of the attending physicians and their judgment of the condition of the individual and the appropriate treatment protocol.

In some embodiments, the compounds described herein or a pharmaceutically acceptable salt, solvate, polymorph, ester, tautomer or prodrug thereof are administered in combination with an antiviral therapeutic. In some embodiments, the compounds described herein or a pharmaceutically acceptable salt, solvate, polymorph, ester, tautomer or prodrug thereof are administered in combination with an anti HIV or AIDS therapeutic. In some embodiments, the compounds described herein or a pharmaceutically acceptable salt, solvate, polymorph, ester, tautomer or prodrug thereof are administered in combination with reverse transcriptase inhibitors, viral protease inhibitors, fusion inhibitors, cytokines, cytokine inhibitors, glycosylation inhibitors, viral mRNA processing inhibitors, entry inhibitors, integrase inhibitors or maturation inhibitors. In some embodiments, the compounds described herein or a pharmaceutically acceptable salt, solvate, polymorph, ester, tautomer or prodrug thereof are administered in combination with adefovir, abacavir, amprenavir, apricitabine, atazanavir, bevirimat, darunavir, delavirdine, didanosine, efavirenz, emtricitabine, elvitegravir, enfuvirtide, etravirine, fosamprenavir, fuseon, indinavir, lamivudine, lopinavir, maraviroc, nelfinavir, nevirapine, racivir, raltegravir, reverset, ritonavir, saquinavir, stavudine, tenofovir, tipranavir, vicriviroc, zalcitabine, zidovudine, interferon-α, interferon-β or interferon-γ, or a combination of two or more thereof. In some embodiments, the compounds described herein or a pharmaceutically acceptable salt, solvate, polymorph, ester, tautomer or prodrug thereof are administered in combination with an anti HIV or AIDS therapeutic presently in clinical trials or in development.

Kits

In some embodiments, the compounds, compositions and methods described herein provide kits for the treatment of disorders, such as the ones described herein. In some embodiments, these kits comprise a compound, compounds or compositions described herein in a container and, optionally, instructions teaching the use of the kit according to the various methods and approaches described herein. In some embodiments, such kits also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. In some embodiments, such information is based on the results of various studies, for example, studies using experimental animals involving in vivo models and studies based on human clinical trials. In some embodiments, kits described herein are provided, marketed and/or promoted to health providers, including physicians, nurses, pharmacists, formulary officials, and the like. In some embodiments, the kits are marketed directly to the consumer.

In some embodiments, the compounds described herein are utilized for diagnostics and as research reagents. For example, the compounds described herein, either alone or in combination with other compounds, are used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. In certain instances, these analyses are performed on stimulated or unstimulated cells and in the presence or absence of other compounds which affect expression patterns.

In some embodiments, the compounds and formulations disclosed herein are useful for veterinary treatment of companion animals, exotic animals and farm animals, including mammals, rodents, and the like. More preferred animals include horses, dogs, and cats.

The examples and preparations provided below further illustrate and exemplify the compounds claimed herein and methods of preparing such compounds. It is to be understood that the scope of the present disclosure is not limited in any way by the scope of the following examples and preparations. In the following examples molecules with a single chiral center, unless otherwise noted, exist as a racemic mixture.

Those molecules with two or more chiral centers, unless otherwise noted, exist as a racemic mixture of diastereomers.

EXAMPLES

I. Chemical Syntheses

Example 1

4-(4-(2,6-Dimethyl-4-(pyridin-4-yl)phenoxy)-5-methyl-5H-pyrrolo[3,2-d]pyrimidin-2-ylamino)benzonitrile

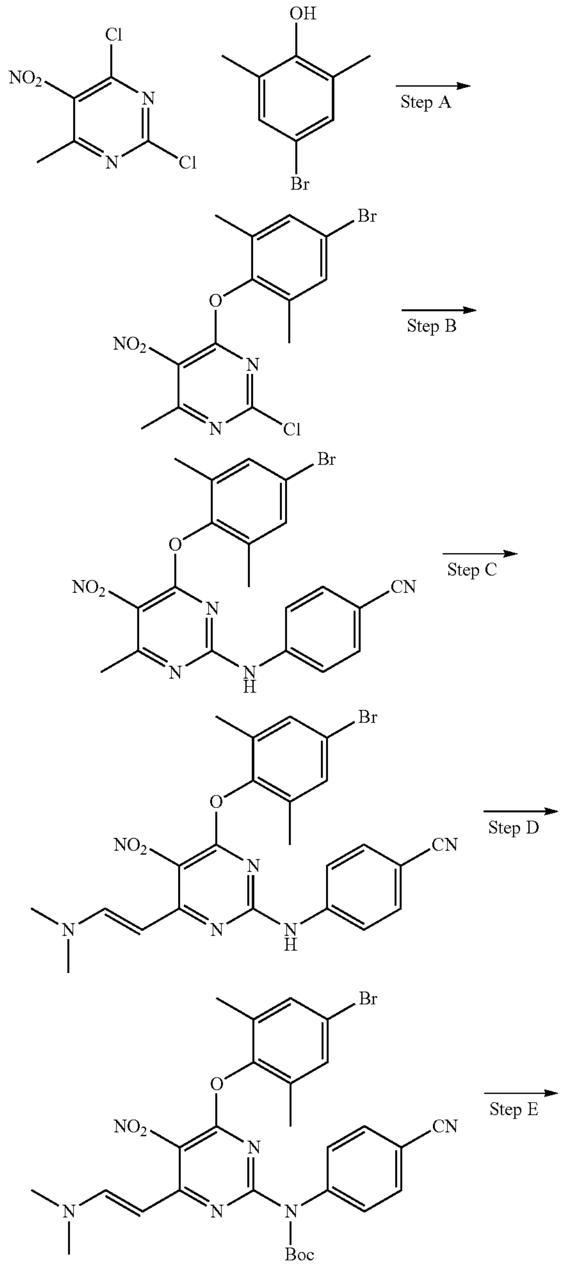

-continued

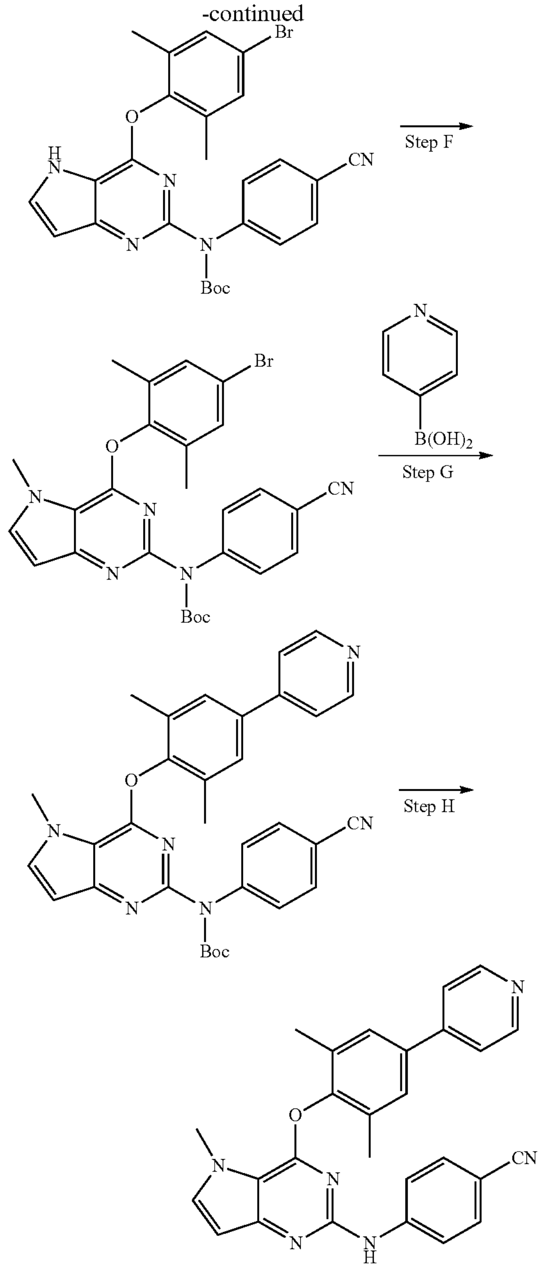

Step A: 4-(4-bromo-2,6-dimethylphenoxy)-2-chloro-6-methyl-5-nitropyrimidine

A solution of LiHMDS in THF (1M, 77 ml, 77 mmol) was added at −78° C. to a mixture of 2,6-dimethoxy-4-bromophenol (14.07 g, 70 mmol) in THF (100 ml) over 15 minutes. The mixture was stirred for an additional 2 hours. Phenoxide salt was observed as solid suspension. The mixture was cooled with liquid nitrogen to a temperature around −100° C. and then a solution of 2,6-dichloro-4-methyl-5-nitropyrimidine (17.47 g, 84 mmol) in THF (50 ml) was added rapidly to the mixture, which turned dark red. The reaction was kept at a temperature around −100° C. for 1 hour. After warming to room temperature, the mixture was filtered and the solid was washed with ethanol to yield 16.75 g of the title product. The filtrate was concentrated and crystallized to obtain an additional 5.60 giving a total amount of 22.35 g of desired compound (60 mmol, 85%). $^1$H NMR ($CDCl_3$, 400 MHz) δ 2.11 (s, 6H), 2.63 (s, 3H), 7.27 (s, 2H).

Step B: 4-(4-(4-bromo-2,6-dimethylphenoxy)-6-methyl-5-nitropyrimidin-2-ylamino)benzonitrile A mixture of 4-(4-bromo-2,6-dimethylphenoxy)-2-chloro-6-methyl-5-nitropyrimidine (22.0 g, 59.3 mmol), 4-aminobenzonitrile (7.7 g. 65.2 mmol) and pyridine (4.8 ml, 59.3 mmol) in THF (300 ml) was heated to 80° C. for 10 hours. The reaction mixture was dissolved in methanol, washed with brine and extracted with ethyl acetate. The organic layer was washed twice with brine, dried over $MgSO_4$ and concentrated to dryness. The solid was washed with a mixture of hexane:ethyl acetate (80:20) before filtration. After filtration, the solid was washed again with methanol. The filtrate was concentrated again until dryness. The second round of precipitation was collected following the same procedure. The operation was repeated until total product was recovered. The combined solids were recrystallized from acetone to obtain the title compound (22.72 g, 50 mmol, 84%). $^1$H NMR ($CDCl_3$, 400 MHz) δ 2.14 (s, 6H), 2.60 (s, 3H), 7.22 (d, J=8.8 Hz, 2H), 7.26 (d, J=8.9, 2H), 7.27 (s, 2H), 12.75 (bs, 1H).

Step C: (E)-4-(4-(4-bromo-2,6-dimethylphenoxy)-6-(2-(dimethylamino)vinyl)-5-nitropyrimidin-2-ylamino)benzonitrile To a homogenous mixture of 4-(4-(4-bromo-2,6-dimethylphenoxy)-6-methyl-5-nitropyrimidin-2-ylamino)benzonitrile (22.71 g, 50 mmol) in DMF (300 ml) was added tert-butoxybis (dimethylamino) methane (12.39 ml, 60 mmol) over 15 minutes. The mixture was stirred at room temperature overnight. DMF was partially removed. The residue was washed with water and extracted with ethyl acetate (×3). The organic layers were combined, washed with brine, dried ($MgSO_4$) and concentrated to dryness yielding to the desired product as a yellow solid (23.41 g, 46.0 mmol, 92%) which was used in next step without further purification. $^1$H NMR ($CDCl_3$, 400 MHz) δ 2.14 (s, 6H), 2.98 (bs, 3H), 3.13 (bs, 3H), 5.54 (d, J=12.4 Hz, 1H), 7.03 (s, 1H), 7.27 (d, J=8.6, 2H), 7.28 (s, 2H), 7.40 (d, J=8.6, 2H), 8.03 (d, J=12.2 Hz, 1H).

Step D: (E)-tert-butyl 4-(4-bromo-2,6-dimethylphenoxy)-6-(2-(dimethylamino)vinyl)-5-nitropyrimidin-2-yl(4-cyanophenyl)carbamate To a heterogeneous mixture of (E)-4-(4-(4-bromo-2,6-dimethylphenoxy)-6-(2-(dimethylamino)vinyl)-5-nitropyrimidin-2-ylamino)benzonitrile (23.41 g, 46.0 mmol), potassium carbonate (8.88 g, 64.4 mmol), 4-dimethylaminopyridine (0.56 g, 4.6 mmol) in dichloromethane (300 ml) was added a solution of $Boc_2O$ (11.43 g, 50.6 mmol) in DCM (100 ml) over 30 minutes. The mixture was stirred for 3 hours at room temperature. The reaction mixture was washed with brine and extracted with dichloromethane (×3). The organic layer were combined, dried over $MgSO_4$ and concentrated to dryness to yield to the title compound as a yellow solid (28.0 g, 45.9 mmol, 99%), which was used for the next step without further purification.

Step E: tert-butyl 4-(4-bromo-2,6-dimethylphenoxy)-5H-pyrrolo[3,2-d]pyrimidin-2-yl(4-cyanophenyl) carbamate A solution of $Na_2S_2O_4$ (40.04 g, 230 mmol) in water (100 ml) was added to a solution of (E)-tert-butyl 4-(4-bromo-2,6-dimethylphenoxy)-6-(2-(dimethylamino)vinyl)-5-nitropyrimidin-2-yl(4-cyanophenyl)carbamate (28.0 g, 45.9 mmol) in THF (300 ml). The mixture was stirred at room temperature of 2 days. The reaction mixture was concentrated. The residue was washed with water and extracted with ethyl acetate. The organic layer was concentrated and the product was obtained by crystallization from a mixture of water and methanol (18.15 g (mmol, 74%). $^1$H NMR ($CDCl_3$, 400 MHz) δ 1.33 (s, 9H), 2.05 (s, 6H), 6.73 (d, J=3.8 Hz, 1H), 7.18 (d, J=8.8 Hz, 2H), 7.21 (s, 2H), 7.49 (d, J=8.8, 2H), 7.55 (d, J=3.8 Hz, 1H), 9.09 (s, 1H).

Step F: tert-butyl 4-(4-bromo-2,6-dimethylphenoxy)-5-methyl-5H-pyrrolo[3,2-d]pyrimidin-2-yl(4-cyanophenyl)carbamate To a cold mixture of tert-butyl 4-(4-bromo-2,6-dimethylphenoxy)-5H-pyrrolo[3,2-d]pyrimidin-2-yl(4-cyanophenyl)carbamate (0.81 g, 1.5 mmol) in THF (5 ml) at −78° C. was added a solution of LiHMDS (1M, 2 ml, 2 mmol). The mixture was warmed to 0° C. over 2 hours and then was cooled to −78° C. Idomethane (0.37 ml, 6 mmol) was added and the mixture was warmed to room temperature over 2 hours and then stirred at this temperature for an additional 2 hours. The mixture was washed with brine, extracted with ethyl acetate (×3). The organic layers were combined dried over $MgSO_4$ and concentrated to dryness. The crude material was purified by chromatography on silica to obtain the title compound (0.782 g, 1.42 mmol, 95%). $^1$H NMR ($CDCl_3$, 400 MHz) δ 1.32 (s, 9H), 2.07 (s, 6H), 4.18 (s, 3H), 6.65 (d, J=3.8 Hz, 1H), 7.15 (d, J=8.8 Hz, 2H), 7.21 (s, 2H), 7.37 (d, J=3.8 Hz, 1H), 7.49 (d, J=8.8, 2H).

Step G: tert-butyl 4-(2,6-dimethyl-4-(pyridin-4-yl)phenoxy)-5-methyl-5H-pyrrolo[3,2-d]pyrimidin-2-yl4-cyanophenylcarbamate tert-Butyl 4-(4-bromo-2,6-dimethylphenoxy)-5-methyl-5H-pyrrolo[3,2-d]pyrimidin-2-yl(4-cyanophenyl)carbamate (400 mg, 0.729 mmol) was combined with pyridine-4-boronic acid (179 mg, 1.46 mmol) and tetrakis(triphenylphosphine)palladium(0) (84 mg, 0.0729 mmol) in a two dram vial. The vial was sealed and flushed with argon. Degassed THF (5.0 mL), and aqueous $Na_2CO_3$ (2 M, 1.5 mL, 3.0 mmol) were injected, and the mixture was agitated on a shaker at 80° C. for 10 h. The mixture was diluted with EtOAc and extracted with aqueous $Na_2CO_3$ (0.5 M, ×2). The organic layer was collected, concentrated, and the product purified by chromatography ($SiO_2$, 1:4 hexanes/EtOAc) to give the Boc protected derivative as a solid (340 mg, 85%).

Step H: 4-(4-(2,6-dimethyl-4-(pyridin-4-yl)phenoxy)-5-methyl-5H-pyrrolo[3,2-d]pyrimidin-2-ylamino)benzonitrile tert-Butyl 4-(2,6-dimethyl-4-(pyridin-4-yl)phenoxy)-5-methyl-5H-pyrrolo[3,2-d]pyrimidin-2-yl-4-cyanophenylcarbamate was treated with TFA (10 mL) at 25° C. for 2 h. TFA was evaporated, the obtained residue dissolved in EtOAc, and extracted with saturated aqueous $NaHCO_3$ (×2). The organic layer was collected, concentrated, and the product purified by chromatography ($SiO_2$, 1:4 hexanes/EtOAc) to give the title compound as a solid (277 mg, 100%). $^1$H NMR (400 MHz, $CDCl_3$-$CD_3OD$ (5:1), 25° C.) δ 8.67 (bs, 2H), 7.63 (m, 3H), 7.50 (s, 2H), 7.43 (d, J=8.8 Hz, 2H), 7.32 (d, J=3.0 Hz, 1H), 7.26 (d, J=8.7 Hz, 2H), 6.43 (d, J=2.9 Hz, 1H), 4.16 (s, 3H), 2.27 (s, 6H).

Examples 2-17

4-(4-(2,6-Dimethyl-4-($R^P$)phenoxy)-5-methyl-5H-pyrrolo[3,2-d]pyrimidin-2-ylamino)benzonitrile The compounds in the table below were prepared following the same procedures as described for example 1, steps G and H. tert-butyl 4-(4-bromo-2,6-dimethylphenoxy)-5-methyl-5H-pyrrolo[3,2-d]pyrimidin-2-yl(4-cyanophenyl)carbamate (prepared in step F, example 1 above) was coupled with the appropriate boronic acid derivative, to produce the final compounds.

| Eg | Compound Name | Boronic acid starting material | Structure | $^1$H NMR (400 MHz) 25° C. δ |
|---|---|---|---|---|
| 2 | 4-(4-(4-(3-Fluoropyridin-4-yl)-2,6-dimethylphenoxy)-5-methyl-5H-pyrrolo[3,2-d]pyrimidin-2-ylamino)benzonitrile | 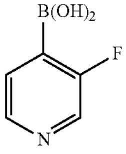 | 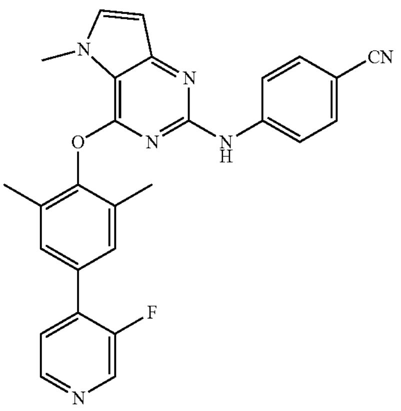 [SMILES: Cc1cc(-c2ccncc2F)cc(C)c1Oc1nc(Nc2ccc(C#N)cc2)nc2ccn(C)c12] | [a)] 8.57 (s, 1H), 8.49 (m, 1H), 7.52 (m, 1H), 7.47 (s, 2H), 7.42 (d, J = 8.9 Hz, 2H), 7.34 (d, J = 3.0 Hz, 1H), 7.30 (d, J = 9.0 Hz, 2H), 6.43 (d, J = 3.0 Hz, 1H), 4.17 (s, 3H), 2.27 (s, 6H) |
| 3 | 4-(4-(4-(2-Fluoropyridin-4-yl)-2,6-dimethylphenoxy)-5-methyl-5H-pyrrolo[3,2-d]pyrimidin-2-ylamino)benzonitrile | 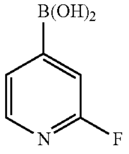 | 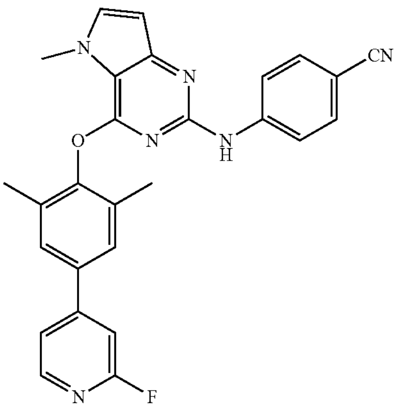 | [a)] 8.30 (d, J = 5.3 Hz, 1H), 7.53 (m, 3H), 7.47 (s, 2H), 7.43 (d, J = 9.1 Hz, 2H), 7.36 (d, J = 3.0 Hz, 1H), 7.26 (m, 3H), 6.44 (d, J = 3.0 Hz, 1H), 4.18 (s, 3H), 2.29 (s, 6H) |
| 4 | 4-(4-(4-(2,6-Difluoropyridin-4-yl)-2,6-dimethylphenoxy)-5-methyl-5H-pyrrolo[3,2-d]pyrimidin-2-ylamino)benzonitrile | 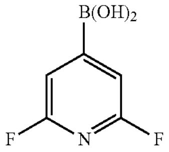 | 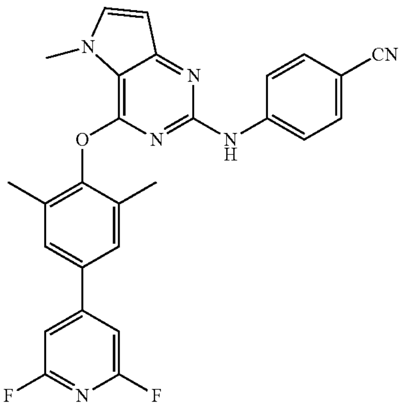 [SMILES: Cc1cc(-c2cc(F)nc(F)c2)cc(C)c1Oc1nc(Nc2ccc(C#N)cc2)nc2ccn(C)c12] | [a)] 7.46 (m, 5H), 7.30 (m, 3H), 7.08 (s, 2H), 6.45 (d, J = 3.0 Hz, 1H), 4.15 (s, 3H), 2.27 (s, 6H) |

-continued

| Eg | Compound Name | Boronic acid starting material | Structure | $^1$H NMR (400 MHz) 25° C. δ |
|---|---|---|---|---|
| 5 | 4-(4-(2-(4-Cyanophenylamino)-5-methyl-5H-pyrrolo[3,2-d]pyrimidin-4-yloxy)-3,5-dimethylphenyl) nicotinonitrile | 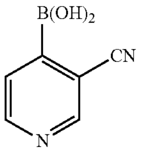 [SMILES: N#Cc1cnccc1B(O)O] | 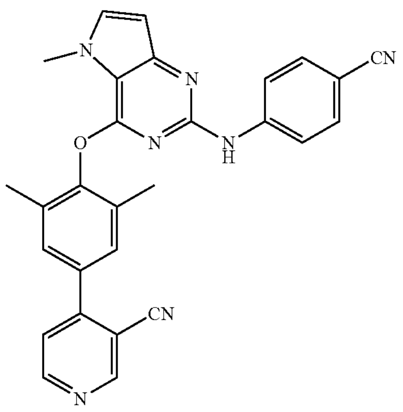 [SMILES: Cc1cc(-c2ccncc2C#N)cc(C)c1Oc1nc(Nc2ccc(C#N)cc2)nc2ccn(C)c12] | [a] 9.04 (bs, 1H) 8.90 (bs, 1H), 7.60 (s, 1H), 7.47 (m, 4H), 7.34 (m, 3H), 6.46 (s, 1H), 4.17 (s, 3H), 2.30 (s, 6H) |
| 6 | 4-(4-(2-(4-Cyanophenylamino)-5-methyl-5H-pyrrolo[3,2-d]pyrimidin-4-yloxy)-3,5-dimethylphenyl) picolinonitrile | 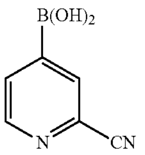 [SMILES: N#Cc1cc(B(O)O)ccn1] | 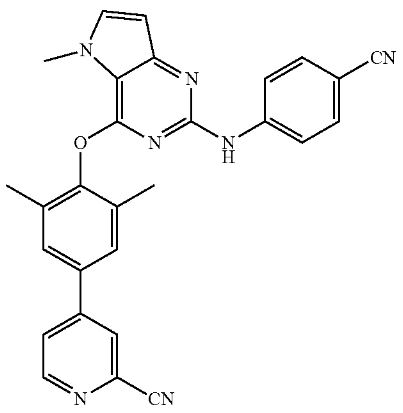 [SMILES: Cc1cc(-c2ccnc(C#N)c2)cc(C)c1Oc1nc(Nc2ccc(C#N)cc2)nc2ccn(C)c12] | [a] 8.81 (m, 1H), 8.02 (s, 1H), 7.82 (m, 1H), 7.51 (s, 2H), 7.45 (m, 2H), 7.33 (m, 1H), 7.28 (m, 2H), 6.45 (m, 1H), 4.17 (s, 3H), 2.29 (s, 6H) |
| 7 | 4-(4-(2,6-Dimethyl-4-(3-methylpyridin-4-yl)phenoxy)-5-methyl-5H-pyrrolo[3,2-d]pyrimidin-2-ylamino)benzonitrile | 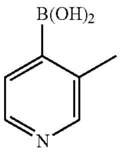 | 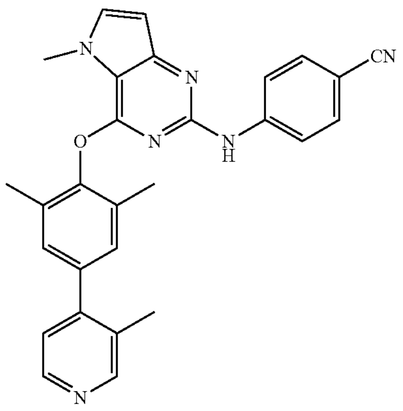 [SMILES: Cc1cnccc1-c1cc(C)c(Oc2nc(Nc3ccc(C#N)cc3)nc3ccn(C)c23)c(C)c1] | [a] 8.50 (bs, 2H), 7.48 (m, 2H), 7.35 (m, 4H), 7.20 (s, 2H), 6.44 (s, 1H), 4.18 (s, 3H), 2.41 (s, 3H), 2.27 (s, 6H) |

-continued

| Eg | Compound Name | Boronic acid starting material | Structure | $^1$H NMR (400 MHz) 25° C. δ |
|---|---|---|---|---|
| 8 | 4-(4-(2,6-Dimethyl-4-(2-methylpyridin-4-yl)phenoxy)-5-methyl-5H-pyrrolo[3,2-d]pyrimidin-2-ylamino)benzonitrile | 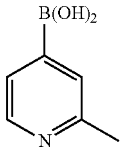 | 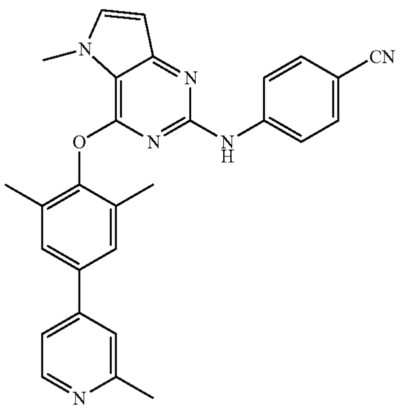 [SMILES: Cc1cc(-c2cc(C)c(Oc3nc(Nc4ccc(C#N)cc4)nc4ccn(C)c34)c(C)c2)ccn1] | [a] 8.53 (m, 1H), 7.48 (m, 3H), 7.41 (m, 4H), 7.32 (m, 1H), 7.26 (m, 2H), 6.43 (m, 1H), 4.16 (s, 3H), 2.68 (s, 3H), 2.27 (s, 6H) |
| 9 | 4-(4-(4-(3-Methoxypyridin-4-yl)-2,6-dimethylphenoxy)-5-methyl-5H-pyrrolo[3,2-d]pyrimidin-2-ylamino)benzonitrile | 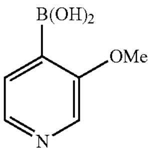 [SMILES: COc1cnccc1B(O)O] | 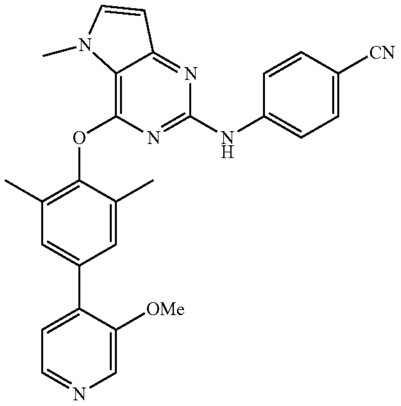 [SMILES: COc1cnccc1-c1cc(C)c(Oc2nc(Nc3ccc(C#N)cc3)nc3ccn(C)c23)c(C)c1] | [a] 8.39 (bs, 1H), 8.32 (bs, 1H), 7.42 (m, 2H), 7.40 (m, 1H), 7.33 (m, 5H), 6.43 (d, J = 3.1 Hz, 1H), 4.16 (s, 3H), 4.05 (s, 3H), 2.25 (s, 6H) |
| 10 | 4-(4-(4-(2-Methoxypyridin-4-yl)-2,6-dimethylphenoxy)-5-methyl-5H-pyrrolo[3,2-d]pyrimidin-2-ylamino)benzonitrile | 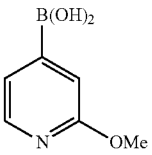 [SMILES: COc1cc(B(O)O)ccn1] | 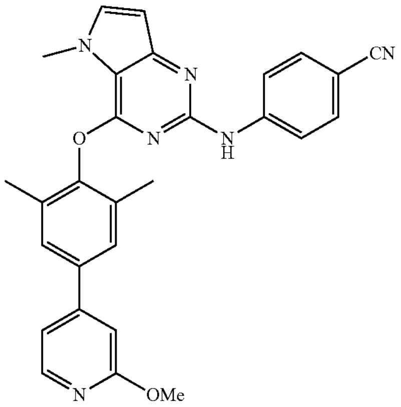 [SMILES: COc1cc(-c2cc(C)c(Oc3nc(Nc4ccc(C#N)cc4)nc4ccn(C)c34)c(C)c2)ccn1] | [a] 8.25 (bs, 1H), 7.47 (s, 2H), 7.42 (d, J = 8.6 Hz, 2H), 7.32 (m, 1H), 7.27 (d, J = 8.7 Hz, 2H), 7.20 (d, J = 4.5 Hz, 1H), 7.04 (bs, 1H), 6.44 (s, 1H), 4.16 (s, 3H), 4.02 (s, 3H), 2.26 (s, 6H) |

-continued

| Eg | Compound Name | Boronic acid starting material | Structure | $^1H$ NMR (400 MHz) 25° C. δ |
|---|---|---|---|---|
| 11 | 4-(4-(4-(3-Chloropyridin-4-yl)-2,6-dimethylphenoxy)-5-methyl-5H-pyrrolo[3,2-d]pyrimidin-2-ylamino)benzonitrile | 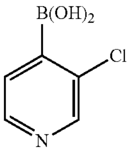 | 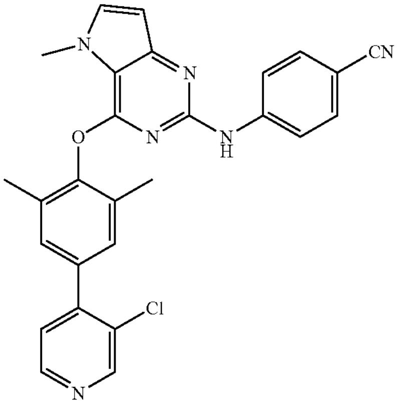 [SMILES: Cc1cc(-c2ccncc2Cl)cc(C)c1Oc1nc(Nc2ccc(C#N)cc2)nc2ccn(C)c12] | [a] 8.69 (s, 1H), 8.55 (d, J = 4.9 Hz, 1H), 7.47 (m, 1H), 7.45 (m, 1H), 7.43 (m, 1H), 7.42 (m, 1H), 7.36 (m, 3H), 7.34 (m, 1H), 7.32 (m, 1H), 6.43 (m, 1H), 4.18 (s, 3H), 2.28 (s, 6H) |
| 12 | 4-(4-(2,6-Dimethyl-4-(pyridin-3-yl)phenoxy)-5-methyl-5H-pyrrolo[3,2-d]pyrimidin-2-ylamino)benzonitrile | 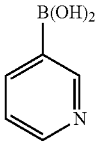 | 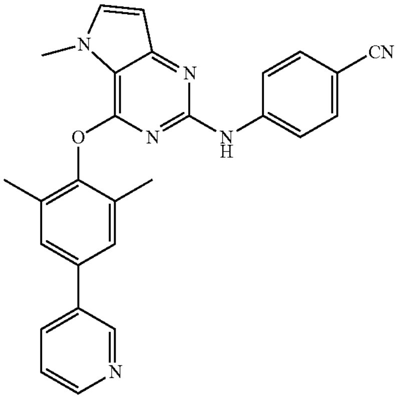 [SMILES: Cc1cc(-c2cccnc2)cc(C)c1Oc1nc(Nc2ccc(C#N)cc2)nc2ccn(C)c12] | [b] 8.92 (bs, 1H), 8.67 (bs, 1H), 7.93 (d, J = 7.7 Hz, 1H), 7.71 (s, 1H), 7.43 (d, J = 8.7 Hz, 2H), 7.40 (s, 2H), 7.27 (m, 3H), 6.43 (d, J = 2.7 Hz, 1H), 4.15 (s, 3H), 2.26 (s, 6H) |
| 13 | 4-(4-(4-(Furan-3-yl)-2,6-dimethylphenoxy)-5-methyl-5H-pyrrolo[3,2-d]pyrimidin-2-ylamino)benzonitrile | 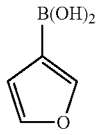 | 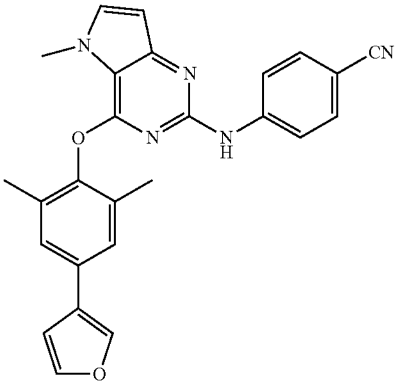 [SMILES: Cc1cc(-c2ccoc2)cc(C)c1Oc1nc(Nc2ccc(C#N)cc2)nc2ccn(C)c12] | [b] 7.78 (s, 1H), 7.53 (m, 1H), 7.46 (bs, 1H), 7.39 (d, J = 8.8 Hz, 2H), 7.31 (s, 2H), 7.28 (s, 1H), 7.26 (m, 2H), 6.74 (s, 1H), 6.41 (d, J = 2.9 Hz, 1H), 4.14 (s, 3H), 2.20 (s, 6H) |

-continued

| Eg | Compound Name | Boronic acid starting material | Structure | $^1$H NMR (400 MHz) 25° C. δ |
|---|---|---|---|---|
| 14 | 4-(4-(2,6-dimethyl-4-(pyrimidin-5-yl)phenoxy)-5-methyl-5H-pyrrolo[3,2-d]pyrimidin-2-ylamino)benzonitrile | 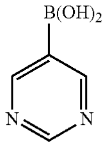 | 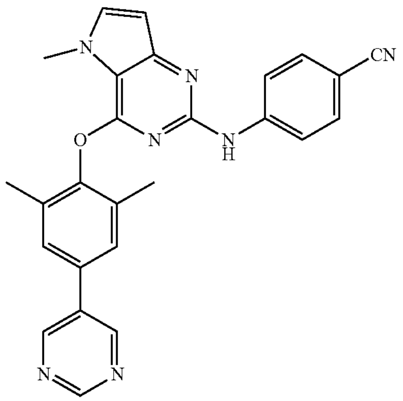 [SMILES: Cc1cc(-c2cncnc2)cc(C)c1Oc1nc(Nc2ccc(C#N)cc2)nc2ccn(C)c12] | b) 8.78 (s, 2H), 7.53 (bs, 1H), 7.48 (d, J = 8.8 Hz, 1H), 7.33 (s, 2H), 7.31 (d, J = 8.8 Hz, 2H), 7.28 (d, J = 3.0 Hz, 1H), 6.44 (d, J = 2.9 Hz, 1H), 4.15 (s, 3H), 4.10 (s, 3H), 2.26 (s, 6H). |
| 15 | 4-(4-(2,6-Dimethyl-4-(thiophen-3-yl)phenoxy)-5-methyl-5H-pyrrolo[3,2-d]pyrimidin-2-ylamino)benzonitrile | 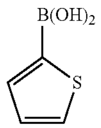 | 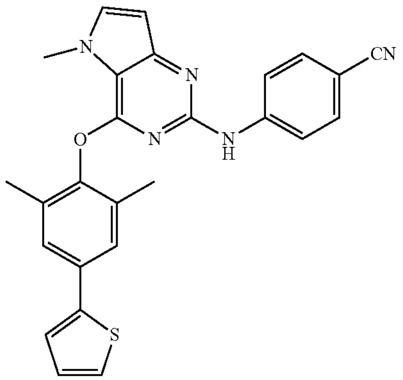 [SMILES: Cc1cc(-c2cccs2)cc(C)c1Oc1nc(Nc2ccc(C#N)cc2)nc2ccn(C)c12] | c) 2.18 (s, 6H) 4.11 (s, 3H) 6.39 (d, J = 2.90 Hz, 1H) 7.36 (d, J = 8.91 Hz, 2H) 7.56-7.72 (m, 6H) 7.88-7.95 (m, 2H) 9.58 (s, 1H) |
| 16 | 4'-(2-(4-Cyanophenylamino)-5-methyl-5H-pyrrolo[3,2-d]pyrimidin-4-yloxy)-3'-5'-dimethylbiphenyl-3-carbonitrile | 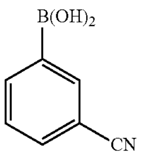 [SMILES: N#Cc1cccc(B(O)O)c1] | 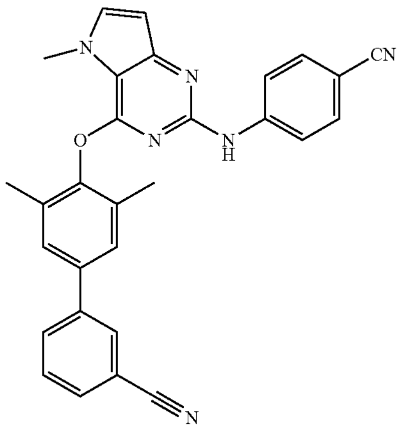 [SMILES: Cc1cc(-c2cccc(C#N)c2)cc(C)c1Oc1nc(Nc2ccc(C#N)cc2)nc2ccn(C)c12] | c) 2.28 (s, 6H) 4.23 (s, 3H) 6.49 (d, J = 2.90 Hz, 1H) 7.27-7.34 (m, 2H) 7.38-7.45 (m, 2H) 7.57 (s, 2H) 7.67-7.74 (m, 2H) 7.74-7.80 (m, 1H) 8.00-8.06 (m, 1H) 8.07 (s, 1H). |

-continued

| Eg | Compound Name | Boronic acid starting material | Structure | $^1H$ NMR (400 MHz) 25° C. δ |
|---|---|---|---|---|
| 17 | 6-(4-(2-(4-Cyanophenylamino)-5-methyl-5H-pyrrolo[3,2-d]pyrimidin-4-yloxy)-3,5-dimethylphenyl) picolinonitrile | 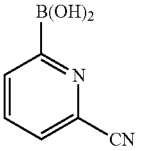 [SMILES: N#Cc1cccc(B(O)O)n1] | 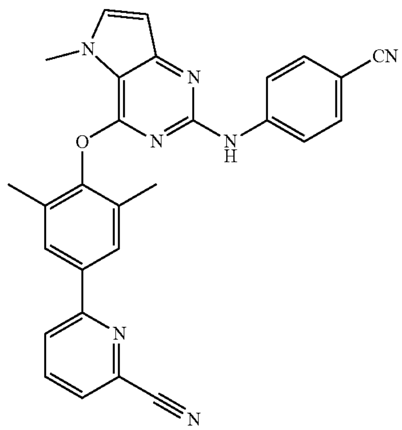 [SMILES: Cc1cc(-c2cccc(C#N)n2)cc(C)c1Oc1nc(Nc2ccc(C#N)cc2)nc2ccn(C)c12] | [c] 2.29 (s, 6H) 4.24 (s, 3H) 6.63 (d, J = 2.90 Hz, 1H) 7.11-7.18 (m, 2H) 7.29-7.35 (m, 2H) 7.44 (d, J = 2.90 Hz, 1H) 7.74 (dd, J = 5.60, 2.90 Hz, 1H) 7.93 (s, 2H) 7.99 8.04 (m, 2H) 12.41 (br. s., 1H). |

[a] $CDCl_3$—$CD_3OD$ (5:1)
[b] $CDCl_3$
[c] d6-DMSO

Example 18

4-(7-Chloro-4-(2,6-dimethyl-4-(pyridin-4-yl)phenoxy)-5-methyl-5H-pyrrolo[3,2-d]pyrimidin-2-ylamino)benzonitrile

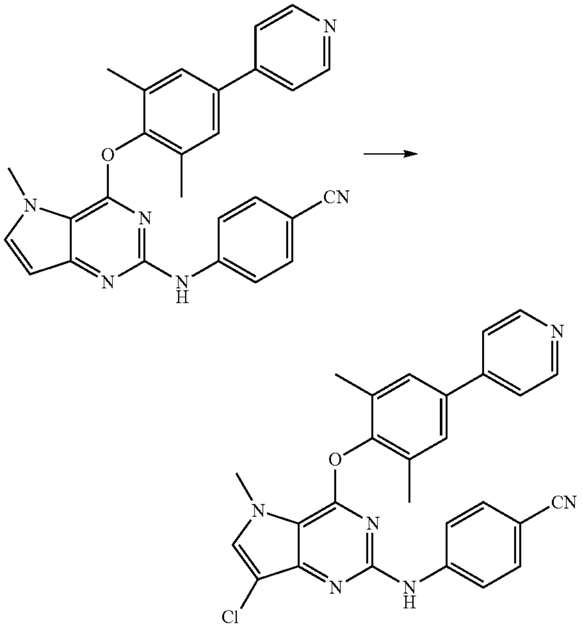

4-(4-(2,6-Dimethyl-4-(pyridin-4-yl)phenoxy)-5-methyl-5H-pyrrolo[3,2-d]pyrimidin-2-ylamino)benzonitrile (example 1) (310 mg, 0.567 mmol) was combined with NCS (76 mg, 0.567 mmol) in DMF/THF (3:2) mixture (5 mL). The mixture was stirred at 25° C. for 15 h under an atmosphere of argon and more NCS (120 mg, 0.90 mmol) was added. The mixture was stirred at 25° C. for another 24 h, diluted with ethyl acetate, and extracted with $H_2O$ (×2). The organic layer was collected, concentrated, and the product purified by preparatory thin layer chromatography (1:1 hexanes/ethyl acetate) to give the Boc-protected chlorinated analog as a solid. The obtained product was then treated with TFA (10 mL) at 25° C. for 2 h. TFA was evaporated, the obtained residue dissolved in ethyl acetate, and extracted with saturated aqueous $NaHCO_3$ (×2). The organic layer was collected, concentrated, and the product purified by chromatography ($SiO_2$, ethyl acetate) to give the title compound as a solid (10 mg, 4%, two steps). $^1H$ NMR (400 MHz, $CDCl_3$-$CD_3OD$ (5:1), 25° C.) δ 8.67 (bs, 2H), 7.65 (m, 2H), 7.51 (s, 2H), 7.43 (d, J=8.8 Hz, 2H), 7.35 (d, J=8.7 Hz, 1H), 7.27 (d, J=8.8 Hz, 2H), 4.15 (s, 3H), 2.26 (s, 6H).

Example 19

4-(4-(2,6-Dimethyl-4-(pyridin-4-yl)phenylamino)-5-methyl-5H-pyrrolo[3,2-d]pyrimidin-2-ylamino)benzonitrile

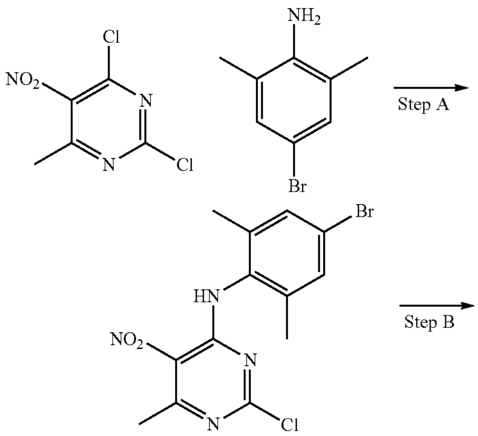

-continued

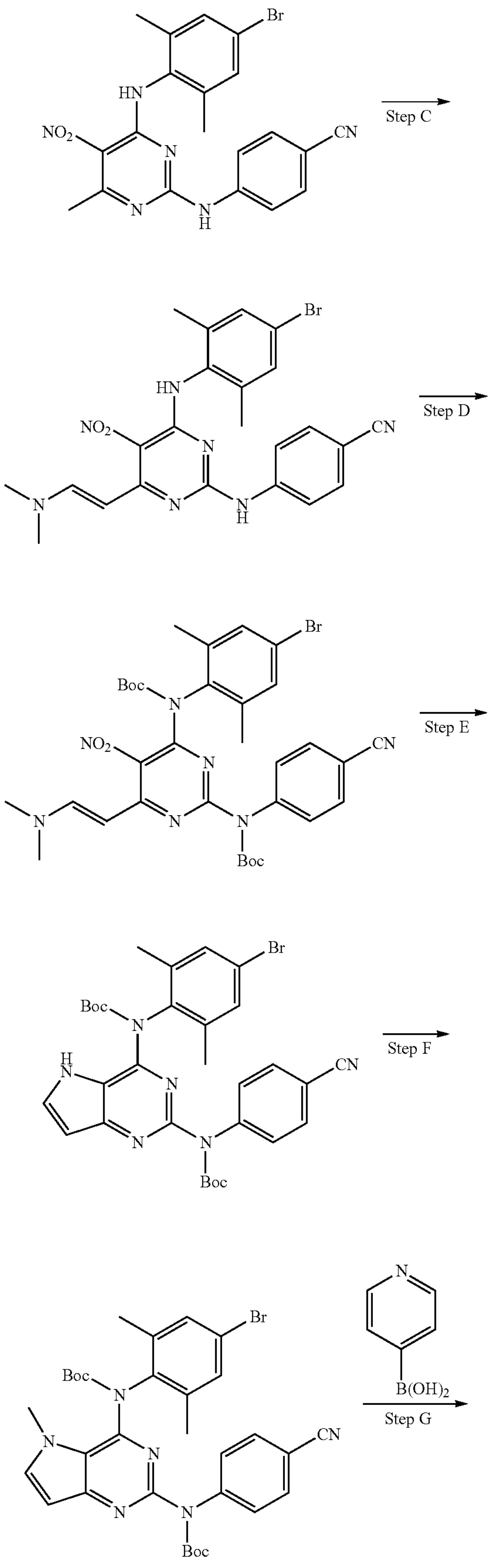

-continued

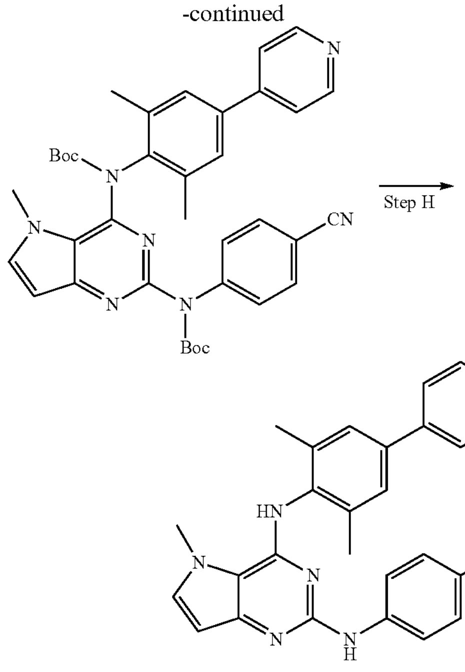

Step A: N-(4-bromo-2,6-dimethylphenyl)-2-chloro-6-methyl-5-nitropyrimidin-4-amine To a solution of 4-bromo-2,6-dimethylaniline (19.8 m g, 99.0 mmol) and 3,4-dichloro-6-methyl-5-nitropyrimimidine (20.6 g, 99.0 mmol) in THF (198 ml) at ambient temperature was added diisopropylethylamine (18.0 ml, 108.9 mmol). The reaction mixture was heated to 60° C. and stirred for 2 days. Upon completion, the volatiles were removed in vacuo. The resulting crude was slurried in cold ethanol and filtered. The resulting solids were washed 2× with cold ethanol and dried under vacuum overnight to give 18.6 g (51%) of N-(4-bromo-2,6-dimethylphenyl)-2-chloro-6-methyl-5-nitropyrimidin-4-amine as an orange powder. $^1H$ NMR (400 MHz, $CDCl_3$) δ ppm 2.18 (s, 6H) 2.80 (s, 3H) 7.31 (s, 2H) 9.23 (br. s., 1H).

Step B: methyl 4-(4-(4-bromo-2,6-dimethylphenylamino)-6-methyl-5-nitropyrimidin-2-ylamino)benzonitrile To a solution of N-(4-bromo-2,6-dimethylphenyl)-2-chloro-6-methyl-5-nitropyrimidin-4-amine (18.5 g, 49.8 mmol) and 4-aminobenzonitrile (5.9 g, 49.8 mmol) in THF (250 ml) at ambient temperature was added pyridine (4.0 ml, 49.8 mmol). The reaction mixture was heated to reflux and stirred for 2 days under argon. Upon completion half of the solvent was removed in vacuo. The solids were dissolved in methanol and 250 ml brine was added. The aqueous layer was extracted with ethyl acetate (3×125 ml) and the collected organic fractions were dried with $MgSO_4$, filtered and reduced in vacuo. The resulting solids were slurried in methanol and $Et_2O$ and filtered. The filtrand was washed 3× with cold $Et_2O$ and dried overnight under vacuum to give 14.4 g (64%) of methyl 4-(4-(4-bromo-2,6-dimethylphenylamino)-6-methyl-5-nitropyrimidin-2-ylamino)benzonitrile as a brown powder. m/z=453 [M+1].

Step C: (E)-4-(4-(4-bromo-2,6-dimethylphenylamino)-6-(2-(dimethylamino)vinyl)-5-nitropyrimidin-2-ylamino)benzonitrile A dried flask under argon was charged with methyl 4-(4-(4-bromo-2,6-dimethylphenylamino)-6-methyl-5-nitropyrimidin-2-ylamino)benzonitrile (4.3 g, 9.5 mmol) dissolved in anhydrous DMF (95 ml) followed by tert-butoxybis(dimethylamino)methane (2.4 ml, 11.4 mmol). The reaction mixture was heated to 60° C. and stirred overnight under argon. Upon completion the reaction was cooled to ambient temperature, concentrated to half volume, and quenched with $H_2O$ (100 ml). The aqueous solution was extracted with ethyl acetate (3×70 ml) and the collected organic fractions were washed with brine (100 ml), dried with $MgSO_4$, filtered and concentrated. Silica gel chromatography (ethyl acetate:Hexanes=50:50) yielded (E)-4-(4-(4-bromo-2,6-dimethylphenylamino)-6-(2-(dimethylamino)vinyl)-5-nitropyrimidin-2-ylamino)benzonitrile (3.21 g, 67%) as a brown solid. m/z=508 [M+1].

Step D: di-boc protected (E)-4-(4-(4-bromo-2,6-dimethylphenylamino)-6-(2-(dimethylamino)vinyl)-5-nitropyrimidin-2-ylamino)benzonitrile To a solution of (E)-4-(4-(4-bromo-2,6-dimethylphenylamino)-6-(2-(dimethylamino)vinyl)-5-nitropyrimidin-2-ylamino)benzonitrile (3.2 g, 6.3 mmol) in anhydrous DMF (25 ml) was added diisopropylethylamine (5.2 ml, 31.6 mmol) followed by 4-diethylaminopyridine (386.1 mg, 3.2 mmol). The reaction was stirred under argon, and once the DMAP is completely in solution, di-tert-butyl dicarbonate (5.5 g, 25.3 mmol) previously dissolved in 2 ml of anhydrous DMF was added dropwise over 15 min. The reaction was stirred for 3 h, diluted with ethyl acetate (75 ml), and extracted with aq. HCl (0.5 M, 3×35 ml) followed by $H_2O$ (35 ml). The collected aqueous fractions were extracted with ethyl acetate (2×20 ml). The collected organic fractions were washed with brine (75 ml), dried with $Na_2SO_4$, filtered and concentrated in vacuo to yield 4.7 g of di-boc protected (E)-4-(4-(4-bromo-2,6-dimethylphenylamino)-6-(2-(dimethylamino)vinyl)-5-nitropyrimidin-2-ylamino)benzonitrile red-brown syrup. m/z=708 [M+1].

Step E: di-boc protected 4-(4-(4-bromo-2,6-dimethylphenylamino)-5H-pyrrolo[3,2-d]pyrimidin-2-ylamino)benzonitrile To a solution of di-boc protected (E)-4-(4-(4-bromo-2,6-dimethylphenylamino)-6-(2-(dimethylamino)vinyl)-5-nitropyrimidin-2-ylamino)benzonitrile (4.5 g, 6.4 mmol) in THF (42 ml) was added sodium dithionite (6.5 g, 31.8 mmol) slurried in $H_2O$ (14 ml). Stirring was commenced and 5 more equivalents of sodium dithionite (1 eq=1.3 g) was added over the next 2 days. Upon completion, the solution was diluted with $H_2O$ (30 ml) and extracted with ethyl acetate (3×35 ml). The collected organic fractions were washed with brine (50 ml), dried with $MgSO_4$, filtered and concentrated in vacuo to yield 3.9 g (97%) of di-boc protected 4-(4-(4-bromo-2,6-dimethylphenylamino)-5H-pyrrolo[3,2-d]pyrimidin-2-ylamino)benzonitrile as a red-brown viscous oil. m/z=633 [M+1].

Step F: Di-boc protected 4-(4-(4-bromo-2,6-dimethylphenylamino)-5-methyl-5H-pyrrolo[3,2-d]pyrimidin-2-ylamino)benzonitrile To a solution of di-boc protected 4-(4-(4-bromo-2,6-dimethylphenylamino)-5H-pyrrolo[3,2-d]pyrimidin-2-ylamino)benzonitrile (4.2 g, 6.7 mmol) in anhydrous THF (22 ml) at −78° C. was added lithium bis(trimethylsilyl)amide (1.0 M in THF, 8.65 ml, 8.6 mmol) dropwise over 5 min. Upon completion, the reaction was allowed to warm to 0° C. After stirring for 0.5 h at 0° C., the reaction was again cooled to −78° C. and iodomethane (1.7 ml, 26.6 mmol) was added dropwise over 10 min. The reaction was allowed to warm to room temperature and stirred overnight. The solution was diluted with ethyl acetate (60 ml) and extracted with $H_2O$ (3×30 ml). The collected aqueous fractions were extracted with ethyl acetate (2×20 ml) and the combined organic fractions were washed with brine (50 ml), dried with $MgSO_4$, filtered and concentrated in vacuo. Silica gel chromatography (ethyl acetate: Hexanes=33:67) yielded 1.69 g (39%) of di-boc protected 4-(4-(4-bromo-2,6-dimethylphenylamino)-5-methyl-5H-pyrrolo[3,2-d]pyrimidin-2-ylamino)benzonitrile as a brown foam. $^1H$ NMR (400 MHz, $CDCl_3$) δ ppm 1.19 (s, 11H) 1.44 (s, 11H) 2.17 (s, 6H) 4.08 (s, 3H) 6.66 (d, J=3.11 Hz, 1H) 7.15-7.22 (m, 4H) 7.30 (s, 1H) 7.47 (d, J=3.11 Hz, 1H) 7.50 (d, J=8.50 Hz, 2H).

Step G: Di-boc protected 4-(4-(2,6-dimethyl-4-(pyridin-4-yl)phenylamino)-5-methyl-5H-pyrrolo[3,2-d]pyrimidin-2-ylamino)benzonitrile Di-boc protected 4-(4-(4-bromo-2,6-dimethylphenylamino)-5-methyl-5H-pyrrolo[3,2-d]pyrimidin-2-ylamino)benzonitrile (400 mg, 0.729 mmol) is combined with pyridine-4-boronic acid (179 mg, 1.46 mmol) and tetrakis(triphenylphosphine)palladium(0) (84 mg, 0.0729 mmol) in a two dram vial. The vial is sealed and flushed with argon. Degassed THF (5.0 mL), and aqueous $Na_2CO_3$ (2 M, 1.5 mL, 3.0 mmol) are injected, and the mixture agitated on a shaker at 80° C. for 10 h. The mixture is diluted with ethyl acetate and extracted with aqueous $Na_2CO_3$ (0.5 M, ×2). The organic layer is collected, concentrated, and the product purified by chromatography ($SiO_2$, 1:4 hexanes/ethyl acetate) to give the di-boc protected compound.

Step H: 4-(4-(2,6-Dimethyl-4-(pyridin-4-yl)phenylamino)-5-methyl-5H-pyrrolo[3,2-d]pyrimidin-2-ylamino)benzonitrile Di-boc protected 4-(4-(2,6-Dimethyl-4-(pyridin-4-yl)phenylamino)-5-methyl-5H-pyrrolo[3,2-d]pyrimidin-2-ylamino)benzonitrile is treated with TFA (10 mL) at 25° C. for 2 h. TFA is evaporated, the obtained residue dissolved in ethyl acetate, and extracted with saturated aqueous $NaHCO_3$ (×2). The organic layer is collected, concentrated, and the product purified by chromatography ($SiO_2$, 1:4 hexanes/EtOAc) to give the title compound.

Examples 20-95

Examples 20-95 were synthesized in a similar fashion to example 1 or example 19 using the appropriate boronic acid/ester and other starting materials.

| Eg | Compound Name | Boronic Acid starting material | Structure | $^1$H NMR (400 MHz) 25° C. δ MS (ESI) |
|---|---|---|---|---|
| 20 | 4-(4-(4-(2-Methoxypyrimidin-5-yl)-2,6-dimethylphenoxy)-5-methyl-5H-pyrrolo[3,2-d]pyrimidin-2-ylamino)benzonitrile | 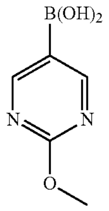 | 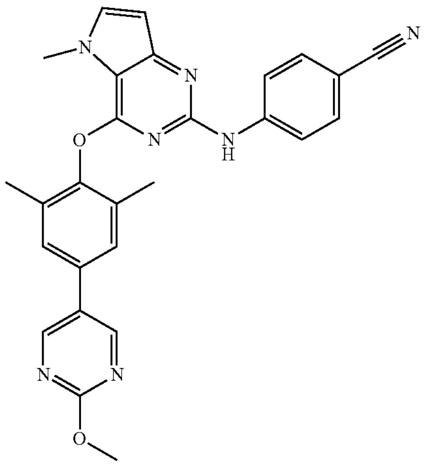 | b) 8.78 (s, 1H), 7.50 (m, 4H), 7.30 (m, 5H), 6.44 (d, 1H), 4.15 (s, 3H), 4.10 (s, 3H), 2.26 (s, 6H); MS (m/z): 478 [M + H]$^+$. |
| 21 | 4-(4-(2,6-Dimethyl-4-(1,3,5-trimethyl-1H-pyrazol-4-yl)phenoxy)-5-methyl-5H-pyrrolo[3,2-d]pyrimidin-2-ylamino)benzonitrile | 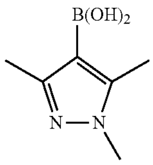 | 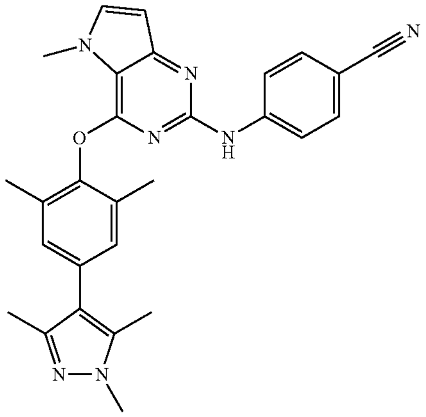 [SMILES: Cc1cc(-c2c(C)nn(C)c2C)cc(C)c1Oc1nc(Nc2ccc(C#N)cc2)nc2ccn(C)c12] | b) 7.85 (s, 1H), 7.44 (d, 2H), 7.28 (d, 2H), 7.10 (s, 2H), 6.42 (s, 1H), 4.22 (s, 3H), 3.85 (s, 3H), 2.40 (m, 6H); 2.32 (s, 6H); MS (m/z): 478 [M + H]$^+$. |
| 22 | 4-(4-(4'-(Dimethylamino)-3,5-dimethylbiphenyl-4-yloxy)-5-methyl-5H-pyrrolo[3,2-d]pyrimidin-2-ylamino)benzonitrile | 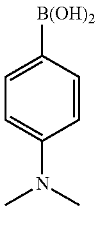 | 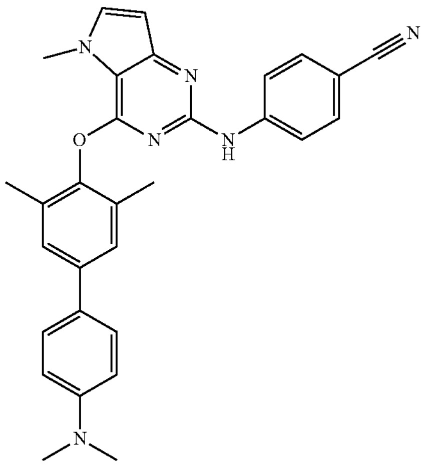 [SMILES: Cc1cc(-c2ccc(N(C)C)cc2)cc(C)c1Oc1nc(Nc2ccc(C#N)cc2)nc2ccn(C)c12] | b) 7.85 (s, 1H), 7.54 (d, 2H), 7.37 (m, 4H), 7.25 (d, 2H), 6.85 (d, 2H), 6.39 (s, 1H), 4.13 (s, 3H), 3.10 (s, 6H), 2.22 (m, 6H); MS (m/z): 489 [M + H]$^+$. |

-continued

| Eg | Compound Name | Boronic Acid starting material | Structure | $^{1}$H NMR (400 MHz) 25° C. δ MS (ESI) |
|---|---|---|---|---|
| 23 | 4-(4-(2-(4-Cyanophenylamino)-5-methyl-5H-pyrrolo[3,2-d]pyrimidin-4-yloxy)-3,5-dimethylphenyl) nicotinonitrile | 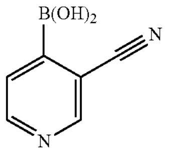 [SMILES: N#Cc1cnccc1B(O)O] | 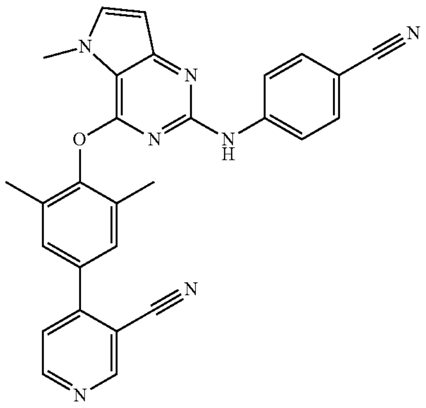 [SMILES: Cc1cc(-c2ccncc2C#N)cc(C)c1Oc1nc(Nc2ccc(C#N)cc2)nc2ccn(C)c12] | [a] 8.90 (m, 2H), 7.60 (m, 2H), 7.48 (m, 4H), 7.34 (m, 2H), 6.45 (s, 1H), 4.17 (s, 3H), 2.29 (s, 6H); MS (m/z): 472 $[M + H]^+$. |
| 24 | 4-(4-(2,6-Dimethyl-4-(1H-pyrazol-4-yl)phenoxy)-5-methyl-5H-pyrrolo[3,2-d]pyrimidin-2-ylamino)benzonitrile | 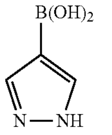 | 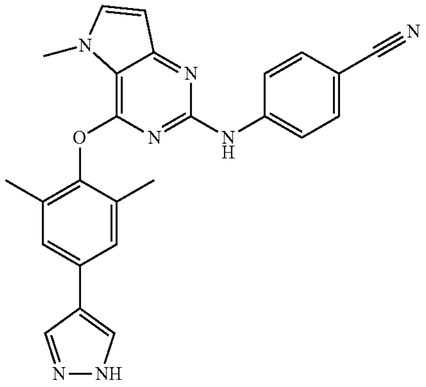 [SMILES: Cc1cc(-c2cn[nH]c2)cc(C)c1Oc1nc(Nc2ccc(C#N)cc2)nc2ccn(C)c12] | [a] 7.95 (m, 2H), 7.35 (m, 7H), 6.42 (s, 1H), 4.20 (s, 3H), 2.25 (s, 6H); MS (m/z): 436 $[M + H]^+$. |
| 25 | 4-(4-(2,6-Dimethyl-4-(1-methyl-1H-pyrazol-5-yl)phenoxy)-5-methyl-5H-pyrrolo[3,2-d]pyrimidin-2-ylamino)benzonitrile | 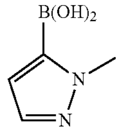 | 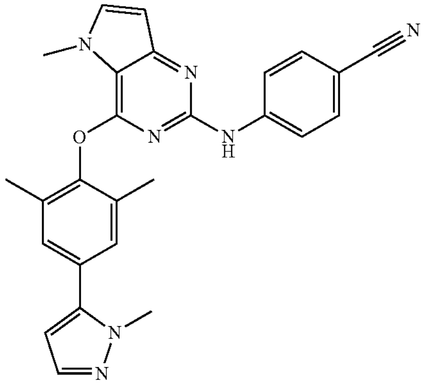 [SMILES: Cc1cc(-c2ccnn2C)cc(C)c1Oc1nc(Nc2ccc(C#N)cc2)nc2ccn(C)c12] | [b] 7.55 (s, 2H), 7.45 (d, 2H), 7.30 (m, 4H), 6.40 (s, 1H), 6.35 (s, 1H), 4.15 (s, 3H), 3.90 (s, 3H), 2.25 (s, 6H); MS (m/z): 450 $[M + H]^+$. |

-continued

| Eg | Compound Name | Boronic Acid starting material | Structure | $^1$H NMR (400 MHz) 25° C. δ MS (ESI) |
|---|---|---|---|---|
| 26 | 4-(4-(4-(Benzo[c][1,2,5]oxodiazol-5-yl)-2,6-dimethylphenoxy)-5-methyl-5H-pyrrolo[3,2-d]pyrimidin-2-ylamino)benzonitrile | 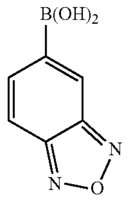 [SMILES: OB(O)c1ccc2nonc2c1] | 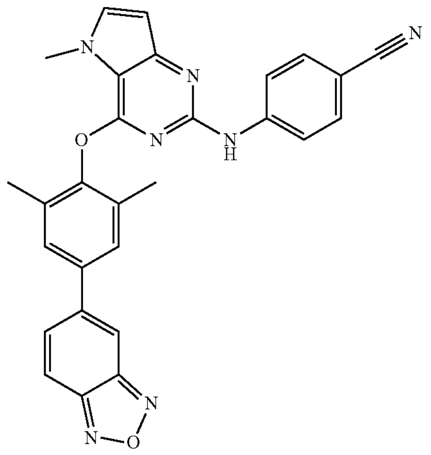 [SMILES: Cc1cc(-c2ccc3nonc3c2)cc(C)c1Oc1nc(Nc2ccc(C#N)cc2)nc2ccn(C)c12] | [b] 8.00 (m, 3H), 7.75 (d, 2H), 7.45 (m, 4H), 7.30 (m, 2H), 6.40 (s, 1H), 4.15 (s, 3H), 2.25 (s, 6H); MS (m/z): 488 $[M + H]^+$. |
| 27 | 4-(4-(2,6-Dimethyl-4-(1H-pyrrol-2-yl)phenoxy)-5-methyl-5H-pyrrolo[3,2-d]pyrimidin-2-ylamino)benzonitrile | 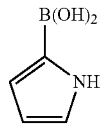 | 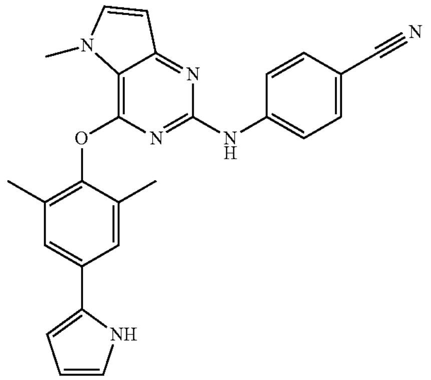 [SMILES: Cc1cc(-c2ccc[nH]2)cc(C)c1Oc1nc(Nc2ccc(C#N)cc2)nc2ccn(C)c12] | [b] 8.52 (s, 1H), 7.45 (m, 3H), 7.32 (m, 5H), 6.85 (s, 1H), 6.53 (s, 1H), 6.40 (s, 1H), 6.35 (s, 1H), 4.16 (s, 3H), 2.22 (s, 6H); MS (m/z): 435 $[M + H]^+$. |
| 28 | 4-(4-(4-(2-(Dimethylamino)pyrimidin-5-yl)-2,6-dimethylphenoxy)-5-methyl-5H-pyrrolo[3,2-d]pyrimidin-2-ylamino)benzonitrile | 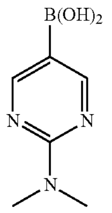 | 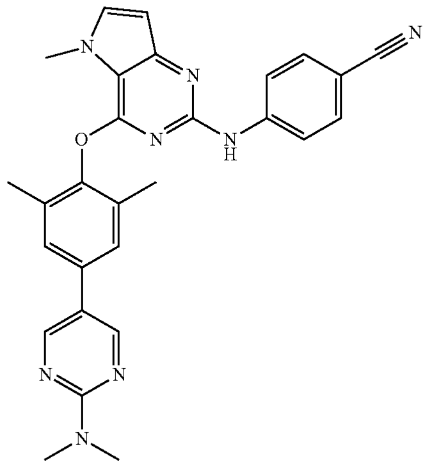 [SMILES: Cc1cc(-c2cnc(N(C)C)nc2)cc(C)c1Oc1nc(Nc2ccc(C#N)cc2)nc2ccn(C)c12] | [a] 8.65 (s, 2H), 7.48 (m, 2H), 7.32 (m, 5H), 6.42 (s, 1H), 4.22 (s, 3H), 3.32 (s, 6H), 2.26 (s, 6H); MS (m/z): 491 $[M + H]^+$. |

-continued

| Eg | Compound Name | Boronic Acid starting material | Structure | $^1$H NMR (400 MHz) 25° C. δ MS (ESI) |
|---|---|---|---|---|
| 29 | 4-(6-(2,6-Dimethyl-4-(pyridin-4-yl)phenoxy)-7H-purin-2-ylamino)benzonitrile | 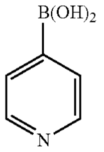 | 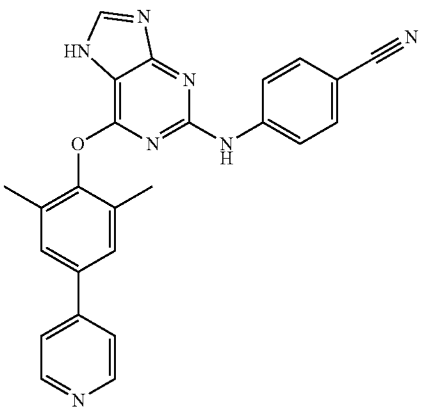 [SMILES: Cc1cc(-c2ccncc2)cc(C)c1Oc1nc(Nc2ccc(C#N)cc2)nc2nc[nH]c12] | [c] 13.21 (s, 1H), 9.93 (s, 1H), 8.69 (d, 2H), 8.26 (s, 1H), 7.80 (d, 2H), 7.74 (s, 2H), 7.64 (d, 2H), 7.39 (d, 2H), 2.20 (s, 6H); MS (m/z): 434 [M + H]$^+$. |
| 30 | 5-(4-(2-(4-Cyanophenylamino)-5-methyl-5H-pyrrolo[3,2-d]pyrimidin-4-yloxy)-3,5-dimethylphenyl)pyrimidine-2-carbonitrile | 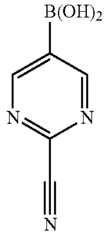 | 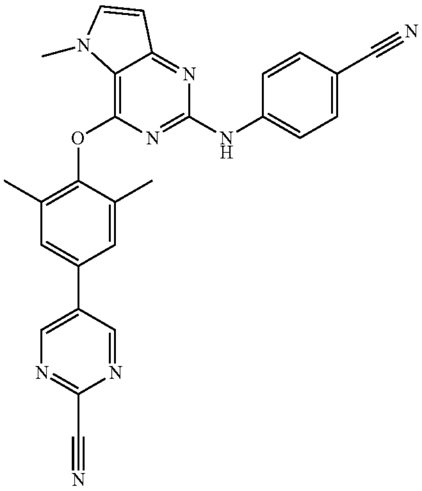 [SMILES: Cc1cc(-c2cnc(C#N)nc2)cc(C)c1Oc1nc(Nc2ccc(C#N)cc2)nc2ccn(C)c12] | [a] 9.24 (s, 2H), 7.40 (m, 7H), 6.42 (s, 1H), 4.24 (s, 3H), 2.30 (s, 6H); MS (m/z): 473 [M + H]$^+$. |
| 31 | 4-(4-(7-Chloro-2-(4-cyanophenylamino)-5-methyl-5H-pyrrolo[3,2-d]pyrimidin-4-yloxy)-3,5-dimethylphenyl) nicotinonitrile | 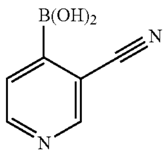 [SMILES: N#Cc1cnccc1B(O)O] | 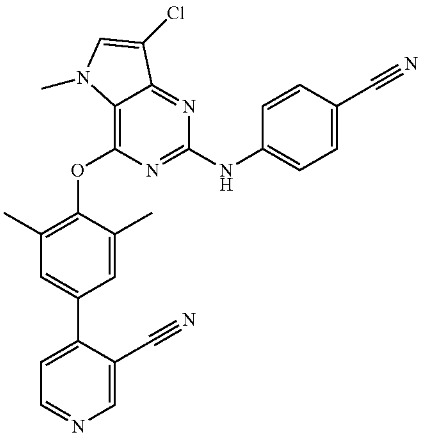 [SMILES: Cc1cc(-c2ccncc2C#N)cc(C)c1Oc1nc(Nc2ccc(C#N)cc2)nc2c(Cl)cn(C)c12] | [a] 8.97 (m, 2H), 7.47 (m, 8H), 4.15 (s, 3H), 2.29 (s, 6H); MS (m/z): 506 [M + H]$^+$. |

-continued

| Eg | Compound Name | Boronic Acid starting material | Structure | $^1H$ NMR (400 MHz) 25° C. δ MS (ESI) |
|---|---|---|---|---|
| 32 | 4-(7-Chloro-4-(2,6-dimethyl-4-(1H-pyrazol-4-yl)phenoxy)-5-methyl-5H-pyrrolo[3,2-d]pyrimidin-2-ylamino)benzonitrile | 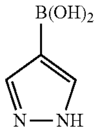 | 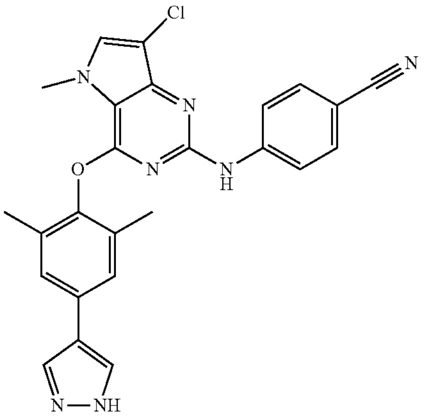 [SMILES: Cc1cc(-c2cn[nH]c2)cc(C)c1Oc1nc(Nc2ccc(C#N)cc2)nc2c(Cl)cn(C)c12] | [a] 7.96 (s, 1H), 7.36 (m, 8H), 4.15 (s, 3H), 2.21 (s, 6H); MS (m/z): 470 [M + H]$^+$. |
| 33 | 4-(4-(3'-(Dimethylamino)-3,5-dimethylbipyenyl-4-yloxy)-5-methyl-5H-pyrrolo[3,2-d]pyrimidin-2-ylamino)benzonitrile | 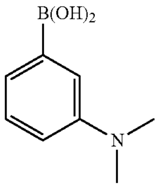 | 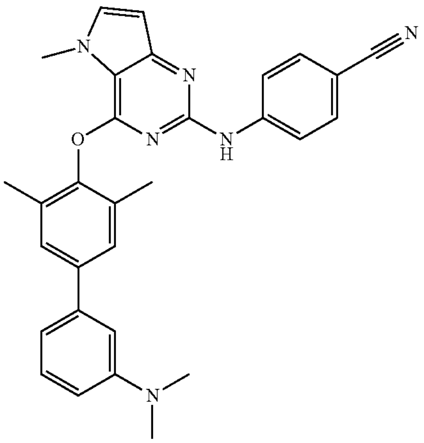 [SMILES: Cc1cc(-c2cccc(N(C)C)c2)cc(C)c1Oc1nc(Nc2ccc(C#N)cc2)nc2ccn(C)c12] | [a] 7.71 (s, 1H), 7.35 (m, 8H), 6.97 (m, 1H), 6.80 (m, 1H), 6.42 (s, 1H), 4.16 (s, 3H), 3.07 (s, 6H), 2.25 (s, 6H); MS (m/z): 489 [M + H]$^+$. |
| 34 | 3-(4-(2-(4-Cyanophenylamino)-5-methyl-5H-pyrrolo[3,2-d]pyrimidin-4-yloxy)-3,5-dimethylphenyl)thiophene-2-carbonitrile | 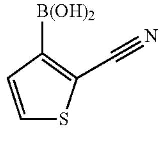 | 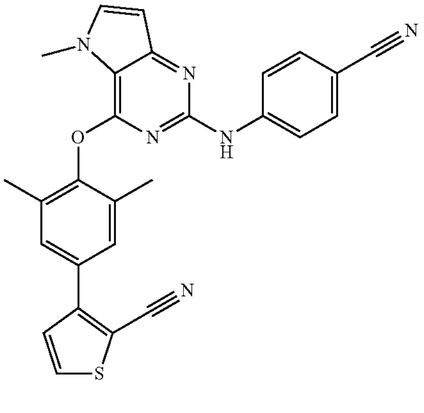 [SMILES: Cc1cc(-c2ccsc2C#N)cc(C)c1Oc1nc(Nc2ccc(C#N)cc2)nc2ccn(C)c12] | [a] 8.11 (s, 1H), 7.41 (m, 8H), 6.43 (s, 1H), 4.15 (s, 3H), 2.25 (s, 6H); MS (m/z): 477 [M + H]$^+$. |

-continued

| Eg | Compound Name | Boronic Acid starting material | Structure | $^1$H NMR (400 MHz) 25° C. δ MS (ESI) |
|---|---|---|---|---|
| 35 | 4-(4-(4-(3,5-Dimethylisoxazol-4-yl)-2,6-dimethylphenoxy)-5-methyl-5H-pyrrolo[3,2-d]pyrimidin-2-ylamino)benzonitrile | 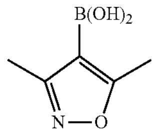 | 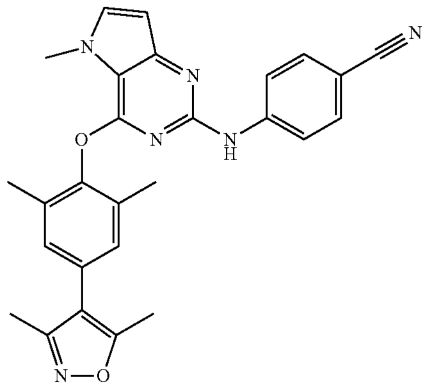 [SMILES: Cc1cc(-c2c(C)noc2C)cc(C)c1Oc1nc(Nc2ccc(C#N)cc2)nc2ccn(C)c12] | [a] 7.47 (d, 2H), 7.33 (m, 3H), 7.08 (s, 2H), 6.45 (s, 1H), 4.14 (s, 3H), 2.49 (s, 3H), 2.35 (s, 3H), 2.24 (s, 6H); MS (m/z): 465 [M + H]$^+$. |
| 36 | 4'-(2-(4-Cyanophenylamino)-5-methyl-5H-pyrrolo[3,2-d]pyrimidin-4-yloxy)-N,N,3',5'-tetramethylbiphenyl-3-carboxamide | 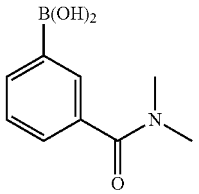 | 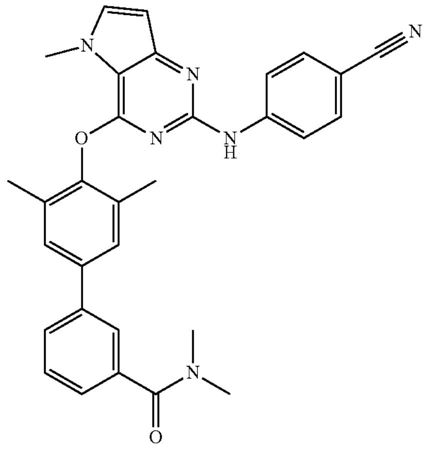 [SMILES: Cc1cc(-c2cccc(C(=O)N(C)C)c2)cc(C)c1Oc1nc(Nc2ccc(C#N)cc2)nc2ccn(C)c12] | [a] 7.73 (m, 3H), 7.53 (t, 1H), 7.40 (m, 4H), 7.25 (m, 3H), 6.41 (d, 1H), 4.15 (s, 3H), 3.17 (s, 3H), 3.09 (s, 3H), 2.24 (s, 6H); MS (m/z): 517 [M + H]$^+$. |
| 37 | 4-(4-(2,6-Dimethyl-4-(quinolin-4-yl)phenoxy)-5-methyl-5H-pyrrolo[3,2-d]pyrimidin-2-ylamino)benzonitrile | 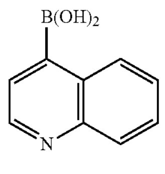 [SMILES: OB(O)c1ccnc2ccccc12] | 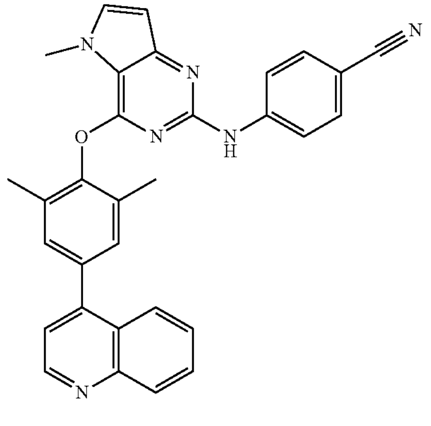 [SMILES: Cc1cc(-c2ccnc3ccccc23)cc(C)c1Oc1nc(Nc2ccc(C#N)cc2)nc2ccn(C)c12] | [b] 9.02 (s, 1H), 8.23 (d, 1H), 8.00 (d, 1H), 7.79 (m, 1H), 7.58 (m, 1H), 7.50 (d, 2H), 7.34 (m, 7H), 6.42 (s, 1H), 4.18 (s, 3H), 2.25 (s, 6H); MS (m/z): 497 [M + H]$^+$. |

-continued

| Eg | Compound Name | Boronic Acid starting material | Structure | $^1$H NMR (400 MHz) 25° C. δ MS (ESI) |
|---|---|---|---|---|
| 38 | 4-(4-(2,6-Dimethyl-4-(quinolin-5-yl)phenoxy)-5-methyl-5H-pyrrolo[3,2-d]pyrimidin-2-ylamino)benzonitrile | 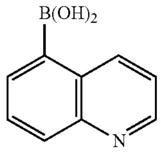 [SMILES: OB(O)c1cccc2ncccc12] | 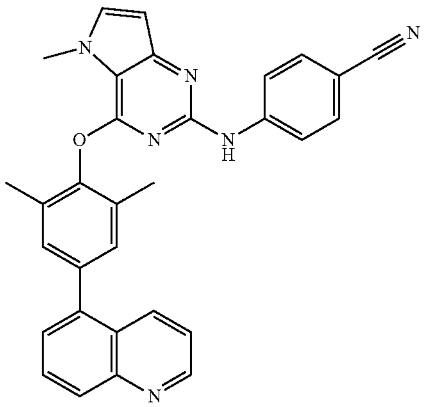 [SMILES: Cc1cc(-c2cccc3ncccc23)cc(C)c1Oc1nc(Nc2ccc(C#N)cc2)nc2ccn(C)c12] | [b)] 9.24 (s, 1H), 8.42 (m, 1H), 8.02 (m, 1H), 7.81 (m, 1H), 7.73 (m, 2H), 7.44 (d, 2H), 7.28 (m, 6H), 6.40 (s, 1H), 4.14 (s, 3H), 2.24 (s, 6H); MS (m/z): 497 [M + H]$^+$. |
| 39 | 4-(4-(4-(Isoquinolin-5-yl)-2,6-dimethylphenoxy)-5-methyl-5H-pyrrolo[3,2-d]pyrimidin-2-ylamino)benzonitrile | 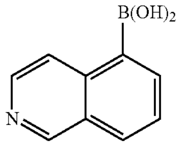 [SMILES: OB(O)c1cccc2cnccc12] | 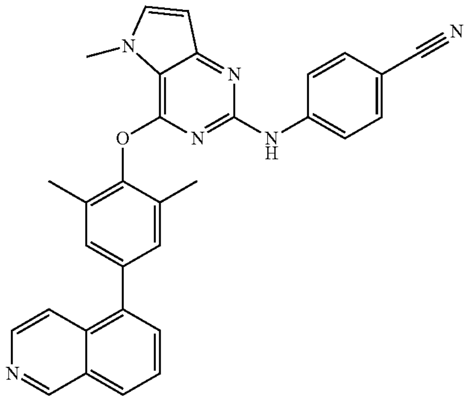 [SMILES: Cc1cc(-c2cccc3cnccc23)cc(C)c1Oc1nc(Nc2ccc(C#N)cc2)nc2ccn(C)c12] | [b)] 9.02 (m, 1H), 8.26 (d, 1H), 7.86 (d, 1H), 7.78 (d, 1H), 7.66 (m, 1H), 7.50 (m, 7H), 7.28 (d, 2H), 6.45 (s, 1H), 4.17 (s, 3H), 2.27 (s, 6H); MS (m/z): 497 [M + H]$^+$. |
| 40 | 4-(4-(4-(Isoquinolin-4-yl)-2,6-dimethylphenoxy)-5-methyl-5H-pyrrolo[3,2-d]pyrimidin-2-ylamino)benzonitrile | 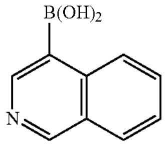 [SMILES: OB(O)c1cncc2ccccc12] | 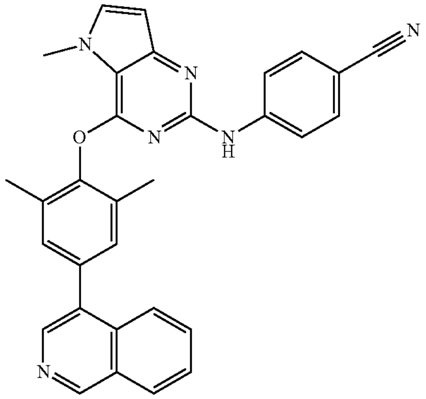 [SMILES: Cc1cc(-c2cncc3ccccc23)cc(C)c1Oc1nc(Nc2ccc(C#N)cc2)nc2ccn(C)c12] | [b)] 9.32 (s, 1H), 8.58 (s, 1H), 8.10 (m, 1H), 8.00 (m, 1H), 7.72 (m, 2H), 7.52 (d, 2H), 7.30 (m, 6H), 6.45 (s, 1H), 4.16 (s, 3H), 2.28 (s, 6H); MS (m/z): 497 [M + H]$^+$. |

-continued

| Eg | Compound Name | Boronic Acid starting material | Structure | $^1$H NMR (400 MHz) 25° C. δ MS (ESI) |
|---|---|---|---|---|
| 41 | 4-(4-(2,6-Dimethyl-4-(quinolin-3-yl)phenoxy)-5-methyl-5H-pyrrolo[3,2-d]pyrimidin-2-ylamino)benzonitrile | 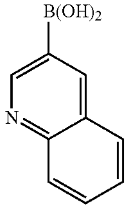 [SMILES: OB(O)c1cnc2ccccc2c1] | 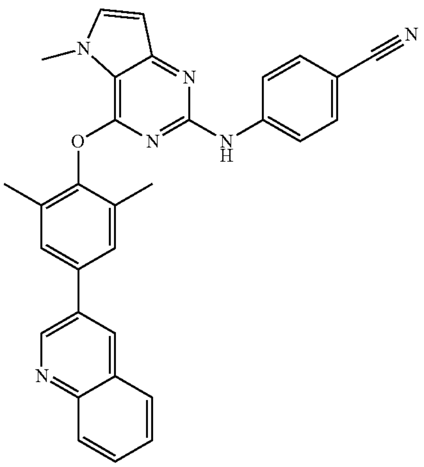 [SMILES: Cc1cc(-c2cnc3ccccc3c2)cc(C)c1Oc1nc(Nc2ccc(C#N)cc2)nc2ccn(C)c12] | [b)] 9.26 (s, 1H), 8.37 (s, 1H), 8.18 (d, 1H), 7.96 (d, 1H), 7.78 (m, 1H), 7.65 (m, 1H), 7.52 (m, 4H), 7.35 (d, 2H), 7.28 (d, 2H), 6.44 (s, 1H), 4.16 (s, 3H), 2.32 (s, 6H); MS (m/z): 497 $[M + H]^+$. |
| 42 | 4'-(2-(4-Cyanophenylamino)-5-methyl-5H-pyrrolo[3,2-d]pyrimidin-4-yloxy)-N,N,3',5'-tetramethylbiphenyl-4-sulfonamide | 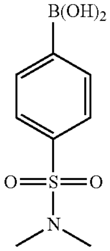 | 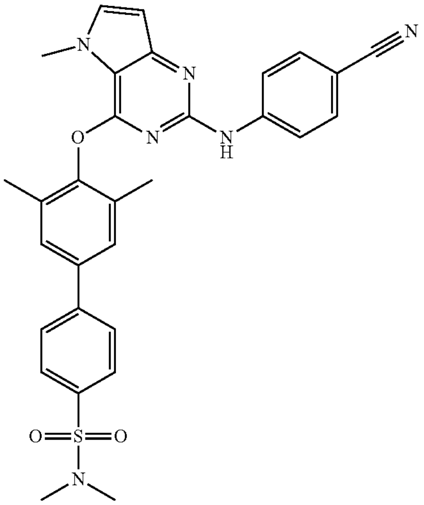 [SMILES: Cc1cc(-c2ccc(S(=O)(=O)N(C)C)cc2)cc(C)c1Oc1nc(Nc2ccc(C#N)cc2)nc2ccn(C)c12] | [a)] 7.92 (m, 4H), 7.40 (m, 7H), 6.46 (s, 1H), 4.20 (s, 3H), 2.83 (s, 6H), 2.20 (s, 6H); MS (m/z): 553 $[M + H]^+$. |
| 43 | 4-(4-(2,6-Dimethyl-4-(quinolin-8-yl)phenoxy)-5-methyl-5H-pyrrolo[3,2-d]pyrimidin-2-ylamino)benzonitrile | 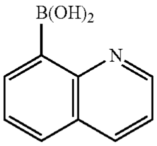 [SMILES: OB(O)c1cccc2cccnc12] | 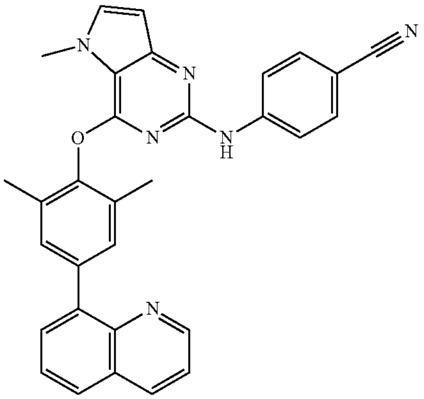 [SMILES: Cc1cc(-c2cccc3cccnc23)cc(C)c1Oc1nc(Nc2ccc(C#N)cc2)nc2ccn(C)c12] | [a)] 7.84 (m, 4H), 7.48 (m, 6H), 7.28 (m, 3H), 6.48 (s, 1H), 4.22 (s, 3H), 2.21 (s, 6H); MS (m/z): 497 $[M + H]^+$. |

-continued

| Eg | Compound Name | Boronic Acid starting material | Structure | $^1$H NMR (400 MHz) 25° C. δ MS (ESI) |
|---|---|---|---|---|
| 44 | 4'-(2-(4-Cyanophenylamino)-5-methyl-5H-pyrrolo[3,2-d]pyrimidin-4-yloxy)-3',5'-dimethylbiphenyl-4-carbonitrile | 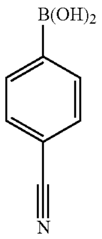 [SMILES: N#Cc1ccc(B(O)O)cc1] | 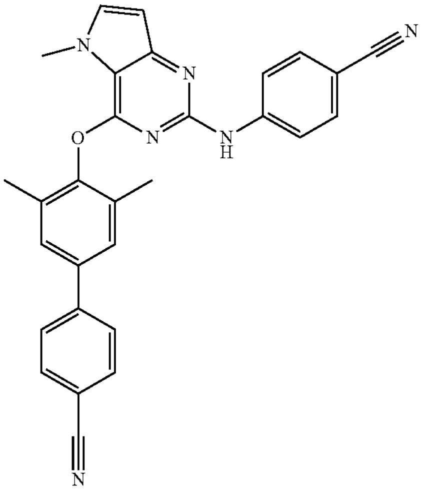 [SMILES: Cc1cc(-c2ccc(C#N)cc2)cc(C)c1Oc1nc(Nc2ccc(C#N)cc2)nc2ccn(C)c12] | [b)] 9.60 (s, 1H), 7.99 (m, 4H), 7.69 (m, 4H), 7.38 (d, 2H), 6.40 (s, 1H), 4.11 (s, 3H), 2.22 (s, 6H); MS (m/z): 471 [M + H]$^+$. |
| 45 | 4'-(2-(4-Cyanophenylamino)-7H-purin-6-yloxy)-3',5'-dimethylbiphenyl-4-carboxamide | 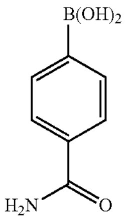 | 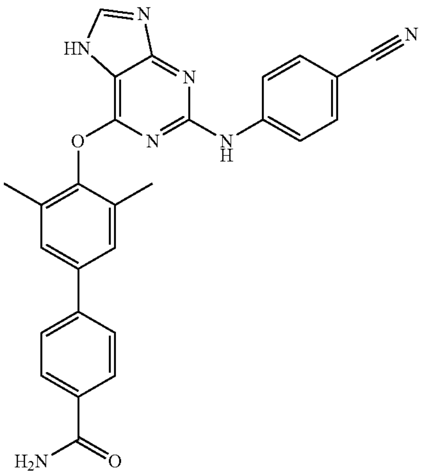 [SMILES: Cc1cc(-c2ccc(C(N)=O)cc2)cc(C)c1Oc1nc(Nc2ccc(C#N)cc2)nc2nc[nH]c12] | [c)] 13.22 (s, 1H), 9.90 (s, 1H), 8.28 (s, 1H), 8.05 (m, 4H), 7.86 (d, 2H), 7.66 (m, 4H), 7.40 (d, 2H), 2.19 (s, 6H); MS (m/z): 476 [M + H]$^+$. |
| 46 | 4'-(2-(4-Cyanophenylamino)-7H-purin-6-yloxy)-3',5'-dimethylbiphenyl-4-sulfonamide | 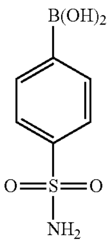 | 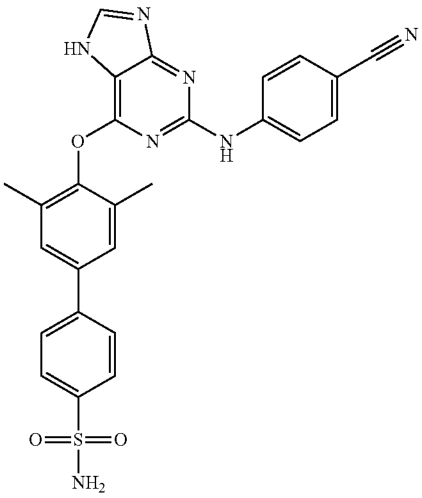 [SMILES: Cc1cc(-c2ccc(S(N)(=O)=O)cc2)cc(C)c1Oc1nc(Nc2ccc(C#N)cc2)nc2nc[nH]c12] | [c)] 13.24 (s, 1H), 9.90 (s, 1H), 8.28 (s, 1H), 7.97 (m, 4H), 7.67 (m, 4H), 7.43 (m, 4H), 2.24 (s, 6H); MS (m/z): 512 [M + H]$^+$. |

-continued

| Eg | Compound Name | Boronic Acid starting material | Structure | $^1$H NMR (400 MHz) 25° C. δ MS (ESI) |
|---|---|---|---|---|
| 47 | 4-(6-(2,6-Dimethyl-4-(1-methyl-1H-pyrazol-5-yl)phenoxy)-7H-purin-2-ylamino)benzonitrile | 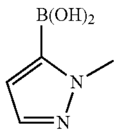 | 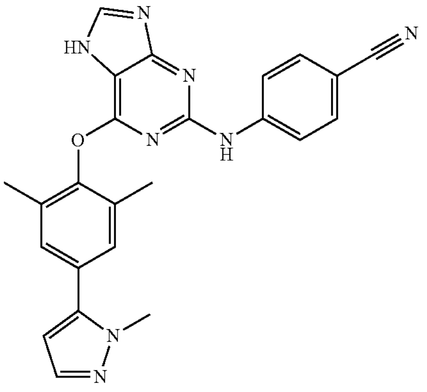 [SMILES: Cc1cc(-c2ccnn2C)cc(C)c1Oc1nc(Nc2ccc(C#N)cc2)nc2nc[nH]c12] | c) 13.24 (s, 1H), 9.92 (s, 1H), 8.29 (s, 1H), 7.64 (d, 2H), 7.53 (s, 1H), 7.41 (m, 4H), 6.48 (s, 1H), 3.93 (s, 3H), 2.17 (s, 6H); MS (m/z): 437 [M + H]$^+$. |
| 48 | 4-(4-(2,6-Dimethyl-4-(pyrimidin-4-yl)phenoxy-5-methyl-5H-pyrrolo[3,2-d]pyrimidin-2-ylamino)benzonitrile | 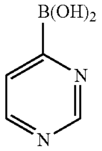 | 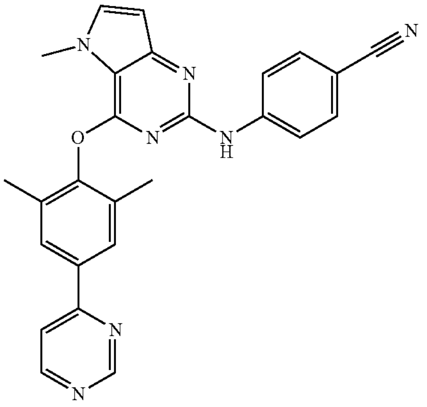 [SMILES: Cc1cc(-c2ccncn2)cc(C)c1Oc1nc(Nc2ccc(C#N)cc2)nc2ccn(C)c12] | b) 9.34 (s, 1H), 8.84 (s, 1H), 7.94 (s, 2H), 7.79 (m, 1H), 7.46 (d, 2H), 7.31 (m, 4H), 6.46 (s, 1H), 4.17 (s, 3H), 2.30 (s, 6H); MS (m/z): 448 [M + H]$^+$. |
| 49 | 4'-(2-(4-Cyanophenylamino)-7-(4-methoxybenzyl)-7H-purin-6-yloxy)-3',5'-dimethylbiphenyl-4-carboxamide | 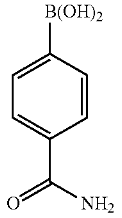 | 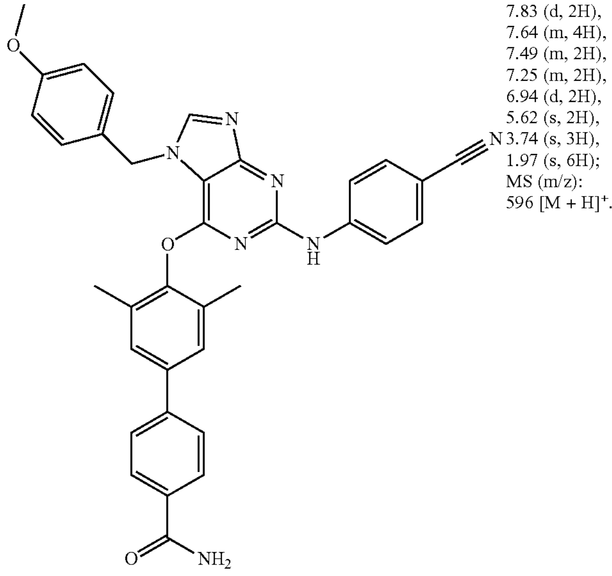 | b) 9.88 (s, 1H), 8.72 (s, 1H), 8.04 (m, 4H), 7.83 (d, 2H), 7.64 (m, 4H), 7.49 (m, 2H), 7.25 (m, 2H), 6.94 (d, 2H), 5.62 (s, 2H), 3.74 (s, 3H), 1.97 (s, 6H); MS (m/z): 596 [M + H]$^+$. |

-continued

| Eg | Compound Name | Boronic Acid starting material | Structure | $^1$H NMR (400 MHz) 25° C. δ MS (ESI) |
|---|---|---|---|---|
| 50 | 4'-(2-(4-Cyanophenylamino)-5-methyl-5H-pyrrolo[3,2-d]pyrimidin-4-yloxy)-2-fluoro-3',5'-dimethylbiphenyl-4-carboxamide | 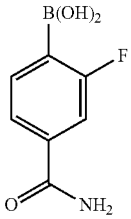 [SMILES: NC(=O)c1ccc(B(O)O)c(F)c1] | 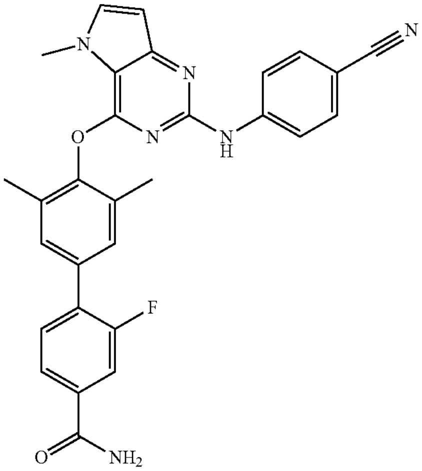 | [c)] 8.75 (m, 2H), 7.60 (m, 8H), 7.36 (s, 2H), 4.10 (s, 3H), 2.28 (s, 6H); MS (m/z): 448 [M + H]$^+$. |
| 51 | 4-(4-(2,6-Dimethyl-4-(pyridin-4-yl)phenoxy)-1-methyl-1H-pyrazolo[3,4-d]pyrimidin-6-ylamino)benzonitrile | 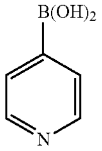 | 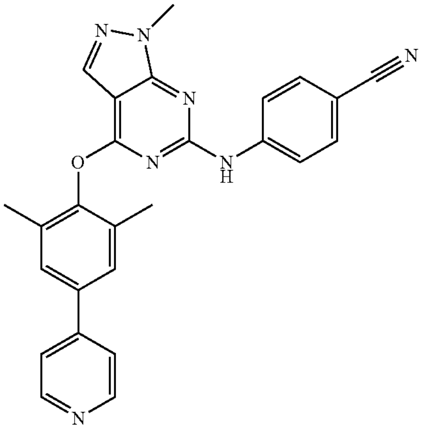 [SMILES: Cc1cc(-c2ccncc2)cc(C)c1Oc1nc(Nc2ccc(C#N)cc2)nc2c1cnn2C] | [b)] 9.34 (s, 1H), 8.84 (s, 1H), 7.94 (s, 2H), 7.79 (m, 1H), 7.46 (d, 2H), 7.31 (m, 4H), 6.46 (s, 1H), 4.17 (s, 3H), 2.30 (s, 6H); MS (m/z): 448 [M + H]$^+$. |
| 52 | 4'-(2-(4-Cyanophenylamino)-9-methyl-9H-purin-6-yloxy)-3',5'-dimethylbiphenyl-4-sulfonamide | 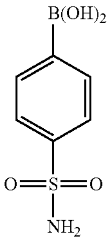 | 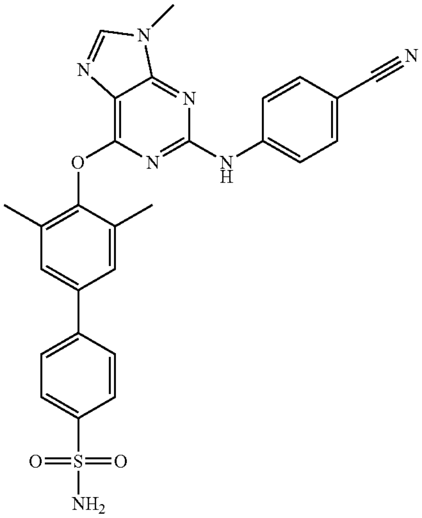 [SMILES: Cc1cc(-c2ccc(S(N)(=O)=O)cc2)cc(C)c1Oc1nc(Nc2ccc(C#N)cc2)nc2c1ncn2C] | [c)] 10.14 (s, 1H), 8.28 (s, 1H), 7.95 (m, 4H), 7.64 (m, 4H), 7.48 (s, 2H), 7.40 (d, 2H), 3.75 (s, 3H), 2.26 (s, 6H); MS (m/z): 526 [M + H]$^+$. |

-continued

| Eg | Compound Name | Boronic Acid starting material | Structure | $^{1}$H NMR (400 MHz) 25° C. δ MS (ESI) |
|---|---|---|---|---|
| 53 | 4'-(2-(4-Cyanophenylamino)-7-methyl-7H-purin-6-yloxy)-3',5'-dimethylbiphenyl-4-sulfonamide | 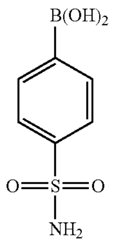 | 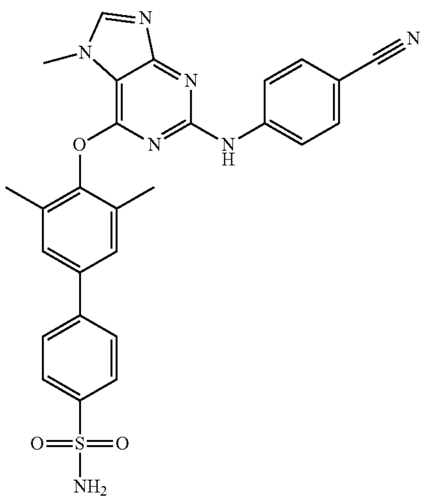 [SMILES: Cc1cc(-c2ccc(S(N)(=O)=O)cc2)cc(C)c1Oc1nc(Nc2ccc(C#N)cc2)nc2ncn(C)c12] | [c] 9.80 (s, 1H), 8.45 (s, 1H), 7.96 (m, 4H), 7.70 (d, 2H), 7.64 (s, 2H), 7.46 (m, 4H), 4.18 (s, 3H), 2.25 (s, 6H); MS (m/z): 526 [M + H]$^+$. |
| 54 | 4-(4-(4'-Amino-3,5-dimethylbiphenyl-4-yloxy)-5-methyl-5H-pyrrolo[3,2-d]pyrimidin-2-ylamino)benzonitrile | 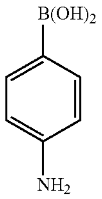 | 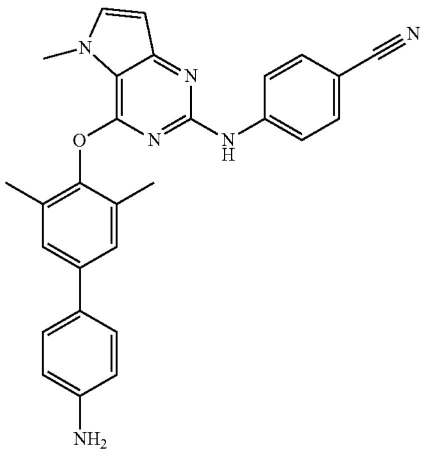 [SMILES: Cc1cc(-c2ccc(N)cc2)cc(C)c1Oc1nc(Nc2ccc(C#N)cc2)nc2ccn(C)c12] | [b] 7.40 (m, 12H), 6.85 (d, 2H), 6.46 (s, 1H), 4.18 (s, 3H), 2.25 (s, 6H); MS (m/z): 461 [M + H]$^+$. |
| 55 | 4'-(2-(4-Cyanophenylamino)-7-methyl-7H-purin-6-yloxy)-2-fluoro-3',5'-dimethylbiphenyl-4-carboxamide | 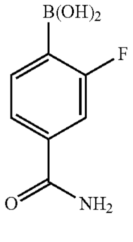 [SMILES: NC(=O)c1ccc(B(O)O)c(F)c1] | 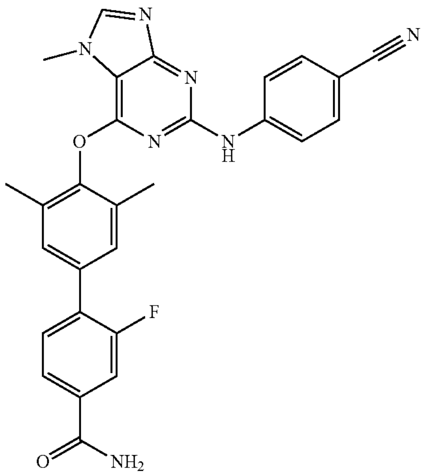 [SMILES: Cc1cc(-c2ccc(C(N)=O)cc2F)cc(C)c1Oc1nc(Nc2ccc(C#N)cc2)nc2ncn(C)c12] | [c] 9.92 (s, 1H), 8.45 (s, 1H), 8.17 (s, 1H), 7.88 (m, 3H), 7.72 (m, 2H), 7.61 (s, 1H), 7.49 (m, 4H), 4.13 (s, 3H), 2.24 (s, 6H); MS (m/z): 508 [M + H]$^+$. |

-continued

| Eg | Compound Name | Boronic Acid starting material | Structure | $^1$H NMR (400 MHz) 25° C. δ MS (ESI) |
|---|---|---|---|---|
| 56 | 4'-(2-(4-Cyanophenylamino)-9-methyl-9H-purin-6-yloxy)-2-fluoro-3',5'-dimethylbiphenyl-4-carboxamide | 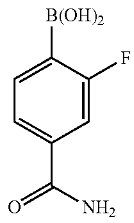 [SMILES: NC(=O)c1ccc(B(O)O)c(F)c1] | 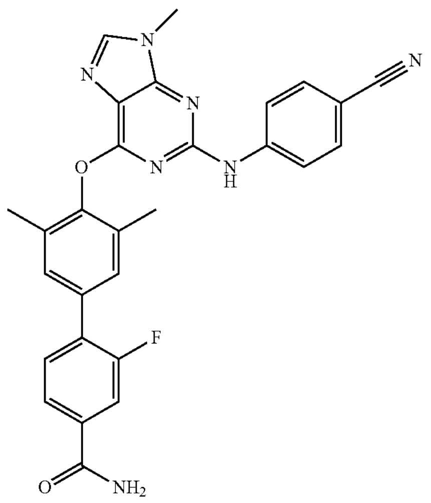 [SMILES: Cc1cc(-c2ccc(C(N)=O)cc2F)cc(C)c1Oc1nc(Nc2ccc(C#N)cc2)nc2c1ncn2C] | c) 10.12 (s, 1H), 8.27 (s, 1H), 8.18 (s, 1H), 7.89 (m, 3H), 7.74 (m, 2H), 7.62 (m, 1H), 7.53 (s, 2H), 7.40 (d, 2H), 3.81 (s, 3H), 2.18 (s, 6H); MS (m/z): 508 [M + H]$^+$. |
| 57 | 4-(4-(2,6-dimethyl-4-(pyridazin-4-yl)phenoxy)-5-methyl-5H-pyrrolo[3,2-d]pyrimidin-2-ylamino)benzonitrile | 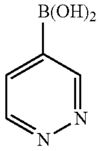 | 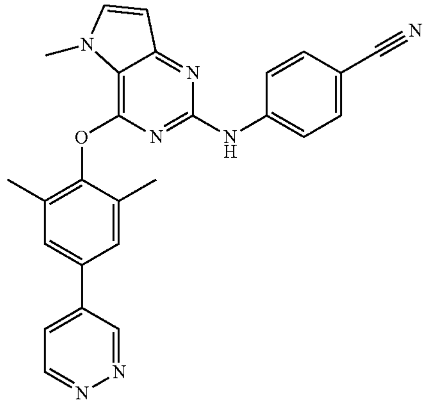 [SMILES: Cc1cc(-c2ccnnc2)cc(C)c1Oc1nc(Nc2ccc(C#N)cc2)nc2ccn(C)c12] | c) 9.77 (s, 1H), 9.63 (s, 1H), 9.34 (s, 1H), 8.12 (m, 1H), 7.90 (s, 2H), 7.72 (m, 3H), 7.43 (d, 2H), 6.44 (s, 1H), 4.14 (s, 3H), 2.26 (s, 6H); MS (m/z): 448 [M + H]$^+$. |
| 58 | 4-(6-(2,6-Dimethyl-4-(pyridazin-4-yl)phenoxy)-7-methyl-7H-purin-2-ylamino)benzonitrile | 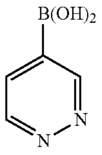 | 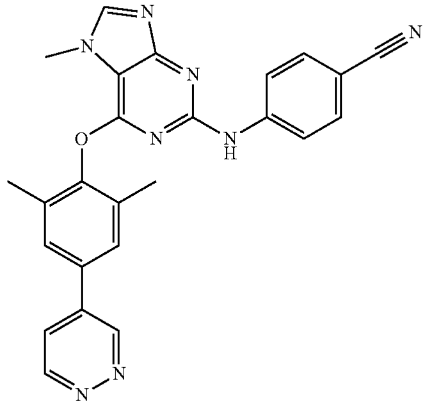 [SMILES: Cc1cc(-c2ccnnc2)cc(C)c1Oc1nc(Nc2ccc(C#N)cc2)nc2ncn(C)c12] | c) 9.88 (s, 1H), 9.77 (s, 1H), 9.34 (m, 1H), 8.46 (s, 1H), 8.12 (m, 1H), 7.91 (s, 2H), 7.72 (d, 2H), 7.47 (d, 2H), 4.13 (s, 3H), 2.27 (s, 6H); MS (m/z): 449 [M + H]$^+$. |

-continued

| Eg | Compound Name | Boronic Acid starting material | Structure | $^1$H NMR (400 MHz) 25° C. δ MS (ESI) |
|---|---|---|---|---|
| 59 | 4-(6-(2,6-Dimethyl-4-(pyridazin-4-yl)phenoxy)-9-methyl-9H-purin-2-ylamino)benzonitrile | 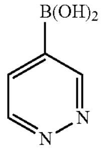 | 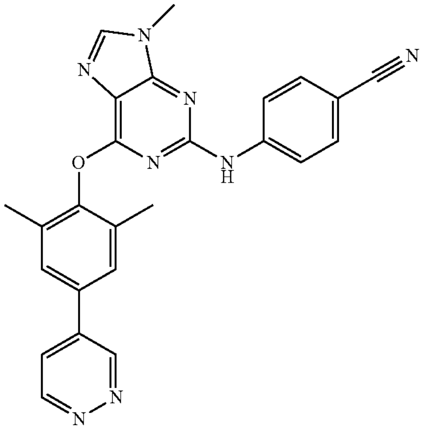 [SMILES: Cc1cc(-c2ccnnc2)cc(C)c1Oc1nc(Nc2ccc(C#N)cc2)nc2c1ncn2C] | $^{c)}$ 10.12 (s, 1H), 9.78 (s, 1H), 9.35 (s, 1H), 8.27 (s, 1H), 8.13 (m, 1H), 7.91 (s, 2H), 7.63 (d, 2H), 7.39 (d, 2H), 3.81 (s, 3H), 2.21 (s, 6H); MS (m/z): 449 $[M + H]^+$. |
| 60 | 5-(4-(2-(4-Cyanophenylamino)-5-methyl-5H-pyrrolo[3,2-d]pyrimidin-4-yloxy)-3,5-dimethylphenyl) picolinamide | 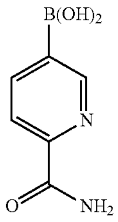 | 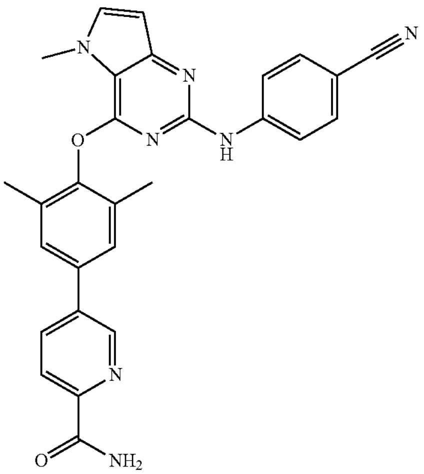 [SMILES: Cc1cc(-c2ccc(C(N)=O)nc2)cc(C)c1Oc1nc(Nc2ccc(C#N)cc2)nc2ccn(C)c12] | $^{c)}$ 9.64 (s, 1H), 9.05 (s, 1H), 8.38 (m, 1H), 8.18 (m, 3H), 7.73 (m, 5H), 7.43 (d, 2H), 6.43 (s, 1H), 4.14 (s, 3H), 2.26 (s, 6H); MS (m/z): 490 $[M + H]^+$. |
| 61 | 6-(4-(2-(4-Cyanophenylamino)-5-methyl-5H-pyrrolo[3,2-d]pyrimidin-4-yloxy)-3,5-dimethylphenyl) nicotinamide | 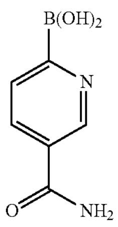 | 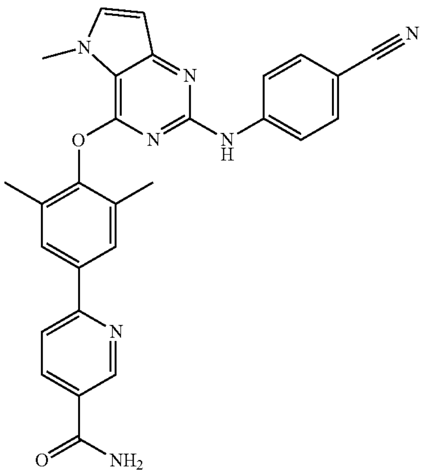 [SMILES: Cc1cc(-c2ccc(C(N)=O)cn2)cc(C)c1Oc1nc(Nc2ccc(C#N)cc2)nc2ccn(C)c12] | $^{c)}$ 9.67 (s, 1H), 9.20 (s, 1H), 8.43 (m, 1H), 8.25 (m, 3H), 8.13 (s, 2H), 7.70 (m, 3H), 7.45 (d, 2H), 6.47 (s, 1H), 4.13 (s, 3H), 2.28 (s, 6H); MS (m/z): 490 $[M + H]^+$. |

-continued

| Eg | Compound Name | Boronic Acid starting material | Structure | $^1$H NMR (400 MHz) 25° C. δ MS (ESI) |
|---|---|---|---|---|
| 62 | 4-(4-(4'-fluoro-3,5-dimethylbiphenyl-4-yloxy)-5-methyl-5H-pyrrolo[3,2-d]pyrimidin-2-ylamino)benzonitrile | 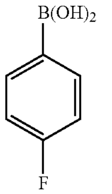 | 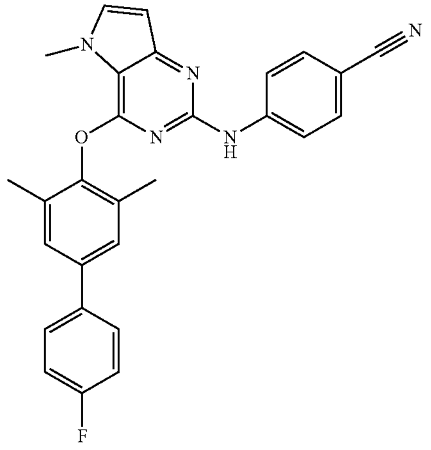 [SMILES: Cc1cc(-c2ccc(F)cc2)cc(C)c1Oc1nc(Nc2ccc(C#N)cc2)nc2ccn(C)c12] | [b] 2.23 (s, 6H) 4.15 (s, 3H) 6.44 (d, J = 2.90 Hz, 1H) 7.18 (t, J = 8.60 Hz, 1H) 7.25-7.29 (m, 2H) 7.41 (d, J = 8.91 Hz, 2H) 7.60 (dd, J = 8.71, 5.39 Hz, 2H) |
| 63 | 4'-(2-(4-cyanophenylamino)-5-methyl-5H-pyrrolo[3,2-d]pyrimidin-4-yloxy)-4-fluoro-3',5'-dimethylbiphenyl-3-carbonitrile | 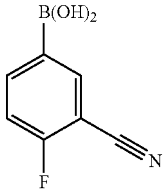 [SMILES: N#Cc1cc(B(O)O)ccc1F] | 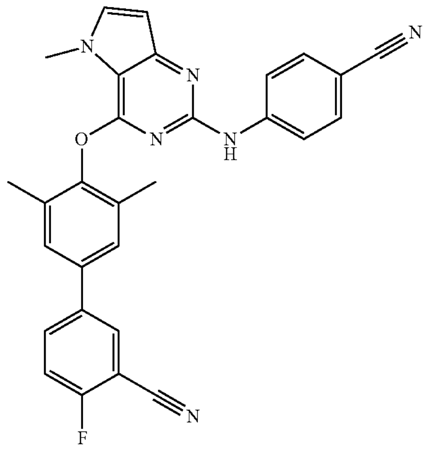 [SMILES: Cc1cc(-c2ccc(F)c(C#N)c2)cc(C)c1Oc1nc(Nc2ccc(C#N)cc2)nc2ccn(C)c12] | [b] 2.25 (s, 6H) 4.15 (s, 3H) 6.45 (d, J = 3.11 Hz, 1H) 7.16 (s, 1H) 7.27-7.31 (m, 3H) 7.32-7.37 (m, 3H) 7.44 (d, J = 8.71 Hz, 2H) 7.87 (d, J = 5.39 Hz, 2H), |
| 64 | 3-(4-(2-(4-cyanophenylamino)-5-methyl-5H-pyrrolo[3,2-d]pyrimidin-j4-yloxy)-3,5-dimethylphenyl) isonicotinonitrile | 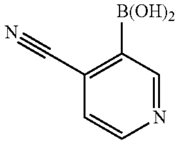 [SMILES: N#Cc1ccncc1B(O)O] | 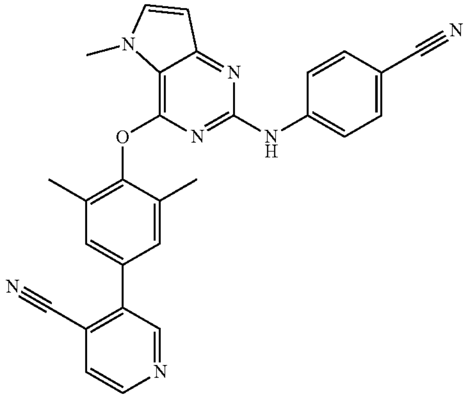 [SMILES: Cc1cc(-c2cnccc2C#N)cc(C)c1Oc1nc(Nc2ccc(C#N)cc2)nc2ccn(C)c12] | [b] 2.28 (s, 6H) 4.15 (s, 3H) 6.46 (d, J = 2.90 Hz, 1H) 7.28 (d, J = 2.90 Hz, 2H) 7.36-7.43 (m, 3H) 7.51 (d, J = 8.91 Hz, 2H) 7.67 (d, J = 4.98 Hz, 1H) 8.79 (d, J = 4.98 Hz, 1H) 8.93 (s, 1H) |

-continued

| Eg | Compound Name | Boronic Acid starting material | Structure | $^1$H NMR (400 MHz) 25° C. δ MS (ESI) |
|---|---|---|---|---|
| 65 | 4-(4-(3',5'-difluoro-3,5-dimethylbiphenyl-4-yloxy)-5-methyl-5H-pyrrolo[3,2-d]pyrimidin-2-ylamino)benzonitrile | 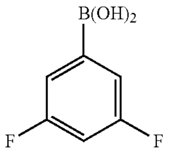 | 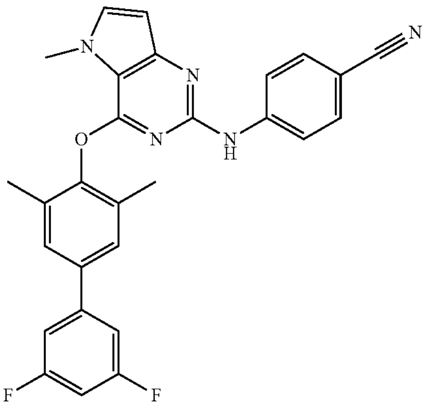 [SMILES: Cc1cc(-c2cc(F)cc(F)c2)cc(C)c1Oc1nc(Nc2ccc(C#N)cc2)nc2ccn(C)c12] | b) 2.24 (s, 6H) 4.14 (s, 3H) 6.44 (d, J = 2.90 Hz, 1H) 6.78-6.87 (m, 1H) 7.13-7.20 (m, 3H) 7.27 (d, J = 2.90 Hz, 1H) 7.31 (d, J = 8.71 Hz, 2H) 7.38 (s, 2H) 7.44 (d, J = 8.71 Hz, 2H) |
| 66 | 4-(5-methyl-4-(3',4',5'-trifluoro-3,5-dimethylphenyl-4-yloxy)-5H-pyrrolo[3,2-d]pyrimidin-2-ylamino)benzonitrile | 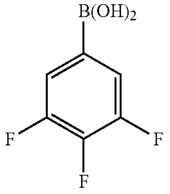 | 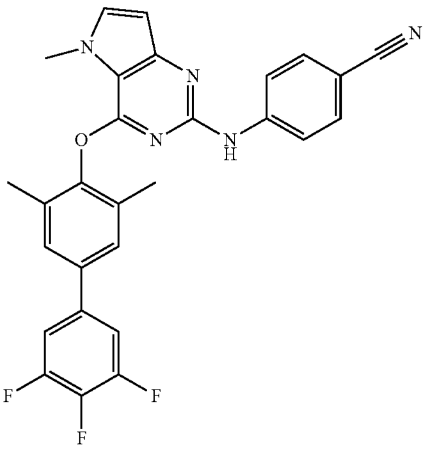 [SMILES: Cc1cc(-c2cc(F)c(F)c(F)c2)cc(C)c1Oc1nc(Nc2ccc(C#N)cc2)nc2ccn(C)c12] | b) 2.24 (s, 6H) 4.14 (s, 3H) 6.45 (d, J = 2.90 Hz, 1H) 7.16 (br. s., 1H) 7.22-7.29 (m, 4H) 7.30 (s, 1H) 7.32 (s, 2H) 7.44 (d, J = 8.71 Hz, 2H) |
| 67 | 4-(4-(3',5'-difluoro-2'-methoxy-3,5-dimethylbiphenyl-4-yloxy)-5-methyl-5H-pyrrolo[3,2-d]pyrimidin-2-ylamino)benzonitrile | 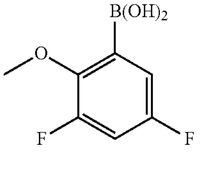 | 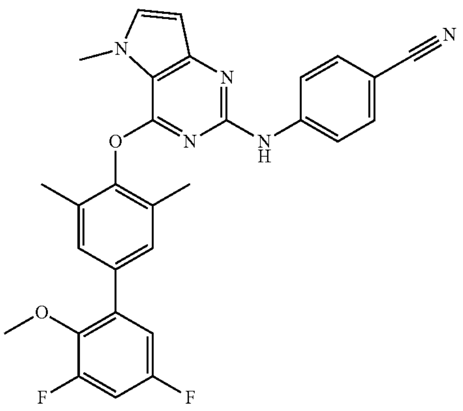 [SMILES: COc1c(F)cc(F)cc1-c1cc(C)c(Oc2nc(Nc3ccc(C#N)cc3)nc3ccn(C)c23)c(C)c1] | b) 2.23 (s, 6H) 3.79 (d, J = 1.24 Hz, 3H) 4.15 (s, 3H) 6.44 (d, J = 3.11 Hz, 1H) 6.84-6.95 (m, 2H) 7.21 (br. s., 1H) 7.27 (d, J = 2.90 Hz, 1H) 7.32-7.38 (m, 4H) 7.46 (d, J = 8.71 Hz, 2H) |

-continued

| Eg | Compound Name | Boronic Acid starting material | Structure | $^1$H NMR (400 MHz) 25° C. δ MS (ESI) |
|---|---|---|---|---|
| 68 | 4-(4-(4-(2,3-dihydrobenzo[b][1,4]dioxin-6-yl)-2,6-dimethylphenoxy)-5-methyl-5H-pyrrolo[3,2-d]pyrimidin-2-ylamino)benzonitrile | 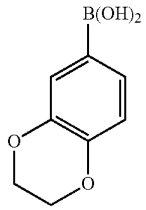 [SMILES: OB(O)c1ccc2c(c1)OCCO2] | 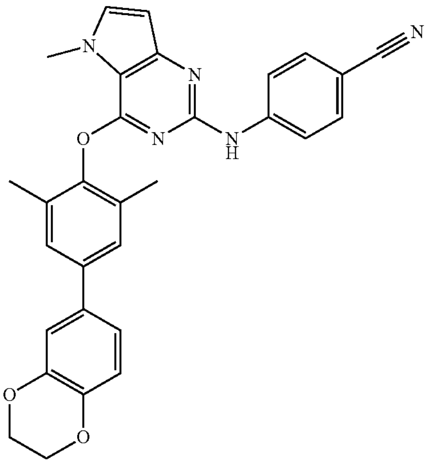 [SMILES: Cc1cc(-c2ccc3c(c2)OCCO3)cc(C)c1Oc1nc(Nc2ccc(C#N)cc2)nc2ccn(C)c12] | [b)] 2.21 (s, 6H) 4.14 (s, 3H) 4.33 (s, 4H) 6.43 (d, J = 3.11 Hz, 1H) 6.98 (d, J = 8.29 Hz, 1H) 7.10-7.15 (m, 1H) 7.16 (d, J = 2.28 Hz, 1H) 7.23-7.27 (m, 2H) 7.29 (d, J = 8.91 Hz, 2H) 7.35 (s, 2H) 7.37-7.43 (m, 2H) |
| 69 | 4-(4-(4-(benzo[d][1,3]dioxol-5-yl)-2,6-dimethylphenoxy)-5-methyl-5H-pyrrolo[3,2-d]pyrimdin-2-ylamino)benzonitrile | 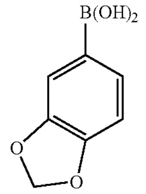 [SMILES: OB(O)c1ccc2c(c1)OCO2] | 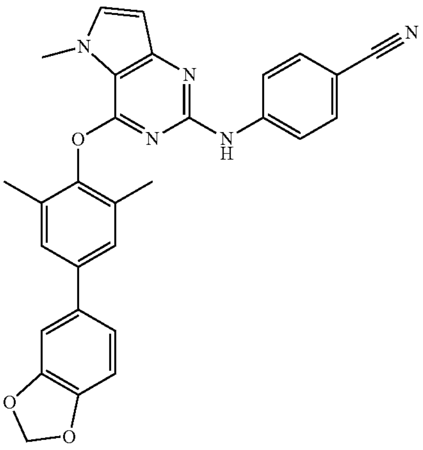 [SMILES: Cc1cc(-c2ccc3c(c2)OCO3)cc(C)c1Oc1nc(Nc2ccc(C#N)cc2)nc2ccn(C)c12] | [b)] 2.22 (s, 6H) 4.14 (s, 3H) 6.03 (s, 2H) 6.43 (d, J = 3.11 Hz, 1H) 6.93 (d, J = 8.50 Hz, 1H) 7.08-7.15 (m, 2H) 7.25-7.27 (m, 2H), 7.29 (d, J = 8.71 Hz, 2H) 7.33 (s, 2H) 7.37-7.43 (m, 2H) |
| 70 | 4-(4-(4-(2-aminopyrimidin-5-yl)-2,6-dimethylphenoxy)-5-methyl-5H-pyrrolo[3,2-d]pyrimidin-2-ylamino)benzonitrile | 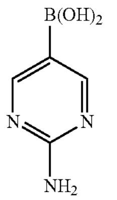 | 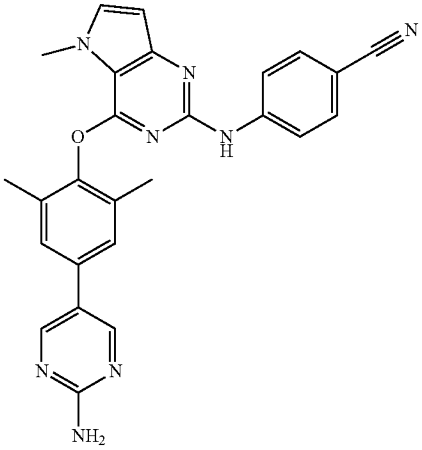 [SMILES: Cc1cc(-c2cnc(N)nc2)cc(C)c1Oc1nc(Nc2ccc(C#N)cc2)nc2ccn(C)c12] | [b)] 2.24 (s, 6H) 4.14 (s, 3H) 5.18 (s, 2H) 6.45 (d, J = 2.90 Hz, 1H) 7.25-7.28 (m, 2H) 7.30 (s, 2H) 7.33 (d, J = 8.91 Hz, 2H) 7.48 (d, J = 8.71 Hz, 2H) 8.59 (s, 2H) |

-continued

| Eg | Compound Name | Boronic Acid starting material | Structure | $^1$H NMR (400 MHz) 25° C. δ MS (ESI) |
|---|---|---|---|---|
| 71 | 4'-(2-(4-cyanophenylamino)-5-methyl-5H-pyrrolo[3,2-d]pyrimidin-4-yloxy)-3',5'-dimethylbiphenyl-3-sulfonamide | 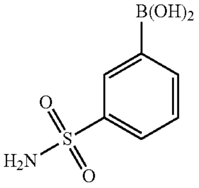 [SMILES: NS(=O)(=O)c1cccc(B(O)O)c1] | 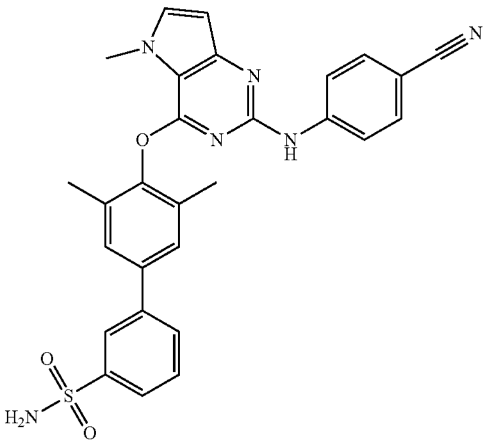 [SMILES: Cc1cc(-c2cccc(S(N)(=O)=O)c2)cc(C)c1Oc1nc(Nc2ccc(C#N)cc2)nc2ccn(C)c12] | [b] 2.25 (s, 6H) 3.37 (dd, J = 3.21, 1.55 Hz, 2H) 4.18 (s, 3H) 6.38-6.47 (m, 1H) 7.16-7.25 (m, 2H) 7.29-7.39 (m, 4H) 7.47 (s, 2H) 7.61-7.70 (m, 1H) 7.83-7.91 (m, 1H) 7.91-7.97 (m, 1H) 8.22 (d, J = 1.24 Hz, 1H) |
| 72 | 4'-(2-(4-cyanophenylamino)-5-methyl-5H-pyrrolo[3,2-d]pyrimidin-4-yloxy)-3',5'-dimethylbiphenyl-4-sulfonamide | 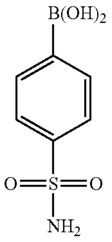 | 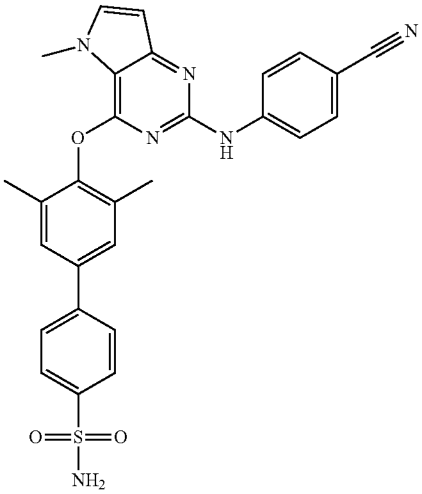 [SMILES: Cc1cc(-c2ccc(S(N)(=O)=O)cc2)cc(C)c1Oc1nc(Nc2ccc(C#N)cc2)nc2ccn(C)c12] | [b] 2.25 (s, 6H) 3.34 (s, 2H) 4.17 (s, 3H) 6.42 (d, J = 2.90 Hz, 1H) 7.20 (d, J = 8.71 Hz, 2H) 7.29-7.39 (m, 4H) 7.46 (s, 2H) 7.79 (d, J = 8.50 Hz, 2H) 8.05 (d, J = 8.29 Hz, 2H) |
| 73 | 4'-(2-(4-cyanophenylamino)-5-methyl-5H-pyrrolo[3,2-d]pyrimidin-4-yloxy)-3',5'-dimethylbiphenyl-2-sulfonamide | 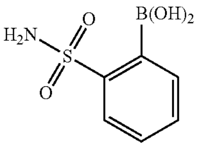 [SMILES: NS(=O)(=O)c1ccccc1B(O)O] | 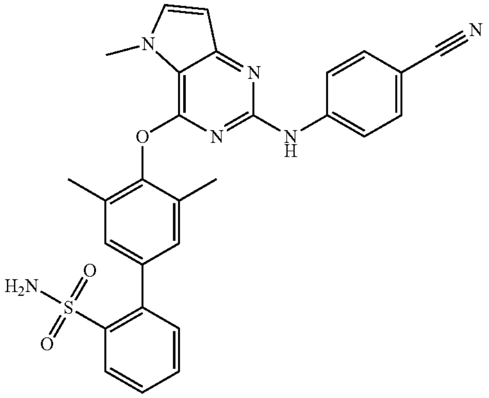 [SMILES: Cc1cc(-c2ccccc2S(N)(=O)=O)cc(C)c1Oc1nc(Nc2ccc(C#N)cc2)nc2ccn(C)c12] | [b] 2.23 (s, 6H) 4.15 (s, 3H) 4.54 (br. s., 2H) 6.44 (d, J = 2.90 Hz, 1H) 7.28 (d, J = 2.90 Hz, 1H) 7.31 (s, 2H) 7.38-7.46 (m, 4H) 7.50-7.59 (m, 3H) 7.63-7.72 (m, 1H) 8.20 (d, J = 7.88 Hz, 1H) |

-continued

| Eg | Compound Name | Boronic Acid starting material | Structure | $^{1}$H NMR (400 MHz) 25° C. δ MS (ESI) |
|---|---|---|---|---|
| 74 | N-tert-butyl-4'-(2-(4-cyanophenylamino)-5-methyl-5H-pyrrolo[3,2-d]pyrimidin-4-yloxy)-3',5'-dimethylbiphenyl-2-sulfonamide | 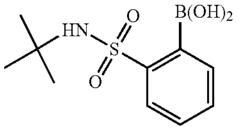 [SMILES: CC(C)(C)NS(=O)(=O)c1ccccc1B(O)O] | 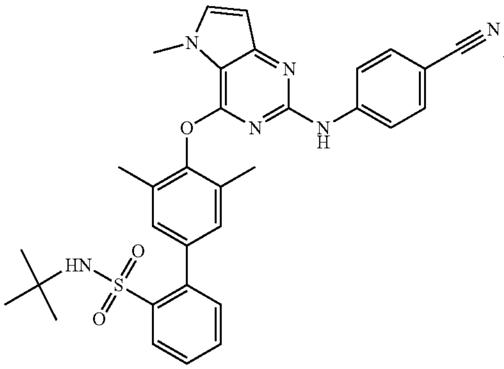 [SMILES: Cc1cc(-c2ccccc2S(=O)(=O)NC(C)(C)C)cc(C)c1Oc1nc(Nc2ccc(C#N)cc2)nc2ccn(C)c12] | [b] 1.10 (s, 9H) 2.23 (s, 6H) 4.16 (s, 3H) 6.45 (d, J = 2.90 Hz, 1H) 7.28 (d, J = 2.90 Hz, 1H) 7.30 (s, 2H) 7.34-7.47 (m, 4H) 7.48-7.58 (m, 3H) 7.60-7.67 (m, 1H) 8.17-8.23 (m, 1H) |
| 75 | 4'-(2-(4-cyanophenylamino)-5-methyl-5H-pyrrolo[3,2-d]pyrimidin-4-yloxy)-3',5'-dimethylbiphenyl-4-carboxylic acid | 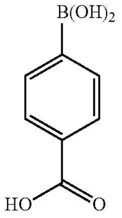 | 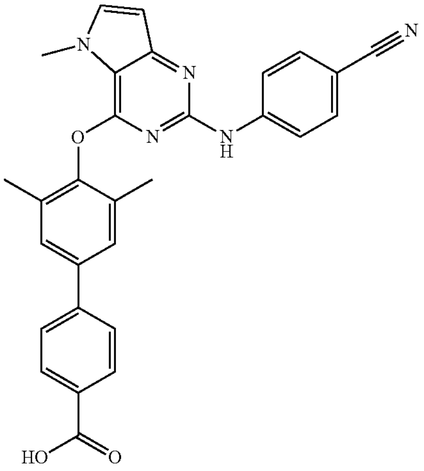 [SMILES: Cc1cc(-c2ccc(C(=O)O)cc2)cc(C)c1Oc1nc(Nc2ccc(C#N)cc2)nc2ccn(C)c12] | [b] 2.22 (d, J = 2.28 Hz, 6H) 4.13 (d, J = 2.28 Hz, 3H) 6.37 (t, J = 2.80 Hz, 1H) 7.22 (dd, J = 9.02, 2.38 Hz, 2H) 7.30 (t, J = 2.59 Hz, 1H) 7.35-7.41 (m, 4H) 7.44 (d, J = 1.45 Hz, 2H) 7.69 (dd, J = 8.40, 2.18 Hz, 2H) 8.13 (dd, J = 8.29, 2.28 Hz, 2H) |
| 76 | 4-(4-(4-(1-benzyl-1H-pyrazol-4-yl)-2,6-dimethylphenoxy)-5-methyl-5H-pyrrolo[3,2-d]pyrimidin-2-ylamino)benzonitrile | 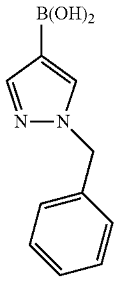 [SMILES: OB(O)c1cnn(Cc2ccccc2)c1] | 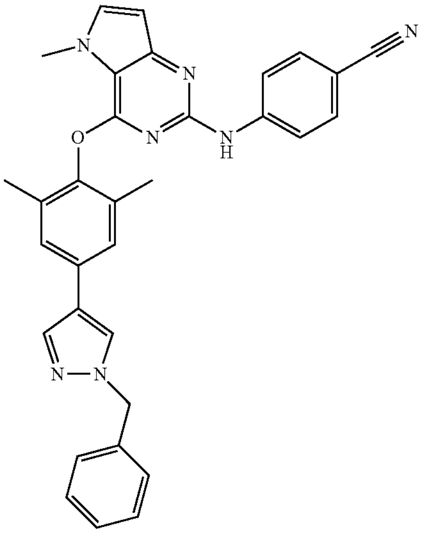 [SMILES: Cc1cc(-c2cnn(Cc3ccccc3)c2)cc(C)c1Oc1nc(Nc2ccc(C#N)cc2)nc2ccn(C)c12] | [b] 2.17 (s, 6H) 4.13 (s, 3H) 5.39 (s, 2H) 6.42 (d, J = 2.90 Hz, 1H) 7.20 (br. s., 1H) 7.23-7.37 (m, 8H) 7.37-7.45 (m, 4H) 7.66 (s, 1H) 7.86 (s, 1H) |

-continued

| Eg | Compound Name | Boronic Acid starting material | Structure | $^1$H NMR (400 MHz) 25° C. δ MS (ESI) |
|---|---|---|---|---|
| 77 | 4'-(2-(4-cyanophenylamino)-5-methyl-5H-pyrrolo[3,2-d]pyrimidin-4-yloxy)-3',5'-dimethylbiphenyl-3-carboxamide | 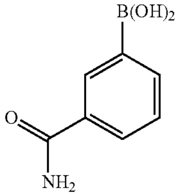 [SMILES: NC(=O)c1cccc(B(O)O)c1] | 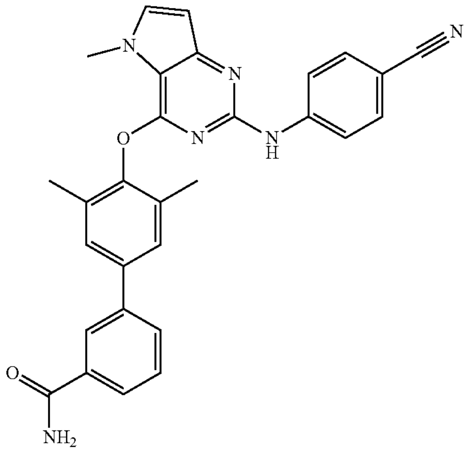 [SMILES: Cc1cc(-c2cccc(C(N)=O)c2)cc(C)c1Oc1nc(Nc2ccc(C#N)cc2)nc2ccn(C)c12] | [b)] 2.23 (s, 6H) 4.12 (s, 3H) 6.40 (d, J = 2.90 Hz, 1H) 7.38 (d, J = 8.91 Hz, 2H) 7.47 (s, 1H) 7.58 (t, J = 7.67 Hz, 2H) 7.64 (s, 2H) 7.69 (dd, J = 6.01, 2.90 Hz, 2H) 7.90 (dt, J = 7.67, 1.76 Hz, 2H) 8.14 (s, 1H) 8.24 (s, 1H) 9.60 (s, 1H) |
| 78 | 4'-(2-(4-cyanophenylamino)-5-methyl-5H-pyrrolo[3,2-d]pyrimidin-4-yloxy)-3',5'-dimethylbiphenyl-4-carboxamide | 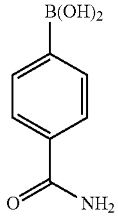 | 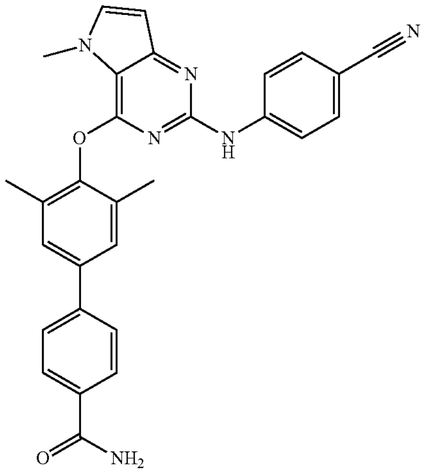 [SMILES: Cc1cc(-c2ccc(C(N)=O)cc2)cc(C)c1Oc1nc(Nc2ccc(C#N)cc2)nc2ccn(C)c12] | [b)] 2.26 (s, 6H) 4.17 (s, 3H) 6.42 (d, J = 3.11 Hz, 1H) 7.24 (d, J = 8.91 Hz, 2H) 7.34 (d, J = 3.11 Hz, 1H) 7.37 (s, 2H) 7.40 (s, 1H) 7.47 (s, 2H) 7.74 (d, J = 8.29 Hz, 2H) 7.99 (d, J = 8.29 Hz, 2H) |
| 79 | 4-(4-(4-(3-chloro-2-morpholinopyridin-4-yl)-2,6-dimethylphenoxy)-5-methyl-5H-pyrrolo[3,2-d]pyrimidin-2-ylamino)benzonitrile | 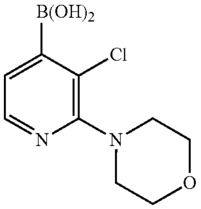 [SMILES: OB(O)c1ccnc(N2CCOCC2)c1Cl] | 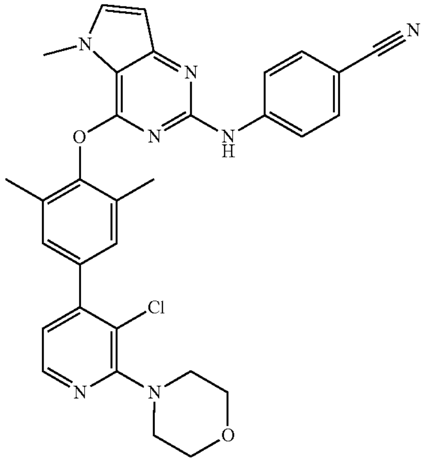 [SMILES: Cc1cc(-c2ccnc(N3CCOCC3)c2Cl)cc(C)c1Oc1nc(Nc2ccc(C#N)cc2)nc2ccn(C)c12] | [b)] 2.24 (s, 6H) 3.40-3.46 (m, 4H) 3.88-3.94 (m, 4H) 4.15 (s, 3H) 6.43 (d, J = 3.11 Hz, 1H) 6.96 (d, J = 4.98 Hz, 1H) 7.26 (s, 2H) 7.28 (d, J = 3.11 Hz, 1H) 7.32-7.37 (m, 2H) 7.39 (s, 1H) 7.40-7.45 (m, 2H) 8.27 (d, J = 4.77 Hz, 1H) |

-continued

| Eg | Compound Name | Boronic Acid starting material | Structure | $^1$H NMR (400 MHz) 25° C. δ MS (ESI) |
|---|---|---|---|---|
| 80 | 4-(4-(4-(2-chloropyridin-3-yl)-2,6-dimethylphenoxy)-5-methyl-5H-pyrrolo[3,2-d]pyrimidin-2-ylamino)benzonitrile | 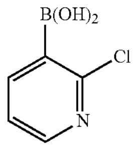 | 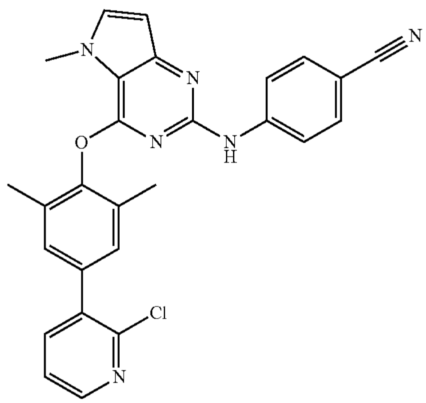 [SMILES: Cc1cc(-c2cccnc2Cl)cc(C)c1Oc1nc(Nc2ccc(C#N)cc2)nc2ccn(C)c12] | b) 2.25 (s, 6H) 4.15 (s, 3H) 6.44 (d, J = 2.90 Hz, 1H) 7.27-7.31 (m, 3H) 7.33-7.37 (m, 2H) 7.38 (d, J = 4.77 Hz, 1H) 7.40 (d, J = 4.77 Hz, 1H) 7.43-7.48 (m, 2H) 7.74 (dd, J = 7.46, 1.87 Hz, 1H) 8.45 (dd, J = 4.66, 1.76 Hz, 1H) |
| 81 | 4'-(2-(4-cyanophenylamino)-5-methyl-5H-pyrrolo[3,2-d]pyrimidin-4-yloxy)-3-methoxy-3',5'-dimethylbiphenyl-2-carbonitrile | 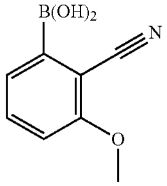 | 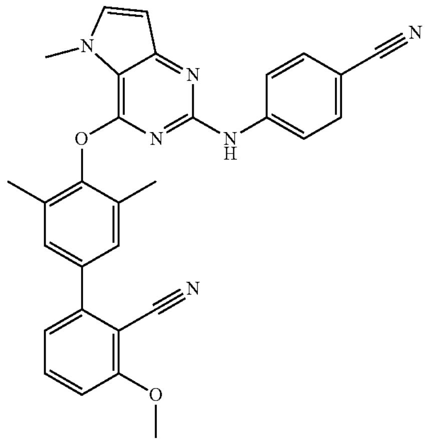 [SMILES: COc1cccc(-c2cc(C)c(Oc3nc(Nc4ccc(C#N)cc4)nc4ccn(C)c34)c(C)c2)c1C#N] | b) 2.24 (s, 6H) 4.02 (s, 3H) 4.14 (s, 3H) 6.43 (d, J = 2.90 Hz, 1H) 7.01 (d, J = 8.50 Hz, 1H) 7.12 (d, J = 7.67 Hz, 1H) 7.27 (d, J = 3.11 Hz, 1H) 7.30-7.36 (m, 3H) 7.38 (s, 2H) 7.41-7.47 (m, 2H) 7.63 (t, J = 8.09 Hz, 1H) |
| 82 | 4-(4-(4-(6-methoxypyridin-3-yl)-2,6-dimethylphenoxy)-5-methyl-5H-pyrrolo[3,2-d]pyrimidin-2-ylamino)benzonitrile | 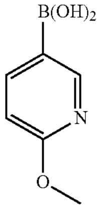 | 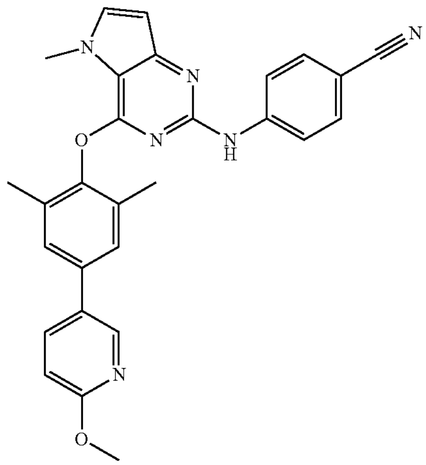 [SMILES: COc1ccc(-c2cc(C)c(Oc3nc(Nc4ccc(C#N)cc4)nc4ccn(C)c34)c(C)c2)cn1] | b) 2.24 (s, 6H) 4.01 (s, 3H) 4.15 (s, 3H) 6.44 (d, J = 2.90 Hz, 1H) 6.88 (d, J = 8.50 Hz, 1H) 7.27 (d, J = 3.11 Hz, 1H) 7.28-7.32 (m, 2H) 7.34 (s, 2H) 7.44 (d, J = 8.91 Hz, 2H) 7.84 (dd, J = 8.50, 2.49 Hz, 1H) 8.44 (d, J = 2.49 Hz, 1H) |

-continued

| Eg | Compound Name | Boronic Acid starting material | Structure | $^1$H NMR (400 MHz) 25° C. δ MS (ESI) |
|---|---|---|---|---|
| 83 | 4'-(2-(4-cyanophenylamino)-5-methyl-5H-pyrrolo[3,2-d]pyrimidin-4-yloxy)-6-methoxy-3',5'-dimethylbiphenyl-2-carbonitrile | 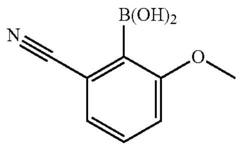 | 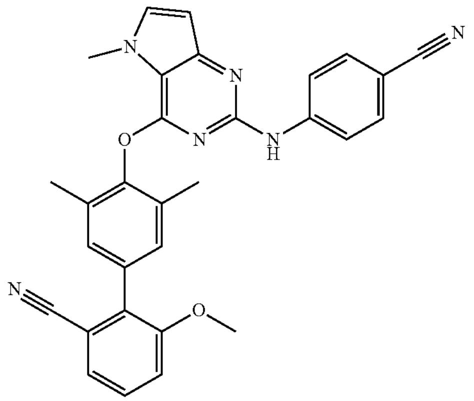 [SMILES: COc1cccc(C#N)c1-c1cc(C)c(Oc2nc(Nc3ccc(C#N)cc3)nc3ccn(C)c23)c(C)c1] | [b] 2.23 (s, 6H) 3.89 (s, 3H) 4.15 (s, 3H) 6.40 (d, J = 2.90 Hz, 1H) 7.25 (s, 2H) 7.25-7.29 (m, 2H) 7.35-7.41 (m, 4H) 7.42-7.47 (m, 2H) 7.81 (br. s., 1H) |
| 84 | 5-(4-(2-(4-cyanophenylamino)-5-methyl-5H-pyrrolo[3,2-d]pyrimidin-4-yloxy)-3,5-dimethylphenyl) picolinonitrile | 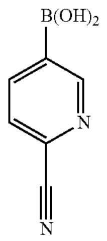 [SMILES: N#Cc1ccc(B(O)O)cn1] | 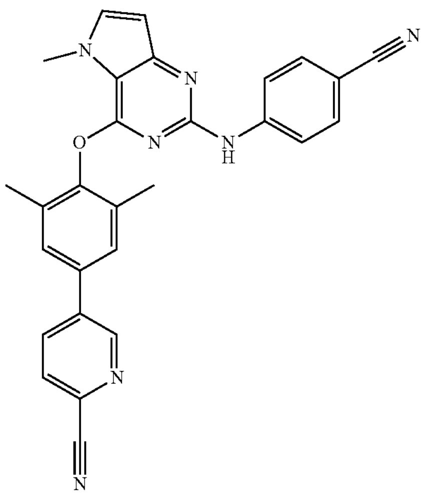 [SMILES: Cc1cc(-c2ccc(C#N)nc2)cc(C)c1Oc1nc(Nc2ccc(C#N)cc2)nc2ccn(C)c12] | [b] 2.26-2.31 (m, 6H) 4.16 (s, 3H) 6.46 (d, J = 3.11 Hz, 1H) 7.28-7.34 (m, 3H) 7.44 (s, 2H) 7.44-7.49 (m, 2H) 7.83 (d, J = 8.09 Hz, 1H) 8.07 (dd, J = 8.09, 2.28 Hz, 1H) 9.01 (d, J = 1.66 Hz, 1H) |
| 85 | 4'-(2-(4-cyanophenylamino)-5-methyl-5H-pyrrolo[3,2-d]pyrimidin-4-yloxy)-6-cyclopropyl-3',5'-dimethylbiphenyl-4-sulfonamide | 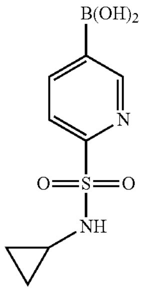 [SMILES: O=S(=O)(NC1CC1)c1ccc(B(O)O)cn1] | 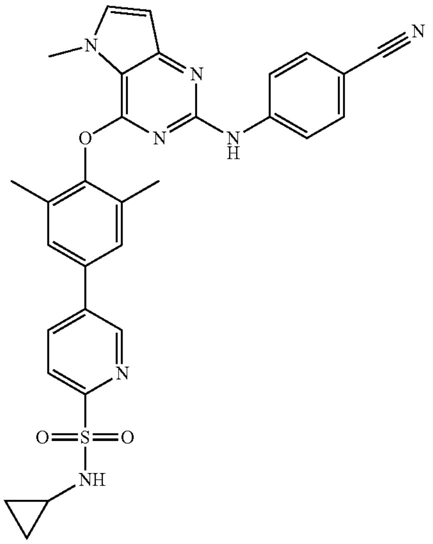 [SMILES: Cc1cc(-c2ccc(S(=O)(=O)NC3CC3)nc2)cc(C)c1Oc1nc(Nc2ccc(C#N)cc2)nc2ccn(C)c12] | [b] 0.62-0.75 (m, 5H) 2.26 (s, 6H) 4.16 (s, 3H) 5.47 (br. s., 1H) 6.42 (br. s., 1H) 7.19 (d, J = 8.71 Hz, 2H) 7.30 (s, 1H) 7.34 (d, J = 8.91 Hz, 2H) 7.47 (s, 2H) 7.81 (d, J = 8.50 Hz, 2H) 8.05 (d, J = 8.50 Hz, 2H) 8.39 (br. s., 1H) |

-continued

| Eg | Compound Name | Boronic Acid starting material | Structure | $^1$H NMR (400 MHz) 25° C. δ MS (ESI) |
|---|---|---|---|---|
| 86 | 4-(4-(4-(1H-indol-2-yl)-2,6-dimethylphenoxy)-5-methyl-5H-pyrrolo[3,2-d]pyrimidin-2-ylamino)benzonitrile | 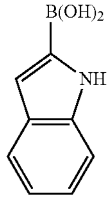 | 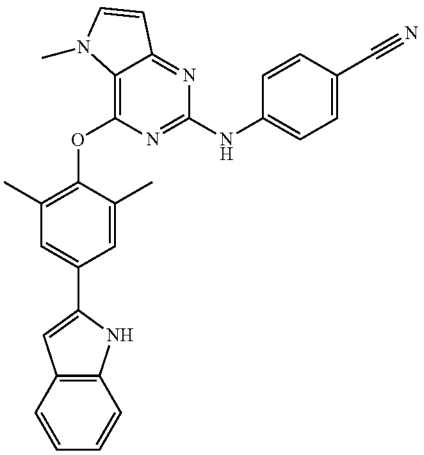 [SMILES: Cc1cc(-c2cc3ccccc3[nH]2)cc(C)c1Oc1nc(Nc2ccc(C#N)cc2)nc2ccn(C)c12] | [b] 2.27 (s, 6H) 4.17 (s, 3H) 6.47 (d, J = 3.11 Hz, 1H) 6.89 (d, J = 1.45 Hz, 1H) 7.14-7.21 (m, 1H) 7.20-7.27 (m, 1H) 7.20-7.27 (m, 1H) 7.30 (d, J = 2.90 Hz, 1H) 7.35 (d, J = 8.71 Hz, 2H) 7.39 (br. s., 1H) 7.43-7.50 (m, 3H) 7.52 (s, 2H) 7.69 (d, J = 7.46 Hz, 1H) 8.47 (br. s., 1H) |
| 87 | 4-(4-(4-(5-methoxypyridin-3-yl)-2,6-dimethylphenoxy)-5-methyl-5H-pyrrolo[3,2-d]pyrimidin-2-ylamino)benzonitrile | 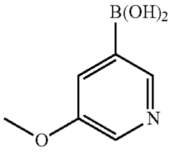 | 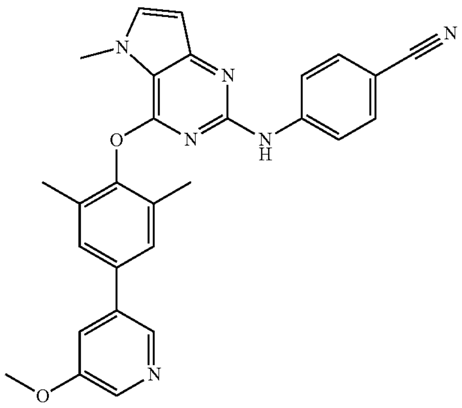 [SMILES: COc1cncc(-c2cc(C)c(Oc3nc(Nc4ccc(C#N)cc4)nc4ccn(C)c34)c(C)c2)c1] | [b] 2.28 (s, 6H) 4.00 (s, 3H) 4.18 (s, 3H) 6.47 (d, J = 2.90 Hz, 1H) 7.20-7.37 (m, 4H) 7.38-7.53 (m, 5H) 8.37 (s, 1H) 8.53 (s, 1H) |
| 88 | 4'-(7-chloro-2-(4-cyanophenylamino)-5-methyl-5H-pyrrolo[3,2-d]pyrimidin-4-yloxy)-3',5'-dimethylbiphenyl-4-carboxamide | 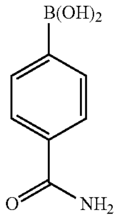 | 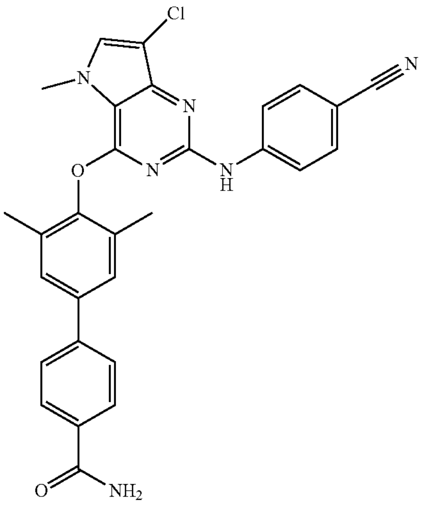 [SMILES: Cc1cc(-c2ccc(C(N)=O)cc2)cc(C)c1Oc1nc(Nc2ccc(C#N)cc2)nc2c(Cl)cn(C)c12] | [c] 2.23 (s, 6H) 4.12 (s, 3H) 7.35 (d, J = 8.91 Hz, 2H) 7.43 (br. s., 1H) 7.62 (d, J = 8.71 Hz, 2H) 7.67 (s, 2H) 7.86 (d, J = 8.29 Hz, 2H) 7.94 (s, 1H) 8.03 (d, J = 8.29 Hz, 2H) 8.08 (br. s., 1H) 9.95 (s, 1H) |

-continued

| Eg | Compound Name | Boronic Acid starting material | Structure | $^1$H NMR (400 MHz) 25° C. δ MS (ESI) |
|---|---|---|---|---|
| 89 | 4'-(2-(4-cyanophenylamino)-5-methyl-5H-pyrrolo[3,2-d]pyrimidin-4-yloxy)-N,N,3',5'-tetramethylbiphenyl-4-carboxamide | 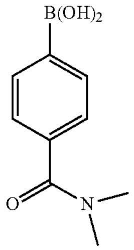 | 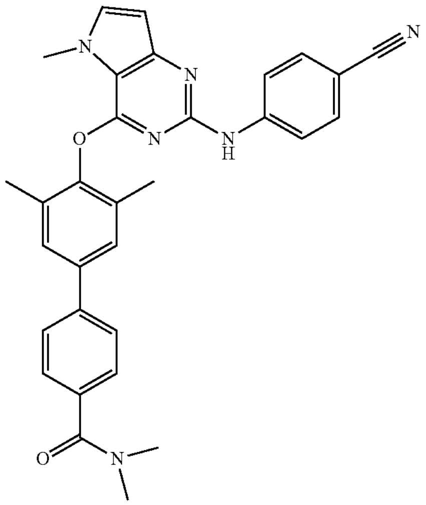 [SMILES: Cc1cc(-c2ccc(C(=O)N(C)C)cc2)cc(C)c1Oc1nc(Nc2ccc(C#N)cc2)nc2ccn(C)c12] | [b)] 2.25 (s, 6H) 3.06-3.20 (m, 6H) 4.25 (s, 3H) 6.60 (d, J = 1.87 Hz, 1H) 7.18-7.22 (m, 2H) 7.27-7.30 (m, 2H) 7.48 (s, 3H) 7.57-7.64 (m, 2H) 7.65-7.72 (m, 2H) 11.47 (s, 1H) |
| 90 | 4-(4-(4'-(azetidine-1-carbonyl)-3,5-dimethylbiphenyl-4-yloxy)-5-methyl-5H-pyrrolo[3,2-d]pyrimidin-2-ylamino)benzonitrile | 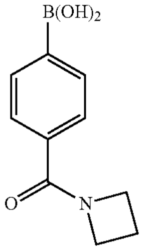 [SMILES: O=C(c1ccc(B(O)O)cc1)N1CCC1] | 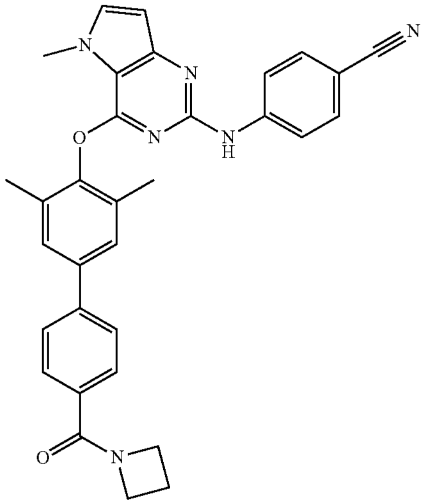 [SMILES: Cc1cc(-c2ccc(C(=O)N3CCC3)cc2)cc(C)c1Oc1nc(Nc2ccc(C#N)cc2)nc2ccn(C)c12] | [b)] 2.22 (s, 6H) 2.38 (quin, J = 7.77 Hz, 2H) 4.22 (s, 3H) 4.22-4.29 (m, 2H) 4.42 (t, J = 7.57 Hz, 2H) 6.66 (d, J = 2.28 Hz, 1H) 7.17 (d, J = 8.50 Hz, 2H) 7.26 (s, 2H) 7.46 (s, 2H) 7.48 (d, J = 2.28 Hz, 1H) 7.67 (d, J = 8.29 Hz, 2H) 7.74-7.78 (m, 2H) |
| 91 | 1-(4'-(2-(4-cyanophenylamino)-5-methyl-5H-pyrrolo[3,2-d]pyrimidin-4-yloxy)-3',5'-dimethylbiphenylcarbonyl)pyrrolidine-3-carbonitrile | 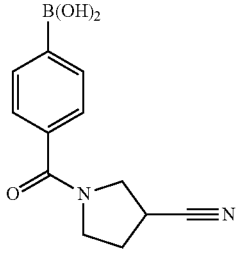 [SMILES: N#CC1CCN(C(=O)c2ccc(B(O)O)cc2)C1] | 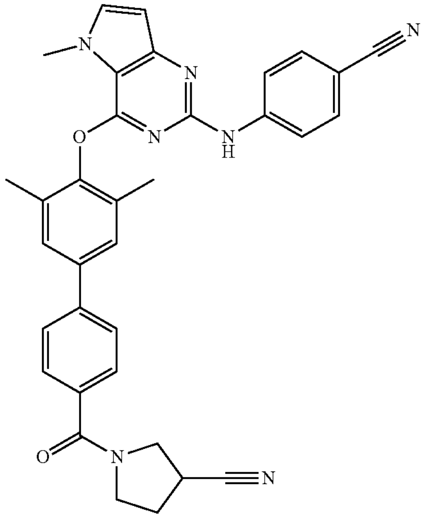 [SMILES: Cc1cc(-c2ccc(C(=O)N3CCC(C#N)C3)cc2)cc(C)c1Oc1nc(Nc2ccc(C#N)cc2)nc2ccn(C)c12] | [b)] 2.27 (s, 6H) 2.30-2.47 (m, 2H) 3.16-3.31 (m, 1H) 3.71-4.01 (m, 4H) 4.18 (s, 3H) 6.45 (d, J = 2.90 Hz, 1H) 7.23-7.27 (m, 2H) 7.30 (d, J = 3.11 Hz, 1H) 7.37 (d, J = 8.71 Hz, 2H) 7.41 (s, 1H) 7.46 (s, 2H) 7.66-7.72 (m, 2H) 7.72-7.76 (m, 2H) |

-continued

| Eg | Compound Name | Boronic Acid starting material | Structure | $^1$H NMR (400 MHz) 25° C. δ MS (ESI) |
|---|---|---|---|---|
| 92 | 4'-(2-(4-cyanophenylamino)-5-methyl-5H-pyrrolo[3,2-d]pyrimidin-4-yloxy)-N-cyclopropyl-3',5'-dimethylbiphenyl-4-carboxamide | 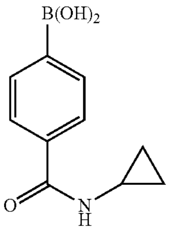 [SMILES: O=C(NC1CC1)c1ccc(B(O)O)cc1] | 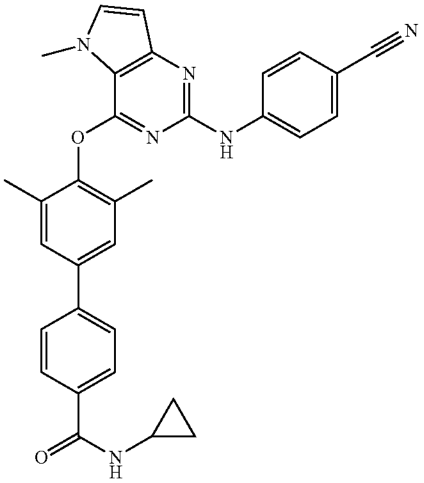 [SMILES: Cc1cc(-c2ccc(C(=O)NC3CC3)cc2)cc(C)c1Oc1nc(Nc2ccc(C#N)cc2)nc2ccn(C)c12] | [b] 0.66-0.73 (m, 2H) 0.86-0.96 (m, 2H) 2.26 (s, 6H) 2.92-3.02 (m, 1H) 4.17 (s, 3H) 6.44 (d, J = 2.90 Hz, 2H) 7.26 (d, J = 8.91 Hz, 2H) 7.30 (d, J = 2.90 Hz, 1H) 7.39 (d, J = 8.71 Hz, 2H) 7.44 (s, 2H) 7.50 (br.s., 1H) 7.71 (d, J = 8.29 Hz, 2H) 7.89 (d, J = 8.50 Hz, 2H) |
| 93 | 4-(4-(3,5-dimethyl-4'-(pyrrolidine-1-carbonyl)biphenyl-4-yloxy)-5-methyl-5H-pyrrolo[3,2-d]pyrimidin-2-ylamino)benzonitrile | 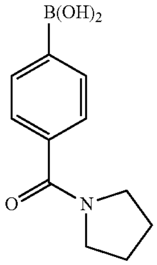 [SMILES: O=C(c1ccc(B(O)O)cc1)N1CCCC1] | 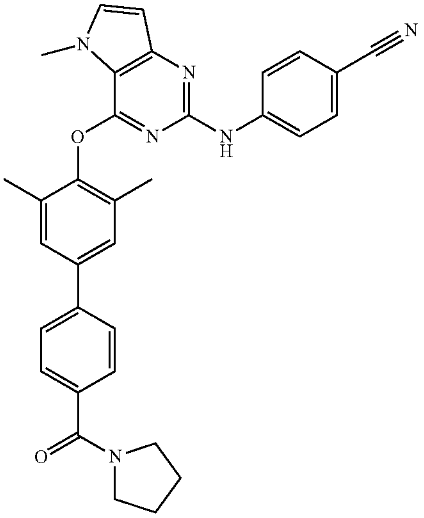 [SMILES: Cc1cc(-c2ccc(C(=O)N3CCCC3)cc2)cc(C)c1Oc1nc(Nc2ccc(C#N)cc2)nc2ccn(C)c12] | [b] 1.86-2.06 (m, 4H) 2.23 (s, 6H) 3.54 (t, J = 6.43 Hz, 2H) 3.67 (t, J = 6.84 Hz, 2H) 4.15 (s, 3H) 6.47 (d, J = 2.49 Hz, 1H) 7.24 (d, J = 2.90 Hz, 1H) 7.39 (d, J = 8.91 Hz, 2H) 7.43 (s, 2H) 7.60-7.71 (m, 4H) 8.66 (br. s., 1H) |
| 94 | 4-(4-(4'-(3-hydroxypyrrolidine-1-carbonyl)-3,5-dimethylbiphenyl-4-yloxy)-5-methyl-5H-pyrrolo[3,2-d]pyrimidin-2-ylamino)benzonitrile | 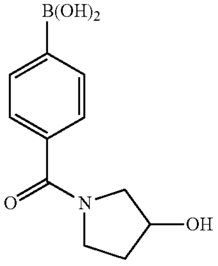 [SMILES: O=C(c1ccc(B(O)O)cc1)N1CCC(O)C1] | 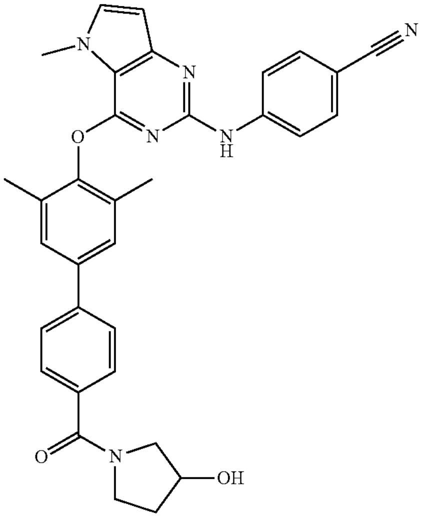 [SMILES: Cc1cc(-c2ccc(C(=O)N3CCC(O)C3)cc2)cc(C)c1Oc1nc(Nc2ccc(C#N)cc2)nc2ccn(C)c12] | [b] 1.92-2.14 (m, 2H) 2.23 (s, 6H) 3.52-3.92 (m, 4H) 4.14 (d, J = 4.35 Hz, 3H) 4.36-4.57 (m, 1H) 6.40 (t, J = 3.52 Hz, 1H) 7.14 (d, J = 8.71 Hz, 1H) 7.24 (d, J = 8.71 Hz, 1H) 7.26-7.31 (m, 3H) 7.38 (d, J = 8.91 Hz, 1H) 7.44 (d, J = 9.33 Hz, 2H) 7.58-7.75 (m, 4H) |

-continued
| Eg | Compound Name | Boronic Acid starting material | Structure | $^{1}$H NMR (400 MHz) 25° C. δ MS (ESI) |
|---|---|---|---|---|
| 95 | 4-(4-(3,5-Dimethylbiphenyl-4-yloxy)-5-methyl-5H-pyrrolo[3,2-d]pyrimidin-2-ylamino)benzonitrile | 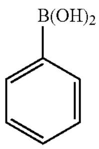 | 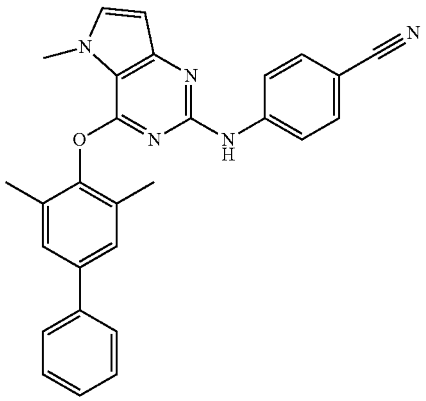 [SMILES: Cc1cc(-c2ccccc2)cc(C)c1Oc1nc(Nc2ccc(C#N)cc2)nc2ccn(C)c12] | b) 7.67 (d, 2H), 7.52 (t, 2H), 7.43 (m, 5H), 7.30 (m, 4H), 6.46 (d, 1H), 4.17 (s, 3H), 2.26 (s, 6H); MS (ESI): m/z 446 (M + 1)$^{+}$. |
a) $CDCl_3$—$CD_3OD$ (3:1)
b) $CDCl_3$
c) d6-DMSO
Example 96
4-(6-(4-(Pyridin-4-yl)phenoxy)-7H-purin-2-ylamino)benzonitrile
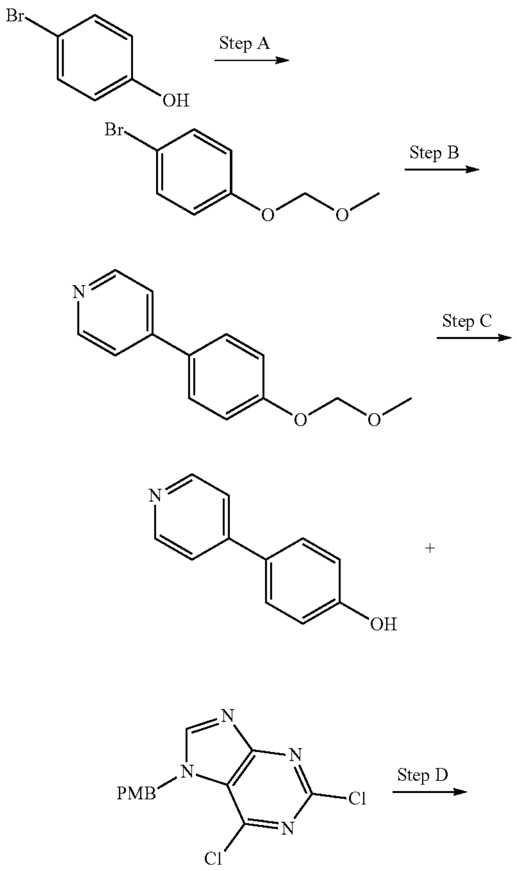
-continued
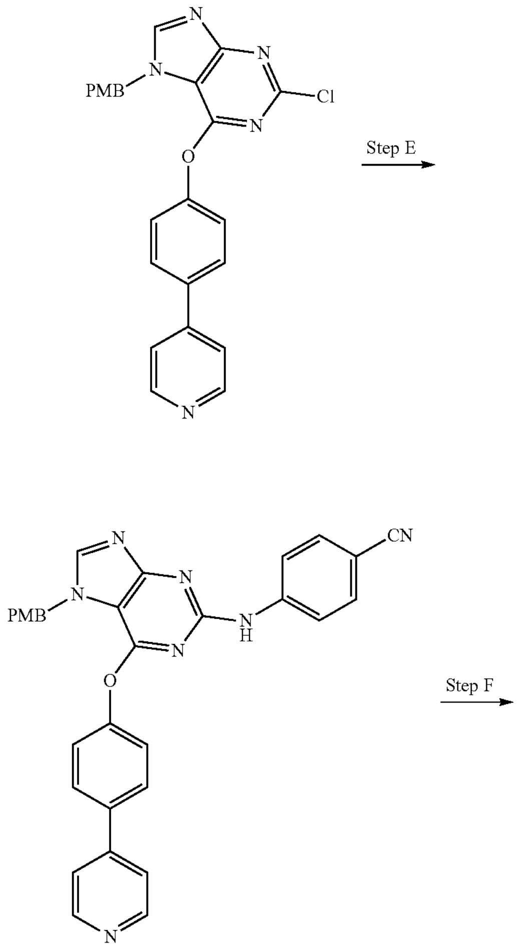

-continued

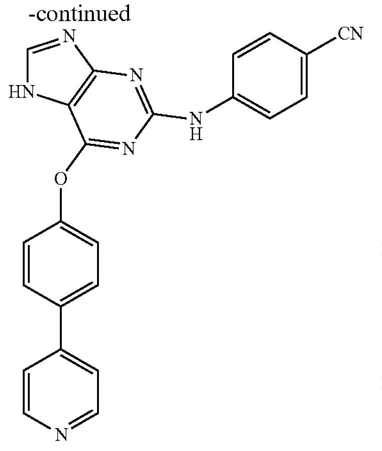

Step A: 1-bromo-4-(methoxymethoxy)benzene

To a solution of 4-bromophenol (0.50 g, 2.89 mmol) and dimethoxymethane (2.6 mL, 29.39 mmol) in DCM (60 mL) was added $P_2O_5$ (1.50 g, 10.57 mmol). The reaction mixture was stirred at for 1 h and insoluble precipitate was filtered off. Solid $Na_2CO_3$ was added to the solution and stirred for additional 10 min. The solid was filtered off and the solution was concentrated. Purification on a silica gel column gave the desired product as a clear oil (363 mg). NMR ($CDCl_3$): 7.38 (d, 2H), 6.93 (d, 2H), 5.15 (s, 2H), 3.47 (s, 3H).

Step B: 4-(4-(methoxymethoxy)phenyl)pyridine

To a degassed solution of 1-bromo-4-(methoxymethoxy) benzene (360 mg, 1.66 mmol), pyridin-4-ylboronic acid (307 mg, 2.50 mmol), and $Cs_2CO_3$ (1.09 g, 3.35 mmol) in THF (5 mL) was added $Pd(PPh_3)_4$ (190 mg, 0.16 mmol). The reaction mixture was heated at 80° C. overnight and diluted with EtOAc (50 mL). It was washed with $H_2O$ (2×25 mL), dried over $Na_2SO_4$, and concentrated. Purification on a silica gel column gave the desired product as a white solid (265 mg). NMR ($CDCl_3$): 8.63 (d, 2H), 7.67 (d, 2H), 7.47 (d, 2H), 7.16 (d, 2H), 5.24 (s, 2H), 3.52 (s, 3H).

Step C: 4-(pyridin-4-yl)phenol

A solution of 4-(4-(methoxymethoxy)phenyl)pyridine (240 mg, 1.11 mmol) in aqueous HCl (1N, 2.8 mL) was stirred at rt overnight. The reaction was neutralized with saturated $NaHCO_3$ and the precipitate was collected by filtration to yield the desired compound as a white solid (150 mg). NMR (MeOH-$d^4$): 8.49 (d, 2H), 7.65 (m, 4H), 6.92 (d, 2H).

Step D: 2-Chloro-7-(4-methoxybenzyl)-6-(4-(pyridin-4-yl)phenoxy)-7H-purine

To a solution of 4-(pyridin-4-yl)phenol (160 mg, 0.93 mmol) in THF (5 mL) was added KO$^t$Bu (115 mg, 1.03 mmol) and stirred for 20 min. 2,6-Dichloro-9-(4-methoxybenzyl)-9H-purine (300 mg, 0.97 mmol) in THF (20 mL) was added and stirred at rt over night. The reaction mixture was diluted with EtOAc (50 mL), washed with $H_2O$ (2×25 mL), and dried over $Na_2SO_4$. Purification on a silica gel column gave the desired product as a white solid (110 mg). NMR ($CDCl_3$): 8.70 (d, 2H), 7.94 (s, 1H), 7.73 (d, 2H), 7.54 (d, 2H), 7.43 (d, 2H), 7.31 (d, 2H), 6.92 (d, 2H), 5.36 (s, 2H), 3.82 (s, 3H); MS (ESI): m/z 444 $(M+1)^+$.

Step E: 4-(7-(4-methoxybenzyl)-6-(4-(pyridin-4-yl)phenoxy)-7H-purin-2-ylamino)benzonitrile A solution of 2-chloro-7-(4-methoxybenzyl)-6-(4-(pyridin-4-yl)phenoxy)-7H-purine (48 mg, 0.11 mmol), 4-aminobenzonitrile (20 mg, 0.17 mmol), $Pd(OAc)_2$ (2 mg, 0.009 mmol), BINAP (9 mg, 0.014 mmol), and $Cs_2CO_3$ (43 mg, 0.13 mmol) in toluene (2 mL) was degassed by bubbling nitrogen for 15 min then heated at 80° C. overnight. The desired product was precipitated with EtOAc (10 mL) and saturated $NaHCO_3$. NMR (DMSO-$d^6$): 10.00 (s, 1H), 8.70 (d, 2H), 8.41 (s, 1H), 7.98 (d, 2H), 7.82 (d, 2H), 7.75 (d, 2H), 7.53 (m, 4H), 7.38 (d, 2H), 6.98 (d, 2H), 5.38 (s, 2H), 3.74 (s, 3H); MS (ESI): m/z 526 $(M+1)^+$.

Step F: 4-(6-(4-(Pyridin-4-yl)phenoxy)-7H-purin-2-ylamino)benzonitrile

A solution of 4-(7-(4-methoxybenzyl)-6-(4-(pyridin-4-yl)phenoxy)-7H-purin-2-ylamino)benzonitrile (38 mg, 0.07 mmol) in TFA (0.5 mL) was heated at 60° C. overnight. The desired product was precipitated with EtOAc (2 mL) and collected by filtration. NMR (DMSO-$d^6$): 9.98 (s, 1H), 8.95 (d, 2H), 8.38 (d, 2H), 8.35 (d, 2H), 8.20 (d, 2H), 7.76 (d, 2H), 7.63 (d, 2H), 7.53 (d, 2H).

Example 97

4-(7-(4-Methoxybenzyl)-6-(2-methyl-4-(pyridin-4-yl)phenoxy)-7H-purin-2-ylamino)benzonitrile Synthesized in a similar fashion to example 96 using the appropriate starting material.

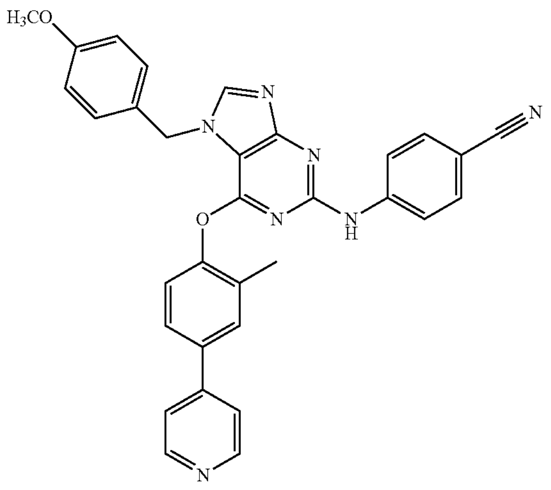 [SMILES: COc1ccc(Cn2cnc3nc(Nc4ccc(C#N)cc4)nc(Oc4ccc(-c5ccncc5)cc4C)c32)cc1]

NMR (DMSO-$d_6$): δ 10.01 (s, 1H), 8.69 (d, 2H), 8.41 (s 1H), 7.91 (m, 1H), 7.81 (m, 3H), 7.69 (d, 2H), 7.43 (m, 3H), 7.38 (d, 2H), 6.97 (d, 2H), 5.37 (s, 2H), 3.74 (s, 3H); MS (ESI): m/z 540 $(M+1)^+$.

Example 98

4-(6-(2-Methyl-4-(pyridin-4-yl)phenoxy)-7H-purin-2-ylamino)benzonitrile

Synthesized in a similar fashion to example 96 using the appropriate starting material.

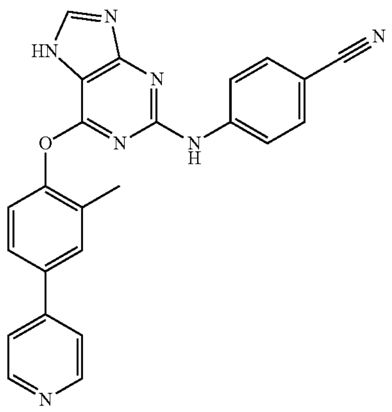 [SMILES: Cc1cc(-c2ccncc2)ccc1Oc1nc(Nc2ccc(C#N)cc2)nc2nc[nH]c12]

NMR (DMSO-$d_6$): δ 9.50 (s, 1H), 8.67 (d, 2H), 7.95 (s 1H), 7.88 (s, 1H), 7.80 (d, 2H), 7.75 (m, 3H), 7.39 (d, 2H), 7.35 (d, 1H), 2.25 (s, 3H); MS (ESI): m/z 420 $(M+1)^+$.

Example 99

4-(6-(2-chloro-6-methyl-4-(pyridin-4-yl)phenoxy)-7-(4-methoxybenzyl)-7H-purin-2-ylamino)benzonitrile Synthesized in a similar fashion to example 96 using the appropriate starting material.

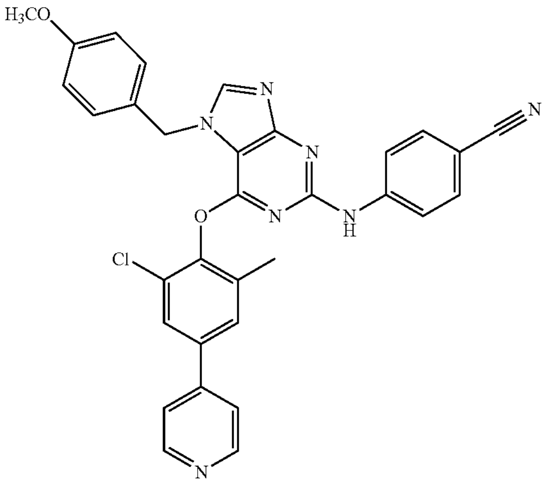 [SMILES: COc1ccc(Cn2cnc3nc(Nc4ccc(C#N)cc4)nc(Oc4c(C)cc(-c5ccncc5)cc4Cl)c32)cc1]

NMR (DMSO-$d_6$): δ 10.01 (s, 1H), 8.71 (d, 2H), 8.44 (s, 1H), 8.01 (m, 1H), 7.93 (m, 1H), 7.85 (d, 2H), 7.68 (d, 2H), 7.45 (d, 2H), 7.40 (d, 2H), 6.98 (d, 2H), 5.37 (s, 2H), 3.74 (s, 3H), 2.27 (s, 3H); MS (ESI): m/z 574 $(M+1)^+$.

Example 100

4-(6-(2-Chloro-6-methyl-4-(pyridin-4-yl)phenoxy)-7H-purin-2-ylamino)benzonitrile Synthesized in a similar fashion to example 96 using the appropriate starting material.

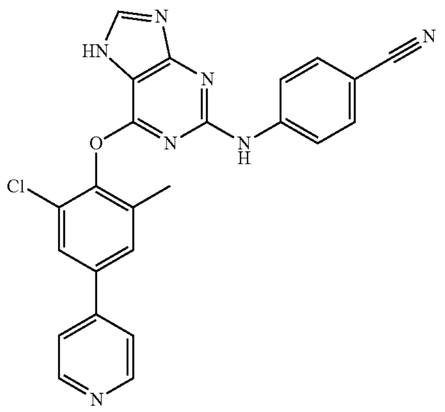 [SMILES: Cc1cc(-c2ccncc2)cc(Cl)c1Oc1nc(Nc2ccc(C#N)cc2)nc2nc[nH]c12]

NMR ($CDCl_3$/MeOH-$d^4$): δ 8.80 (s, 2H), 8.00 (s, 1H), 7.63 (m, 3H), 7.47 (m, 3H), 7.30 (m, 4H), 2.29 (s, 3H); MS (ESI): m/z 454 $(M+1)^+$.

Example 101

4-(6-(2-Chloro-4-(pyridin-4-yl)phenoxy)-7-(4-methoxybenzyl)-7H-purin-2-ylamino)benzonitrile Synthesized in a similar fashion to example 96 using the appropriate starting material.

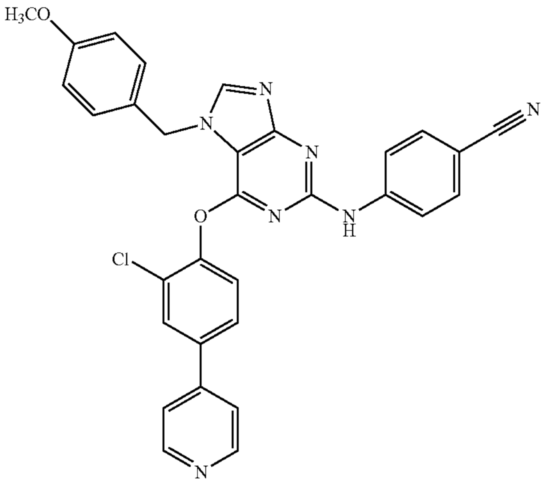 [SMILES: COc1ccc(Cn2cnc3nc(Nc4ccc(C#N)cc4)nc(Oc4ccc(-c5ccncc5)cc4Cl)c32)cc1]

NMR (DMSO-$d_6$): δ 10.05 (s, 1H), 8.72 (d, 2H), 8.44 (s 1H), 8.20 (d, 1H), 7.98 (dd, 1H), 7.87 (d, 2H), 7.70 (m, 3H), 7.48 (d, 2H), 7.39 (d, 2H), 6.97 (d, 2H), 5.38 (s, 2H), 3.74 (s, 3H); MS (ESI): m/z 560 $(M+1)^+$.

Example 102

4-(6-(2-Chloro-4-(pyridin-4-yl)phenoxy)-7H-purin-2-ylamino)benzonitrile

Synthesized in a similar fashion to example 96 using the appropriate starting material.

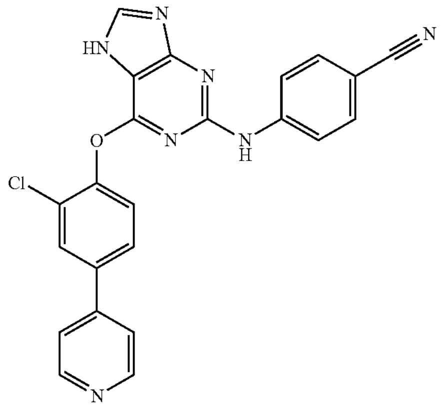 [SMILES: N#Cc1ccc(Nc2nc(Oc3ccc(-c4ccncc4)cc3Cl)c3[nH]cnc3n2)cc1]

NMR (DMSO-$d_6$): δ 9.66 (s, 1H), 8.71 (m, 2H), 7.17 (d, 1H), 8.06 (s, 1H), 7.95 (dd, 1H), 7.87 (m, 2H), 7.72 (d, 2H), 7.61 (d, 1H), 7.41 (d, 2H); MS (ESI): m/z 440 $(M+1)^+$.

Example 103

4-(6-(2,6-Dichloro-4-(pyridin-4-yl)phenoxy)-7-(4-methoxybenzyl)-7H-purin-2-ylamino)benzonitrile Synthesized in a similar fashion to example 96 using the appropriate starting material.

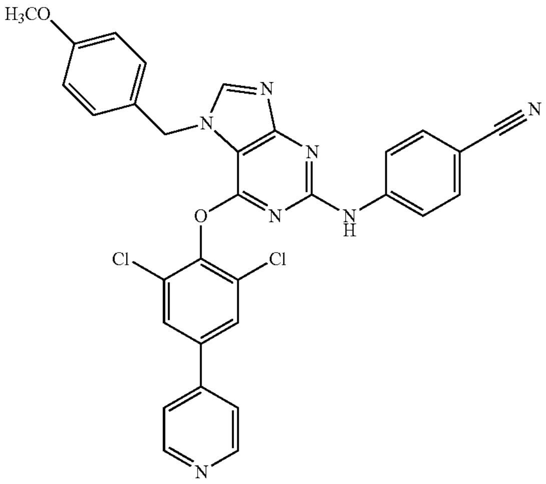 [SMILES: COc1ccc(Cn2cnc3nc(Nc4ccc(C#N)cc4)nc(Oc4c(Cl)cc(-c5ccncc5)cc4Cl)c32)cc1]

NMR (DMSO-$d_6$): δ 10.11 (s, 1H), 8.74 (d, 2H), 8.47 (s 1H), 8.23 (s, 2H), 7.93 (d, 2H), 7.67 (d, 2H), 7.52 (d, 2H), 7.41 (d, 2H), 6.98 (d, 2H), 5.38 (s, 2H), 3.74 (s, 3H); MS (ESI): m/z 594 $(M+1)^+$.

Example 104

4-(6-(2,6-Dichloro-4-(pyridin-4-yl)phenoxy)-7H-purin-2-ylamino)benzonitrile

Synthesized in a similar fashion to example 96 using the appropriate starting material.

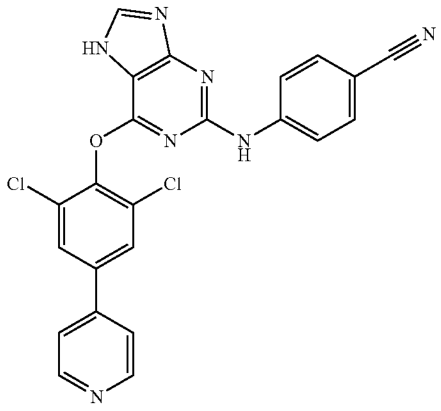 [SMILES: N#Cc1ccc(Nc2nc(Oc3c(Cl)cc(-c4ccncc4)cc3Cl)c3[nH]cnc3n2)cc1]

NMR (DMSO-$d_6$): δ 8.65 (s, 2H), 7.98 (s, 1H), 7.68 (s, 2H), 7.54 (m, 2H), 7.46 (d, 2H), 7.27 (d, 2H); MS (ESI): m/z 474 $(M+1)^+$.

Example 105

4-(9-(4-Methoxybenzyl)-6-(4-(pyridin-4-yl)phenoxy)-9H-purin-2-ylamino)-3,5-dimethylbenzonitrile Synthesized in a similar fashion to example 96 using the appropriate starting material.

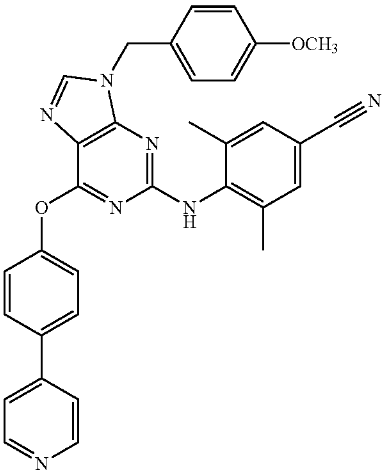 [SMILES: COc1ccc(Cn2cnc3c(Oc4ccc(-c5ccncc5)cc4)nc(Nc4c(C)cc(C#N)cc4C)nc32)cc1]

NMR (DMSO-$d_6$): δ 8.83 (s, 1H), 8.66 (d, 2H), 8.18 (s, 1H), 7.83 (d, 2H), 7.74 (d, 2H), 7.54 (s, 1H), 7.39 (d, 2H), 7.20 (d, 2H), 6.90 (d, 2H), 5.09 (s, 2H), 3.76 (s, 3H), 2.08 (s, 6H); MS (ESI): m/z 554 $(M+1)^+$.

Example 106

3,5-Dimethyl-4-(6-(4-(pyridin-4-yl)phenoxy)-9H-purin-2-ylamino)benzonitrile

Synthesized in a similar fashion to example 96 using the appropriate starting material.

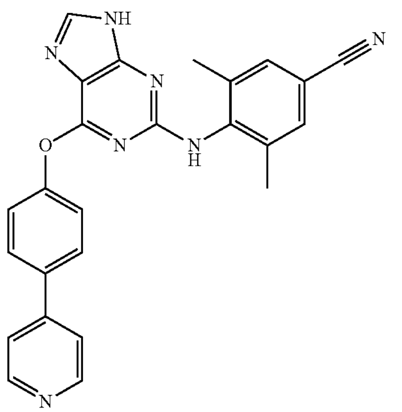 [SMILES: Cc1cc(C#N)cc(C)c1Nc1nc(Oc2ccc(-c3ccncc3)cc2)c2nc[nH]c2n1]

NMR (DMSO-$d_6$): δ 8.70 (m, 3H), 8.07 (s, 1H), 7.90 (d, 2H), 7.82 (d, 2H), 7.52 (s, 2H), 7.44 (d, 2H), 2.15 (s, 6H); MS (ESI): m/z 434 $(M+1)^+$.

Example 107

4-(6-(2,6-Dimethyl-4-(pyridin-4-yl)phenoxy)-7-methyl-7H-purin-2-ylamino)benzonitrile Synthesized in a similar fashion to example 96 using the appropriate starting material.

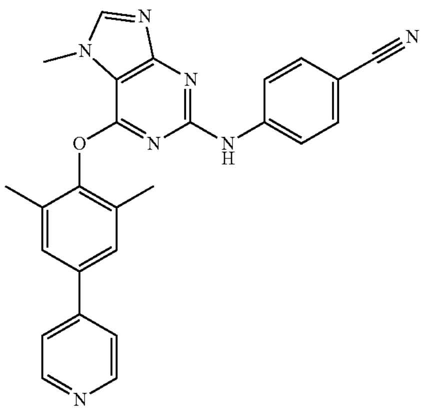 [SMILES: Cc1cc(-c2ccncc2)cc(C)c1Oc1nc(Nc2ccc(C#N)cc2)nc2ncn(C)c12]

NMR (DMSO-$d_6$): δ 9.86 (s, 1H), 8.69 (d, 2H), 8.44 (s, 1H), 7.81 (d, 2H), 7.75 (s, 2H), 7.69 (d, 2H), 7.43 (d, 2H), 4.12 (s, 3H), 2.25 (s, 6H); MS (ESI): m/z 448 $(M+1)^+$.

Example 108

4-(6-(2,6-dimethyl-4-(pyridin-4-yl)phenoxy)-9-methyl-9H-purin-2-ylamino)benzonitrile Synthesized in a similar fashion to example 96 using the appropriate starting material.

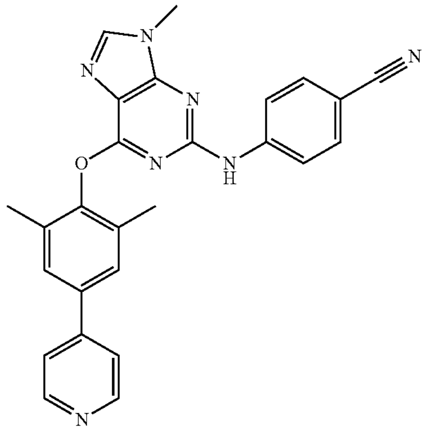 [SMILES: Cc1cc(-c2ccncc2)cc(C)c1Oc1nc(Nc2ccc(C#N)cc2)nc2c1ncn2C]

NMR (DMSO-$d_6$): δ 10.10 (s, 1H), 8.69 (d, 2H), 8.26 (s, 1H), 7.82 (d, 2H), 7.75 (s, 2H), 7.60 (d, 2H), 7.34 (d, 2H), 3.80 (s, 3H), 2.19 (s, 6H); MS (ESI): m/z 448 $(M+1)^+$.

Example 109

4'-(2-(4-cyanophenylamino)-9-methyl-9H-purin-6-yloxy)-3',5'-dimethylbiphenyl-4-carboxamide

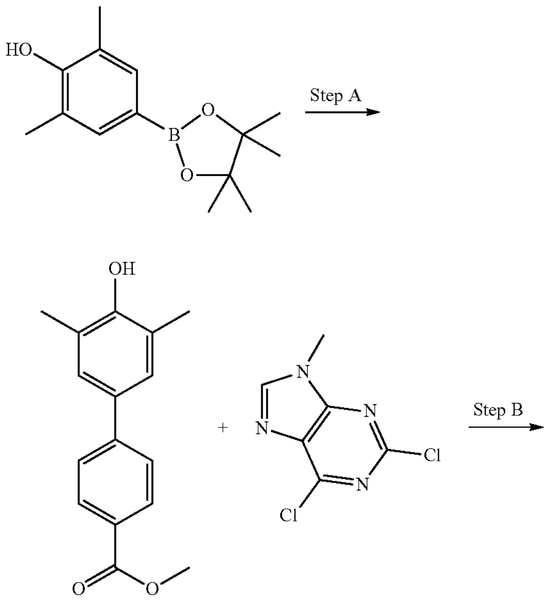

-continued

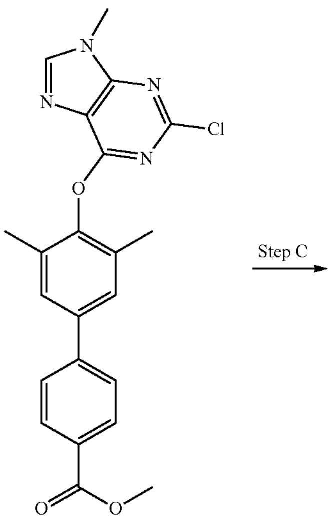

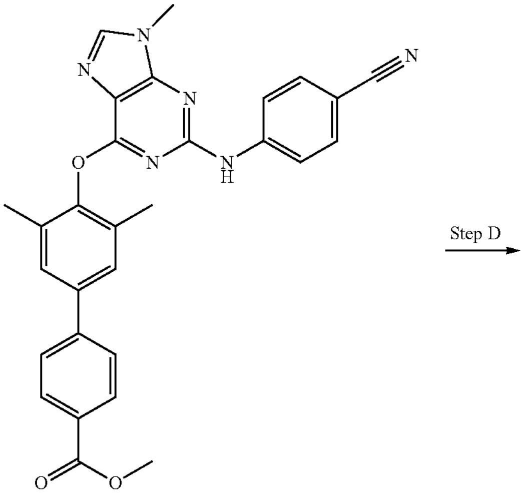

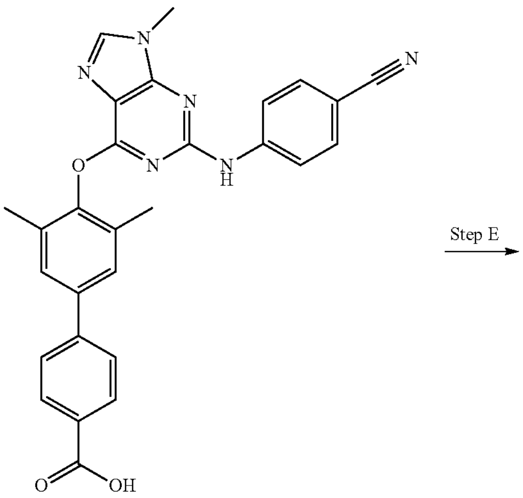

-continued

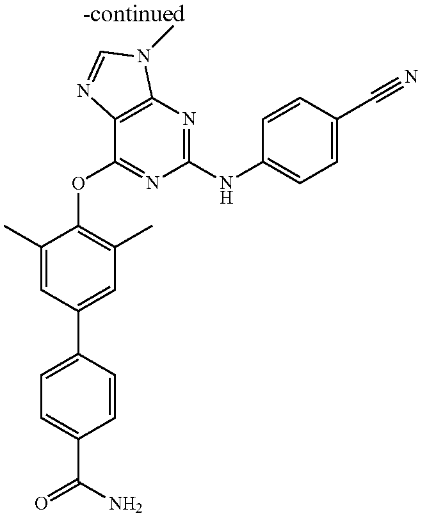

Step A: Methyl 4'-hydroxy-3',5'-dimethylbiphenyl-4-carboxylate

A solution of 2,6-dimethyl-4-(4,4,5,5-tetramethyl-1,3,2-dioxaborolan-2-yl)phenol (525 mg, 2.12 mmol), methyl 4-bromobenzoate (460 mg, 2.14 mmol), $PdCl_2$(dppf) (80 mg, 0.11 mmol) and $Cs_2CO_3$ (1.40 g, 4.31 mmol) in DMF (10 mL, 5% $H_2O$) was heated at 80° C. for 1 h. The reaction mixture was diluted with EtOAc (50 mL), washed with $H_2O$ (2×50 mL), and dried over $Na_2SO_4$. Purification on a silica gel column gave the desired product as a pale yellow solid (430 mg). NMR ($CDCl_3$): δ 8.08 (d, 2H), 7.62 (d, 2H), 7.29 (s, 2H), 4.75 (s, 1H), 3.95 (s, 3H), 2.35 (s, 6H).

Step B: Methyl 4'-(2-chloro-9-methyl-9H-purin-6-yloxy)-3',5'-dimethylbiphenyl-4-carboxylate A solution of methyl 4'-hydroxy-3',5'-dimethylbiphenyl-4-carboxylate (134 mg, 0.52 mmol), 2,6-dichloro-9-methyl-9H-purine (103 mg, 0.51 mmol), and $K_2CO_3$ (215 mg, 1.56 mmol) in DME (5 mL) was heated at 80° C. overnight. The desired product was precipitated with $H_2O$ and collected by filtration (186 mg). NMR ($CDCl_3$): δ 8.12 (d, 2H), 8.01 (s, 1H), 7.70 (d, 2H), 7.40 (s, 2H), 3.97 (s, 3H), 3.93 (s, 3H), 2.24 (s, 6H).

Step C: Methyl 4'-(2-(4-cyanophenylamino)-9-methyl-9H-purin-6-yloxy)-3',5'-dimethylbiphenyl-4-carboxylate A degassed solution of methyl 4'-(2-chloro-9-methyl-9H-purin-6-yloxy)-3',5'-dimethylbiphenyl-4-carboxylate (180 mg, 0.43 mmol), 4-aminobenzonitrile (105 mg, 0.89 mmol), $Pd(OAc)_2$ (10 mg, 0.044 mmol), BINAP (57 mg, 0.092 mmol), and $Cs_2CO_3$ (280 mg, 0.88 mmol) in toluene (2 mL) was heated at 80° C. overnight. The desired product was precipitated with EtOAc (2 mL) and saturated $NaHCO_3$ (2 mL) and the resulting precipitate was collected by filtration (210 mg). NMR (DMSO-$d^6$): δ 10.10 (s, 1H), 8.25 (s, 1H), 8.10 (d, 2H), 7.95 (d, 2H), 7.68 (s, 2H), 7.60 (d, 2H), 7.34 (d, 2H), 3.91 (s, 3H), 3.80 (s, 3H), 2.18 (s, 6H); MS (ESI): m/z 505 $(M+1)^+$.

Step D: 4'-(2-(4-Cyanophenylamino)-9-methyl-9H-purin-6-yloxy)-3',5'-dimethylbiphenyl-4-carboxylic acid A solution of methyl 4'-(2-(4-cyanophenylamino)-9-methyl-9H-purin-6-yloxy)-3',5'-dimethylbiphenyl-4-carboxylate (110 mg, 0.22 mmol) and lithium hydroxide (100 mg, 2.38 mmol) in) in a mixture of THF (3 mL), MeOH (1 mL), and $H_2O$ (1 mL) was stirred at rt for 3 h. The reaction mixture was diluted with $H_2O$ (5 mL) and acidified (1 N HCl). The resulting precipitate was collected by filtration to yield the desired compound (90 mg). MS (ESI): m/z 491 $(M+1)^+$.

Step E: 4'-(2-(4-cyanophenylamino)-9-methyl-9H-purin-6-yloxy)-3',5'-dimethylbiphenyl-4-carboxamide To a solution of 4'-(2-(4-cyanophenylamino)-9-methyl-9H-purin-6-yloxy)-3',5'-dimethylbiphenyl-4-carboxylic acid (40 mg, 0.082 mmol), HOAt (23 mg, 0.18 mmol), and EDCI (35 mg, 0.18 mmol) was added ammonium chloride (25 mg, 0.47 mmol) followed by TEA (0.1 mL, 0.72 mmol) at rt. The reaction mixture was heated at 80° C. for 1 h and added $H_2O$. The solid material which precipitated was collected by filtration and purified on silica gel preparative TLC to yield the desired compound. NMR (DMSO-$d^6$): δ 10.10 (s, 1H), 8.25 (s, 1H), 8.08 (s, 1H), 8.03 (d, 2H), 7.87 (d, 2H), 7.66 (s, 2H), 7.62 (d, 2H), 7.43 (s, 1H), 7.35 (d, 2H), 3.80 (s, 3H), 2.18 (s, 6H); MS (ESI): m/z 490 $(M+1)^+$.

Example 110

4'-(2-(4-Cyanophenylamino)-7-methyl-7H-purin-6-yloxy)-3',5'-dimethylbiphenyl-4-carboxylic acid Synthesized in a similar fashion to example 109 using the appropriate starting material.

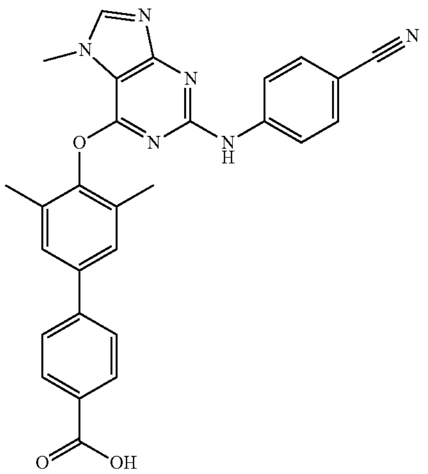 [SMILES: Cc1cc(-c2ccc(C(=O)O)cc2)cc(C)c1Oc1nc(Nc2ccc(C#N)cc2)nc2ncn(C)c12]

NMR (DMSO-$d_6$): δ 9.86 (s, 1H), 8.44 (s, 1H), 8.05 (d, 2H), 7.88 (d, 2H), 7.70 (d, 2H), 7.66 (s, 2H), 7.45 (d, 2H), 4.12 (s, 3H), 2.24 (s, 6H); MS (ESI): m/z 491 $(M+1)^+$.

Example 111

4'-(2-(4-Cyanophenylamino)-7-methyl-7H-purin-6-yloxy)-3',5'-dimethylbiphenyl-4-carboxamide Synthesized in a similar fashion to example 109 using the appropriate starting material.

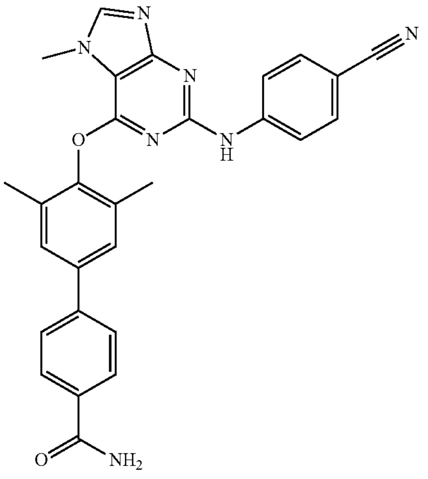 [SMILES: Cc1cc(-c2ccc(C(N)=O)cc2)cc(C)c1Oc1nc(Nc2ccc(C#N)cc2)nc2ncn(C)c12]

NMR (DMSO-$d_6$): δ 9.86 (s, 1H), 8.44 (s, 1H), 8.07 (s, 1H), 8.03 (d, 2H), 7.86 (d, 2H), 7.72 (d, 2H), 7.66 (s, 2H), 7.44 (m, 3H), 4.12 (s, 3H), 2.24 (s, 6H); MS (ESI): m/z 490 $(M+1)^+$.

Example 112

3',5'-dichloro-4'-(2-(4-cyanophenylamino)-7-methyl-7H-purin-6-yloxy)biphenyl-4-carboxamide Synthesized in a similar fashion to example 109 using the appropriate starting material.

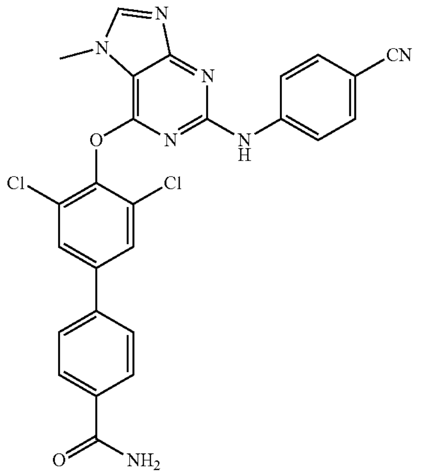

$^1H$ NMR (Acetone $d_6$, 400 MHz) δ 4.26 (s, 3H), 6.8 (bs, 1H), 7.52 (d, J=8.6 Hz, 2H), 7.63 (bs, 1H), 7.86 (d, J=8.6 Hz, 2H), 8.01 (d 7, J=8.8 Hz, 2H), 8.09 (s, 2H), 8.17 (d 7, J=8.8 Hz, 2H), 8.38 (s, 1H), 9.06 (s, 1H). MS (ESI): m/z 531.03 $(M+2)^+$.

Example 113

3'-chloro-4'-(2-(4-cyanophenylamino)-9-methyl-9H-purin-6-yloxy)-5'-methylbiphenyl-4-sulfonamide Synthesized in a similar fashion to example 109 using the appropriate starting material.

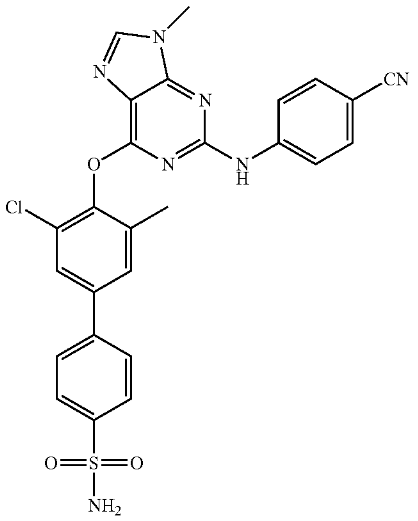 [SMILES: Cc1cc(-c2ccc(S(N)(=O)=O)cc2)cc(Cl)c1Oc1nc(Nc2ccc(C#N)cc2)nc2c1ncn2C]

$^1$H NMR (DMSO $d_6$, 400 MHz) δ 2.27 (s, 3H), 3.82 (s, 3H), 7.42 (d, J=8.5 Hz, 2H), 7.49 (bs, 2H), 7.65 (d, J=8.5 Hz, 2H), 7.88 (d, J=2.6 Hz, 1H), 7.94 (d, J=2.6 Hz, 1H), 7.96 (d, J=8.7 Hz, 2H), 8.04 (d, J=8.7 Hz, 2H), 8.28 (s, 1H), 10.21 (s, 1H). MS (ESI): m/z 546.06 $(M+1)^+$.

Example 114

3',5'-dichloro-4'-(2-(4-cyanophenylamino)-9-methyl-9H-purin-6-yloxy)biphenyl-4-carboxamide Synthesized in a similar fashion to example 109 using the appropriate starting material.

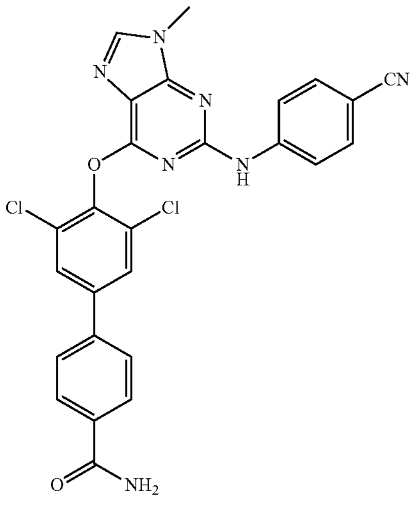 [SMILES: Cn1cnc2c(Oc3c(Cl)cc(-c4ccc(C(N)=O)cc4)cc3Cl)nc(Nc3ccc(C#N)cc3)nc21]

$^1$H NMR (DMSO $d_6$, 400 MHz) δ 3.82 (s, 3H), 7.43 (d, J=8.6 Hz, 2H), 7.50 (bs, 1H), 7.67 (d, J=8.6 Hz, 2H), 7.98 (d,

J=8.7 Hz, 2H), 8.06 (d, J=8.7 Hz, 2H), 8.15 (bs, 1H), 8.18 (s, 2H), 10.23 (s, 1H). MS (ESI): m/z 531.01 $(M+2)^+$.

Example 115

3'-chloro-4'-(2-(4-cyanophenylamino)-7-methyl-7H-purin-6-yloxy)-5'-methylbiphenyl-4-sulfonamide Synthesized in a similar fashion to example 109 using the appropriate starting material.

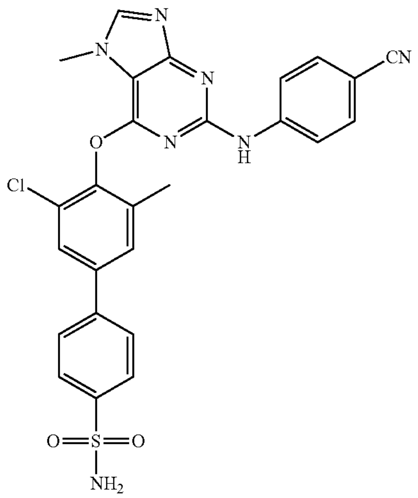 [SMILES: Cc1cc(-c2ccc(S(N)(=O)=O)cc2)cc(Cl)c1Oc1nc(Nc2ccc(C#N)cc2)nc2ncn(C)c12]

$^1$H NMR (DMSO $d_6$, 400 MHz) δ 2.35 (s, 3H), 4.12 (s, 3H), 7.48 (bs, 2H), 7.49 (d, J=8.5 Hz, 2H), 7.74 (d, J=8.5, 2H), 7.88 (d, J=2.6 Hz, 1H), 7.96 (d, J=2.6 Hz, 1H), 7.97 (d, J=8.7 Hz, 2H), 8.04 (d, J=8.7 Hz, 2H), 8.48 (s, 1H), 9.93 (s, 1H). MS (ESI): m/z 546.06 $(M+1)^+$.

Example 116

3'-chloro-4'-(2-(4-cyanophenylamino)-7-methyl-7H-purin-6-yloxy)-5'-methylbiphenyl-4-carboxamide Synthesized in a similar fashion to example 109 using the appropriate starting material.

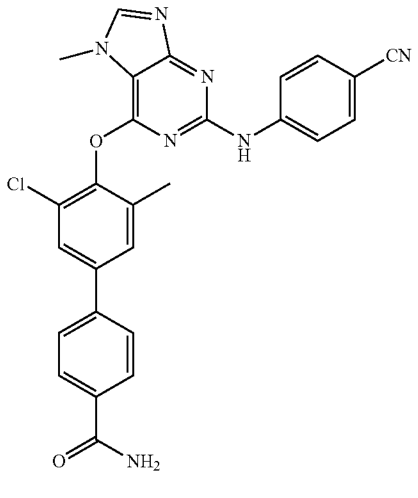 [SMILES: Cc1cc(-c2ccc(C(N)=O)cc2)cc(Cl)c1Oc1nc(Nc2ccc(C#N)cc2)nc2ncn(C)c12]

$^1$H NMR (DMSO $d_6$, 400 MHz) δ 2.11 (s, 3H), 4.12 (s, 3H), 7.45 (bs, 1H), 7.46 (d, J=8.5 Hz, 2H), 7.71 (d, J=8.5 Hz, 2H), 7.87 (d, J=2.6 Hz, 1H), 7.92 (d, J=8.7 Hz, 2H), 7.96 (d, J=2.6 Hz, 1H), 8.04 (d, J=8.7 Hz, 2H), 8.12 (s, 1H), 8.48 (s, 1H), 9.95 (s, 1H). MS (ESI): m/z 511.04 $(M+2)^+$.

Example 117

3'-chloro-4'-(2-(4-cyanophenylamino)-9-methyl-9H-purin-6-yloxy)-5'-methylbiphenyl-4-carboxamide Synthesized in a similar fashion to example 109 using the appropriate starting material.

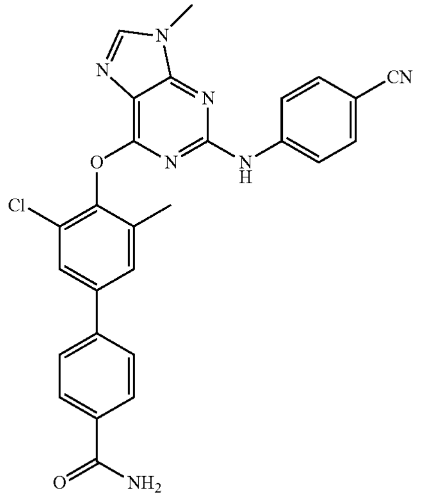 [SMILES: Cc1cc(-c2ccc(C(N)=O)cc2)cc(Cl)c1Oc1nc(Nc2ccc(C#N)cc2)nc2c1ncn2C]

$^1$H NMR (DMSO $d_6$, 400 MHz) δ 2.27 (s, 3H), 3.82 (s, 3H), 7.39 (d, J=8.5 Hz, 2H), 7.47 (bs, 1H), 7.64 (d, J=8.5 Hz, 2H), 7.87 (d, J=2.6 Hz, 1H), 7.93 (d, J=8.7 Hz, 2H), 7.94 (d, J=2.6 Hz, 1H), 8.05 (d, J=8.7 Hz, 2H), 8.12 (s, 1H), 8.24 (s, 1H), 10.16 (s, 1H). MS (ESI): m/z 511.04 $(M+2)^+$.

Example 118

5-(4-(2-(4-cyanophenylamino)-7-methyl-7H-purin-6-yloxy)-3,5-dimethylphenyl)picolinamide Synthesized in a similar fashion to example 109 using the appropriate starting material.

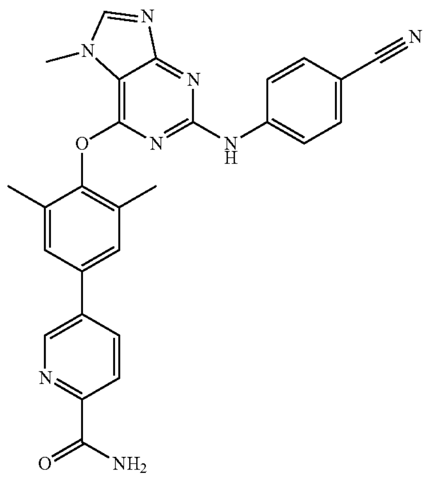 [SMILES: Cc1cc(-c2ccc(C(N)=O)nc2)cc(C)c1Oc1nc(Nc2ccc(C#N)cc2)nc2ncn(C)c12]

$^1$H NMR (DMSO $d_6$, 400 MHz) δ 2.26 (s, 6H), 4.13 (s, 3H), 7.46 (d, J=8.6 Hz, 2H), 7.73 (d, J=8.6 Hz, 2H), 7.74 (bs, 1H), 7.75 (s, 2H), 8.18 (d, J=8.3 Hz, 1H), 8.19 (bs, 1H), 8.37 (dd, J=8.3, 2.6 Hz, 1H), 8.45 (s, 1H), 9.05 (d, J=2.6 Hz, 1H), 9.87 (s, 1H). MS (ESI): m/z 491.13 $(M+1)^+$.

Example 119

5-(4-(2-(4-cyanophenylamino)-9-methyl-9H-purin-6-yloxy)-3,5-dimethylphenyl)picolinamide Synthesized in a similar fashion to example 109 using the appropriate starting material.

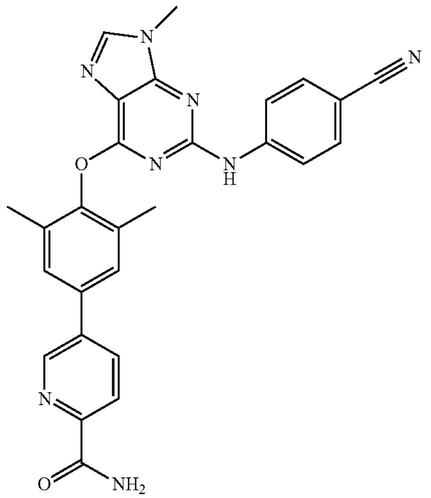 [SMILES: Cc1cc(-c2ccc(C(N)=O)nc2)cc(C)c1Oc1nc(Nc2ccc(C#N)cc2)nc2c1ncn2C]

$^1$H NMR (DMSO $d_6$, 400 MHz) δ 2.21 (s, 6H), 3.81 (s, 3H), 7.39 (d, J=8.6 Hz, 2H), 7.65 (d, J=8.6 Hz, 2H), 7.75 (bs, 1H), 7.76 (s, 2H), 8.17 (d, J=8.3 Hz, 1H), 8.21 (bs, 1H), 8.27 (s, 1H), 8.38 (dd, J=8.3, 2.6 Hz, 1H), 9.06 (d, J=2.6 Hz, 1H), 10.11 (s, 1H). MS (ESI): m/z 491.13 $(M+1)^+$.

Example 120

Ethyl 5-(4-(2-(4-cyanophenylamino)-7H-purin-6-yloxy)-3,5-dimethylphenyl)picolinate Synthesized in a similar fashion to example 109 using the appropriate starting material.

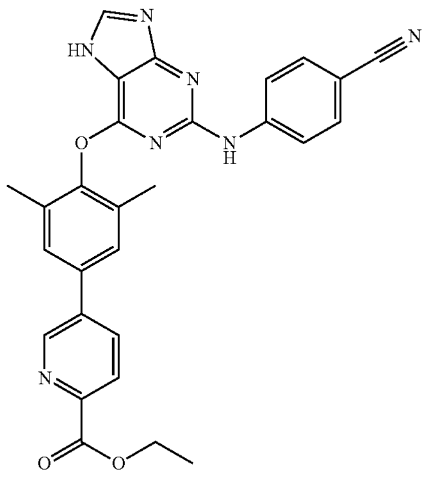 [SMILES: CCOC(=O)c1ccc(-c2cc(C)c(Oc3nc(Nc4ccc(C#N)cc4)nc4nc[nH]c34)c(C)c2)cn1]

$^1$H NMR (DMSO $d_6$, 400 MHz) δ 1.40 (t, J=8.0 Hz, 3H), 2.22 (s, 6H), 4.43 (t, J=8.0 Hz, 2H), 7.48 (d, J=8.6 Hz, 2H), 7.66 (d, J=8.6 Hz, 2H), 7.76 (s, 2H), 8.21 (d, J=8.2 Hz, 1H), 8.32 (s, 1H), 8.41 (dd, J=8.3, 2.6 Hz, 1H), 9.14 (d, J=2.6 Hz, 1H), 9.91 (s, 1H). MS (ESI): m/z 506.18 (M+1)$^+$.

Example 121

6-(4-(2-(4-cyanophenylamino)-9H-purin-6-yloxy)-3,5-dimethylphenyl)nicotinic acid Synthesized in a similar fashion to example 109 using the appropriate starting material.

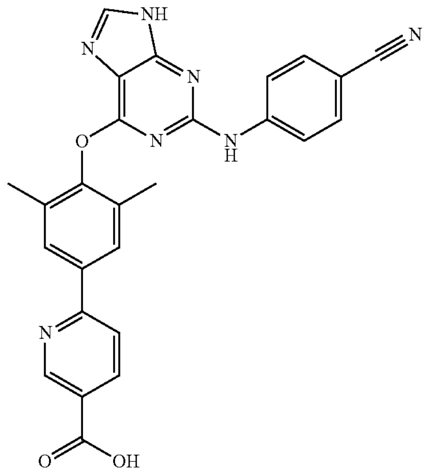 [SMILES: Cc1cc(-c2ccc(C(=O)O)cn2)cc(C)c1Oc1nc(Nc2ccc(C#N)cc2)nc2[nH]cnc12]

$^1$H NMR (DMSO $d_6$, 400 MHz) δ 2.18 (s, 6H), 7.28 (d, J=8.6 Hz, 2H), 7.65 (d, J=8.6 Hz, 2H), 7.71 (s, 1H), 7.88-7.91 (m, 4H), 8.20 (dd, J=8.3, 2.6 Hz, 1H), 9.06 (s, 1H), 9.19 (bs, 1H). MS (ESI): m/z 478.10 (M+1)$^+$.

Example 122

1-(6-(4-(2-(4-cyanophenylamino)-9H-purin-6-yloxy)-3,5-dimethylphenyl)nicotinoyl)pyrrolidine-3-carboxamide Synthesized in a similar fashion to example 109 using the appropriate starting material.

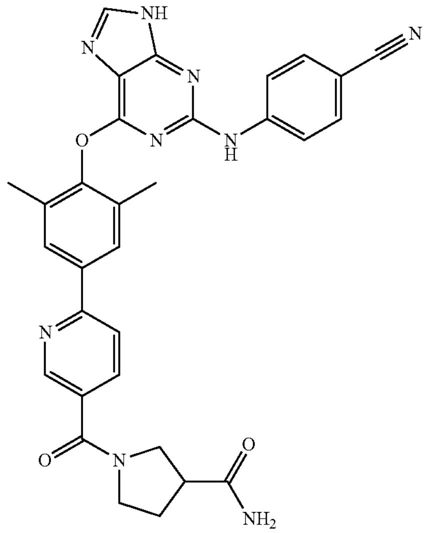 [SMILES: Cc1cc(-c2ccc(C(=O)N3CCC(C(N)=O)C3)cn2)cc(C)c1Oc1nc(Nc2ccc(C#N)cc2)nc2[nH]cnc12]

$^1$H NMR ($CD_3OD$, 400 MHz) δ 1.92-2.29 (m, 2H), 2.23 (s, 6H), 3.15-3.23 (m, 1H), 3.81-3.90 (m, 4H), 7.31 (d, J=8.6 Hz, 2H), 7.55-7.61 (m, 3H), 7.91 (s, 1H), 7.92 (s, 2H), 8.03-8.12 (m, 3H), 8.21 (s, 1H), 8.88 (s, 1H). MS (ESI): m/z 574.21 (M+1)$^+$.

Example 123

6-(4-(2-(4-cyanophenylamino)-7-methyl-7H-purin-6-yloxy)-3,5-dimethylphenyl)nicotinamide Synthesized in a similar fashion to example 109 using the appropriate starting material.

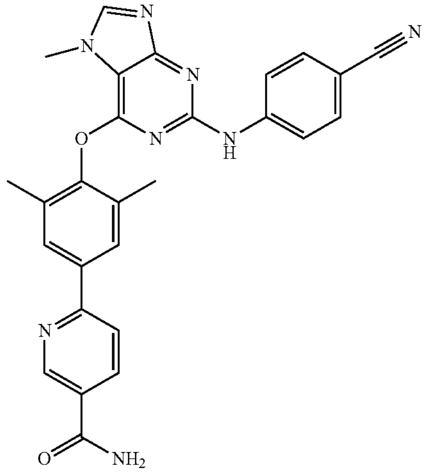 [SMILES: Cc1cc(-c2ccc(C(N)=O)cn2)cc(C)c1Oc1nc(Nc2ccc(C#N)cc2)nc2ncn(C)c12]

$^1$H NMR (DMSO $d_6$, 400 MHz) δ 2.26 (s, 6H), 4.13 (s, 3H), 7.43 (d, J=8.6 Hz, 2H), 7.65 (bs, 1H), 7.70 (d, J=8.6 Hz, 2H), 8.06 (s, 2H), 8.16 (d, J=8.4 Hz, 1H), 8.24 (bs, 1H), 8.36 (dd, J=8.4, 2.6 Hz, 1H), 8.44 (s, 1H), 9.16 (d, J=2.6 Hz, 1H), 9.85 (s, 1H). MS (ESI): m/z 492.07 (M+2)$^+$.

Example 124

6-(4-(2-(4-cyanophenylamino)-9-methyl-9H-purin-6-yloxy)-3,5-dimethylphenyl)nicotinamide Synthesized in a similar fashion to example 109 using the appropriate starting material.

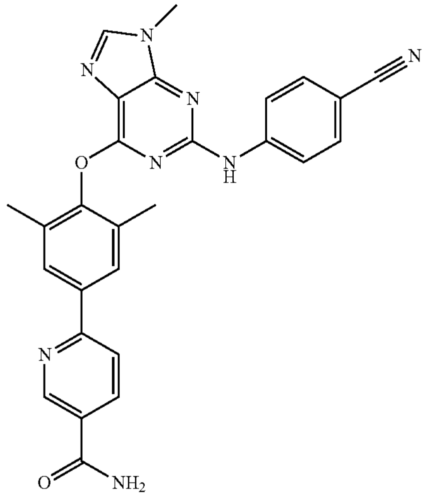 [SMILES: Cc1cc(-c2ccc(C(N)=O)cn2)cc(C)c1Oc1nc(Nc2ccc(C#N)cc2)nc2c1ncn2C]

$^1$H NMR (DMSO $d_6$, 400 MHz) δ 2.27 (s, 6H), 3.92 (s, 3H), 6.95 (bs, 1H), 7.43 (d, J=8.6 Hz, 2H), 7.78 (bs, 1H), 7.79 (d, J=8.6 Hz, 2H), 8.08 (s, 2H), 8.18 (d, J=8.4 Hz, 1H), 8.22 (s,

1H), 8.44 (dd, J=8.4, 2.6 Hz, 1H), 9.21 (s, 1H), 9.28 (d, J=2.6 Hz, 1H). MS (ESI): m/z 492.07 $(M+2)^+$.

Example 125

4-(6-(4-(5-(azetidine-1-carbonyl)pyridin-2-yl)-2,6-dimethylphenoxy)-9H-purin-2-ylamino)benzonitrile Synthesized in a similar fashion to example 109 using the appropriate starting material.

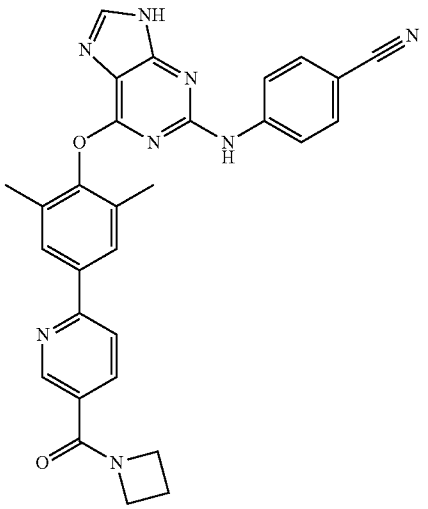 [SMILES: Cc1cc(-c2ccc(C(=O)N3CCC3)cn2)cc(C)c1Oc1nc(Nc2ccc(C#N)cc2)nc2[nH]cnc12]

$^1$H NMR (DMSO $d_6$, 400 MHz) δ 2.20 (s, 6H), 2.30-2.34 (m, 2H), 4.12 (t, J=6.8 Hz, 2H), 4.44 (t, J=6.8 Hz, 2H), 7.35 (d, J=8.6 Hz, 2H), 7.61 (d, J=8.6 Hz, 2H), 8.02 (s, 2H), 8.13 (s, 2H), 8.18 (s, 1H), 8.93 (s, 1H), 9.78 (s, 1H). MS (ESI): m/z 517.11 $(M+1)^+$.

Example 126

6-(4-(2-(4-cyanophenylamino)-9H-purin-6-yloxy)-3,5-dimethylphenyl)nicotinamide

Synthesized in a similar fashion to example 109 using the appropriate starting material.

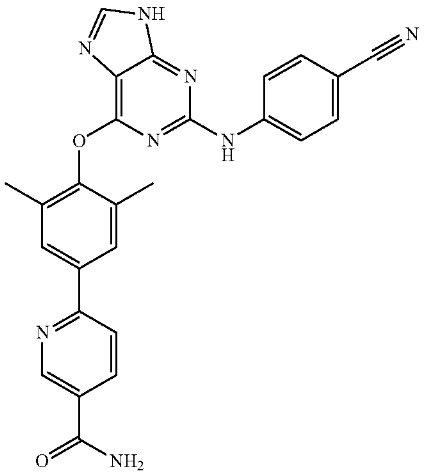 [SMILES: Cc1cc(-c2ccc(C(N)=O)cn2)cc(C)c1Oc1nc(Nc2ccc(C#N)cc2)nc2[nH]cnc12]

$^1$H NMR (DMSO $d_6$, 400 MHz) δ 2.20 (s, 6H), 7.35 (d, J=8.6 Hz, 2H), 7.64 (d, J=8.6 Hz, 2H), 7.66 (bs, 1H), 8.03 (s, 2H), 8.10 (s, 1H), 8.15 (d, J=8.4 Hz, 1H), 8.26 (bs, 1H), 8.36 (dd, J=8.4, 2.6 Hz, 1H), 9.16 (d, J=2.6 Hz, 1H), 9.69 (s, 1H). MS (ESI): m/z 478.03 $(M+2)^+$.

Example 127

1-(6-(4-(2-(4-cyanophenylamino)-9H-purin-6-yloxy)-3,5-dimethylphenyl)nicotinoyl)pyrrolidine-3-carbonitrile Synthesized in a similar fashion to example 109 using the appropriate starting material.

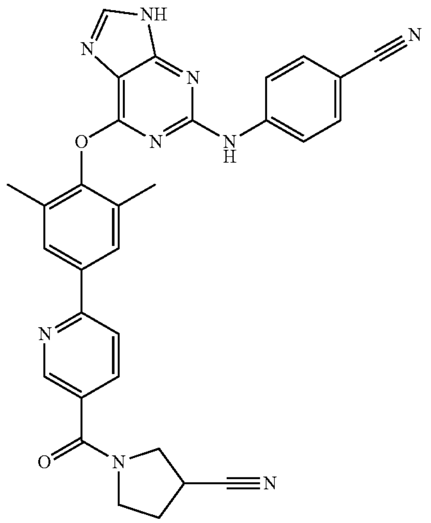 [SMILES: Cc1cc(-c2ccc(C(=O)N3CCC(C#N)C3)cn2)cc(C)c1Oc1nc(Nc2ccc(C#N)cc2)nc2[nH]cnc12]

$^1$H NMR ($CD_3OD$, 400 MHz) δ 2.27 (s, 6H), 2.30-2.45 (m, 2H), 3.43-3.60 (m, 1H), 3.72-3.89 (m, 3H), 3.95-4.02 (m, 1H), 7.30 (d, J=8.6 Hz, 2H), 7.54 (d, J=8.6 Hz, 2H), 7.94 (s, 2H), 8.05 (d, J=8.4 Hz, 1H), 8.12 (dd, J=8.6, 2.2 Hz, 1H), 8.21 (s, 1H), 8.90 (d, J=2.2 Hz, 1H). MS (ESI): m/z 556.12 $(M+1)^+$.

Example 128

6-(4-(2-(4-cyanophenylamino)-9H-purin-6-yloxy)-3,5-dimethylphenyl)-N,N-dimethylnicotinamide Synthesized in a similar fashion to example 109 using the appropriate starting material.

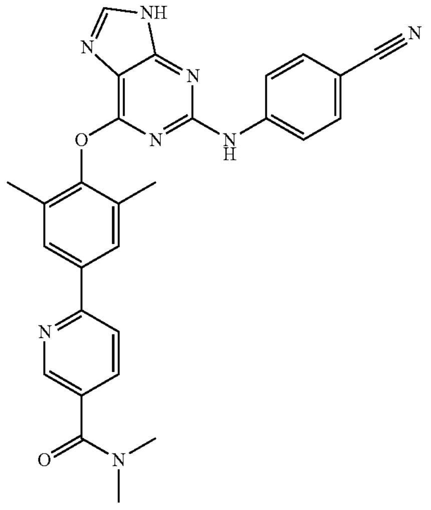 [SMILES: Cc1cc(-c2ccc(C(=O)N(C)C)cn2)cc(C)c1Oc1nc(Nc2ccc(C#N)cc2)nc2[nH]cnc12]

$^1$H NMR (DMSO $d_6$, 400 MHz) δ 2.20 (s, 6H), 3.03 (s, 3H), 3.05 (s, 3H), 7.38 (d, J=8.6 Hz, 2H), 7.61 (d, J=8.6 Hz, 2H), 8.01 (d, J=8.4, 1H), 8.05 (s, 2H), 8.13 (dd, J=8.4, 2.2 Hz, 1H), 8.28 (s, 1H), 8.75 (d, J=2.2 Hz, 1H), 9.90 (s, 1H), 13.28 (bs, 1H). MS (ESI): m/z 505.10 $(M+1)^+$.

Example 129

5-(4-(2-(4-cyanophenylamino)-9H-purin-6-yloxy)-3,5-dimethylphenyl)picolinamide Synthesized in a similar fashion to example 109 using the appropriate starting material.

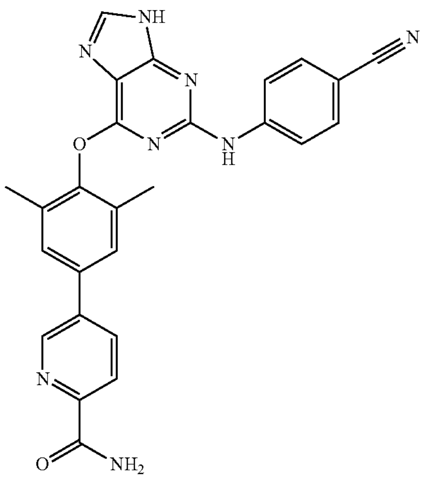 [SMILES: Cc1cc(-c2ccc(C(N)=O)nc2)cc(C)c1Oc1nc(Nc2ccc(C#N)cc2)nc2[nH]cnc12]

$^1$H NMR (DMSO $d_6$, 400 MHz) δ 2.21 (s, 6H), 7.42 (d, J=8.6 Hz, 2H), 7.67 (d, J=8.6 Hz, 2H), 7.70 (bs, 1H), 7.74 (s, 2H), 8.15 (d, J=8.4 Hz, 1H), 8.18 (s, 1H), 8.26 (bs, 1H), 8.37 (dd, J=8.4, 2.6 Hz, 1H), 9.04 (d, J=2.6 Hz, 1H), 9.95 (s, 1H). MS (ESI): m/z 477.09 $(M+1)^+$.

Example 130

Methyl 5-(4-(2-(4-cyanophenylamino)-9H-purin-6-yloxy)-3,5-dimethylphenyl)picolinate Synthesized in a similar fashion to example 109 using the appropriate starting material.

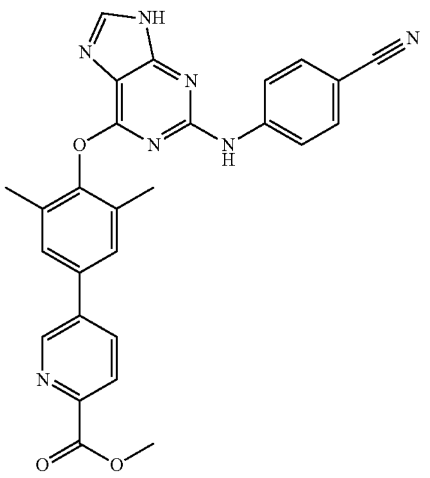 [SMILES: COC(=O)c1ccc(-c2cc(C)c(Oc3nc(Nc4ccc(C#N)cc4)nc4[nH]cnc34)c(C)c2)cn1]

$^1$H NMR ($CDCl_3$, 400 MHz) δ 2.29 (s, 6H), 4.02 (s, 3H), 7.42 (d, J=8.6 Hz, 2H), 7.48 (bs, 1H), 7.68 (d, J=8.6 Hz, 2H), 7.87 (s, 2H), 7.88-8.10 (m, 2H), 8.45 (d, J=8.4 Hz, 1H), 9.38 (s, 1H). MS (ESI): m/z 492.07 $(M+1)^+$.

Example 131

4-(4-(2,6-Dimethyl-4-(pyridin-4-yl)phenylthio)-5-methyl-5H-pyrrolo[3,2-d]pyrimidin-2-ylamino)benzonitrile

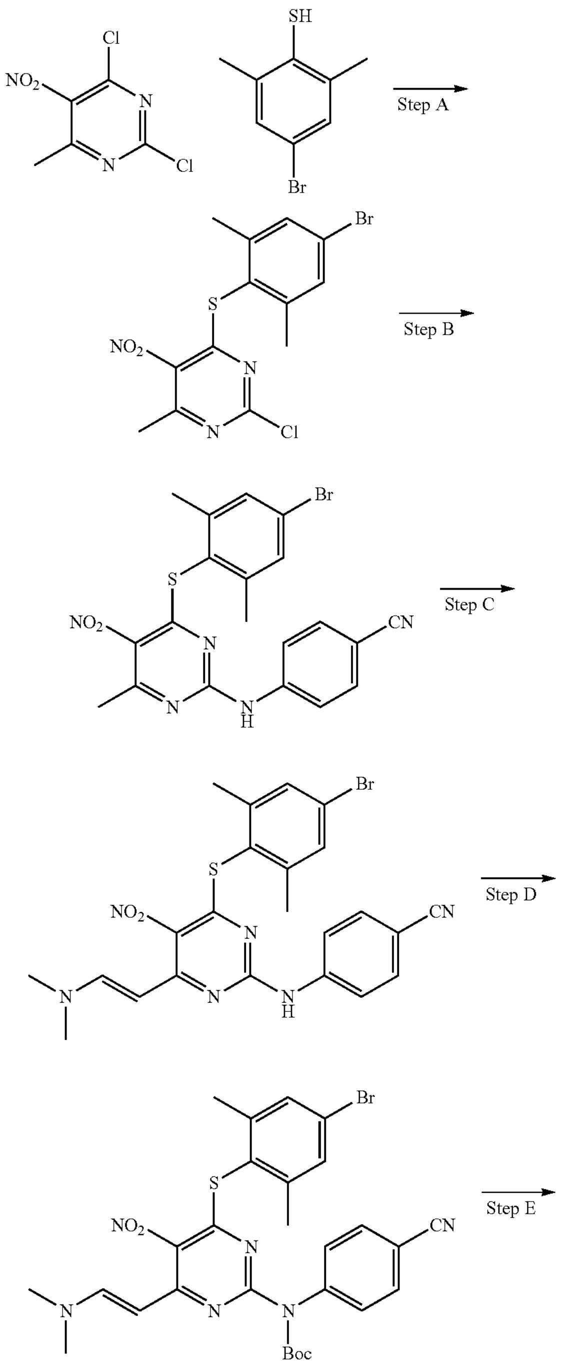

-continued

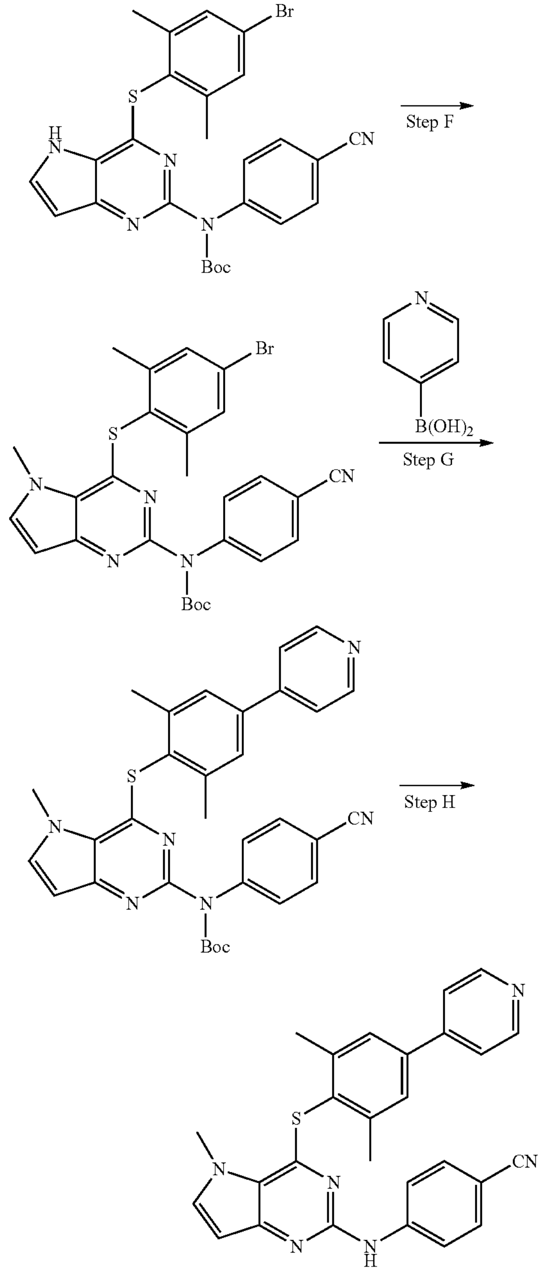

Step A: 4-(4-bromo-2,6-dimethylphenylthio)-2-chloro-6-methyl-5-nitropyrimidine

A solution of LiHMDS in THF (77 mmol) is added to a mixture of 4-bromo-2,6-dimethylbenzenethiol (70 mmol) in THF (100 ml) at −78° C. over 15 minutes and the mixture stirred for an additional 2 hours. The mixture is cooled with liquid nitrogen to around −100° C. and a solution of 2,6-dichloro-4-methyl-5-nitropyrimidine (84 mmol) in THF (50 ml) is added rapidly. The reaction is maintained at around −100° C. for 1 hour and then allowed to warm to room temperature. The mixture is filtered and the isolated solid washed with ethanol. The filtrate may be concentrated and crystallized to obtain additional compound.

Step B: 4-(4-(4-bromo-2,6-dimethylphenylthio)-6-methyl-5-nitropyrimidin-2-ylamino)benzonitrile A mixture of 4-(4-bromo-2,6-dimethylphenylthio)-2-chloro-6-methyl-5-nitropyrimidine (59 mmol), 4-aminobenzonitrile (65 mmol) and pyridine (59 mmol) in THF (300 ml) is heated to 80° C. for 10 hours. The reaction mixture is dissolved in methanol, washed with brine and extracted with ethyl acetate. The organic layer is washed twice with brine, dried over $MgSO_4$ and concentrated to dryness. The solid is washed with a mixture of hexane:ethyl acetate (80:20) before filtration. After filtration, the solid is washed again with methanol. The filtrate may be concentrated and additional rounds of precipitation performed following the same procedure, until all product is recovered. The combined solids are recrystallized from acetone.

Step C: 4-(4-(4-bromo-2,6-dimethylphenylthio)-6-((E)-2-(dimethylamino)vinyl)-5-nitropyrimidin-2-ylamino)benzonitrile To a mixture of 4-(4-(4-bromo-2,6-dimethylphenylthio)-6-methyl-5-nitropyrimidin-2-ylamino)benzonitrile (50 mmol) in DMF (300 ml) is added tert-butoxybis (dimethylamino) methane (60 mmol) over 15 minutes. The mixture is stirred at room temperature overnight. DMF is partially removed. The residue is washed with water and extracted with ethyl acetate (×3). The combined organic layers are washed with brine, dried ($MgSO_4$) and concentrated to dryness to give the desired product which is used in next step without further purification.

Step D: tert-butyl 4-(4-bromo-2,6-dimethylphenylthio)-6-((E)-2-(dimethylamino)vinyl)-5-nitropyrimidin-2-yl4-cyanophenylcarbamate To a mixture of 4-(4-(4-bromo-2,6-dimethylphenylthio)-6-((E)-2-(dimethylamino)vinyl)-5-nitropyrimidin-2-ylamino)benzonitrile (46 mmol), potassium carbonate (64 mmol) and 4-dimethylaminopyridine (5 mmol) in dichloromethane (300 ml) is added a solution of $Boc_2O$ (51 mmol) in DCM (100 ml) over 30 minutes. The mixture is stirred for 3 hours at room temperature, washed with brine and extracted with dichloromethane (×3). The combined organic layers are dried over $MgSO_4$ and concentrated to dryness to yield to the title compound which is used for the next step without further purification.

Step E: tert-butyl 4-(4-bromo-2,6-dimethylphenylthio)-5H-pyrrolo[3,2-d]pyrimidin-2-yl4-cyanophenylcarbamate A solution of $Na_2S_2O_4$ (230 mmol) in water (100 ml) is added to a solution of tert-butyl 4-(4-bromo-2,6-dimethylphenylthio)-6-((E)-2-(dimethylamino)vinyl)-5-nitropyrimidin-2-yl4-cyanophenylcarbamate (46 mmol) in THF (300 ml). The mixture is stirred at room temperature for 2 days and then concentrated. The residue is washed with water and extracted with ethyl acetate. The organic layer is concentrated and the product obtained by crystallization from a mixture of water and methanol.

Step F: tert-butyl 4-(4-bromo-2,6-dimethylphenylthio)-5-methyl-5H-pyrrolo[3,2-d]pyrimidin-2-yl4-cyanophenylcarbamate To a cold mixture of tert-butyl 4-(4-bromo-2,6-dimethylphenylthio)-5H-pyrrolo[3,2-d]pyrimidin-2-yl(4-cyanophenyl)carbamate (1.5 mmol) in THF (5 ml) at −78° C. is added a solution of LiHMDS (2 mmol). The mixture is warmed to 0° C. over 2 hours and then cooled to −78° C. Iodomethane (6 mmol) is added and the mixture warmed to room temperature over 2 hours and then stirred at room temperature for an additional 2 hours. The mixture is washed with brine and extracted with ethyl acetate (×3). The combined organic layers are dried over $MgSO_4$ and concentrated to dryness. The crude material is purified by chromatography on silica.

Step G: tert-butyl 4-(2,6-dimethyl-4-(pyridin-4-yl)phenylthio)-5-methyl-5H-pyrrolo[3,2-d]pyrimidin-2-yl4-cyanophenylcarbamate tert-Butyl 4-(4-bromo-2,6-dimethylphenylthio)-5-methyl-5H-pyrrolo[3,2-d]pyrimidin-2-yl(4-cyanophenyl)carbamate (0.729 mmol) is combined with pyridine-4-boronic acid (1.46 mmol) and tetrakis(triphenylphosphine)palladium(0) (0.0729 mmol) in a two dram vial. The vial is sealed and flushed with argon. Degassed THF (5.0 mL) and aqueous $Na_2CO_3$ (2 M, 1.5 mL, 3.0 mmol) are injected, and the mixture agitated on a shaker at 80° C. for 10 h. The mixture is diluted with ethyl acetate and extracted with aqueous $Na_2CO_3$ (0.5 M, ×2). The organic layer is collected, concentrated, and the residue purified by chromatography ($SiO_2$, 1:4 hexanes/EtOAc).

Step H: 4-(4-(2,6-dimethyl-4-(pyridin-4-yl)phenylthio)-5-methyl-5H-pyrrolo[3,2-d]pyrimidin-2-ylamino)benzonitrile tert-Butyl 4-(2,6-dimethyl-4-(pyridin-4-yl)phenylthio)-5-methyl-5H-pyrrolo[3,2-d]pyrimidin-2-yl4-cyanophenylcarbamate is treated with TFA (10 mL) at 25° C. for 2 h. TFA is removed and the obtained residue dissolved in ethyl acetate, and extracted with saturated aqueous $NaHCO_3$ (×2). The organic layer is collected, concentrated, and the purified by chromatography ($SiO_2$, 1:4 hexanes/EtOAc).

Examples 132-144

4-(4-(2,6-Dimethyl-4-($R^P$)phenylthio)-5-methyl-5H-pyrrolo[3,2-d]pyrimidin-2-ylamino)benzonitrile The compounds in the table below are prepared following the same procedures as described for above example 131, steps G and H. tert-butyl 4-(4-bromo-2,6-dimethylphenylthio)-5-methyl-5H-pyrrolo[3,2-d]pyrimidin-2-yl(4-cyanophenyl)carbamate is coupled with the appropriate boronic acid derivative, to produce the final compounds indicated.

| Eg | Compound Name | Boronic acid starting material | Structure |
|---|---|---|---|
| 132 | 4-(4-(4-(3-fluoropyridin-4-yl)-2,6-dimethylphenylthio)-5-methyl-5H-pyrrolo[3,2-d]pyrimidin-2-ylamino)benzonitrile | 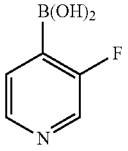 | 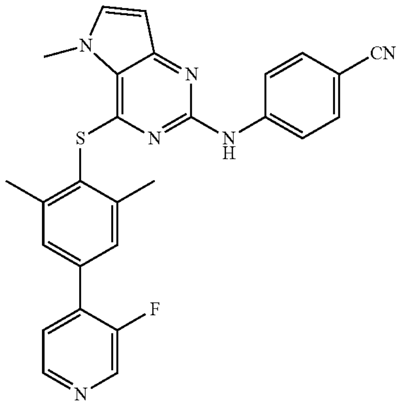 |
| 133 | 4-(4-(4-(2-fluoropyridin-4-yl)-2,6-dimethylphenylthio)-5-methyl-5H-pyrrolo[3,2-d]pyrimidin-2-ylamino)benzonitrile | 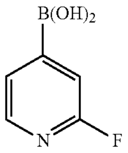 | 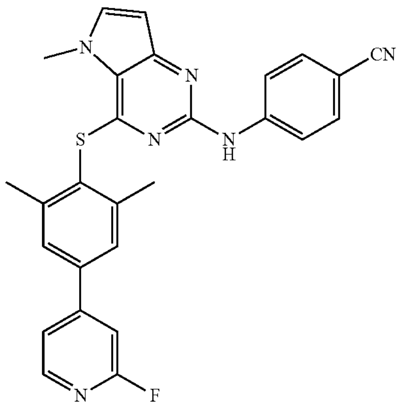 |

-continued

| Eg | Compound Name | Boronic acid starting material | Structure |
|---|---|---|---|
| 134 | 4-(4-(4-(2,6-difluoropyridin-4-yl)-2,6-dimethylphenylthio)-5-methyl-5H-pyrrolo[3,2-d]pyrimidin-2-ylamino)benzonitrile | 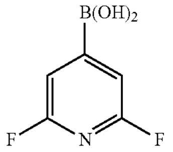 | 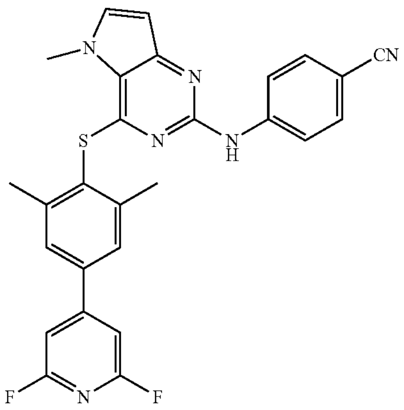 [SMILES: Cc1cc(-c2cc(F)nc(F)c2)cc(C)c1Sc1nc(Nc2ccc(C#N)cc2)nc2ccn(C)c12] |
| 135 | 4-(4-((2-(4-cyanophenylamino)-5-methyl-5H-pyrrolo[3,2-d]pyrimidin-4-yl)sulfanyl)-3,5-dimethylphenyl)pyridine-3-carbonitrile | 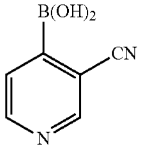 | 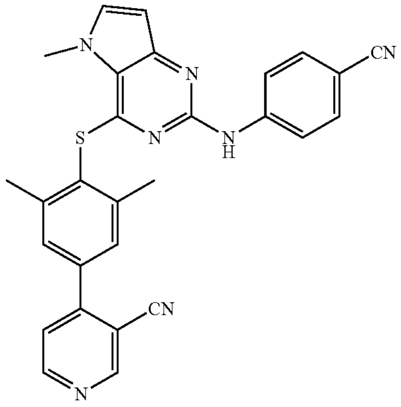 |
| 136 | 4-(4-((2-(4-cyanophenylamino)-5-methyl-5H-pyrrolo[3,2-d]pyrimidin-4-yl)sulfanyl)-3,5-dimethylphenyl)pyridine-2-carbonitrile | 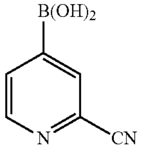 | 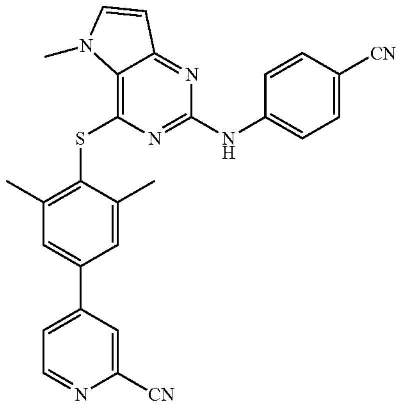 |

-continued
| Eg | Compound Name | Boronic acid starting material | Structure |
|---|---|---|---|
| 137 | 4-(4-(2-methyl-4-(3-methylpyridin-4-yl)phenylthio)-5-methyl-5H-pyrrolo[3,2-d]pyrimidin-2-ylamino)benzonitrile | 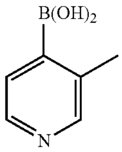 | 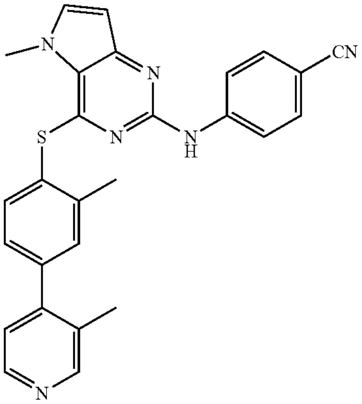 [SMILES: Cc1cc(-c2ccncc2C)ccc1Sc1nc(Nc2ccc(C#N)cc2)nc2ccn(C)c12] |
| 138 | 4-(4-(2,6-dimethyl-4-(2-methylpyridin-4-yl)phenylthio)-5-methyl-5H-pyrrolo[3,2-d]pyrimidin-2-ylamino)benzonitrile | 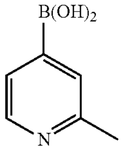 | 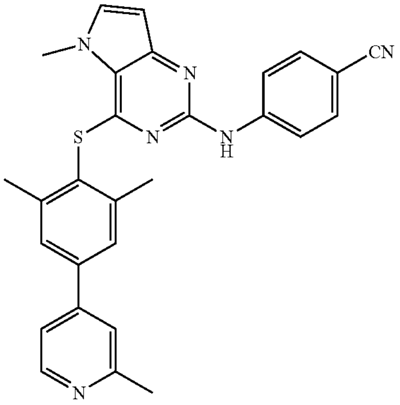 |
| 139 | 4-(4-(4-(3-methoxypyridin-4-yl)-2,6-dimethylphenylthio)-5-methyl-5H-pyrrolo[3,2-d]pyrimidin-2-ylamino)benzonitrile | 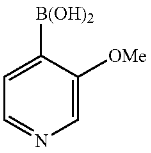 [SMILES: COc1cnccc1B(O)O] | 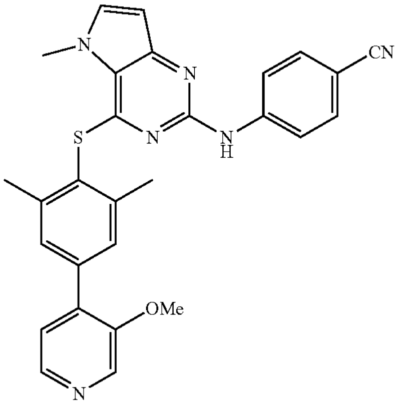 |

-continued
| Eg | Compound Name | Boronic acid starting material | Structure |
|---|---|---|---|
| 140 | 4-(4-(4-(2-methoxypyridin-4-yl)-2,6-dimethylphenylthio)-5-methyl-5H-pyrrolo[3,2-d]pyrimidin-2-ylamino)benzonitrile | 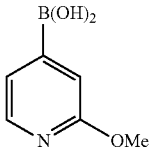 [SMILES: COc1cc(B(O)O)ccn1] | 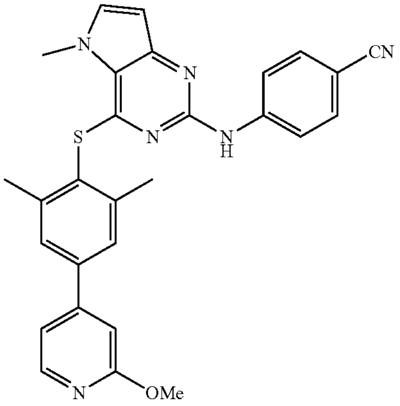 |
| 141 | 4-(4-(4-(3-chloropyridin-4-yl)-2,6-dimethylphenylthio)-5-methyl-5H-pyrrolo[3,2-d]pyrimidin-2-ylamino)benzonitrile | 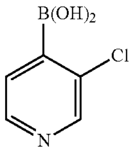 | 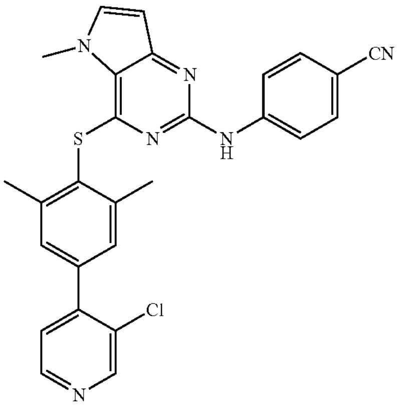 |
| 142 | 4-(4-(2,6-dimethyl-4-(pyridin-3-yl)phenylthio)-5-methyl-5H-pyrrolo[3,2-d]pyrimidin-2-ylamino)benzonitrile | 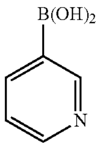 | 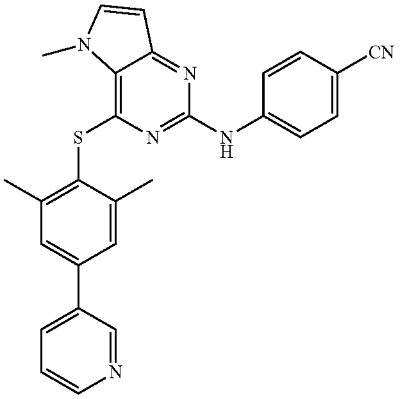 |

-continued

| Eg | Compound Name | Boronic acid starting material | Structure |
|---|---|---|---|
| 143 | 4-(4-(4-(furan-3-yl)-2,6-dimethylphenylthio)-5-methyl-5H-pyrrolo[3,2-d]pyrimidin-2-ylamino)benzonitrile | 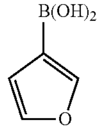 | 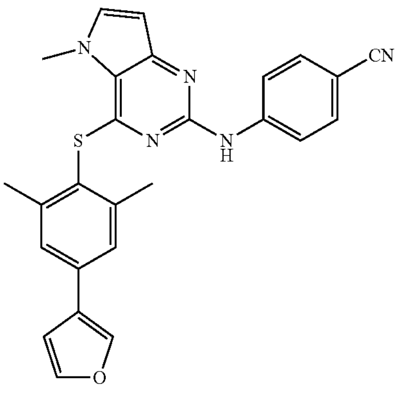 |
| 144 | 4-(4-(4-(2-methoxypyrimidin-5-yl)-2,6-dimethylphenylthio)-5-methyl-5H-pyrrolo[3,2-d]pyrimidin-2-ylamino)benzonitrile | 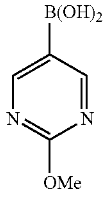 | 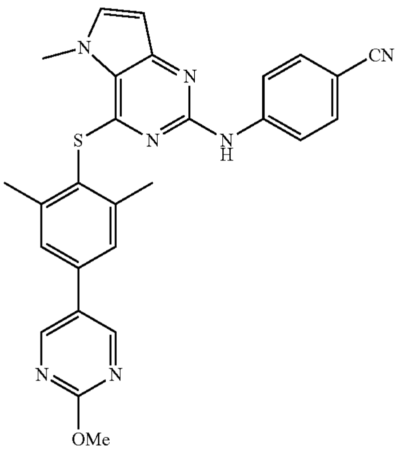 [SMILES: COc1ncc(-c2cc(C)c(Sc3nc(Nc4ccc(C#N)cc4)nc4ccn(C)c34)c(C)c2)cn1] |

Example 145

4-(7-(2,6-dimethyl-4-(pyridin-4-yl)phenoxy)-1H-1,2,31-triazolo[4,5-d]pyrimidin-5-ylamino)benzonitrile

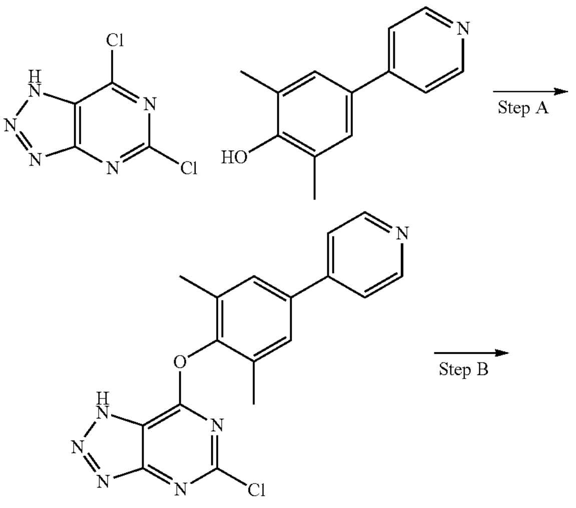

-continued

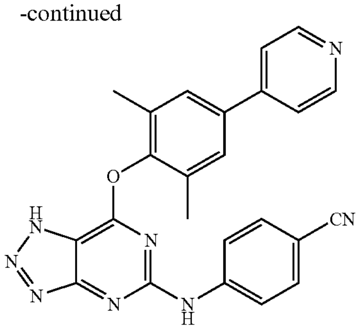

Step A: 7-(2,6-Dimethyl-4-(pyridin-4-yl)phenoxy)-5-chloro-1H-1,2,31-triazolo[4,5-d]pyrimidine Sodium hydride (1.2 eq) is added to 2,6-dimethyl-4-(pyridin-4-yl)phenol (prepared according to literature procedures, see Combellas et al., *Tetrahedron Letters,* 1992, 33, 4923) (1.2 eq) in 1-methyl-2-pyrridone (2 ml/mmol) at 0° C. The reaction mixture is stirred at room temperature for 30 min and a solution of 5,7-dichloro-1H-[1,2,3]triazolo[4,5-d]pyrimidine (see *Helvetica Chimica Acta,* 1951, 34, 835) (1 eq) in 1-methyl-2-pyrridone (1 ml/mmol) is added. The resulting mixture is heated to 100° C. for 16 h, cooled to room temperature, poured into ice water and extracted with $CHCl_3$ (×3). The combined organic layers are washed with water and brine, dried ($Na_2SO_4$), concentrated to dryness and purified by silica gel chromatography.

Step B: 4-(7-(2,6-dimethyl-4-(pyridin-4-yl)phenoxy)-1H-1,2,31-triazolo[4,5-d]pyrimidin-5-ylamino)benzonitrile Trifluoroacetic acid (8 eq) is added to a suspension of 7-(2,6-dimethyl-4-(pyridin-4-yl)phenoxy)-5-chloro-1H-[1,2,3]triazolo[4,5-d]pyrimidine (1 eq) and 4-aminobenzonitrile (4 eq) in 2,2,2-trifluoroethanol (1 ml/0.1 mmol) in a sealed tube. The resulting mixture is heated at 90° C. for 3 days. The reaction is cooled to room temperature, concentrated to dryness and purified by silica gel chromatography.

Example 146

4-(4-(2,6-dimethyl-4-(pyridin-4-yl)phenoxy)-1H-pyrazolo[3,4-d]pyrimidin-6-ylamino)benzonitrile

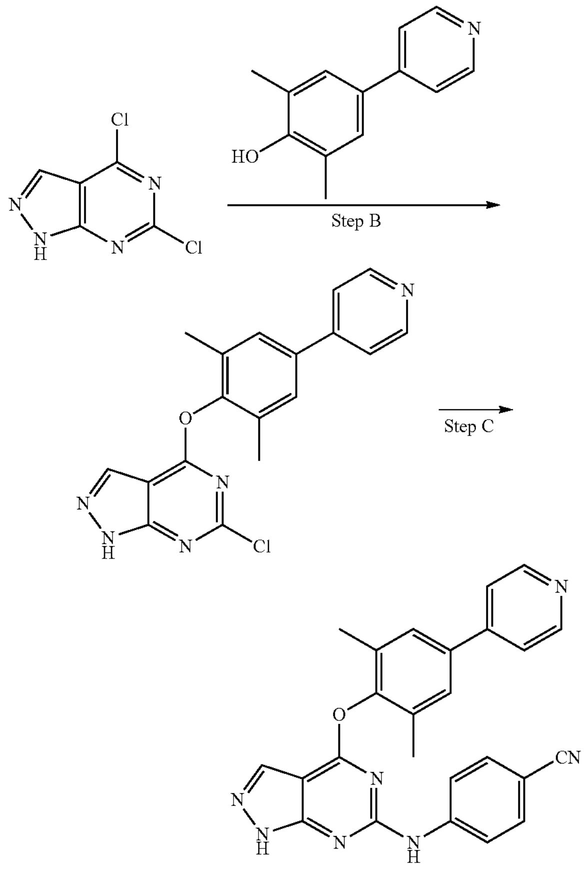

Step A: 4,6-Dichloro-1H-pyrazolo[3,4-d]pyrimidine 4,6-Dichloro-1H-pyrazolo[3,4-d]pyrimidine can be prepared according to previously described procedures (see Takamuro et al., EP 1 772 454 A1, filed Jul. 22, 2005) according to the scheme below:

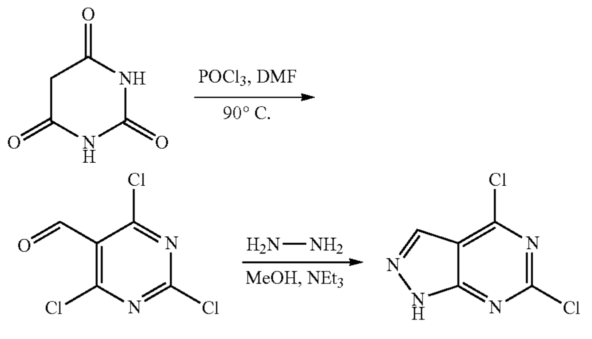

Step B: 4-(2,6-Dimethyl-4-(pyridin-4-yl)phenoxy)-6-chloro-1H-pyrazolo[3,4-d]pyrimidine Sodium hydride (1.2 eq) is added to 2,6-dimethyl-4-(pyridin-4-yl)phenol (prepared according to literature procedures, see Combellas et al., *Tetrahedron Letters,* 1992, 33, 4923) (1.2 eq) in 1-methyl-2-pyrridone (2 ml/mmol) at 0° C. The reaction mixture is stirred at room temperature for 30 min and a solution of 4,6-dichloro-1H-pyrazolo[3,4-d]pyrimidine (1 eq) in 1-methyl-2-pyrridone (1 ml/mmol) is added. The resulting mixture is heated to 100° C. for 16 h, cooled to room temperature, poured into ice water and extracted with $CHCl_3$ (×3). The combined organic layers are washed with water and brine, dried ($Na_2SO_4$), concentrated to dryness and purified by silica gel chromatography.

Step C: 4-(4-(2,6-dimethyl-4-(pyridin-4-yl)phenoxy)-1H-pyrazolo[3,4-d]pyrimidin-6-ylamino)benzonitrile Trifluoroacetic acid (8 eq) is added to a suspension of 7-(2,6-dimethyl-4-(pyridin-4-yl)phenoxy)-5-chloro-1H-[1,2,3]triazolo[4,5-d]pyrimidine (1 eq) and 4-aminobenzonitrile (4 eq) in 2,2,2-trifluoroethanol (1 ml/0.1 mmol) in a sealed tube. The resulting mixture is heated at 90° C. for 3 days. The reaction is cooled to room temperature, concentrated to dryness and purified by silica gel chromatography.

II. Biological Activity

Example 51

Generation of $IC_{50}$ Data (HIV-1 RT Enzyme Assay)

RT polymerase activity was determined by measuring the incorporation of radiolabeled dNTPs into a gapped DNA template. RT inhibition assays were carried out in 96-well plates with 1:4 serially diluted compounds. Each reaction (25 μL) contained 1 nM RT, 25 μg/mL activated calf thymus DNA, 10 μM each dCTP, dGTP, and dTTP, 0.25 μM [α-$^{33}$P] dATP (0.25 μCi), 50 mM Tris-HCl, pH 7.5, 10% glycerol, 2 mM DTT, 100 μg/mL BSA, and 5 mM $MgCl_2$. Reactions proceeded for 2.5 h at room temperature and were quenched by addition of 25 μL 20% TCA. The quenched mixtures were filtered onto glass-fiber filter plates (UniFilter®-96, GF/B) and dried. Each well in the filter plates was counted in 40 μL of MicroScint O scintillation fluid in a TopCount Microplate Scintillation Counter. The $IC_{50}$ was determined by fitting the relative rate data to the dose-response curve, $$\%\ \text{Inhibition}=100(1-v_i/v_0)=[I]/[I]+\text{IC50})$$

where $v_i$ is the reaction velocity in the presence of inhibitor and $v_o$ is the reaction velocity in the absence of inhibitor. Non-linear curve-fitting was performed using GraphPad Prism 4 software.

Example 52

Generation of $EC_{50}$ Data

Compounds were screened for inhibitory activity against human immunodeficiency virus type 1 (HIV-1) using a cell-based assay using HIV-1 expressing firefly luciferase as a reporter gene and pseudotyped with vesicular stomatitis virus envelope glycoprotein (VSV-G). Experimental procedures were essentially as previously published (see Connor et al., *Journal of Virology,* 1996, 70, 5306-5311: Characterization of the functional properties of env genes from long-term survivors of human immunodeficiency virus type 1 infection, and Popik et al., *Journal of Virology,* 2002, 76, 4709-4722: Human immunodeficiency virus type 1 uses lipid raft-co-localized CD4 and chemokine receptors for productive entry into CD4+ T cells). It should be particularly appreciated that some of the viruses contain mutations introduced by PCR mutagenesis in the RT gene, such as K103N, L100I, Y188L and Y181C that render the virus highly resistant to current non-nucleoside RT inhibitor HIV-1 drugs. Virus stocks were generated by co-transfection of plasmid DNA encoding VSV-G with vector pNL4-3Env(−)Luc(+) into 293T cells. Sixty-four hours after transfection, virus-containing medium was collected by centrifugation and stored frozen at −80° C.

HeLa cells were infected with the VSV-G pseudotyped virus in the presence of screening compounds in a 384-well or 96-well microtiter plate format. Forty-eight hours after initial infection, Luciferase Assay Reagent (Promega) was added to the cells and luciferase activity was determined using a LJLAnalyst luminometer. As the luciferase gene is carried in the virus genome, its expression level reflects the virus replication level in the presence of a compound.

To evaluate the activity of the compounds against wild type HIV-1, the HeLa-JC53 cell line that expresses high levels of CD4 and CCR5 was modified by isolation of a stable cell line that expresses luciferase under the control of the HIV-1 promoter (long terminal repeat, i.e., LTR). HIV-1 infection of this cell line stimulates the transcription of luciferase from the HIV-1 promoter and the luciferase gene expression level is proportional to the level of virus replication. Procedures for viral infection, compound testing and luciferase activity determination were the same as for the VSV-G pseudotyped HIV-1.

Two approaches have been used to evaluate cytotoxicity. The first employed another modified HeLa-JC53 cell line that constitutively expresses high levels of luciferase without viral infection. The level of luciferase expression in these cells served as an indicator for cell replication in the presence of the compounds. Procedures for compound testing and luciferase activity determination were the same as for the viral infection tests. The other toxicity assay utilized HeLe-JC53 cells and a commercially available cell viability assay kit (Promega) that measures the ATP levels in the cells.

Example 53

Biological Data for Selected Compounds

Select compounds prepared as described above were assayed according to the biological procedures described herein and the results are given in the table below. The results are listed below as $EC_{50}$ values (nM).

| Eg | EC50 | | | | |
|---|---|---|---|---|---|
| | | mutant | | | |
| No. | wild type | K103N | K103N-L100I | K103N-Y181C | Y188L |
| 1 | B | A | B | B | B |
| 2 | B | B | B | B | C |
| 3 | B | B | B | C | C |
| 4 | B | | C | | |
| 5 | A | A | A | B | C |
| 6 | B | B | B | C | C |
| 7 | B | B | B | B | C |
| 8 | B | C | C | C | C |
| 9 | B | | B | | |
| 10 | C | | C | | |
| 11 | A | | A | | |
| 12 | B | | C | | |
| 13 | B | | C | | |
| 14 | A | | B | | |
| 15 | | | | | |
| 16 | B | C | C | C | C |
| 17 | B | B | B | C | C |
| 18 | B | | B | | |
| 19 | A | | B | | |
| 20 | A | | B | | |
| 21 | B | | C | | |
| 22 | B | | C | | |
| 23 | A | | C | | |
| 24 | A | B | B | C | B |
| 25 | A | | A | | |
| 26 | B | | B | | |
| 27 | A | | C | | |
| 28 | | | C | | |
| 29 | A | A | B | B | B |
| 30 | A | | A | | |
| 31 | A | | A | | |
| 32 | B | | C | | |
| 33 | C | | C | | |
| 34 | B | | B | | |
| 35 | B | | B | | |
| 36 | B | | C | | |
| 37 | B | | C | | |
| 38 | B | | B | | |
| 39 | C | | C | | |
| 40 | B | | C | | |
| 41 | B | | C | | |
| 42 | B | | C | | |
| 43 | B | | C | | |
| 44 | B | | B | | |
| 45 | A | B | B | B | B |
| 46 | B | B | C | B | C |
| 47 | B | | C | | |
| 48 | B | | B | | |
| 49 | B | | C | | |
| 50 | B | B | B | B | C |
| 51 | B | | C | | |
| 52 | A | | B | | |
| 53 | B | B | B | B | C |
| 54 | A | | C | | |
| 55 | B | | B | | |
| 56 | B | | B | | |
| 57 | A | | B | | |
| 58 | B | | B | | |
| 59 | B | | C | | |
| 60 | B | | C | | |
| 61 | B | B | B | C | B |
| 62 | B | | C | | |
| 63 | A | | B | | |
| 64 | A | | A | | |
| 65 | A | | C | | |
| 66 | A | | B | | |
| 67 | A | | C | | |
| 68 | A | | C | | |
| 69 | B | | C | | |
| 70 | | | B | | |

-continued

| Eg | EC50 | | | | |
|---|---|---|---|---|---|
| | | mutant | | | |
| No. | wild type | K103N | K103N-L100I | K103N-Y181C | Y188L |
| 71 | | | C | | |
| 72 | B | | A | | |
| 73 | C | | C | | |
| 74 | C | | C | | |
| 75 | A | | B | | |
| 76 | B | | C | | |
| 77 | B | | C | | |
| 78 | B | B | B | B | B |
| 79 | B | | B | | |
| 80 | B | | B | | |
| 81 | B | | C | | |
| 82 | C | | | | |
| 83 | C | | | | |
| 84 | B | | B | | |
| 85 | B | | C | | |
| 86 | C | | C | | |
| 87 | B | | C | | |
| 88 | B | | B | | |
| 89 | B | | C | | |
| 90 | B | | C | | |
| 91 | C | | C | | |
| 92 | C | | C | | |
| 93 | C | | | | |
| 94 | B | | B | | |
| 95 | C | | C | | |
| 96 | | | | | |
| 97 | | | | | |
| 98 | A | | C | | |
| 99 | B | | C | | |
| 100 | B | | C | | |
| 101 | C | | C | | |
| 102 | A | | C | | |
| 103 | B | | C | | |
| 104 | B | | B | | |
| 105 | C | | C | | |
| 106 | C | | C | | |
| 107 | B | | B | | |
| 108 | B | | B | | |
| 109 | A | | B | | |
| 110 | C | | C | | |
| 111 | B | B | B | C | C |
| 112 | A | | B | | |
| 113 | A | | B | | |
| 114 | A | | C | | |
| 115 | A | | A | | |
| 116 | A | | B | | |
| 117 | A | | B | | |
| 118 | B | | B | | |
| 119 | A | | C | | |
| 120 | C | | C | | |
| 121 | C | | | | |
| 122 | C | | | | |
| 123 | B | B | C | C | B |
| 124 | B | | C | | |
| 125 | B | | B | | |
| 126 | B | | | | |
| 127 | C | | C | | |
| 128 | B | | C | | |
| 129 | B | | C | | |
| 130 | B | | C | | |

Table legend:
A is <1 nM;
B is 1 nM-10 nM;
C is >10 nM.
Blank indicates the compound has not been tested The examples and embodiments described herein are for illustrative purposes only and various modifications or changes suggested to persons skilled in the art are to be included within the spirit and purview of this application and scope of the appended claims. It is intended that the methods and structures within the scope of the following claims and their equivalents be covered thereby.

What is claimed is:

1. A compound of formula (I) or a pharmaceutically acceptable salt, or tautomer thereof:

(I)

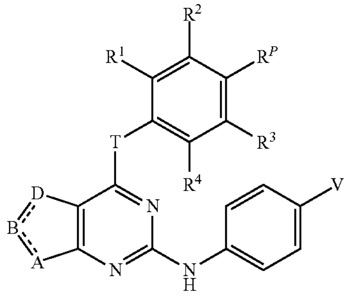

wherein $\overline{\overline{----}}$ represents a double bond between either A and B or B and D;

A is —N═, or —NZ—;

B is —CY═;

D is —N═, —NW—;

wherein

W, Y and Z are each independently selected from H, F, Cl, Br, $C_1$-$C_6$ alkyl, $C_2$-$C_6$ alkenyl, $OC_1$-$C_6$ alkyl, $C_3$-$C_6$ cycloalkyl, $OC_3$-$C_6$ cycloalkyl, phenyl or benzyl, wherein the alkyl, alkenyl, cycloalkyl, phenyl and the phenyl moiety of the benzyl group are optionally substituted with 1-3 substituents selected from F, Cl, Br, I, OH, $CF_3$, $C_1$-$C_3$ alkyl and $OC_1$-$C_3$ alkyl;

V is H, F, Cl, CN, $CF_3$, $SO_2CH_3$, $SO_2NH_2$, $SO_2NHCH_3$, $NH_2$, NH($C_1$-$C_6$ alkyl) or N($C_1$-$C_6$ alkyl);

T is NH, O or S;

$R^P$ is aryl, substituted aryl, heterocyclyl, substituted heterocyclyl, heteroaryl or substituted heteroaryl; and $R^1$, $R^2$, $R^3$ and $R^4$ are independently selected from H, F, Cl, Br, I, $CFH_2$, $CF_2H$, $CF_3$, CN, CH═CHCN, methyl, ethyl, n-propyl, i-propyl, n-butyl, i-butyl, s-butyl, i-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$ and $OC_1$-$C_3$ alkyl.

2. A compound of claim 1, or a pharmaceutically acceptable salt thereof.

3. The compound of claim 1, wherein

V is CN; and

T is O.

4. The compound of claim 1, wherein $R^1$ and $R^4$ are independently selected from Cl, methyl, ethyl, n-propyl and i-propyl; and $R^2$ and $R^3$ are H.

5. The compound of claim 1, wherein W, Y and Z are each independently selected from H, F, Cl, Br, $C_1$-$C_6$ alkyl or $C_1$-$C_6$ alkyl substituted with 1-3 substituents selected from F, Cl, Br, I, OH, and $CF_3$.

6. The compound of claim 1, wherein

Z is H, methyl or ethyl; and

W is H, F, Cl or methyl.

7. The compound of claim 1, wherein $R^P$ is aryl or substituted aryl.

8. The compound of claim 1, wherein $R^P$ is heterocyclyl, substituted heterocyclyl, heteroaryl or substituted heteroaryl.

9. The compound of claim 1, wherein $R^P$ is phenyl, substituted phenyl, heteroaryl or substituted heteroaryl.

10. The compound of claim 1, wherein $R^P$ is substituted pyridyl or substituted phenyl.

11. The compound of claim 1, wherein $R^P$ is substituted pyridyl or substituted phenyl, wherein the substituents are independently selected from F, Cl, Br, I, C(O)R', $CO_2H$, COORS, $CONH_2$, CONHR', CONR'R", $SO_3H$, $S(O)_2R'$, $S(O)_2NH_2$, $S(O)_2NHR'$, $S(O)_2NR'R"$; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl; and R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring.

12. The compound of claim 1, wherein

Y is H;

V is CN; and

T is O.

13. The compound of claim 1, wherein

Y is H;

V is CN;

T is O;

$R^1$ and $R^4$ are independently selected from Cl, methyl, ethyl, n-propyl and i-propyl;

$R^2$ and $R^3$ are H; and $R^P$ is substituted pyridyl or substituted phenyl.

14. A pharmaceutical composition comprising an effective amount of a compound of formula (I) or a pharmaceutically acceptable salt, or tautomer thereof:

(I)

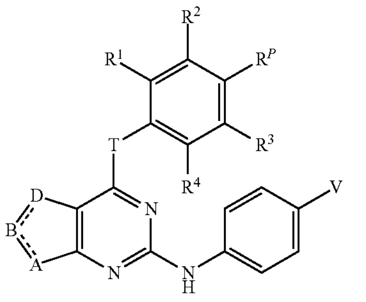

wherein

 represents a double bond between either A and B or B and D;

A is —N═, or —NZ—;

B is —CY═;

D is —N═, —NW—;

wherein

W, Y and Z are each independently selected from H, F, Cl, Br, $C_1$-$C_6$ alkyl, $C_2$-$C_6$ alkenyl, $OC_1$-$C_6$ alkyl, $C_3$-$C_6$ cycloalkyl, $OC_3$-$C_6$ cycloalkyl, phenyl or benzyl, wherein the alkyl, alkenyl, cycloalkyl, phenyl and the phenyl moiety of the benzyl group are optionally substituted with 1-3 substituents selected from F, Cl, Br, I, OH, $CF_3$, $C_1$-$C_3$ alkyl and $OC_1$-$C_3$ alkyl;

V is H, F, Cl, CN, $CF_3$, $SO_2CH_3$, $SO_2NH_2$, $SO_2NHCH_3$, $NH_2$, $NH(C_1$-$C_6$ alkyl) or $N(C_1$-$C_6$ alkyl$)_2$;

T is NH, O or S;

$R^P$ is aryl, substituted aryl, heterocyclyl, substituted heterocyclyl, heteroaryl or substituted heteroaryl; and $R^1$, $R^2$, $R^3$ and $R^4$ are independently selected from H, F, Cl, Br, I, $CFH_2$, $CF_2H$, $CF_3$, CN, CH═CHCN, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$ and $OC_1$-$C_3$ alkyl.

15. The pharmaceutical composition of claim 14, further comprising a pharmaceutically acceptable carrier, diluent or excipient.

16. The pharmaceutical composition of claim 14, further comprising a second therapeutic agent.

17. A method for treating a human immunodeficiency virus (HIV) infection in an individual in need thereof, wherein the treating of a human immunodeficiency virus (HIV) infection is alleviating, ameliorating or inhibiting the human immunodeficiency virus (HIV) infection, the method comprising administering to the individual a therapeutically effective amount of a compound of formula (I) or a pharmaceutically acceptable salt, or tautomer thereof:

(I)

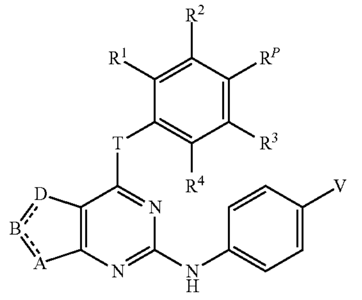

wherein $=\!=\!=$ represents a double bond between either A and B or B and D;

A is —N═, or —NZ—;

B is —CY═;

D is —N═, —NW—;

wherein

W, Y and Z are each independently selected from H, F, Cl, Br, $C_1$-$C_6$ alkyl, $C_2$-$C_6$ alkenyl, $OC_1$-$C_6$ alkyl, $C_3$-$C_6$ cycloalkyl, $OC_3$-$C_6$ cycloalkyl, phenyl or benzyl, wherein the alkyl, alkenyl, cycloalkyl, phenyl and the phenyl moiety of the benzyl group are optionally substituted with 1-3 substituents selected from F, Cl, Br, I, OH, $CF_3$, $C_1$-$C_3$ alkyl and $OC_1$-$C_3$ alkyl;

V is H, F, Cl, CN, $CF_3$, $SO_2CH_3$, $SO_2NH_2$, $SO_2NHCH_3$, $NH_2$, $NH(C_1$-$C_6$ alkyl) or $N(C_1$-$C_6$ alkyl$)_2$;

T is NH, O or S;

$R^P$ is aryl, substituted aryl, heterocyclyl, substituted heterocyclyl, heteroaryl or substituted heteroaryl; and $R^1$, $R^2$, $R^3$ and $R^4$ are independently selected from H, F, Cl, Br, I, $CFH_2$, $CF_2H$, $CF_3$, CN, CH═CHCN, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$ and $OC_1$-$C_3$ alkyl.

18. The method of claim 17, further comprising administering an effective amount of a second anti human immunodeficiency virus (HIV) or acquired immunodeficiency syndrome (AIDS) drug.

19. A method for treating human immunodeficiency virus (HIV) infection in an individual in need thereof with combination therapy, wherein the treating of a human immunodeficiency virus (HIV) infection is alleviating, ameliorating or inhibiting the human immunodeficiency virus (HIV) infection, the method comprising administering to said individual an effective amount of a combination of i) a compound of formula (I); and ii) a compound selected from the group consisting of reverse transcriptase inhibitors, viral protease inhibitors, cytokines, cytokine inhibitors, glycosylation inhibitors, viral mRNA processing inhibitors, entry inhibitors, integrase inhibitors or maturation inhibitors;

(I)

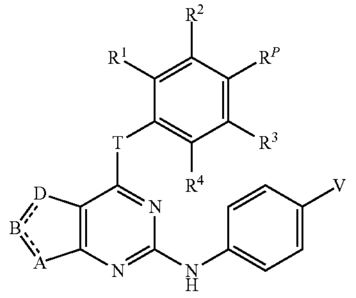

wherein $=\!=\!=$ represents a double bond between either A and B or B and D;

A is —N═, or —NZ—;

B is —CY═;

D is —N═, —NW—;

wherein

W, Y and Z are each independently selected from H, F, Cl, Br, $C_1$-$C_6$ alkyl, $C_2$-$C_6$ alkenyl, $OC_1$-$C_6$ alkyl, $C_3$-$C_6$ cycloalkyl, $OC_3$-$C_6$ cycloalkyl, phenyl or benzyl, wherein the alkyl, alkenyl, cycloalkyl, phenyl and the phenyl moiety of the benzyl group are optionally substituted with 1-3 substituents selected from F, Cl, Br, I, OH, $CF_3$, $C_1$-$C_3$ alkyl and $OC_1$-$C_3$ alkyl;

V is H, F, Cl, CN, $CF_3$, $SO_2CH_3$, $SO_2NH_2$, $SO_2NHCH_3$, $NH_2$, $NH(C_1$-$C_6$ alkyl) or $N(C_1$-$C_6$ alkyl$)_2$;

T is NH, O or S;

$R^P$ is aryl, substituted aryl, heterocyclyl, substituted heterocyclyl, heteroaryl or substituted heteroaryl; and $R^1$, $R^2$, $R^3$ and $R^4$ are independently selected from H, F, Cl, Br, I, $CFH_2$, $CF_2H$, $CF_3$, CN, CH═CHCN, methyl, ethyl, n-propyl, i-propyl, n-butyl, i-butyl, s-butyl, t-butyl, cyclopropyl, cyclobutyl, cyclopentyl, cyclohexyl, cyclopropylmethyl, $NH_2$, NHR', NR'R", OH, OR', SH, SR', C(O)R', $CO_2H$, COOR', $CONH_2$, CONHR', CONR'R", $SO_3H$, $S(O)_2R'$, $S(O)_2NH_2$, $S(O)_2NHR'$, $S(O)_2NR'R"$, aryl, heterocyclyl, heteroaryl; wherein R' is methyl, ethyl, n-propyl, i-propyl, n-butyl, i-butyl, s-butyl, t-butyl, cyclopropyl, cyclobutyl, cyclopentyl, cyclohexyl or cyclopropylmethyl;

R" is methyl, ethyl, n-propyl, i-propyl, n-butyl, i-butyl, s-butyl, t-butyl, cyclopropyl, cyclobutyl, cyclopentyl, cyclohexyl or cyclopropylmethyl; or R' and R" together with the nitrogen atom to which they are attached form an optionally substituted 4-, 5- or 6-membered heterocyclic ring; and the alkyl, cycloalkyl, aryl, heterocyclyl and heteroaryl moieties are optionally substituted with 1-3 substituents selected from F, Cl, Br, I, OH, $NH_2$, CN, $CF_3$ and $OC_1$-$C_3$ alkyl.

20. A compound selected from:
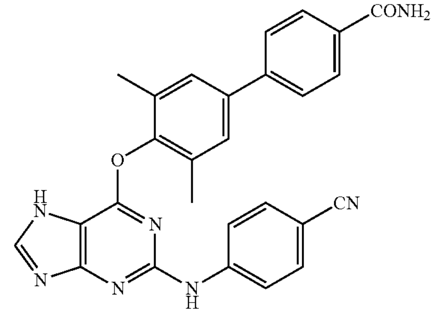
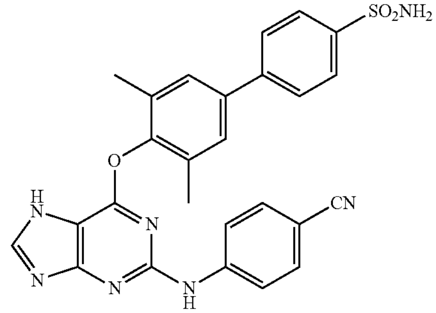
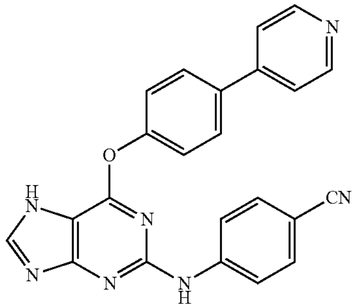
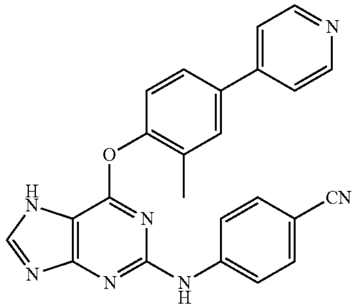
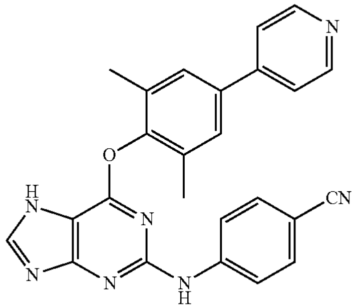
-continued
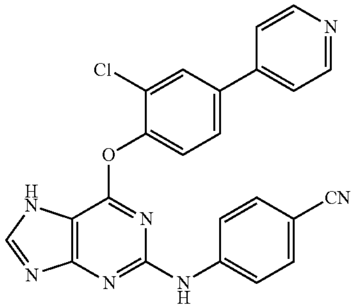
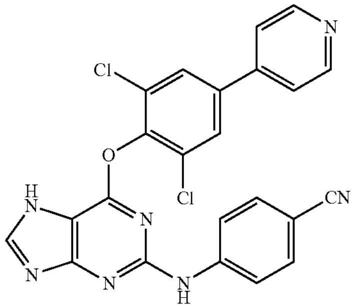
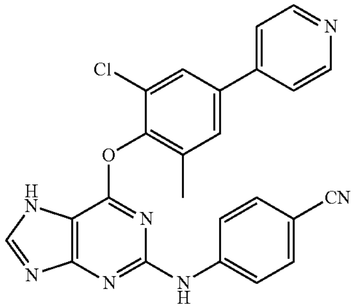
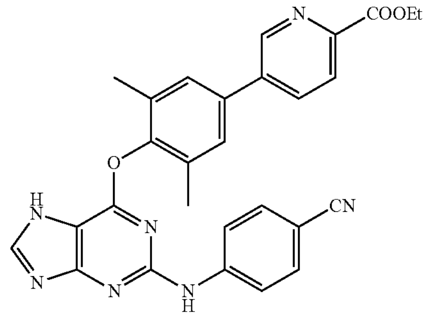
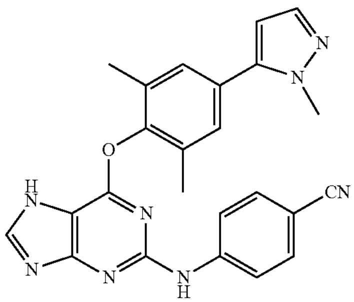

-continued
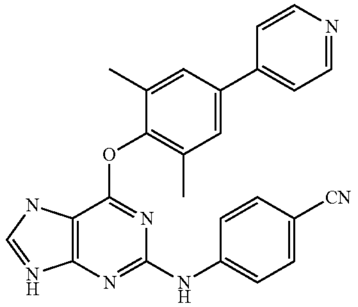
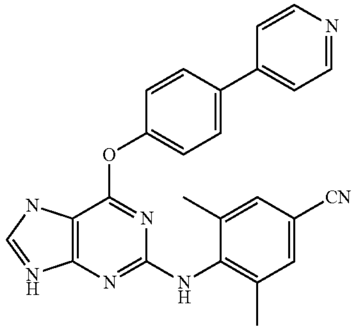
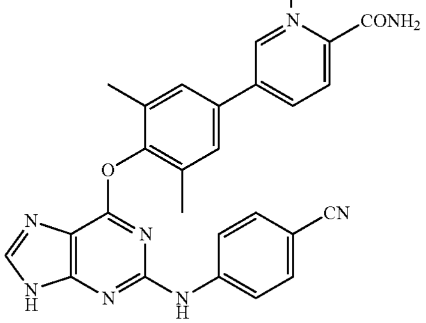
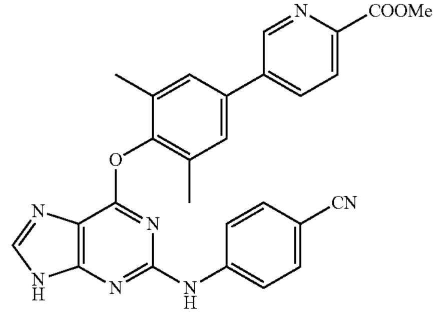
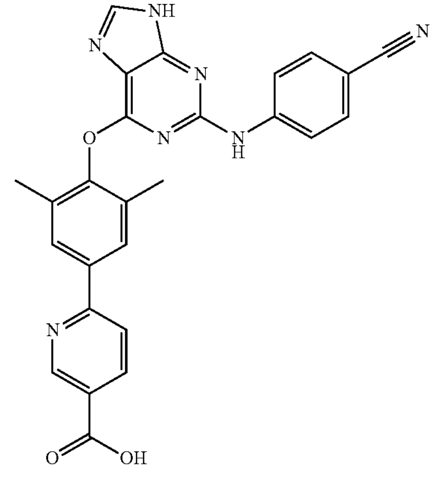
-continued
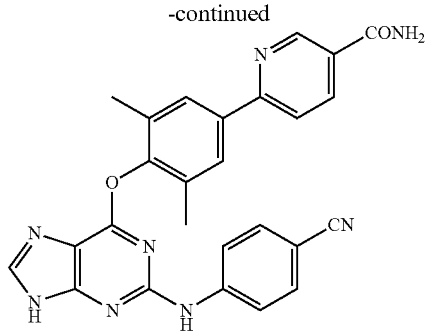
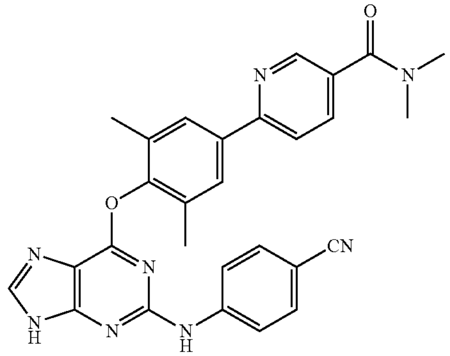
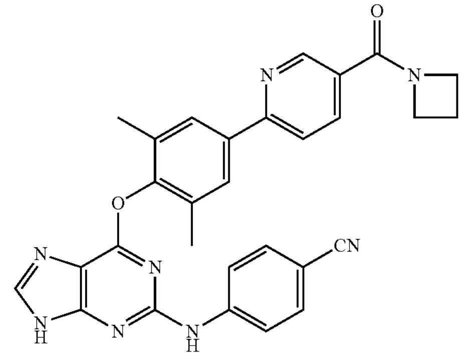
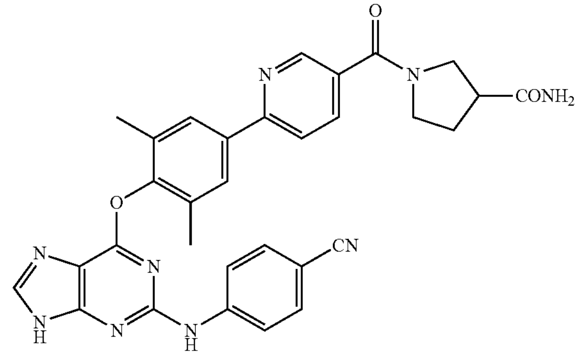
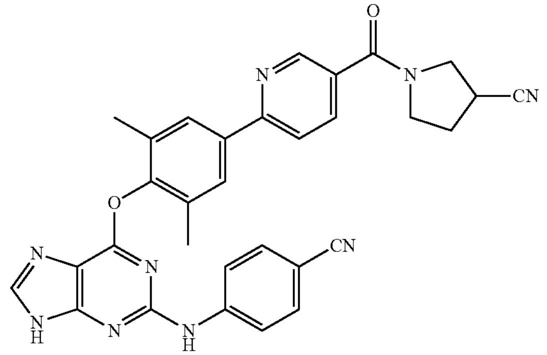

-continued
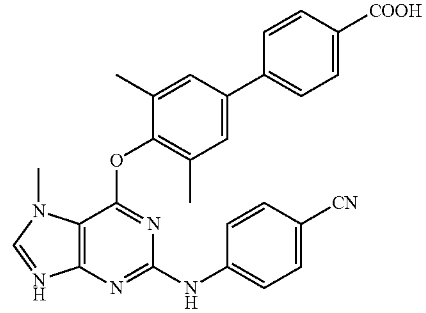
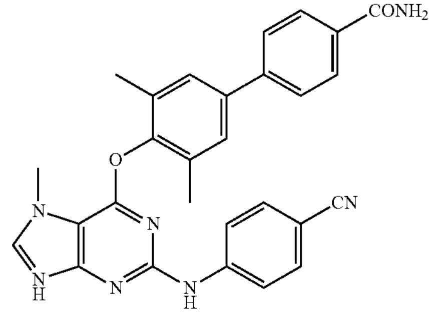
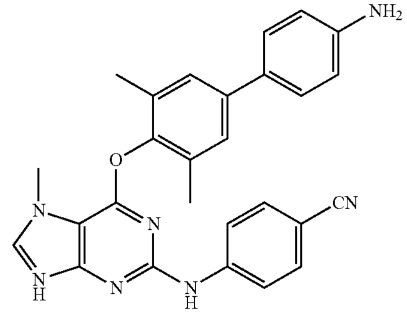
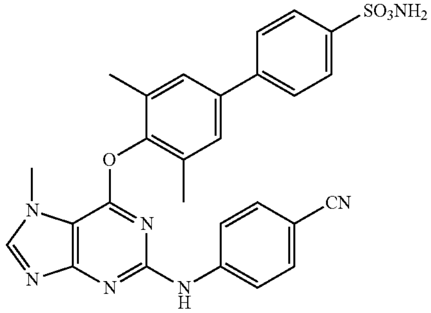
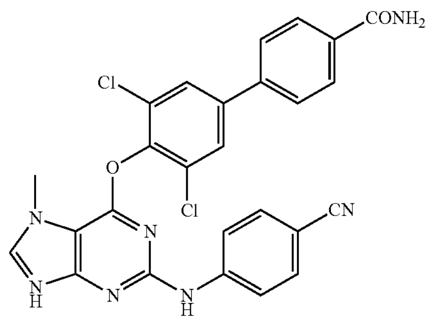
-continued
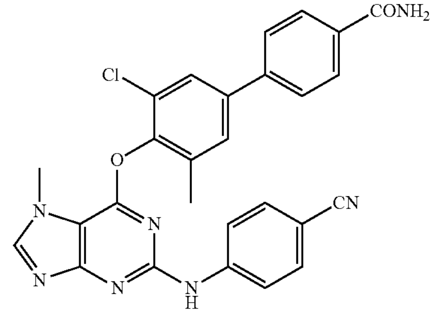
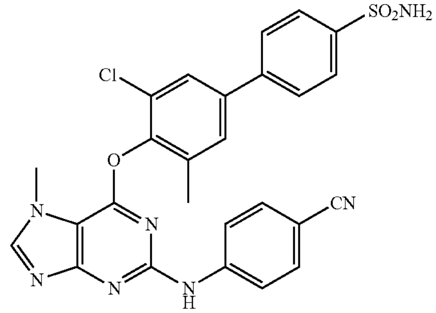
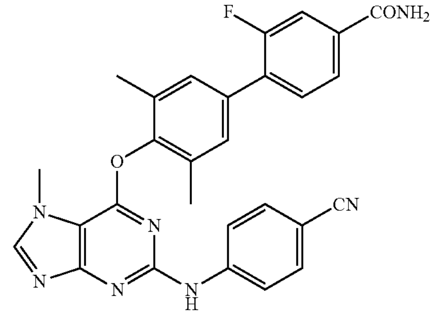
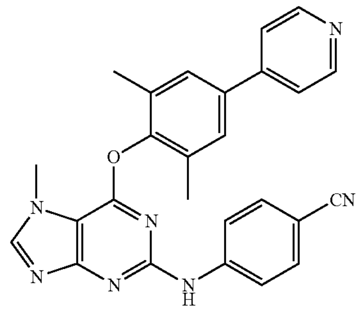
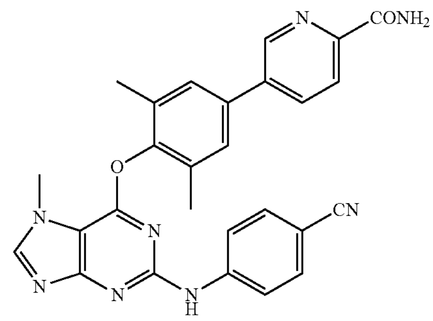

-continued
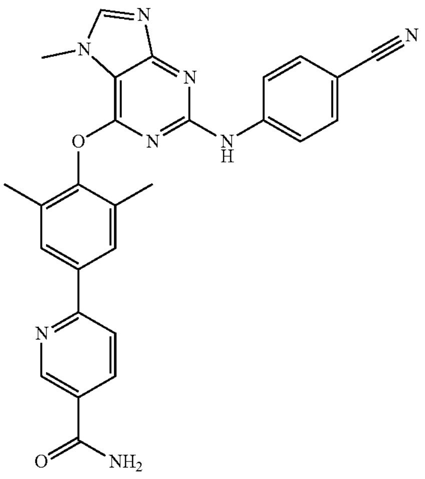
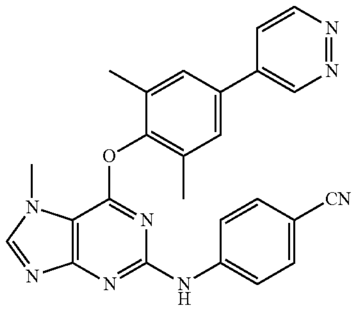
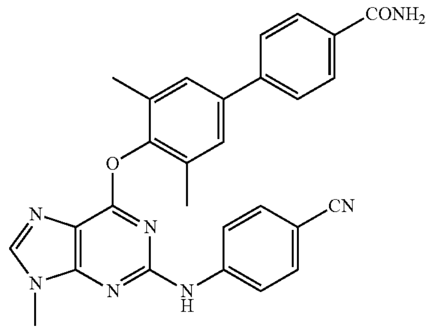
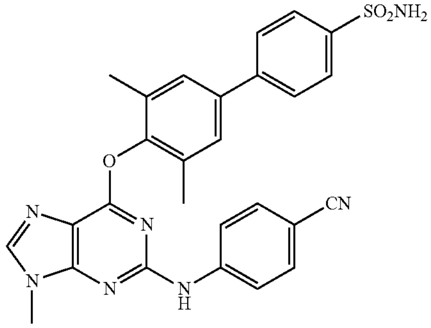
-continued
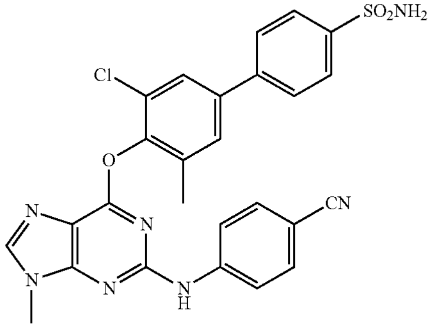
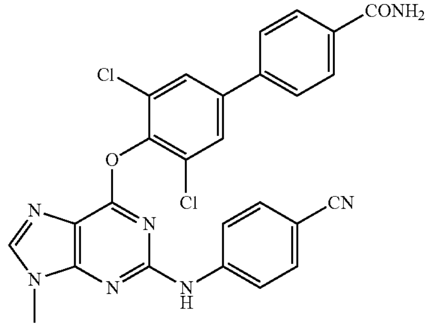
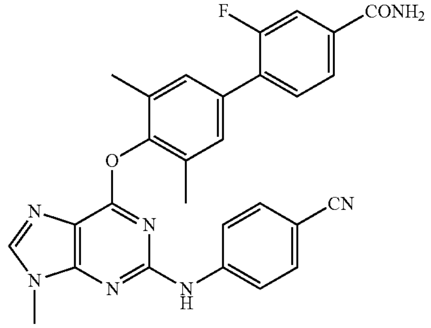
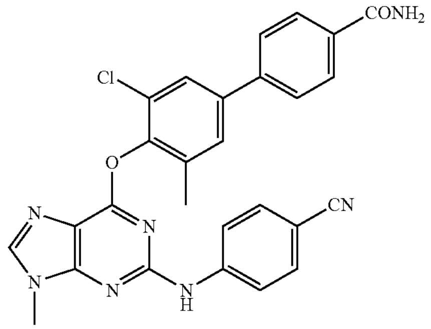
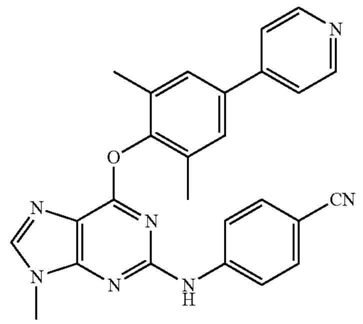

-continued
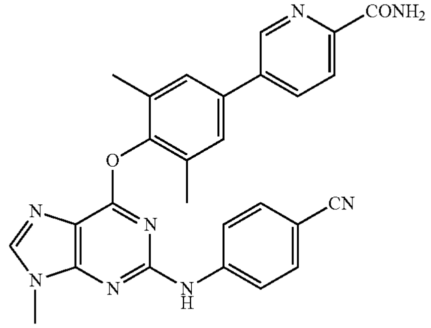
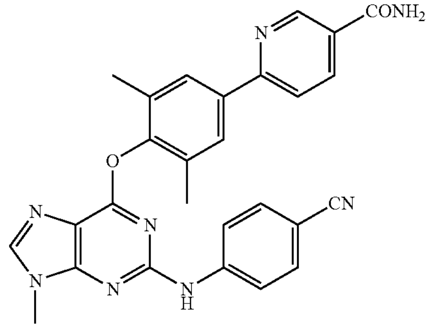
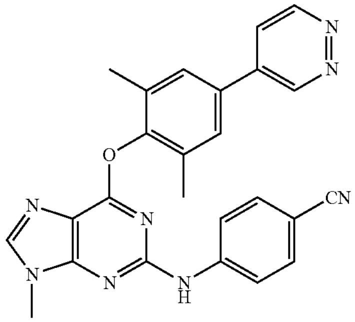
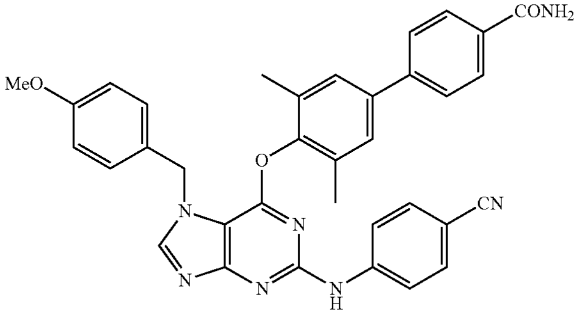
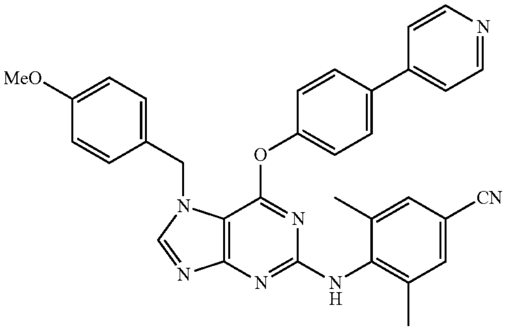
-continued
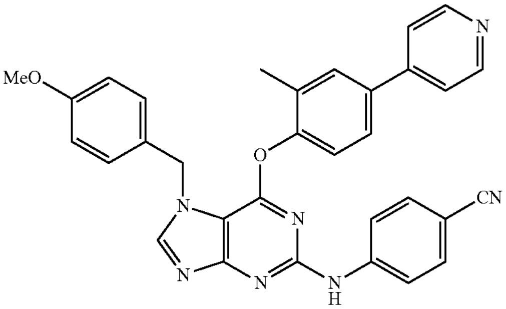
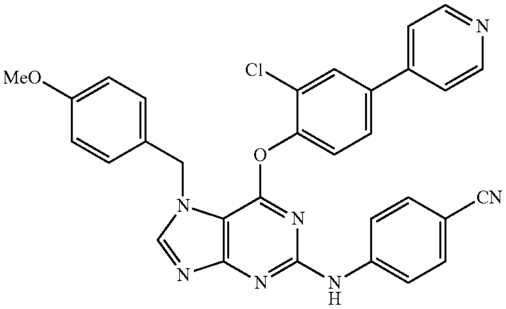
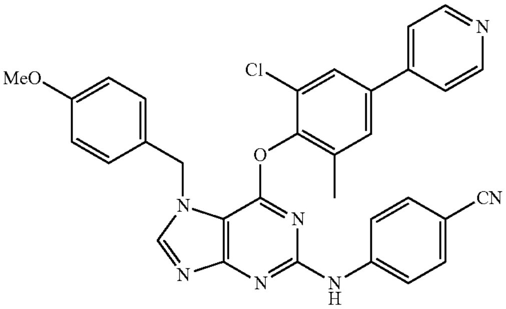
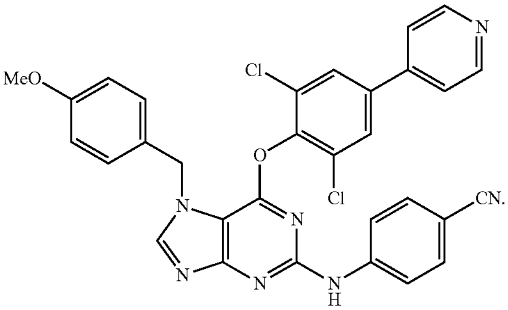
* * * * *